(12) United States Patent
Xiao et al.

(10) Patent No.: US 9,371,283 B2
(45) Date of Patent: Jun. 21, 2016

(54) POLYCYCLIC TETRACYCLINE COMPOUNDS

(75) Inventors: Xiao-Yi Xiao, San Diego, CA (US); Roger Clark, Lexington, MA (US); Diana Hunt, Cambridge, MA (US); Magnus Rönn, Melrose, MA (US); Louis Plamondon, Belmont, MA (US); Minsheng He, Watertown, MA (US); Joyce Sutcliffe, Newton, MA (US); Trudy Grossman, Lexington, MA (US)

(73) Assignee: Tetraphase Pharmaceuticals, Inc., Watertown, MA (US)

( * ) Notice: Subject to any disclaimer, the term of this patent is extended or adjusted under 35 U.S.C. 154(b) by 90 days.

(21) Appl. No.: 13/075,886

(22) Filed: Mar. 30, 2011

(65) Prior Publication Data

US 2011/0269714 A1 Nov. 3, 2011

Related U.S. Application Data

(60) Provisional application No. 61/319,614, filed on Mar. 31, 2010.

(51) Int. Cl.

| *C07D 209/56* | (2006.01) |
|---|---|
| *C07D 209/58* | (2006.01) |
| *C07D 221/18* | (2006.01) |
| *C07D 243/10* | (2006.01) |
| *C07D 405/04* | (2006.01) |
| *C07D 405/06* | (2006.01) |
| *C07D 487/04* | (2006.01) |

(52) U.S. Cl.
CPC ............ *C07D 209/58* (2013.01); *C07D 221/18* (2013.01); *C07D 243/10* (2013.01); *C07D 405/04* (2013.01); *C07D 405/06* (2013.01); *C07D 487/04* (2013.01)

(58) Field of Classification Search
CPC ............................ C07D 221/18; C07D 209/56
USPC .......................................................... 548/418
See application file for complete search history.

(56) References Cited

FOREIGN PATENT DOCUMENTS

| WO | WO/2007/117639 | 10/2007 |
|---|---|---|
| WO | WO2011/123536 | 10/2011 |

OTHER PUBLICATIONS

Notification of Transmittal of the International Search Report and the Written Opinion of the International Searching Authority, or the Declaration for International Patent Application No. PCT/US2011/030532; date of mailing Jul. 12, 2011.

Notification Concerning Transmittal of International Preliminary Report on Patentability for International Patent Application No. PCT/US2011/030532; date of mailing Oct. 11, 2012.

*Primary Examiner* — Barbara P Badio
(74) *Attorney, Agent, or Firm* — Foley Hoag LLP

(57) ABSTRACT

The present invention is directed to a compound represented by Structural Formula (I):

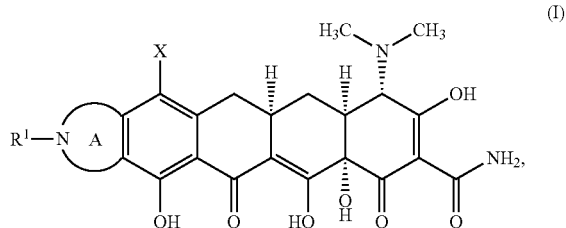

or a pharmaceutically acceptable salt thereof. The variables for Structural Formula (I) are defined herein. Also described is a pharmaceutical composition comprising the compound of Structural Formula (I) and its therapeutic use.

10 Claims, 2 Drawing Sheets

POLYCYCLIC TETRACYCLINE COMPOUNDS

RELATED APPLICATION

This application claims the benefit of U.S. Provisional Application No. 61/319,614, filed on Mar. 31, 2010. The entire teachings of the above application are incorporated herein by reference.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Therefore, there is need for new tetracycline analogs with improved antibacterial activities and efficacies against other tetracycline responsive diseases or disorders.

SUMMARY OF THE INVENTION

A first embodiment of the present invention is directed to a compound represented by Structural Formula (I):

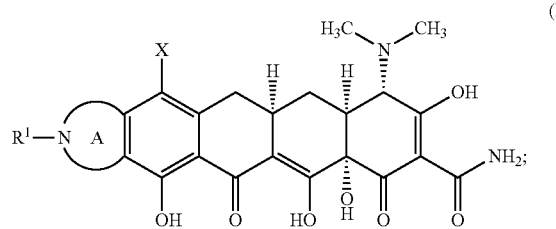

(I)

or a pharmaceutically acceptable salt thereof, wherein:

X is selected from halo, —R, —OR, —SR, —S(O)$_m$R, —N(R)$_2$, —N(R)C(O)R, N(R)C(O)OR', and N(R)S(O)$_m$R', wherein:

each R is independently selected from H, ($C_1$-$C_6$)alkyl, carbocyclyl, or heterocyclyl, or two R groups taken together with the atom or atoms to which they are bound form a 4-7 membered non-aromatic heterocyclyl; and R' is ($C_1$-$C_6$)alkyl, carbocyclyl, or heterocyclyl;

ring A is a 5-7 membered non-aromatic heterocyclic ring optionally containing 1-2 heteroatoms independently selected from N, S and O in addition to the indicated nitrogen atom, wherein:

$R^1$ is selected from hydrogen, —($C_1$-$C_8$)alkyl, —($C_0$-$C_6$)alkylene-carbocyclyl, —($C_0$-$C_6$)alkylene-heterocyclyl, —($C_1$-$C_6$)alkylene-O—($C_1$-$C_6$)alkyl, —($C_2$-$C_6$)alkylene-O-carbocyclyl, —($C_2$-$C_6$)alkylene-O-heterocyclyl, —S(O)$_m$—($C_1$-$C_6$)alkyl, —S(O)$_m$-carbocyclyl, —S(O)$_m$-heterocyclyl, —($C_2$-$C_4$)alkylene-S(O)$_m$-carbocyclyl, —($C_2$-$C_4$)alkylene-S(O)$_m$-heterocyclyl, —C(O)—[C($R^4$)($R^4$)]$_{0-4}$—N($R^2$)($R^3$), —C(O)—($C_1$-$C_6$)alkyl, —C(O)-heterocyclyl, —C(O)-carbocyclyl, —S(O)$_m$-[C($R^4$)($R^4$)]$_{0-4}$—N($R^2$)($R^3$), and —S(O)$_m$—($C_1$-$C_4$)alkylene-carbocyclyl, —S(O)$_m$—($C_1$-$C_4$)alkylene-heterocyclyl, or $R^1$ taken together with a ring atom adjacent to the nitrogen atom to which $R^1$ is bound forms a saturated heterocyclic ring fused to ring A;

each of $R^2$ and $R^3$ is independently selected from hydrogen, ($C_1$-$C_8$)alkyl, —($C_0$-$C_6$) alkylene-carbocyclyl, —($C_0$-$C_6$)alkylene-heterocyclyl, —($C_2$-$C_6$)alkylene-O-carbocyclyl, —($C_2$-$C_6$)alkylene-O-heterocyclyl, —S(O)$_m$—($C_1$-$C_6$)alkyl, —S(O)$_m$-carbocyclyl, —S(O)$_m$-heterocyclyl, —($C_2$-$C_4$)alkylene-S(O)$_m$-carbocyclyl, and —($C_2$-$C_4$)alkylene-S(O)$_m$-heterocyclyl; or $R^2$ and $R^3$, taken together with the nitrogen atom to which they are bound form a heterocyclyl, wherein the heterocyclyl optionally comprises 1 to 4 additional heteroatoms independently selected from N, S and O;

each $R^4$ is independently selected from hydrogen, ($C_1$-$C_6$)alkyl, carbocyclyl, heterocyclyl or a naturally occurring amino acid side chain moiety, or two $R^4$ taken together with a common carbon atom to which they are bound form a 3-7 membered non-aromatic carbocyclyl or a 4-7 membered non-aromatic heterocyclyl, wherein the heterocyclyl formed by two $R^4$ comprises one to three heteroatoms independently selected from N, S and O;

any substitutable carbon atom on ring A is optionally:
  (i) substituted with one to two substituents independently selected from —($C_1$-$C_4$)alkyl, and —($C_0$-$C_4$)alkylene-carbocyclyl; or
  (ii) substituted with =O;
  (iii) taken together with an adjacent ring atom to form a 3-7 membered saturated carbocyclyl or a 4-7 membered saturated heterocyclyl ring; or
  (iv) spyrofused to a 3-7 membered saturated carbocyclyl;

any additional N heteroatom on ring A is substituted with hydrogen, $C_1$-$C_6$ alkyl, carbocyclyl, or heterocyclyl;

each alkyl or alkylene in Structural Formula I is optionally and independently substituted with one or more substituents independently selected from halo, —OH, =O, —O—($C_1$-$C_4$)alkyl, fluoro-substituted-($C_1$-$C_4$) alkyl, —S(O)$_m$—($C_1$-$C_4$)alkyl and —N($R^5$)($R^5$);

each carbocyclyl or heterocyclyl portion of a substituent of ring A or the saturated heterocyclic ring fused to ring A is optionally and independently substituted with one or more substituents independently selected from halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N($R^5$)($R^5$) and CN;

each $R^5$ is independently selected from hydrogen and ($C_1$-$C_4$)alkyl, wherein each alkyl in the group represented by $R^5$ is optionally and independently substituted with one or more substituents independently selected from —($C_1$-$C_4$)alkyl, ($C_3$-$C_6$)cycloalkyl, halo, —OH, —O—($C_1$-$C_4$)alkyl, and —($C_1$-$C_4$)alkylene-O—($C_1$-$C_4$)alkyl; and each m is independently 1 or 2, with the proviso that when X is hydrogen, ring A is not an unsubstituted bivalent piperidine radical.

In one aspect of the first embodiment,

X is selected from halo, —R', —OR, —SR, —S(O)$_m$R, —N(R)$_2$, —N(R)C(O)R, N(R)C(O)OR', and N(R)S(O)$_m$R'; and R' is $(C_1\text{-}C_6)$alkyl, carbocyclyl, or heterocyclyl, wherein the values for the remaining variables are as defined in the first embodiment.

Another embodiment of the present invention is directed to a pharmaceutical composition comprising a pharmaceutically acceptable carrier or diluent and a compound represented by Structural Formula (I) or a pharmaceutically acceptable salt thereof. The pharmaceutical composition is used in therapy, such as treating an infection (e.g., a bacterial infection) in a subject.

Another embodiment of the present invention is a method of treating an infection (e.g., a bacterial infection) in a subject comprising administering to the subject an effective amount of a compound represented by Structural Formula (I) or a pharmaceutically acceptable salt thereof.

Another embodiment of the present invention is a method of preventing an infection (e.g., a bacterial infection) in a subject comprising administering to the subject an effective amount of a compound represented by Structural Formula (I) or a pharmaceutically acceptable salt thereof.

Another embodiment of the present invention is the use of a compound represented by Structural Formula (I) or a pharmaceutically acceptable salt thereof for the manufacture of a medicament for treating an infection (e.g., a bacterial infection) in a subject.

Another embodiment of the present invention is the use of a compound represented by Structural Formula (I) or a pharmaceutically acceptable salt thereof for the manufacture of a medicament for preventing an infection (e.g., a bacterial infection) in a subject.

Another embodiment of the present invention is the use of a compound represented by Structural Formula (I) or a pharmaceutically acceptable salt thereof in therapy, such as treating or preventing an infection (e.g., a bacterial infection) in a subject.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Values and Alternative Values for Variables

Figure 1:
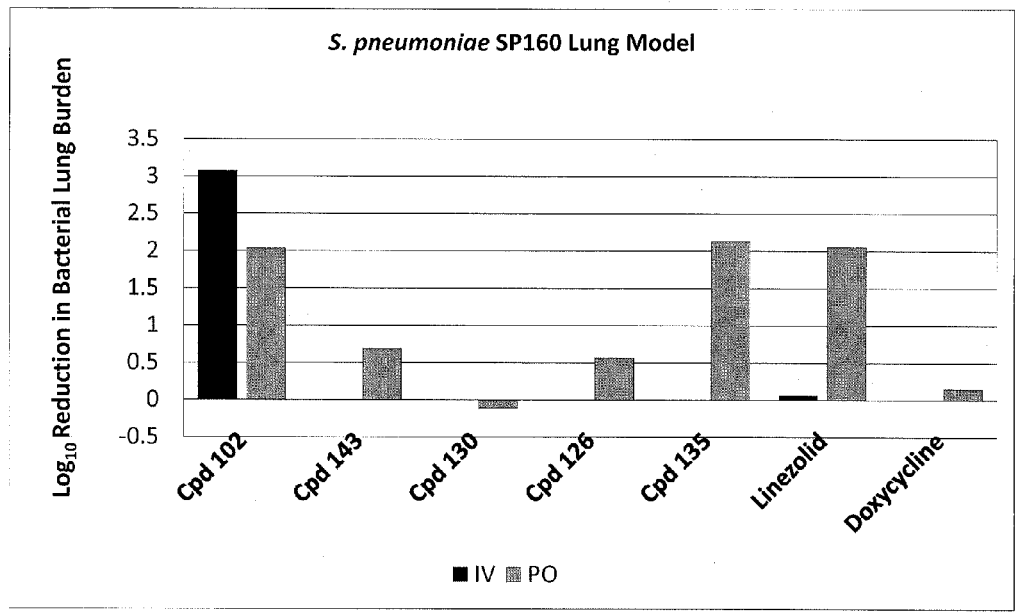
FIG. 1 is a bar graph that demonstrates the efficacy of Compounds 102, 143, 130, 126, and 135 at 10 mg/kg IV, BID and 30 mg/kg, BID orally in a *S. pneumoniae* SP160 lung model. Linezolid at 5 mg/kg IV, BID and 30 mg/kg, BID orally served as a control.

The present invention is directed to a compound represented by Structural Formula (I) or a pharmaceutically acceptable salt thereof. Values and alternative values for the variables in Structural Formula I and for each of the embodiments described herein are provided in the following paragraphs. It is understood that the invention encompasses all combinations of the substituent variables (i.e., $R^1$, $R^2$, $R^3$, etc.) defined herein.

X is selected from halo, —R, —OR, —SR, —S(O)$_m$R, —N(R)$_2$, —N(R)C(O)R, —N(R)C(O)OR', and —N(R)S(O)$_m$R', wherein each R is independently selected from H, $(C_1\text{-}C_6)$alkyl, carbocyclyl, or heterocyclyl; or two R groups taken together with the atom or atoms to which they are bound form a 4-7 membered non-aromatic heterocyclyl; and R' is $(C_1\text{-}C_6)$alkyl, carbocyclyl, or heterocyclyl.

Alternatively, X is selected from halo, —R', —OR, —SR, —S(O)$_m$R, —N(R)$_2$, —N(R)C(O)R, —N(R)C(O)OR', and —N(R)S(O)$_m$R', wherein each R is independently selected from H, $(C_1\text{-}C_6)$alkyl, carbocyclyl, or heterocyclyl; or two R groups taken together with the atom or atoms to which they are bound form a 4-7 membered non-aromatic heterocyclyl; and R' is $(C_1\text{-}C_6)$alkyl, carbocyclyl, or heterocyclyl.

Further, X is selected from fluoro, chloro, hydrogen, methoxy, methyl, trifluoromethyl, trifluoromethoxy and dimethylamino. Alternatively, X is selected from fluoro, chloro, methoxy, methyl, trifluoromethyl, trifluoromethoxy and dimethylamino.

X is selected from fluoro, chloro, methoxy, trifluoromethyl, and dimethylamino. Alternatively, X is methoxy or dimethylamino. Specifically, X is fluoro.

Ring A is a 5-7 membered non-aromatic heterocyclic ring optionally containing 1-2 heteroatoms independently selected from N, S and O in addition to the indicated nitrogen atom.

Ring A is selected from

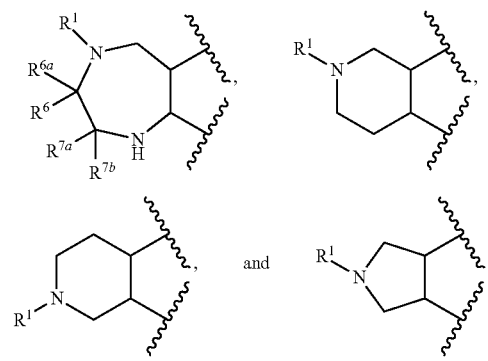

Specifically, ring A is

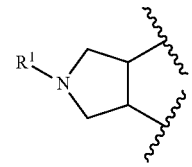

Alternatively, ring A is

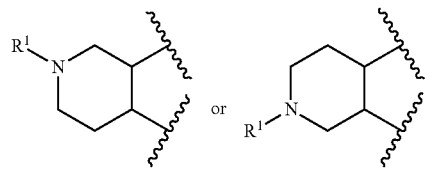

Alternatively, ring A is

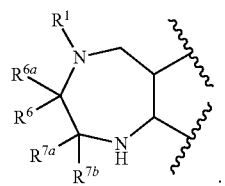

$R^1$ is selected from hydrogen, —$(C_1$-$C_8)$alkyl, —$(C_0$-$C_6)$ alkylene-carbocyclyl, —$(C_0$-$C_6)$alkylene-heterocyclyl, —$(C_1$-$C_6)$alkylene-O—$(C_1$-$C_6)$alkyl, —$(C_2$-$C_6)$alkylene-O-carbocyclyl, —$(C_2$-$C_6)$alkylene-O-heterocyclyl, —$S(O)_m$—$(C_1$-$C_6)$alkyl, —$S(O)_m$-carbocyclyl, —$S(O)_m$-heterocyclyl, —$(C_2$-$C_4)$alkylene-$S(O)_m$-carbocyclyl, —$(C_2$-$C_4)$alkylene-$S(O)_m$-heterocyclyl, —C(O)—[C($R^4$)($R^4$)]$_{0-4}$—N($R^2$)($R^3$), —C(O)—$(C_1$-$C_6)$alkyl, —C(O)-heterocyclyl, —C(O)-carbocyclyl, —$S(O)_m$—[C($R^4$)($R^4$)]$_{0-4}$—N($R^2$)($R^3$), and —$S(O)_m$—$(C_1$-$C_4)$alkylene-carbocyclyl, —$S(O)_m$—$(C_1$-$C_4)$alkylene-heterocyclyl, or $R^1$ taken together with a ring atom adjacent to the nitrogen atom to which $R^1$ is bound forms a saturated heterocyclic ring fused to ring A.

Alternatively, $R^1$ is selected from hydrogen, —$(C_1$-$C_8)$ alkyl, —$(C_2$-$C_4)$alkylene-O—$(C_1$-$C_4)$alkyl, —$(C_0$-$C_3)$alkylene-(saturated heterocycle), —$(C_0$-$C_3)$alkylene-$(C_3$-$C_7)$cycloalkyl, —C(O)—$(C_1$-$C_3)$alkylene-N($R^2$)($R^3$), or $R^1$ taken together with a ring atom adjacent to the nitrogen atom to which $R^1$ is bound forms a saturated heterocyclic ring fused to ring A; wherein any alkyl or alkylene portion of $R^1$ or the saturated heterocyclic ring fused to ring A is optionally substituted with fluoro or hydroxy.

Further, $R^1$ is selected from hydrogen; $(C_1$-$C_3)$ straight alkyl optionally substituted with one or more of: 1 to 5 methyl groups, a single hydroxy group, a single methoxy group, 1 to 3 fluoro groups, a single saturated heterocycle, and a single $(C_3$-$C_7)$cycloalkyl group; $(C_3$-$C_7)$cycloalkyl; tetrahydrofuranyl; and —C(O)—$CH_2$—N($R^2$)($R^3$); or $R^1$ taken together with a ring atom adjacent to the nitrogen atom to which $R^1$ is bound forms a pyrrolidinyl or piperidinyl ring fused to ring A, wherein the pyrrolidinyl or piperidinyl ring fused to ring A is optionally substituted with hydroxy or fluorine.

Alternatively, $R^1$ is selected from ethyl, propyl, $(C_3$-$C_5)$ branched alkyl, $(C_3$-$C_5)$cycloalkyl, $(C_1$-$C_3)$alkylene-cyclopropyl, —C(O)$CH_2$NH-cyclopentyl, and —C(O)$CH_2$-pyrrolidin-1-yl, wherein $R^1$ is optionally substituted with fluoro. Alternatively, $R^1$ is selected from 3-fluoroethyl, propyl, isopropyl, sec-butyl, tert-butyl, $(C_3$-$C_5)$cycloalkyl, —C($CH_3$)$_2$-cyclopropyl, —C(O)$CH_2$NH-cyclopentyl, and —C(O)$CH_2$-(3-fluoropyrrolidin-1-yl). Alternatively, $R^1$ is further selected from tert-pentyl. In another alternative, $R^1$ is selected from hydrogen and $(C_1$-$C_4)$alkyl. Alternatively, $R^1$ is selected from hydrogen, methyl, isobutyl, and tert-butyl.

Each of $R^2$ and $R^3$ is independently selected from hydrogen, $(C_1$-$C_8)$alkyl, —$(C_0$-$C_6)$ alkylene-carbocyclyl, —$(C_0$-$C_6)$alkylene-heterocyclyl, —$(C_2$-$C_6)$alkylene-O-carbocyclyl, —$(C_2$-$C_6)$alkylene-O-heterocyclyl, —$S(O)_m$—$(C_1$-$C_6)$ alkyl, —$S(O)_m$-carbocyclyl, —$S(O)_m$-heterocyclyl, —$(C_2$-$C_4)$alkylene-$S(O)_m$-carbocyclyl, and —$(C_2$-$C_4)$alkylene-$S(O)_m$-heterocyclyl; or $R^2$ and $R^3$, taken together with the nitrogen atom to which they are bound form a heterocyclyl, wherein the heterocyclyl optionally comprises 1 to 4 additional heteroatoms independently selected from N, S and O.

Alternatively, $R^2$ is selected from hydrogen and $(C_1$-$C_3)$ alkyl and $R^3$ is selected from $(C_1$-$C_3)$alkyl and $(C_3$-$C_7)$cycloalkyl, or $R^2$ and $R^3$, taken together with the nitrogen atom to which they are bound form a 4-7 membered saturated heterocyclyl, wherein the heterocyclyl is optionally substituted with fluoro.

In another alternative, $R^2$ and $R^3$ are simultaneously methyl; $R^2$ is hydrogen and $R^3$ is $C_3$-$C_7$ cycloalkyl; or $R^2$ and $R^3$, taken together with the nitrogen atom to which they are bound form a pyrrolidinyl ring optionally substituted with fluoro.

Each $R^4$ is independently selected from hydrogen, $(C_1$-$C_6)$ alkyl, carbocyclyl, heterocyclyl or a naturally occurring amino acid side chain moiety.

Alternatively, two $R^4$ taken together with a common carbon atom to which they are bound form a 3-7 membered non-aromatic carbocyclyl or a 4-7 membered non-aromatic heterocyclyl, wherein the heterocyclyl formed by two $R^4$ comprises one to three heteroatoms independently selected from N, S and O.

Any substitutable carbon atom on ring A is optionally:
(i) substituted with one to two substituents independently selected from —$(C_1$-$C_4)$alkyl, and —$(C_0$-$C_4)$alkylene-carbocyclyl; or
(ii) substituted with =O;
(iii) taken together with an adjacent ring atom to form a 3-7 membered saturated carbocyclyl or a 4-7 membered saturated heterocyclyl ring; or
(iv) spyrofused to a 3-7 membered saturated carbocyclyl.

Any additional N heteroatom on ring A is substituted with hydrogen, $(C_1$-$C_6)$alkyl, carbocyclyl, or heterocyclyl.

Each alkyl or alkylene in Structural Formula I is optionally and independently substituted with one or more substituents independently selected from halo, —OH, =O, —O—$(C_1$-$C_4)$alkyl, fluoro-substituted-$(C_1$-$C_4)$alkyl, —$S(O)_m$—$(C_1$-$C_4)$alkyl and —N($R^5$)($R^5$).

Each carbocyclyl or heterocyclyl portion of a substituent of ring A or the saturated heterocyclic ring fused to ring A is optionally and independently substituted with one or more substituents independently selected from halo, —$(C_1$-$C_4)$ alkyl, —OH, =O, —O—$(C_1$-$C_4)$alkyl, —$(C_1$-$C_4)$alkylene-O—$(C_1$-$C_4)$alkyl, halo-substituted-$(C_1$-$C_4)$alkyl, halo-substituted-O—$(C_1$-$C_4)$alkyl, —C(O)—$(C_1$-$C_4)$alkyl, —C(O)-(fluoro-substituted-$(C_1$-$C_4)$alkyl), —$S(O)_m$—$(C_1$-$C_4)$alkyl, —N($R^5$)($R^5$) and CN.

Each $R^5$ is independently selected from hydrogen and $(C_1$-$C_4)$alkyl, wherein each alkyl in the group represented by $R^5$ is optionally and independently substituted with one or more substituents independently selected from —$(C_1$-$C_4)$alkyl, $(C_3$-$C_6)$cycloalkyl, halo, —OH, —O—$(C_1$-$C_4)$alkyl, and —$(C_1$-$C_4)$alkylene-O—$(C_1$-$C_4)$alkyl.

In one alternative, when X is hydrogen, ring A is not an unsubstituted bivalent piperidine radical.

Each m is independently 1 or 2.

$R^{6a}$ is selected from hydrogen and methyl.

$R^6$ is selected from hydrogen, $(C_1$-$C_4)$alkyl optionally substituted with hydroxy or phenyl; or $R^6$ taken together with $R^1$ and the nitrogen atom and the carbon atom to which they are respectively bound form a pyrrolidinyl or piperidinyl ring fused to ring A, wherein the pyrrolidinyl or piperidinyl ring is optionally substituted with —OH or —F; or $R^6$ and $R^{6a}$ are taken together with the carbon atom to which they are both bound to form a cyclopropyl ring.

Alternatively, $R^6$ is selected from hydrogen, (R)—$(C_1$-$C_4)$ alkyl, or —$CH_2$-phenyl, or $R^1$ and $R^6$ taken together with the nitrogen atom and the carbon atom to which they are respectively bound form a pyrrolidinyl ring fused to ring A. Further, $R^6$ is selected from hydrogen, (R)-methyl, (R)-isobutyl, (R)-sec-butyl, (R)-isopropyl, and —$CH_2$-phenyl. Further, at least one of $R^1$ and $R^6$ is other than hydrogen.

$R^{7a}$ and $R^{7b}$ are each hydrogen. Alternatively, $R^{7a}$ and $R^{7b}$ are taken together to form =O.

A first embodiment of the present invention is directed to a compound represented by Structural Formula (I):

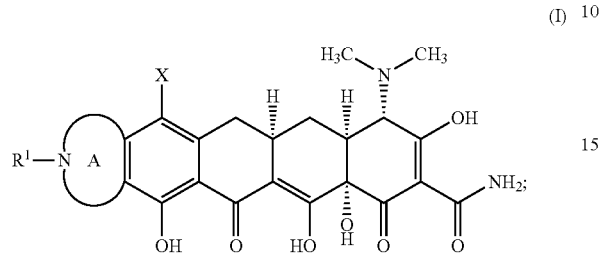

(I)

or a pharmaceutically acceptable salt thereof, wherein:
X is selected from halo, —R, —OR, —SR, —S(O)$_m$R, —N(R)$_2$, —N(R)C(O)R, N(R)C(O)OR', and N(R)S(O)$_m$R', wherein:
  each R is independently selected from H, ($C_1$-$C_6$)alkyl, carbocyclyl, or heterocyclyl, or
  two R groups taken together with the atom or atoms to which they are bound form a 4-7 membered non-aromatic heterocyclyl; and
  R' is ($C_1$-$C_6$)alkyl, carbocyclyl, or heterocyclyl;
ring A is a 5-7 membered non-aromatic heterocyclic ring optionally containing 1-2 heteroatoms independently selected from N, S and O in addition to the indicated nitrogen atom, wherein:
  $R^1$ is selected from hydrogen, —($C_1$-$C_8$)alkyl, —($C_0$-$C_6$)alkylene-carbocyclyl, —($C_0$-$C_6$)alkylene-heterocyclyl, —($C_1$-$C_6$)alkylene-O—($C_1$-$C_6$)alkyl, —($C_2$-$C_6$)alkylene-O-carbocyclyl, —($C_2$-$C_6$)alkylene-O-heterocyclyl, —S(O)$_m$—($C_1$-$C_6$)alkyl, —S(O)$_m$-carbocyclyl, —S(O)$_m$-heterocyclyl, —($C_2$-$C_4$)alkylene-S(O)$_m$-carbocyclyl, —($C_2$-$C_4$)alkylene-S(O)$_m$-heterocyclyl, —C(O)-[C($R^4$)($R^4$)]$_{0-4}$—N($R^2$)($R^3$), —C(O)—($C_1$-$C_6$)alkyl, —C(O)-heterocyclyl, —C(O)-carbocyclyl, —S(O)$_m$—[C($R^4$)($R^4$)]$_{0-4}$—N($R^2$)($R^3$), and —S(O)$_m$—($C_1$-$C_4$)alkylene-carbocyclyl, —S(O)$_m$—($C_1$-$C_4$)alkylene-heterocyclyl, or
  $R^1$ taken together with a ring atom adjacent to the nitrogen atom to which $R^1$ is bound forms a saturated heterocyclic ring fused to ring A;
each of $R^2$ and $R^3$ is independently selected from hydrogen, ($C_1$-$C_8$)alkyl, —($C_0$-$C_6$) alkylene-carbocyclyl, —($C_0$-$C_6$)alkylene-heterocyclyl, —($C_2$-$C_6$)alkylene-O-carbocyclyl, —($C_2$-$C_6$)alkylene-O-heterocyclyl, —S(O)$_m$—($C_1$-$C_6$)alkyl, —S(O)$_m$-carbocyclyl, —S(O)$_m$-heterocyclyl, —($C_2$-$C_4$)alkylene-S(O)$_m$-carbocyclyl, and —($C_2$-$C_4$)alkylene-S(O)$_m$-heterocyclyl; or
  $R^2$ and $R^3$, taken together with the nitrogen atom to which they are bound form a heterocyclyl, wherein the heterocyclyl optionally comprises 1 to 4 additional heteroatoms independently selected from N, S and O;
each $R^4$ is independently selected from hydrogen, ($C_1$-$C_6$) alkyl, carbocyclyl, heterocyclyl or a naturally occurring amino acid side chain moiety, or
  two $R^4$ taken together with a common carbon atom to which they are bound form a 3-7 membered non-aromatic carbocyclyl or a 4-7 membered non-aromatic heterocyclyl, wherein the heterocyclyl formed by two $R^4$ comprises one to three heteroatoms independently selected from N, S and O;
any substitutable carbon atom on ring A is optionally:
  (i) substituted with one to two substituents independently selected from —($C_1$-$C_4$)alkyl, and —($C_0$-$C_4$)alkylene-carbocyclyl; or
  (ii) substituted with =O;
  (iii) taken together with an adjacent ring atom to form a 3-7 membered saturated carbocyclyl or a 4-7 membered saturated heterocyclyl ring; or
  (iv) spyrofused to a 3-7 membered saturated carbocyclyl;
any additional N heteroatom on ring A is substituted with hydrogen, $C_1$-$C_6$ alkyl, carbocyclyl, or heterocyclyl;
each alkyl or alkylene in Structural Formula I is optionally and independently substituted with one or more substituents independently selected from halo, —OH, =O, —O—($C_1$-$C_4$)alkyl, fluoro-substituted-($C_1$-$C_4$)alkyl, —S(O)$_m$—($C_1$-$C_4$)alkyl and —N($R^5$)($R^5$);
each carbocyclyl or heterocyclyl portion of a substituent of ring A or the saturated heterocyclic ring fused to ring A is optionally and independently substituted with one or more substituents independently selected from halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, —C(O)—($C_1$-$C_4$)alkyl, —C(O)-(fluoro-substituted-($C_1$-$C_4$)alkyl), —S(O)$_m$—($C_1$-$C_4$)alkyl, —N($R^5$)($R^5$) and CN;
each $R^5$ is independently selected from hydrogen and ($C_1$-$C_4$)alkyl, wherein each alkyl in the group represented by $R^5$ is optionally and independently substituted with one or more substituents independently selected from —($C_1$-$C_4$)alkyl, ($C_3$-$C_6$)cycloalkyl, halo, —OH, —O—($C_1$-$C_4$)alkyl, and —($C_1$-$C_4$)alkylene-O—($C_1$-$C_4$)alkyl; and
each m is independently 1 or 2,
with the proviso that when X is hydrogen, ring A is not an unsubstituted bivalent piperidine radical.

In one aspect of the first embodiment,
X is selected from fluoro, chloro, hydrogen, methoxy, methyl, trifluoromethyl, trifluoromethoxy and dimethylamino, wherein the values for the remaining variables are as defined in the first embodiment or in the values or alternative values described above.

In a second aspect of the first embodiment,
X is selected from halo, —R', —OR, —SR, —S(O)$_m$R, —N(R)$_2$, —N(R)C(O)R, N(R)C(O)OR', and N(R)S(O)$_m$R'; and
R' is ($C_1$-$C_6$)alkyl, carbocyclyl, or heterocyclyl, wherein the values for the remaining variables are as defined in the first embodiment or in the values or alternative values described above.

In a third aspect of the first embodiment:
X is selected from fluoro, chloro, methoxy, methyl, trifluoromethyl, trifluoromethoxy and dimethylamino; wherein the values for the remaining variables are as defined in the second aspect of the first embodiment or in the values or alternative values described above.

In a fourth aspect of the first embodiment,
$R^1$ is selected from hydrogen, —($C_1$-$C_8$)alkyl, —($C_2$-$C_4$)alkylene-O—($C_1$-$C_4$)alkyl, —($C_0$-$C_3$)alkylene-(saturated heterocycle), —($C_0$-$C_3$)alkylene-($C_3$-$C_7$)cycloalkyl, —C(O)—($C_1$-$C_3$)alkylene-N($R^2$)($R^3$), or R[1] taken together with a ring atom adjacent to the nitrogen atom to which R[1] is bound forms a saturated heterocyclic ring fused to ring A; wherein:
  any alkyl or alkylene portion of R[1] or the saturated heterocyclic ring fused to ring A is optionally substituted with fluoro or hydroxy;
  R[2] is selected from hydrogen and $(C_1-C_3)$alkyl;
  R[3] is selected from $(C_1-C_3)$alkyl and $(C_3-C_7)$cycloalkyl, or R[2] and R[3], taken together with the nitrogen atom to which they are bound form a 4-7 membered saturated heterocyclyl, wherein the heterocyclyl is optionally substituted with fluoro, wherein the values for the remaining variables are as defined in the first embodiment or in the values or alternative values described above.

In a fifth aspect of the first embodiment, wherein: R[1] is selected from hydrogen; $(C_1-C_3)$ straight alkyl optionally substituted with one or more of: 1 to 5 methyl groups, a single hydroxy group, a single methoxy group, 1 to 3 fluoro groups, a single saturated heterocycle, and a single $(C_3-C_7)$cycloalkyl group; $(C_3-C_7)$cycloalkyl; tetrahydrofuranyl; and —C(O)—CH$_2$—N(R[2])(R[3]), wherein R[2] and R[3] are simultaneously methyl; R[2] is hydrogen and R[3] is $C_3-C_7$ cycloalkyl; or R[2] and R[3], taken together with the nitrogen atom to which they are bound form a pyrrolidinyl ring optionally substituted with fluoro, or
  R[1] taken together with a ring atom adjacent to the nitrogen atom to which R[1] is bound forms a pyrrolidinyl or piperidinyl ring fused to ring A, wherein the pyrrolidinyl or piperidinyl ring fused to ring A is optionally substituted with hydroxy or fluorine wherein the values for the remaining variables are as defined in the first embodiment or in the values or alternative values described above.

In a second embodiment, the compound of the present invention is represented by Structural Formula (I), or a pharmaceutically acceptable salt thereof, wherein:
  ring A is selected from

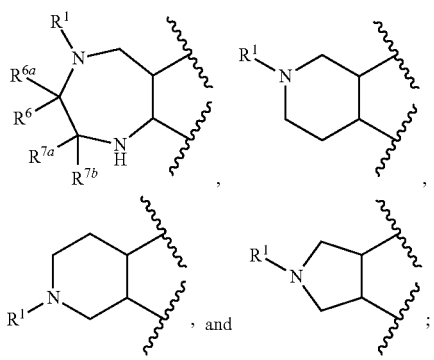

R[6a] is selected from hydrogen and methyl; and
R[6] is selected from hydrogen, $(C_1-C_4)$alkyl optionally substituted with hydroxy or phenyl; or
R[6] taken together with R[1] and the nitrogen atom and the carbon atom to which they are respectively bound form a pyrrolidinyl or piperidinyl ring fused to ring A, wherein the pyrrolidinyl or piperidinyl ring is optionally substituted with —OH or —F; or
R[6] and R[6a] are taken together with the carbon atom to which they are both bound to form a cyclopropyl ring; and
R[7a] and R[7b] are each hydrogen or are taken together to form =O; wherein the values for the remaining variables are as defined in the first embodiment or aspects thereof or in the values or alternative values described above.

For example, the compounds of the second embodiment are represented by Structural Formula (II), (IIIa), (IVa), (Va) or (VIa):

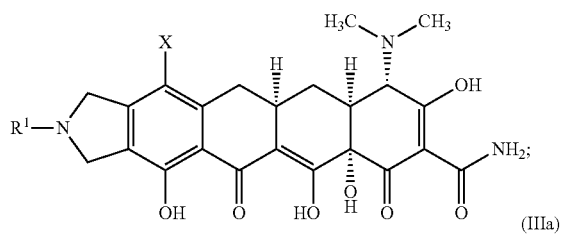
(II)

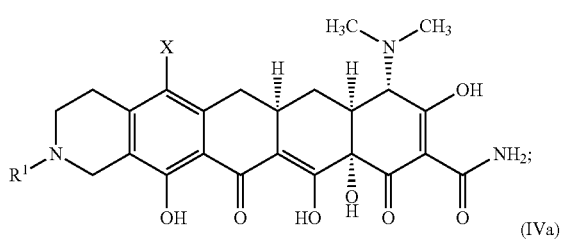
(IIIa)

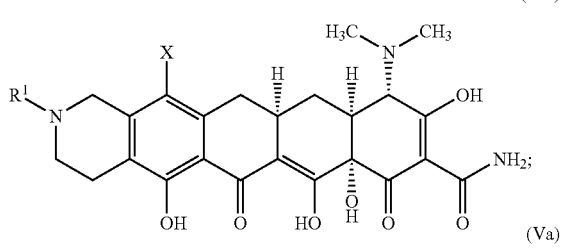
(IVa)

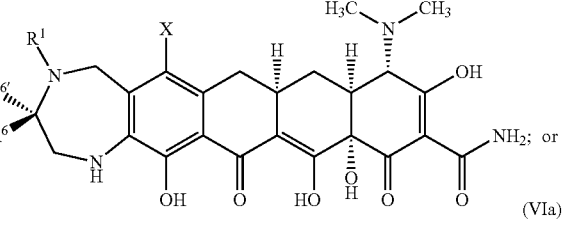
(Va)

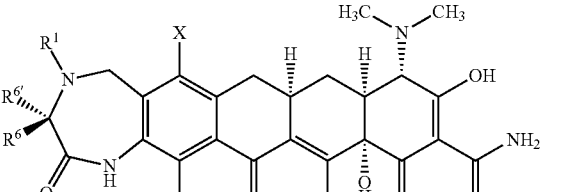
(VIa)

or pharmaceutically acceptable salt thereof, wherein the values for the remaining variables are as defined in the first embodiment or aspects thereof, the second embodiment, or in the values or alternative values described above.

In a third embodiment, the compound of the present invention is represented by Structural Formula (I), or a pharmaceutically acceptable salt thereof, wherein:
  ring A is

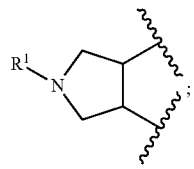

X is selected from fluoro, chloro, methoxy, trifluoromethyl, and dimethylamino; and $R^1$ is selected from ethyl, propyl, ($C_3$-$C_5$) branched alkyl, ($C_3$-$C_5$)cycloalkyl, ($C_1$-$C_3$)alkylene-cyclopropyl, —C(O)CH$_2$NH-cyclopentyl, and —C(O)CH$_2$-pyrrolidin-1-yl, wherein $R^1$ is optionally substituted with fluoro, wherein the values for the remaining variables are as defined in the first or second embodiments or aspects thereof or in the values or alternative values described above.

In a specific aspect of the third embodiment, X is selected from fluoro, chloro, methoxy, trifluoromethyl, and dimethylamino; and $R^1$ is selected from 3-fluoroethyl, propyl, isopropyl, sec-butyl, tert-butyl, ($C_3$-$C_5$)cycloalkyl, —C(CH$_3$)$_2$-cyclopropyl, —C(O)CH$_2$NH-cyclopentyl, —C(O)CH$_2$-(3-fluoropyrrolidin-1-yl); and when X is methoxy or dimethylamino, $R^1$ is further selected from tert-pentyl, wherein the values for the remaining variables are as defined in the first or second embodiments or aspects thereof or in the values or alternative values described above.

In a fourth embodiment, the compound of the present invention is represented by Structural Formula (I), or a pharmaceutically acceptable salt thereof, wherein:

ring A is

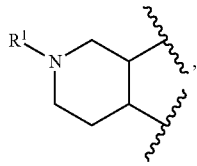

X is fluoro; and $R^1$ is selected from hydrogen, ($C_1$-$C_4$)alkyl, wherein the values for the remaining variables are as defined in the first or second embodiments or aspects thereof or in the values or alternative values described above.

In a specific aspect of the fourth embodiment, $R^1$ is selected from isopropyl, propyl or ethyl, wherein the values for the remaining variables are as defined in the first or second embodiments or aspects thereof or in the values or alternative values described above.

In a fifth embodiment, the compound of the present invention is represented by Structural Formula (I), or a pharmaceutically acceptable salt thereof, wherein:

ring A is

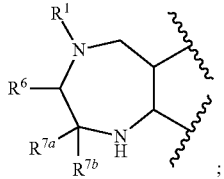

X is fluoro;

$R^1$ is selected from hydrogen, ($C_1$-$C_4$)alkyl;

$R^6$ is selected from hydrogen, (R)—($C_1$-$C_4$)alkyl, or —CH$_2$-phenyl, or $R^1$ and $R^6$ taken together with the nitrogen atom and the carbon atom to which they are respectively bound form a pyrrolidinyl ring fused to ring A;

$R^{7a}$ and $R^{7b}$ are each hydrogen or are taken together to form =O, wherein at least one of $R^1$, and $R^6$ is other than hydrogen, wherein the values for the remaining variables are as defined in the first or second embodiments or aspects thereof or in the values or alternative values described above.

In a specific aspect of the fifth embodiment, $R^1$ is selected from hydrogen, methyl, isobutyl, and tert-butyl; and $R^6$ is selected from hydrogen, (R)-methyl, (R)-isobutyl, (R)-sec-butyl, (R)-isopropyl, and —CH$_2$-phenyl. "(R)" signifies the chirality at the carbon atom to which $R^6$ is attached. Specific structures are as follows:

(R)-methyl:

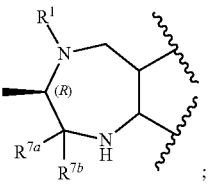

(R)-isobutyl:

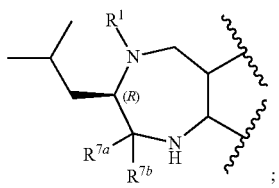

(R)-sec-butyl:

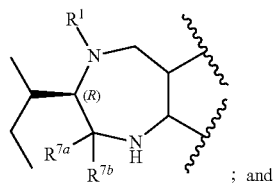

(R)-isopropyl:

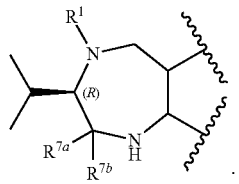

Alternatively, $R^1$ and $R^6$ taken together with the nitrogen atom and the carbon atom to which they are respectively bound form a pyrrolidinyl ring fused to ring A. The values for the remaining variables are as defined in the first or second embodiments or aspects thereof or in the values or alternative values described above.

Exemplary compounds represented by Structural Formula (II) are shown in Tables 1-4 below:

TABLE 1

| | | (II) |
|---|---|---|

![Structure II]

| Compound | X | $R^1$ |
|---|---|---|
| 100 | F | cyclopentyl-CH< |

TABLE 1-continued

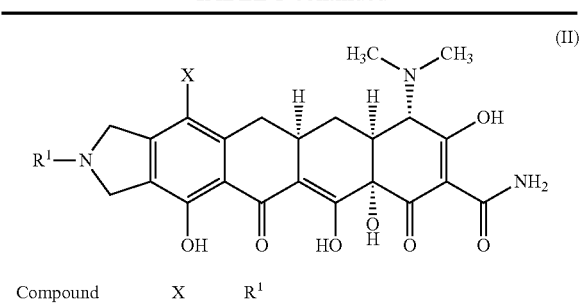

(II)

| Compound | X | R¹ |
|---|---|---|
| 101 | F | (3,3-dimethylbutan-2-yl-like: C(CH₃)(H)C(CH₃)₃... actually neopentyl-methyl) |
| 102 | F | tert-butyl-CH₂- (neopentyl) |
| 103 | N(CH₃)₂ | tert-butyl-CH₂- |
| 104 | F | (tetrahydrofuran-2-yl)methyl |
| 105 | F | H |
| 106 | F | 2,3-dimethylbutan-2-yl |
| 107 | F | 2-fluoroethyl-CH₂- |
| 108 | F | (tetrahydrofuran-2-yl)ethyl |
| 109 | H | tert-butyl-CH₂- |
| 110 | Cl | (S)-2-methylbutan-2-yl |

TABLE 1-continued

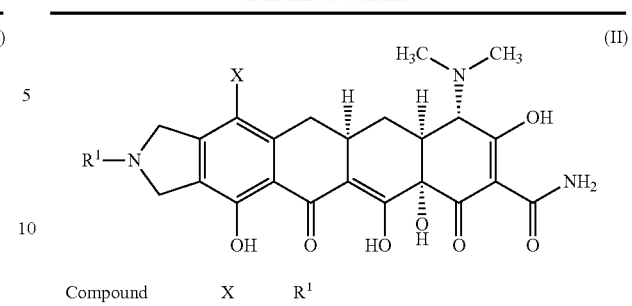

(II)

| Compound | X | R¹ |
|---|---|---|
| 111 | F | cyclopentyl-NH-CH₂-C(=O)-C(CH₃)₂- |
| 112 | CF₃ | 2,3-dimethylbutan-2-yl |
| 113 | CF₃ | (S)-2-methylbutan-2-yl |
| 114 | F | cyclopropyl-C(CH₃)₂- (no, cyclopropyl directly) |
| 115 | N(CH₃)₂ | tert-butyl |
| 116 | CF₃ | cyclopropyl-CH₂- |
| 117 | Cl | (S)-2-methylbutan-2-yl |
| 118 | F | cyclopropyl-C(CH₃)(H)- |
| 119 | OCH₃ | tert-butyl-CH₂- |
| 120 | F | 2-methylbutan-2-yl |
| 121 | F | 3-methylbutan-2-yl |

TABLE 1-continued (II)

| Compound | X | R¹ |
|---|---|---|
| 122 | F | H₃C-C(CH₃)(CH₂F)- |
| 123 | F | H₃C-CH(CH₃)-CH(CH₃)- (with stereo) |
| 124 | N(CH3)₂ | H₃C-CH(CH₃)-CH(CH₃)- (with stereo) |
| 125 | OCH₃ | (H₃C)₂CH-C(CH₃)- |
| 126 | CF₃ | (H₃C)₂CH- |
| 127 | N(CH3)₂ | H₃C-CH(CH₃)-CH(CH₃)- (with stereo) |
| 128 | CF₃ | H₃C-CH(CH₃)-CH(CH₃)- |
| 129 | F | H₃C-C(CH₃)(CH₃)-CH(CH₃)- (with stereo) |
| 130 | F | H₃C-CH(CH₃)-CH(CH₃)- |
| 131 | F | (H₃C)₂N-CH₂-C(=O)- |
| 132 | F | cyclobutyl-CH(CH₃)- |

TABLE 1-continued (II)

| Compound | X | R¹ |
|---|---|---|
| 133 | F | (H₃C)₃C-C(CH₃)- (with stereo) |
| 134 | F | H₃CO-CH₂CH₂- |
| 135 | N(CH3)₂ | (H₃C)₂CH- |
| 136 | F | HO-CH₂-C(CH₃)- (with stereo) |
| 137 | F | (H₃C)₂CH-CH(CH₃)- (with stereo) |
| 138 | OCH₃ | H₃C-CH₂CH₂- |
| 139 | F | pyrrolidinyl-CH₂-C(=O)- |
| 140 | F | tetrahydrofuran-3-yl-C(CH₃)(H)- |
| 141 | CF₃ | H₃C-CH₂CH₂- |
| 142 | F | H₃C-CH₂CH₂- |
| 143 | F | (H₃C)₂CH- |

TABLE 1-continued (II)

| Compound | X | R¹ |
|---|---|---|
| 144 | Cl | tert-butyl (C(CH₃)₃) |
| 145 | OCH₃ | sec-butyl ((S)-CH(CH₃)CH₂CH₃) |
| 146 | F | 2-methyl-2-(pyrrolidin-1-ylmethyl)propyl (neopentyl with CH₂-pyrrolidine) |
| 147 | F | 2-((R)-3-fluoropyrrolidin-1-yl)acetyl-dimethyl group |
| 148 | OCH₃ | (S)-2-methylbutyl (neopentyl-type) |
| 149 | Cl | 2,2-dimethylbutyl |
| 150 | Cl | 2,2-dimethylbutyl (isomer) |

TABLE 2

Exemplary Compounds of Formula III (III)

| Compound | R¹ |
|---|---|
| 200 | tert-butyl (C(CH₃)₃) |
| 201 | 2,2-dimethylbutyl |
| 202 | cyclopentyl-methyl |

TABLE 3

Exemplary Compounds of Formula IV.

(IV)

| Compound | R¹ |
|---|---|
| 300 | isopropyl-methyl (CH(CH₃)₂-C(CH₃)) |
| 301 | sec-butyl-methyl |
| 302 | (S)-sec-butyl-methyl |
| 303 | tert-pentyl (C(CH₃)₂CH(CH₃)) |
| 304 | n-propyl-methyl |

TABLE 3-continued

Exemplary Compounds of Formula IV.

| Compound | R¹ |
|---|---|
| 305 | sec-butyl (H₃C-CH₂-CH(CH₃)-) |
| 306 | isobutyl (H₃C-CH(CH₃)-CH₂-) |
| 307 | ethyl (H₃C-CH₂-) |
| 308 | tert-butyl ((H₃C)₃C-) |

TABLE 4

Exemplary Compounds of Formula V or VI.

| Compound | ring A |
|---|---|
| 400 | (isobutyl-N diazepinone) |
| 401 | (methyl-N, isopropyl diazepinone) |
| 402 | (methyl-N, gem-dimethyl diazepinone) |
| 403 | (HN, isobutyl diazepinone) |
| 404 | (fluoro-pyrrolidine fused diazepinone) |
| 405 | (pyrrolidine fused diazepinone) |

TABLE 4-continued
Exemplary Compounds of Formula V or VI.
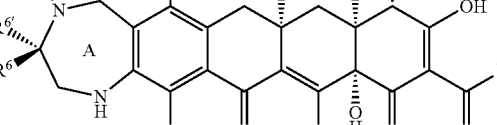
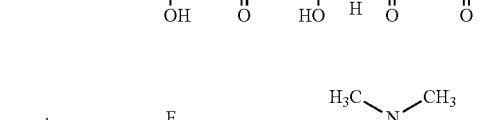
| Compound | ring A |
|---|---|
| 406 | 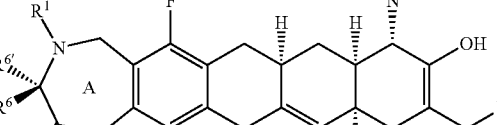 |
| 407 | |
| 408 | |
| 409 | |
| 410 | |
| 411 | 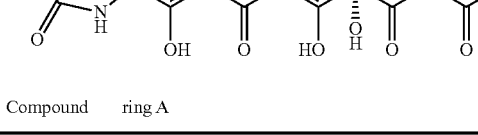 |
| 412 | |
| 413 | |
| 414 | |
| 415 | |

TABLE 4-continued
Exemplary Compounds of Formula V or VI.
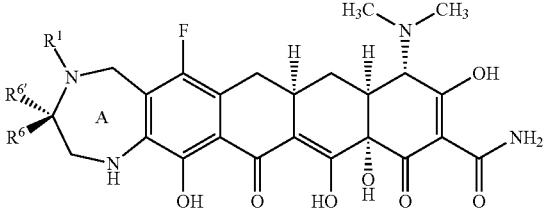
(V) or
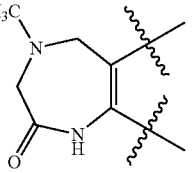
(VI)
| Compound | ring A |
|---|---|
| 416 | 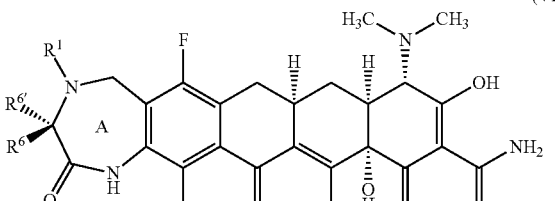 |
| 417 | 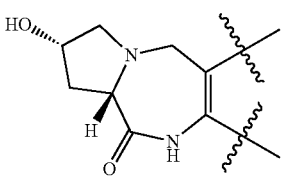 [SMILES: *C1=C(*)NC(=O)[C@@H]2C[C@H](O)CN2C1] |
| 418 | 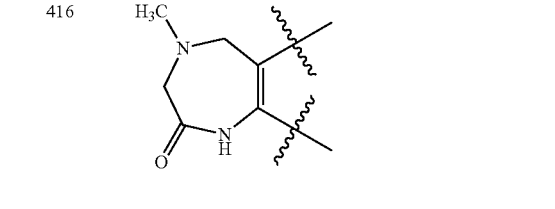 |
| 419 | 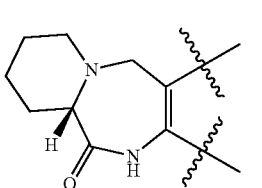 |
| 420 | 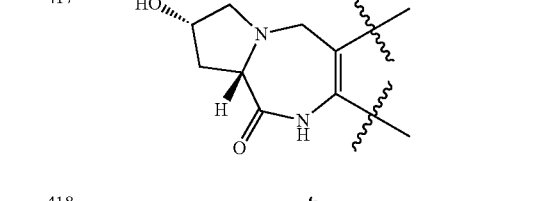 |
| 421 | 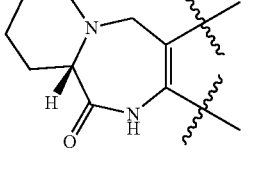 |
| 422 | 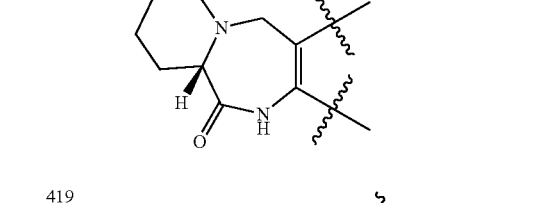 |
| 423 | 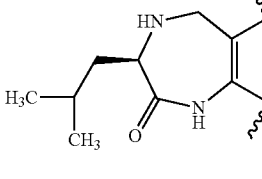 |
| 424 | 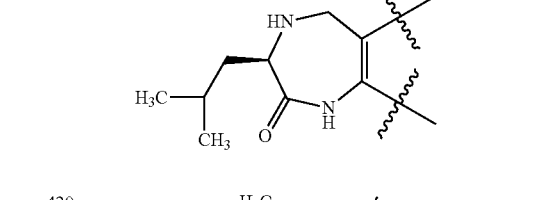 |
| 425 | 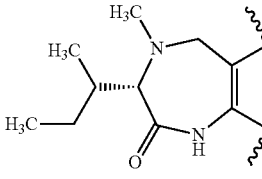 |

TABLE 4-continued

Exemplary Compounds of Formula V or VI.

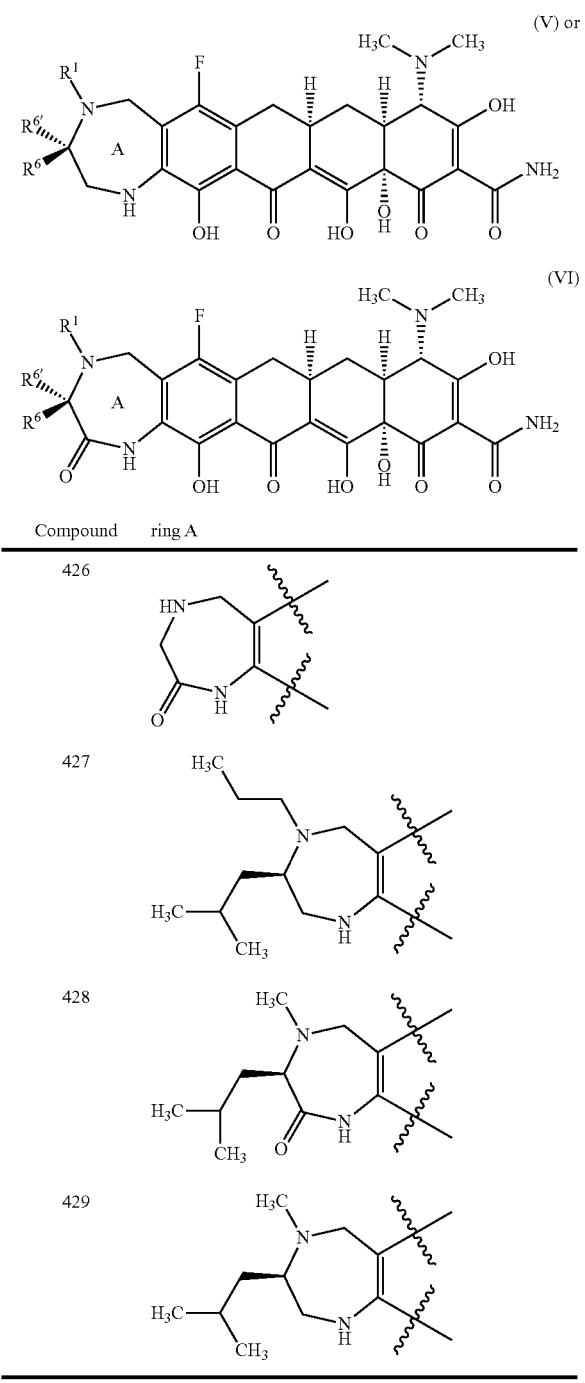

In an eighth embodiment, the compound of the invention is a compound selected from any one of Compounds 300, 304, and 307 or a pharmaceutically acceptable salt thereof.

In a ninth embodiment, the compound of the invention is a compound selected from any one of Compounds 400, 404, 405, 406, 407, 408, 409, 410, 412, 413, 416, 417. 419, 421, 422, 423, 424, 427, 428, and 429 or a pharmaceutically acceptable salt thereof.

Definitions

"Alkyl" means an optionally substituted saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes methyl, ethyl, propyl, butyl, pentyl and hexyl.

"Alkylene" means an optionally substituted saturated aliphatic branched or straight-chain divalent hydrocarbon radical having the specified number of carbon atoms. Thus, "$(C_1-C_6)$alkylene" means a divalent saturated aliphatic radical having from 1-6 carbon atoms in a linear arrangement, e.g., —[$(CH_2)_n$]—, where n is an integer from 1 to 6, "$(C_1-C_6)$ alkylene" includes methylene, ethylene, propylene, butylene, pentylene and hexylene. Alternatively, "$(C_1-C_6)$alkylene" means a divalent saturated radical having from 1-6 carbon atoms in a branched arrangement, for example: —[$CH_2CH_2CH_2CH_2CH(CH_3)$]—, —[$CH_2CH_2CH_2CH_2C(CH_3)_2$]—, —[$CH_2C(CH_3)_2CH(CH_3)$]—, and the like. A specific branched $C_3$-alkylene is

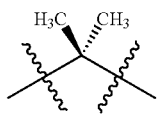

and a specific $C_4$-alkylene is

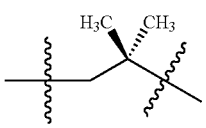

Each alkyl or alkylene in Structural Formula I is optionally and independently substituted with one or more substituents independently selected from halo, —OH, =O, —O—$(C_1-C_4)$alkyl, fluoro-substituted-$(C_1-C_4)$alkyl, —$S(O)_m$—$(C_1-C_4)$alkyl and —$N(R^5)(R^5)$.

"Aryl" or "aromatic" means an aromatic monocyclic or polycyclic (e.g. bicyclic or tricyclic) carbocyclic ring system. In one embodiment, "aryl" is a 6-12 membered monocylic or bicyclic system. Aryl systems include, but are not limited to, phenyl, naphthalenyl, fluorenyl, indenyl, azulenyl, and anthracenyl.

"Carbocyclyl" means a cyclic group with only ring carbon atoms. "Carbocyclyl" includes 3-12 membered saturated or unsaturated aliphatic cyclic hydrocarbon rings or 6-12 membered aryl rings. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

In a sixth embodiment, the compound of the invention is represented by any one of the structural formulas described in Tables 1, 2, 3 or 4, or a pharmaceutically acceptable salt thereof.

In a seventh embodiment, the compound of the invention is a compound selected from any one of Compounds 100, 103, 110, 112, 113, 114, 115, 118, 119, 120, 121, 123, 124, 125, 126, 127, 128, 129, 130, 132, 135, 138, 141, 142, 143, 144, 145, 148, and 149 or a pharmaceutically acceptable salt thereof.

A fused bicyclic carbocyclyl has two rings which have two adjacent ring atoms in common. The first ring is a monocyclic carbocyclyl and the second ring is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl.

A spiro bicyclic carbocyclyl has two rings which have only one ring atom in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remainder of the ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "$C_3$-$C_7$ cycloalkyl" means a hydrocarbon radical of a (3-7 membered) saturated aliphatic cyclic hydrocarbon ring. A $C_3$-$C_7$ cycloalkyl includes, but is not limited to cyclopropyl, cyclobutyl, cyclopentyl, cyclohexyl and cycloheptyl.

"Cycloalkene" means an aliphatic cyclic hydrocarbon ring having one or more double bonds in the ring.

"Cycloalkyne" means an aliphatic cyclic hydrocarbon ring having one or more triple bonds in the ring.

"Hetero" refers to the replacement of at least one carbon atom member in a ring system with at least one heteroatom selected from N, S, and O. "Hetero" also refers to the replacement of at least one carbon atom member in a acyclic system. A hetero ring system or a hetero acyclic system may have 1, 2, 3 or 4 carbon atom members replaced by a heteroatom.

"Heterocyclyl" means a cyclic 4-12 membered saturated or unsaturated aliphatic or aromatic ring containing 1, 2, 3, 4 or 5 heteroatoms independently selected from N, O or S. When one heteroatom is S, it can be optionally mono- or di-oxygenated (i.e. —S(O)— or —S(O)$_2$—). The heterocyclyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a ($C_3$-$C_6$)cycloalkyl. Alternatively, the second ring is phenyl. Example of spiro bicyclic heterocyclyl includes, but are not limited to, azaspiro[4.4]nonane, 7-azaspiro[4.4]nonane, azaspiro[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

Polycyclic heterocyclyls have more than two rings, one of which is a heterocyclyl (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Heteroaryl" or "heteroaromatic ring" means a 5-12 membered monovalent heteroaromatic monocyclic or bicylic ring radical. A herteroaryl contains 1, 2, 3 or 4 heteroatoms independently selected from N, O, and S. Heteroaryls include, but are not limited to furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0]and bicyclo[4.3.0]fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

In a particular embodiment, each carbocyclyl or heterocyclyl portion of a substituent of ring A or the saturated heterocyclic ring fused to ring A is optionally and independently substituted. Exemplary substituents include halo, —($C_1$-$C_4$)alkyl, —OH, =O, —O—($C_1$-$C_4$)alkyl, —($C_1$-$C_4$)alkylene-O—($C_1$-$C_4$)alkyl, halo-substituted-($C_1$-$C_4$)alkyl, halo-substituted-O—($C_1$-$C_4$)alkyl, and —C(O)—($C_1$-$C_4$)alkyl.

"Halogen" used herein refers to fluorine, chlorine, bromine, or iodine.

"Alkoxy" means an alkyl radical attached through an oxygen linking atom. "($C_1$-$C_6$)-alkoxy" includes methoxy, ethoxy, propoxy, butoxy, pentoxy and hexoxy.

Haloalkyl and halocycloalkyl include mono, poly, and perhaloalkyl groups where each halogen is independently selected from fluorine, chlorine, and bromine.

"Halogen" and "halo" are interchangeably used herein and each refers to fluorine, chlorine, bromine, or iodine.

"Fluoro" means —F.

As used herein, fluoro-substituted-$(C_1$-$C_4)$alkyl means a $(C_1$-$C_4)$alkyl substituted with one or more —F groups. Examples of fluoro-substituted-$(C_1$-$C_4)$alkyl include, but are not limited to, —$CF_3$, —$CH_2CF_3$, —$CH_2CF_2H$, —$CH_2CH_2F$ and —$CH_2CH_2CF_3$.

"Naturally occurring amino acid side chain moiety" refers to any amino acid side chain moiety present in a natural amino acid.

Another embodiment of the present invention is a pharmaceutical composition comprising one or more pharmaceutically acceptable carrier and/or diluent and a compound disclosed herein or a pharmaceutically acceptable salt thereof.

"Pharmaceutically acceptable carrier" and "pharmaceutically acceptable diluent" means non-therapeutic components that are of sufficient purity and quality for use in the formulation of a composition of the invention that, when appropriately administered to an animal or human, typically do not produce an adverse reaction, and that are used as a vehicle for a drug substance (i.e. a compound of the present invention).

Pharmaceutically acceptable salts of the compounds of the present invention are also included. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the present invention containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

The invention also includes various isomers and mixtures thereof. Certain of the compounds of the present invention may exist in various stereoisomeric forms. Stereoisomers are compounds which differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. "R" and "S" represent the configuration of substituents around one or more chiral carbon atoms. When a chiral center is not defined as R or S, either a pure enantiomer or a mixture of both configurations is present.

"Racemate" or "racemic mixture" means a compound of equimolar quantities of two enantiomers, wherein such mixtures exhibit no optical activity; i.e., they do not rotate the plane of polarized light.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer that is present divided by the combined weight of the enantiomer that is present and the weight of its optical isomer.

The present invention also provides a method of treating or preventing a subject with a tetracycline-responsive disease or disorder comprising administering to the subject an effective amount of a compound of the present invention or a pharmaceutically acceptable salt thereof.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, prostatitis, tumor growth and invasion, metastasis, diabetes, diabetic proteinuria, panbronchiolitis, aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold, Wegener's granulomatosis; neutrophilic dermatoses and other inflammatory diseases such as dermatitis herpetiformis, leukocytoclastic vasculitis, bullous lupus erythematosus, pustular psoriasis, erythema elevatum diutinum; vitiligo, discoid lupus erythematosus; pyoderma gangrenosum, pustular psoriasis, blepharitis, or meibomianitis, Alzheimer's disease, degenerative maculopathy; acute and chronic gastroenteritis and colitis; acute and chronic cystitis and urethritis; acute and chronic dermatitis; acute and chronic conjunctivitis, acute and chronic serositis, uremic pericarditis; acute and chronic cholecystis, cystic fibrosis, acute and chronic vaginitis, acute and chronic uveitis, drug reactions, insect bites, burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference).

In addition, a method to treat any disease or disease state that could benefit from modulating the expression and/or function of nitric oxide, metalloproteases, proinflammatory mediators and cytokines, reactive oxygen species, components of the immune response, including chemotaxis, lymphocyte transformation, delayed hypersensitivity, antibody production, phagocytosis, and oxidative metabolism of phagocytes. A method to treat any disease or disease state that could benefit from modulating the expression and/or function of C-reactive protein, signaling pathways (e.g., FAK signaling pathway), and/or augment the expression of COX-2 and $PGE_2$ production is covered. A method to treat any disease or disease state that could benefit from inhibition of neovascularization is covered.

Compounds of the invention can be used to prevent or treat important mammalian and veterinary diseases such as diarrhea, urinary tract infections, infections of skin and skin structure including wounds, cellulitis, and abscesses, ear, nose and throat infections, mastitis and the like. In addition, methods for treating neoplasms using tetracycline compounds of the invention are also included (van der Bozert et al., Cancer Res., 48: 6686-6690 (1988)).

Infections that can be treated using compounds of the invention or a pharmaceutically acceptable salt thereof include, but are not limited to, skin infections, GI infections, urinary tract infections, genito-urinary infections, respiratory tract infections, sinuses infections, middle ear infections, systemic infections, intra-abdominal infections, pyelonephritis, pneumonia, bacterial vaginosis, streptococcal sore throat, chronic bacterial prostatitis, gynecological and pelvic infections, sexually transmitted bacterial diseases, ocular and otic infections, cholera, influenza, bronchitis, acne, psoriasis, rosacea, impetigo, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection is a respiratory infection. In a particular aspect, the respiratory infection is Community-Acquired Bacterial Pneumonia (CABP). In a more particular embodiment, the respiratory infection, for example, CABP is caused by a bacterium selected from *S. aureus, S. pneumoniae, S. pyogenes, H. influenza, M. catarrhalis* and *Legionella pneumophila*.

In another embodiment, the infection is a skin infection. In a particular aspect the skin infection is an acute bacterial skin and skin structure infection (ABSSSI). In a more particular embodiment, the skin infection, for example ABSSSI is caused by a bacterium selected from *S. aureus*, CoNS, *S. pyogenes, S. agalactiae, E. faecalis* and *E. faecium*.

In one embodiment, the infection can be caused by a bacterium (e.g. an anaerobic or aerobic bacterium).

In another embodiment, the infection is caused by a Gram-positive bacterium. In a specific aspect of this embodiment, the infection is caused by a Gram-positive bacterium selected from class Bacilli, including, but not limited to, *Staphylococcus* spp., *Streptococcus* spp., *Enterococcus* spp., *Bacillus* spp., *Listeria* spp.; phylum *Actinobacteria*, including, but not limited to, *Propionibacterium* spp., *Corynebacterium* spp., *Nocardia* spp., *Actinobacteria* spp., and class Clostridia, including, but not limited to, *Clostridium* spp.

In another embodiment, the infection is caused by a Gram-positive bacterium selected from *S. aureus*, CoNS, *S. pneumoniae, S. pyogenes, S. agalactiae, E. faecalis* and *E. faecium*.

In another embodiment, the infection is caused by a Gram-negative bacterium. In one aspect of this embodiment, the infection is caused by a phylum Proteobacteria (e.g., Betaproteobacteria and Gammaproteobacteria), including *Escherichia coli, Salmonella, Shigella*, other Enterobacteriaceae, *Pseudomonas, Moraxella, Helicobacter, Stenotrophomonas, Bdellovibrio*, acetic acid bacteria, *Legionella* or alpha-proteobacteria such as *Wolbachia*. In another aspect, the infection is caused by a Gram-negative bacterium selected from cyanobacteria, spirochaetes, green sulfur or green non-sulfur bacteria. In a specific aspect of this embodiment, the infection is caused by a Gram-negative bacteria selected from Enterobactericeae (e.g., *E. coli, Klebsiella pneumoniae* including those containing extended-spectrum β-lactamases and/or carbapenemases), *Bacteroidetes* (e.g., *Bacteroides fragilis*), Vibrionaceae (*Vibrio cholerae*), Pasteurellaceae (e.g., *Haemophilus influenzae*), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of Proteeae, *Acinetobacter* spp., *Helicobacter* spp., and *Campylobacter* spp. In a particular embodiment, the infection is caused by Gram-negative bacterium selected from the group consisting of Enterobactericeae (e.g., *E. coli, Klebsiella pneumoniae*), *Pseudomonas*, and *Acinetobacter* spp. In another embodiment, the infection is caused by an organism selected from the group consisting of *K. pneumoniae, Salmonella, E. hirae, A. baumanii, M. catarrhalis, H. influenzae, P. aeruginosa, E. faecium, E. coli, S. aureus*, and *E. faecalis*.

In another embodiment, the infection is cause by a gram negative bacterium selected from *H. influenza, M. catarrhalis* and *Legionella pneumophila*.

In one embodiment, the infection is caused by an organism that grows intracellularly as part of its infection process.

In another embodiment, the infection is caused by an organism selected from the group consisting of order Rickettsiales; phylum Chlamydiae; order Chlamydiales; *Legionella* spp.; class Mollicutes, including, but not limited to, *Mycoplasma* spp. (e.g. *Mycoplasma pneumoniae*); *Mycobacterium* spp. (e.g. *Mycobacterium tuberculosis*); and phylum Spriochaetales (e.g. *Borrelia* spp. and *Treponema* spp.).

In another embodiment, the infection is caused by a Category A Biodefense organism, Examples of such organisms are described in a list published by the Center for Disease Control and Prevention (CDC). An example of such a list can be found at the CDC website. Examples of Category A organisms include, but are not limited to, *Bacillus anthracis* (anthrax), *Yersinia pestis* (plague), *Clostridium botulinum* (botulism) or *Francisella tularensis* (tularemia). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria.

Additional infections that can be treated using compounds of the invention or a pharmaceutically acceptable salt thereof include, but are not limited to, anthrax, botulism, bubonic plague, and tularemia.

In another embodiment, the infection is caused by a Category B Biodefense organism. Examples of such organisms are described in a list published by the Center for Disease Control and Prevention (CDC). An example of such a list can be found at the CDC website. Examples of Category B organisms include, but are not limited to, *Brucella* spp, *Clostridium perfringens, Salmonella* spp., *Escherichia coli* O157:H7, *Shigella* spp., *Burkholderia mallei, Burkholderia pseudomallei, Chlamydia psittaci, Coxiella burnetii,* Staphylococcal enterotoxin B, *Rickettsia prowazekii, Vibrio cholerae,* and *Cryptosporidium parvum*.

Additional infections that can be treated using compounds of the invention or a pharmaceutically acceptable salt thereof include, but are not limited to, *Brucellosis, Clostridium perfringens*, food-borne illnesses, Glanders, Melioidosis, Psittacosis, Q fever, and water-borne illnesses.

In yet another embodiment, the infection can be caused by one or more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus, Serratia, Staphylococcus* and *Enterococcus* spp., anaerobes (S. E. Dowd, et al., PloS one 2008; 3:e3326, the entire teachings of which are incorporated herein by reference) and respiratory disease (especially in patients that have chronic infections like cystic fibrosis—e.g., *S. aureus* plus *P. aeruginosa* or *H. influenzae*, atypical pathogens), wounds and abscesses (various gram-negative and gram-positive bacteria, notably MSSA/MRSA, coagulase-negative staphylococci, enterococci, *Acinetobacter, P. aeruginosa, E. coli, B. fragilis*), and bloodstream infections (13% were polymicrobial (H. Wisplinghoff, et al., Clin. Infect. Dis. 2004; 39:311-317, the entire teachings of which are incorporated herein by reference)).

In one embodiment, the infection is caused by an organism resistant to one or more antibiotics.

In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline or any other tetracycline derivative. In a particular embodiment, the infection is caused by an organism resistant to tigecycline.

In another embodiment, the infection is caused by an organism resistant to a β-lactam or cephalosporin antibiotic or an organism resistant to penems or carbapenems.

In another embodiment, the infection is caused by an organism resistant to an antimicrobial peptide or a biosimilar therapeutic treatment. Antimicrobial peptides (also called host defense peptides) are an evolutionarily conserved component of the innate immune response and are found among all classes of life. In this case, antimicrobial peptide refers to any naturally occurring molecule or any semi/synthetic molecule that are analogs of anionic peptides, linear cationic α-helical peptides, cationic peptides enriched for specific amino acids (i.e, rich in proline, arginine, phenylalanine, glycine, tryptophan), and anionic and cationic peptides that contain cystein and form disulfide bonds.

In another embodiment, the infection is caused by an organism resistant to macrolides, lincosamides, streptogramin antibiotics, oxazolidinones, and pleuromutilins.

In another embodiment, the infection is caused by an organism resistant to PTK0796 (7-dimethylamino, 9-(2,2-dimethyl-propyl)-aminomethylcycline).

In another embodiment, the infection is caused by a multidrug-resistant pathogen (having intermediate or full resistance to any two or more antibiotics).

In a further embodiment, the tetracycline responsive disease or disorder is not a bacterial infection. In another embodiment, the tetracycline compounds of the invention are essentially non-antibacterial. For example, non-antibacterial compounds of the invention may have MIC values greater than about 4 µg/ml (as measured by assays known in the art and/or the assay given in Example 151. In another embodiment, the tetracycline compounds of the invention have both antibacterial and non-antibacterial effects.

Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity. Examples of matrix metalloproteinase associated states ("MMPAS's") can be treated using compounds of the invention or a pharmaceutically acceptable salt thereof, include, but are not limited to, arteriosclerosis, corneal ulceration, emphysema, osteoarthritis, multiple sclerosis (Liedtke et al., Ann. Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998, 22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compounds of the present invention or a pharmaceutically acceptable salt thereof include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. Nos. 6,100,248; 5,843,925; 5,837,696; or 5,668,122, incorporated herein by reference in their entirety.

Alternatively, the tetracycline compounds may be useful for preventing or reducing the likelihood of cancer recurrence, for example, to treat residual cancer following surgical resection or radiation therapy. The tetracycline compounds useful according to the invention are especially advantageous as they are substantially non-toxic compared to other cancer treatments.

In a further embodiment, the compounds of the invention are administered in combination with standard cancer therapy, such as, but not limited to, chemotherapy.

Examples of tetracycline responsive states can be treated using the compounds of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compounds of the invention or a pharmaceutically acceptable salt thereof include, but are not limited to, juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited to, asthma, cystic fibrosis, chronic obstructive pulmonary disease (COPD), and emphysema. In a further embodiment, the acute and/or chronic lung disorders that can be treated using the compounds of the invention or a pharmaceutically acceptable salt thereof include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke. In a further embodiment, the tetracycline compounds of the invention or a pharmaceutically acceptable salt thereof can be used to treat such disorders as described above and in U.S. Pat. Nos. 6,231,894; 5,773,430; 5,919,775 and 5,789,395, incorporated herein by reference.

In still a further embodiment, the tetracycline compounds of the invention or a pharmaceutically acceptable salt thereof can be used to treat pain, for example, inflammatory, nociceptive or neuropathic pain. The pain can be either acute or chronic.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a tetracycline compound of the invention or a pharmaceutically acceptable salt thereof to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the tetracycline compound of the invention or a pharmaceutically acceptable salt thereof is used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The tetracycline compound or a pharmaceutically acceptable salt thereof may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

The compounds of the invention or a pharmaceutically acceptable salt thereof can be used alone or in combination with one or more therapeutic agent in the methods of the invention disclosed herein.

The language "in combination with" another therapeutic agent or treatment includes co-administration of the tetracycline compound and with the other therapeutic agent or treatment as either a single combination dosage form or as multiple, separate dosage forms, administration of the tetracycline compound first, followed by the other therapeutic agent or treatment and administration of the other therapeutic agent or treatment first, followed by the tetracycline compound.

The other therapeutic agent may be any agent that is known in the art to treat, prevent, or reduce the symptoms of a tetracycline-responsive disease or disorder. The choice of additional therapeutic agent(s) is based upon the particular tetracycline-responsive disease or disorder being treated. Such choice is within the knowledge of a treating physician. Furthermore, the other therapeutic agent may be any agent of benefit to the patient when administered in combination with the administration of a tetracycline compound.

The compounds of the invention or a pharmaceutically acceptable salt thereof can be used alone or in combination with one or more antibiotics and/or immunomodulators (e.g. Deoxycholic acid, Macrokine, Abatacept, Belatacept, Infliximab, Adalimumab, Certolizumab pegol, Afelimomab, Golimumab, and FKBP/Cyclophilin/Calcineurin: Tacrolimus, Ciclosporin, Pimecrolimus).

As used herein, the term "subject" means a mammal in need of treatment or prevention, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of the specified treatment.

As used herein, the term "treating" or 'treatment" refers to obtaining desired pharmacological and/or physiological effect. The effect can include achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome.

As used herein, "preventing" or "prevention" refers to reducing the likelihood of the onset or development of disease, disorder or syndrome.

"Effective amount" means that amount of active compound agent that elicits the desired biological response in a subject. In one embodiment, the effective amount of a compound of the invention is from about 0.01 mg/kg/day to about 1000 mg/kg/day, from about 0.1 mg/kg/day to about 100 mg/kg/day, or from about 0.5 mg/kg/day to about 50 mg/kg/day.

The invention further includes the process for making the composition comprising mixing one or more of the present compounds and an optional pharmaceutically acceptable carrier; and includes those compositions resulting from such a process, which process includes conventional pharmaceutical techniques.

The compositions of the invention include ocular, oral, nasal, transdermal, topical with or without occlusion, intravenous (both bolus and infusion), inhalable, and injection (intraperitoneally, subcutaneously, intramuscularly, intratumorally, or parenterally) formulations. The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally, or by inhalation or insufflation.

Compositions of the invention suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions, and suspensions.

The compositions of the invention may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration. The composition may be administered about 1 to about 5 times per day. Daily administration or post-periodic dosing may be employed.

For oral administration, the composition is preferably in the form of a tablet or capsule containing, e.g., 500 to 0.5 milligrams of the active compound. Dosages will vary depending on factors associated with the particular patient being treated (e.g., age, weight, diet, and time of administration), the severity of the condition being treated, the compound being employed, the mode of administration, and the strength of the preparation.

The oral composition is preferably formulated as a homogeneous composition, wherein the active ingredient is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets may be sugarcoated or filmcoated using standard techniques. Tablets may also be coated or otherwise compounded to provide a prolonged, control-release therapeutic effect. The dosage form may comprise an inner dosage and an outer dosage component, wherein the outer component is in the form of an envelope over the inner component. The two components may further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) may be used.

Compounds of the invention may also be administered via a slow release composition; wherein the composition includes a compound of the invention and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles or nanoemulsions (e.g., in the range of about 1 to 500 nm in diameter, preferably about 50-200 nm in diameter, and most preferably about 100 nm in diameter). In a process for preparing a slow release composition, a slow release carrier and a compound of the invention are first dissolved or dispersed in an organic solvent. The resulting mixture is added into an aqueous solution containing an optional surface-active agent(s) to produce an emulsion. The organic solvent is then evaporated from the emulsion to provide a colloidal suspension of particles containing the slow release carrier and the compound of the invention.

The compound disclosed herein may be incorporated for administration orally or by injection in a liquid form such as aqueous solutions, suitably flavored syrups, aqueous or oil suspensions, flavored emulsions with edible oils such as cottonseed oil, sesame oil, coconut oil or peanut oil and the like, or in elixirs or similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents may also include synthetic and natural gums. For parenteral administration, sterile suspensions and solutions are desired. Isotonic preparations, which generally contain suitable preservatives, are employed when intravenous administration is desired.

The compounds may be administered parenterally via injection. A parenteral formulation may consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil may be employed as a solvent or suspending agent. The parenteral formulation is prepared by dissolving or suspending the active ingredient in the liquid carrier whereby the final dosage unit contains from 0.005 to 10% by weight of the active ingredient. Other additives include preservatives, isotonizers, solubilizers, stabilizers, and pain-soothing agents. Injectable suspensions may also be prepared, in which case appropriate liquid carriers, suspending agents and the like may be employed.

Compounds of the invention may be administered intranasally using a suitable intranasal vehicle.

In another embodiment, the compounds of this invention may be administered directly to the lungs by inhalation.

Compounds of the invention may also be administered topically or enhanced by using a suitable topical transdermal vehicle or a transdermal patch.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably, the compositions are sterile and aqueous based, using purified water. In addition to the compound of the invention, an ophthalmic composition may contain one or more of: a) a surfactant such as a polyoxyethylene fatty acid ester; b) a thickening agents such as cellulose, cellulose derivatives, carboxyvinyl polymers, polyvinyl polymers, and polyvinylpyrrolidones, typically at a concentration n the range of about 0.05 to about 5.0% (wt/vol); c) (as an alternative to or in addition to storing the composition in a container containing nitrogen and optionally including a free oxygen absorber such as Fe), an anti-oxidant such as butylated hydroxyanisol, ascorbic acid, sodium thiosulfate, or butylated hydroxytoluene at a concentration of about 0.00005 to about 0.1% (wt/vol); d) ethanol at a concentration of about 0.01 to 0.5% (wt/vol); and e) other excipients such as an isotonic agent, buffer, preservative, and/or pH-controlling agent. The pH of the ophthalmic composition is desirably within the range of 4 to 8.

In certain embodiments, the composition of this invention includes one or more additional agents. The other therapeutic agent may be ay agent that is capable of treating, preventing or reducing the symptoms of a tetracycline-responsive disease or disorder. Alternatively, the other therapeutic agent may be any agent of benefit to a patient when administered in combination with the tetracycline compound in this invention.

While this invention has been particularly shown and described with references to example embodiments thereof, it will be understood by those skilled in the art that various changes in form and details may be made therein without departing from the scope of the invention encompassed by the appended claims.

Exemplification

The following abbreviations are used in throughout the application.

Ac acetyl
AIBN 2,2'-azobis(2-methylpropionitrile)
aq aqueous
Bn benzyl
Boc tert-butoxycarbonyl
Bu butyl
Cbz benzyloxycarbonyl
Cy tricyclohexylphosphine
dba dibenzylideneacetone
DIBAL-H diisobutylaluminum hydride
DIEA N,N-diisopropylethylamine
DMAP 4-(dimethylamino)pyridine
DME 1,2-dimethoxyethane
DMF N,N-dimethylformamide
DMPU 1,3-dimethyl-3,4-5,6-tetrahydro-2(1H)-pyrimidone
DMSO dimethyl sulfoxide
EDC N-(3-dimethylaminopropyl)-N'-ethylcarbodiimide
ESI electrospray ionization
Et ethyl
EtOAc ethyl acetate
HPLC high performance liquid chromatography
HOBt 1-hydroxybenzotriazole
i iso
IBX 2-iodoxybenzoic acid
LDA lithium diisopropylamide
LHMDS lithium bis(trimethylsilyl)amide
LTMP lithium 2,2,6,6-tetramethylpiperidide
MeOH methanol
Ms methanesulfonyl
MS mass spectrometry
MTBE methyl tert-butyl ether
MW molecular weight
NBS N-bromosuccinimide
NCS N-chlorosuccinimide
NMR nuclear magnetic resonance spectrometry
Ph phenyl
Pr propyl
s secondary
t tertiary
TMEDA N,N,N'N'-tetramethylethylenediamine
TBS tert-butyldimethylsilyl
TEA triethylamine
Tf trifluoromathanesulfonyl
TFA trifluoroacetic acid
TFAA trifluoroacetic anhydride
THF tetrahydrofuran
TLC thin layer chromatography
Ts para-toluenesulfonyl
TsOH para-toluenesulfonic acid
Xantphos 4,5-bis(diphenylphosphino)-9,9-dimethylxanthene Detailed procedures for each of the steps depicted in the following Schemes 1-13 are set forth in the Examples section.

Compounds of Formula II were prepared according to one of Schemes 7-9, depending upon the actual structure. Intermediates used in Scheme 7-9 were prepared by one of Schemes 1-6, as was appropriate for the final structure of the compound.

Compounds of Formula II, wherein X is fluoro were synthesized using a common N-substituted phenyl 4-(benzyloxy)-7-fluoro-6-methylisoindoline-5-carboxylate intermediate, which is prepared according to Scheme 1.

Scheme 1

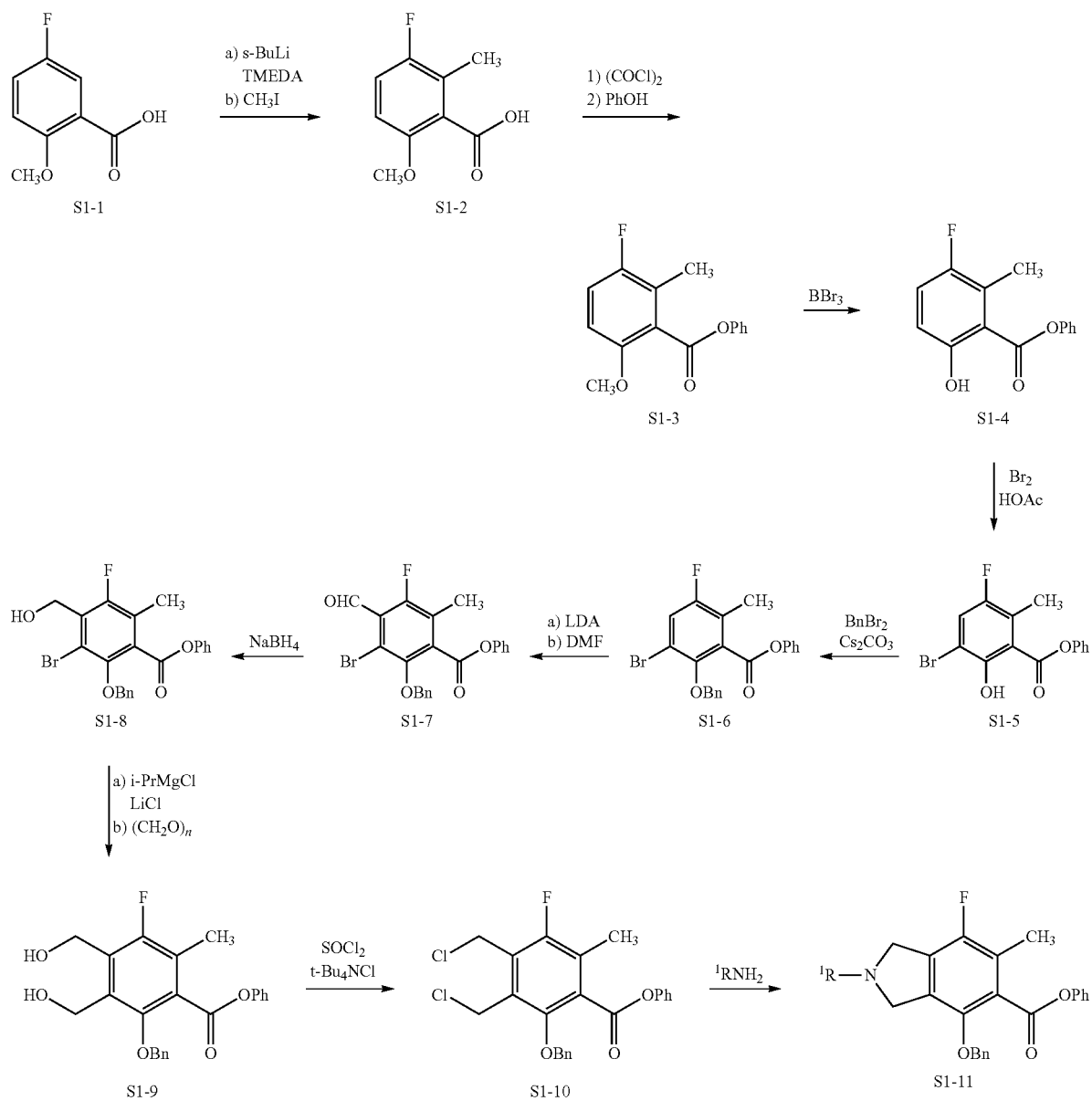

An alternate route to certain N-substituted phenyl 4-(benzyloxy)-7-fluoro-6-methylisoindoline-5-carboxylate intermediates is shown in Scheme 2

Scheme 2

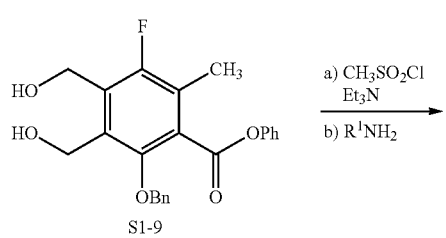

-continued

Compounds of Formula II, wherein X is chloro were synthesized using a common N-substituted phenyl 4-(benzyloxy)-7-chloro-6-methylisoindoline-5-carboxylate intermediate, which is prepared according to Scheme 3.

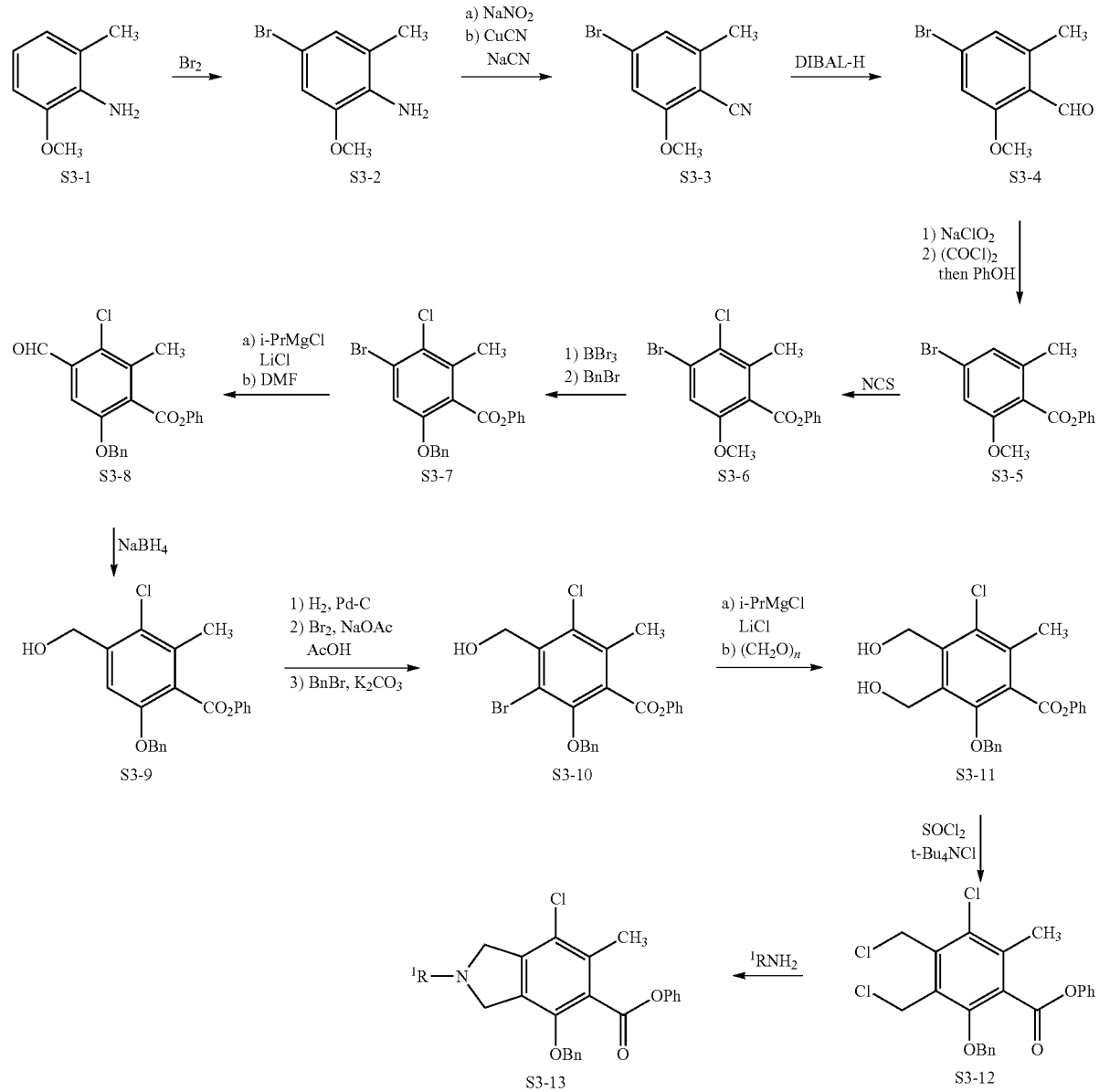
Compounds of Formula II, wherein X is CF$_3$ were synthesized using a common N-substituted phenyl 4-(benzyloxy)-7-trifluoromethyl-6-methylisoindoline-5-carboxylate intermediate, which is prepared according to Scheme 4.
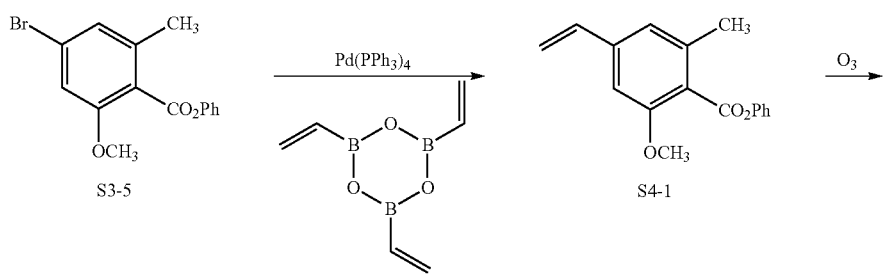

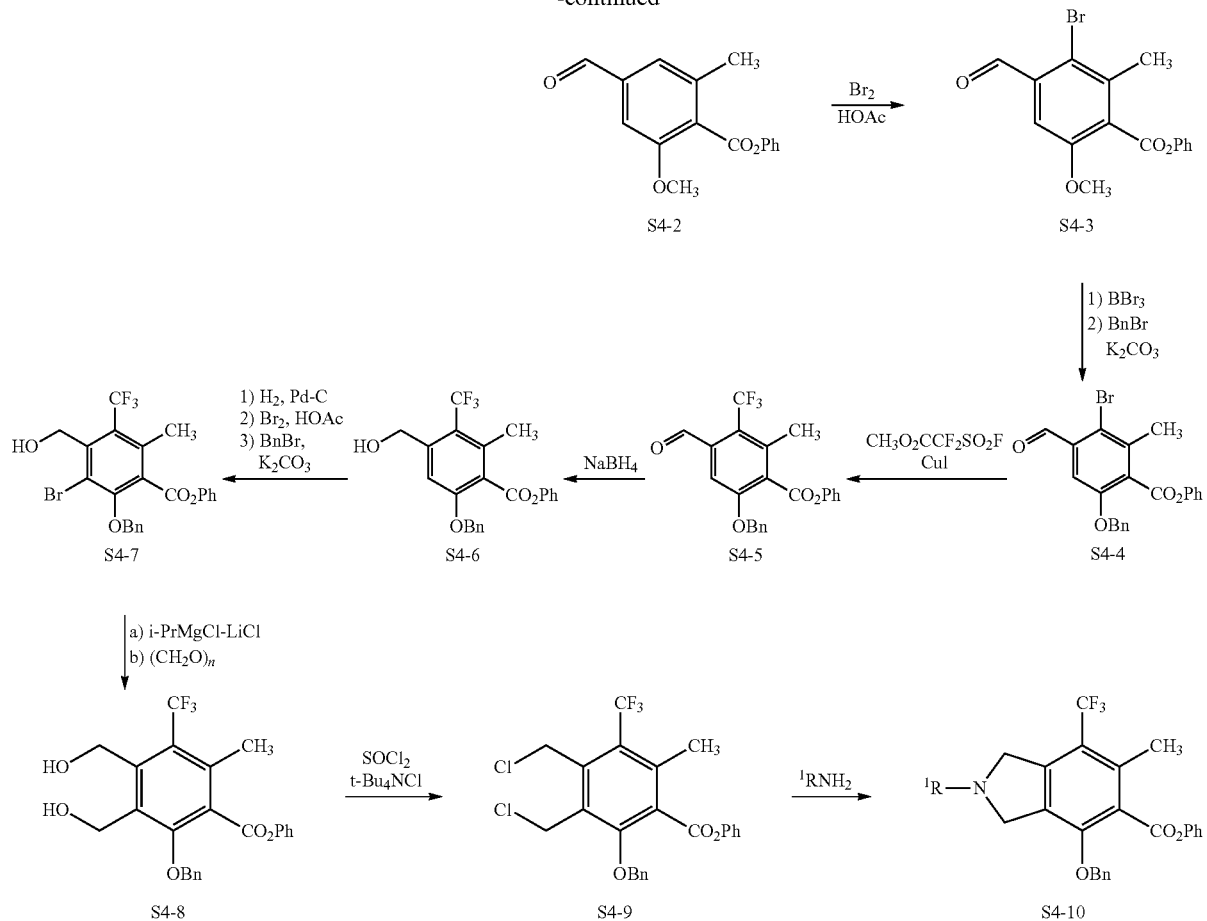
Compounds of Formula II, wherein X is $OCH_3$ were synthesized using a common N-substituted phenyl 4-(benzyloxy)-7-methoxy-6-methylisoindoline-5-carboxylate intermediate, which is prepared according to Scheme 5.
Scheme 5
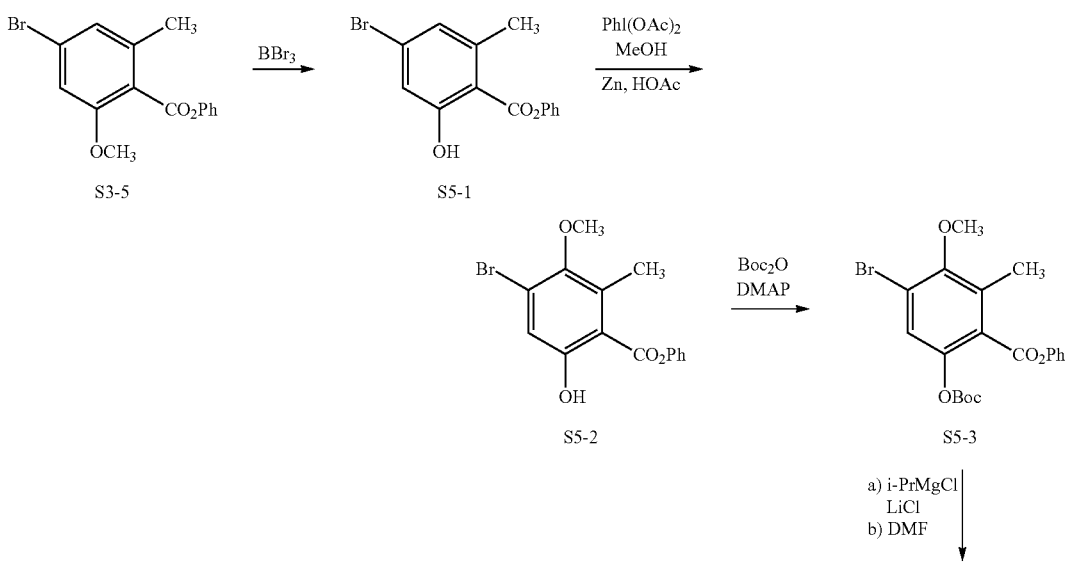

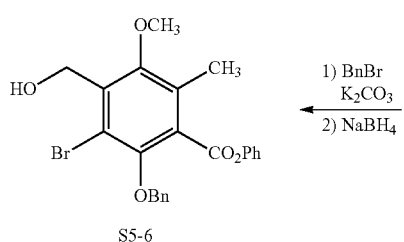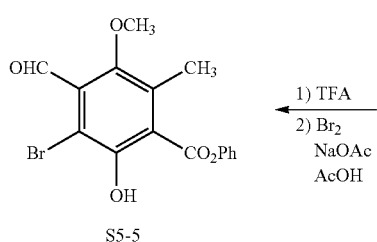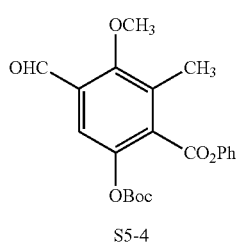

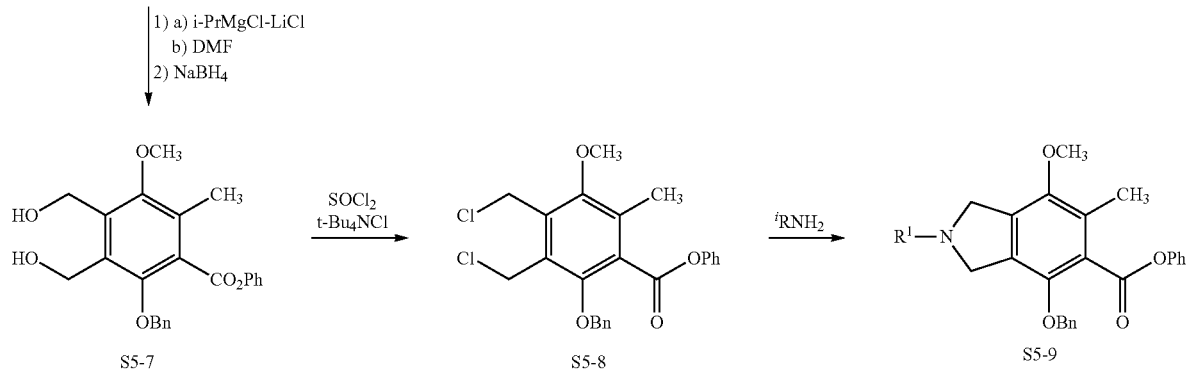

Compounds of Formula II, wherein X is N(CH$_3$)$_2$ were synthesized using a common N-substituted phenyl 4-(benzyloxy)-7-dimethylamino-6-methylisoindoline-5-carboxylate intermediate, which is prepared according to Scheme 6.

Scheme 6

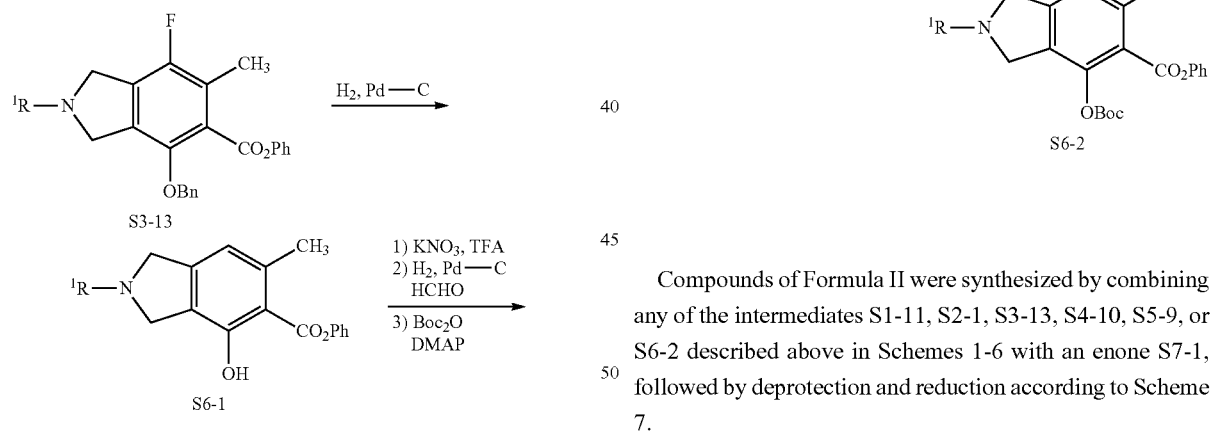

-continued

Compounds of Formula II were synthesized by combining any of the intermediates S1-11, S2-1, S3-13, S4-10, S5-9, or S6-2 described above in Schemes 1-6 with an enone S7-1, followed by deprotection and reduction according to Scheme 7.

Scheme 7

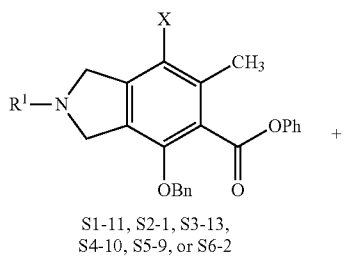

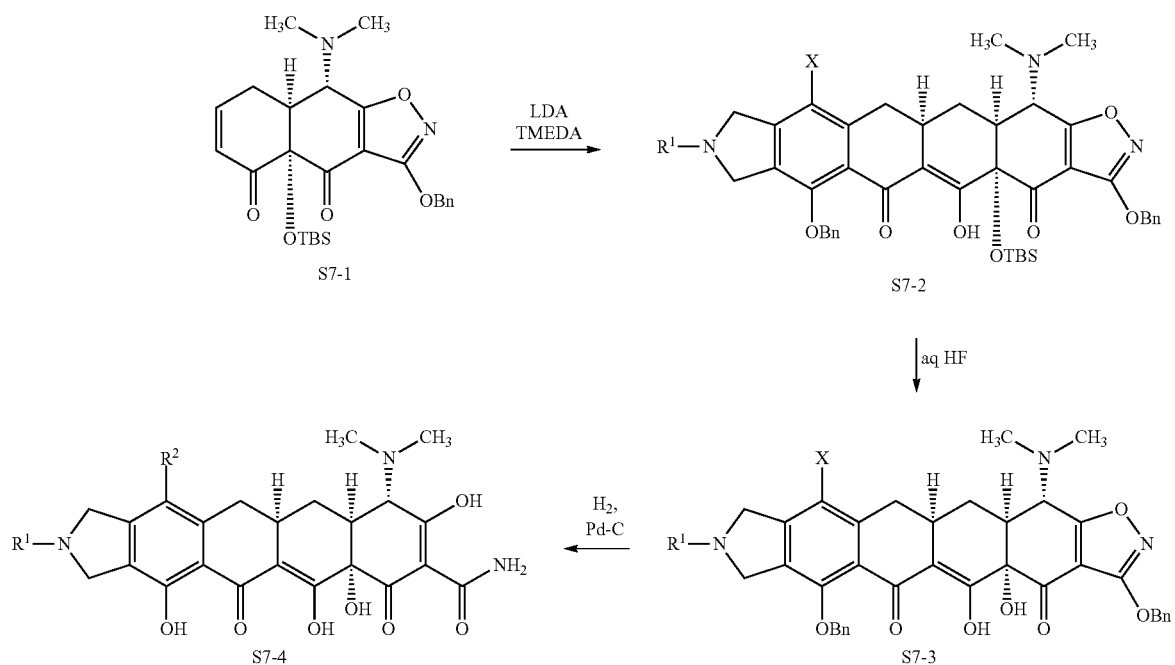
Compounds of Formula II wherein $R^1$ is fluoro and $R^1$ is —C(O)CH$_2$N(R$^2$)(R$^3$) or hydrogen were prepared according to Scheme 8.
Scheme 8
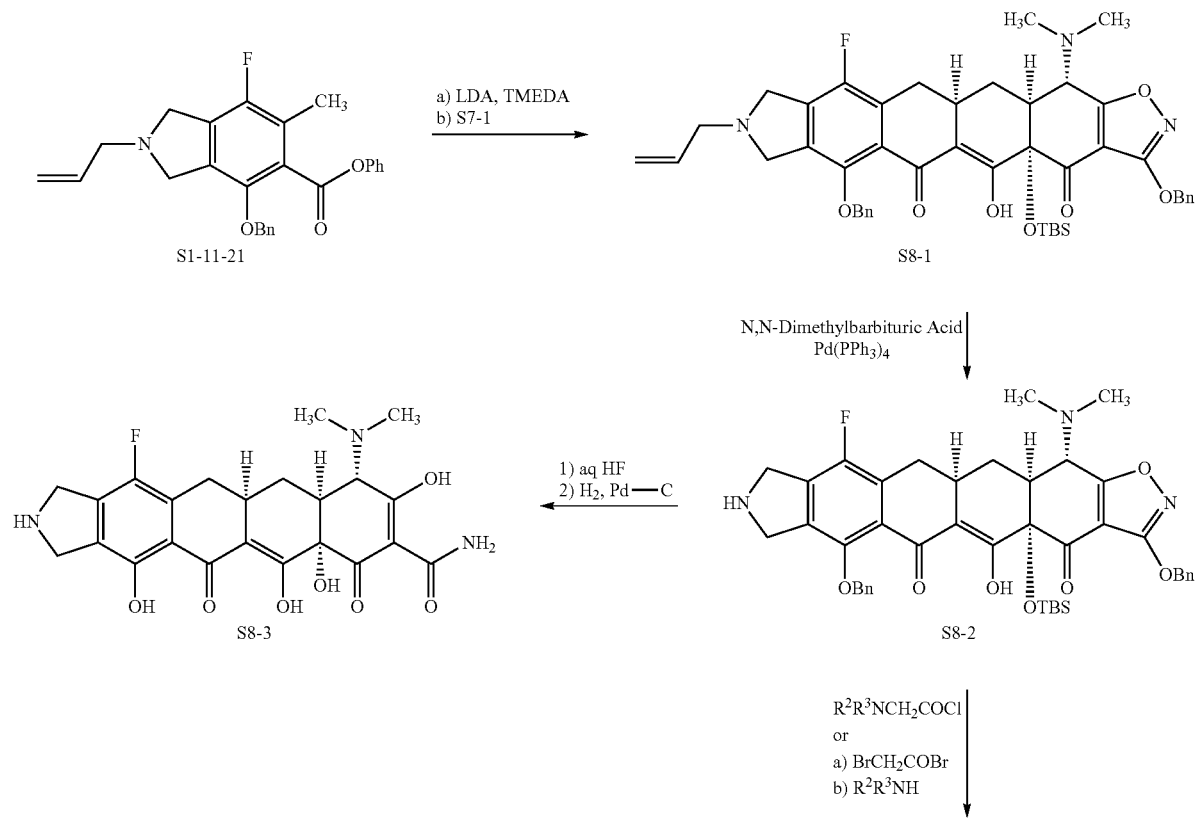

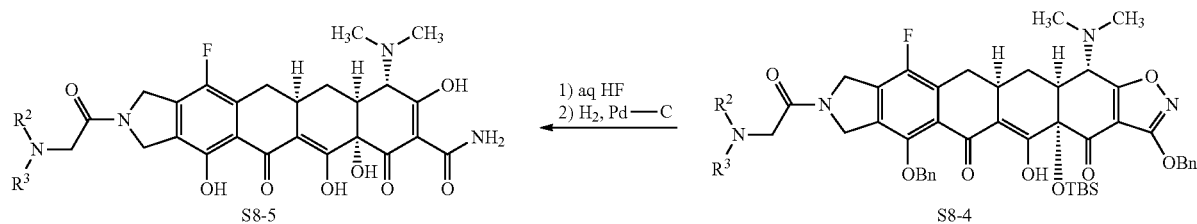
Compound of Formula II wherein X is hydrogen are prepared by reduction of the corresponding compounds wherein X is chloro according to Scheme 9
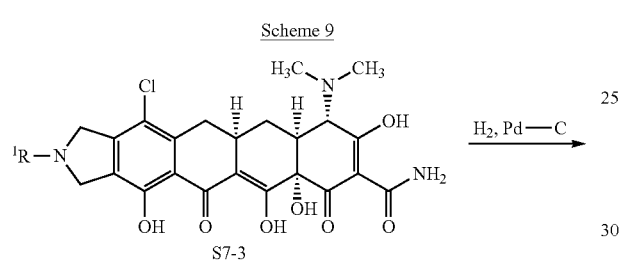
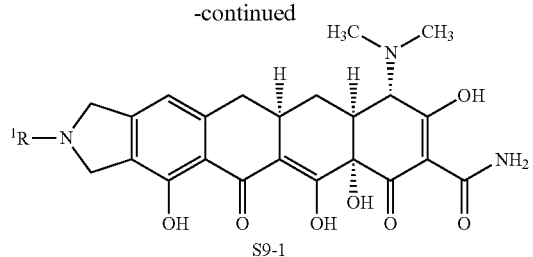
Compounds of Formula III are synthesized through a common N-substituted phenyl 8-(benzyloxy)-5-fluoro-6-methyl-1,2,3,4-tetrahydroisoquinoline-7-carboxylate intermediate (S10-3) according to Scheme 10, below

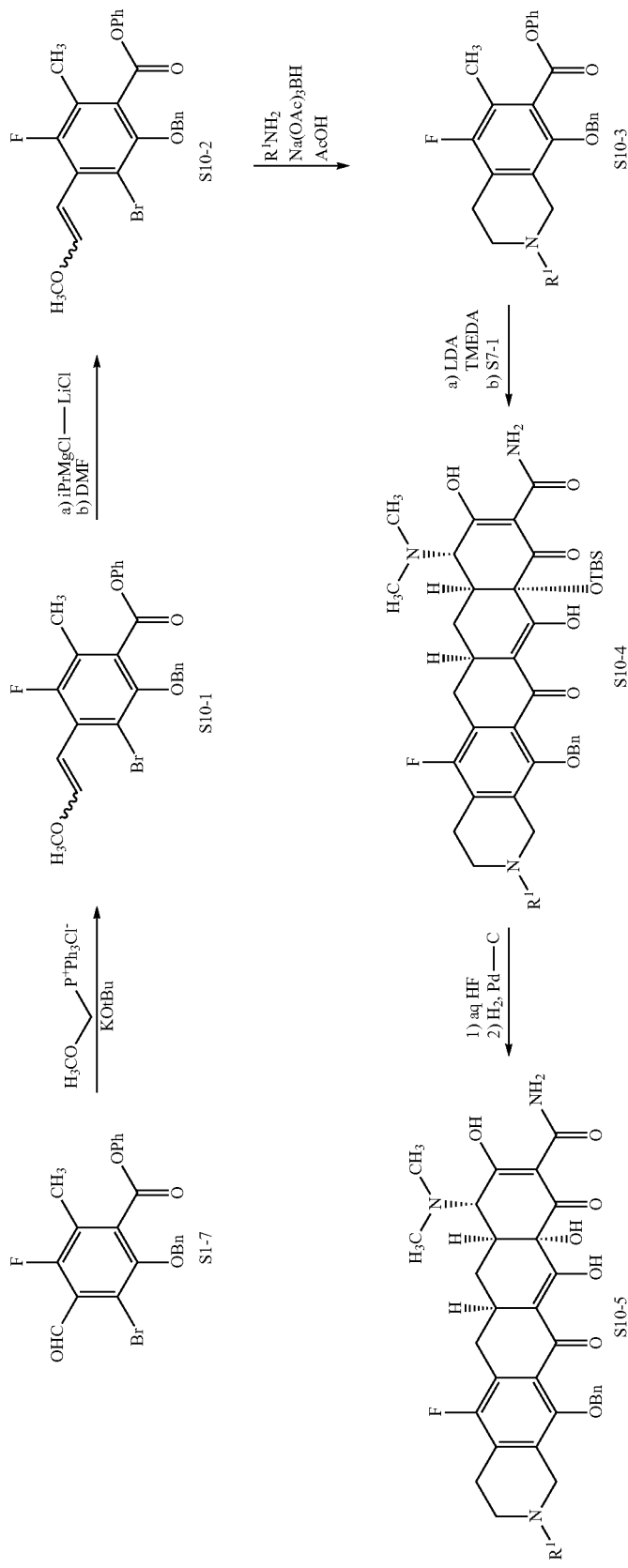

Compounds of Formula IV were prepared using a common N-substituted phenyl 5-(benzyloxy)-8-fluoro-7-methyl-1,2, 3,4-tetrahydroisoquinoline-6-carboxylate intermediate according to Scheme 11
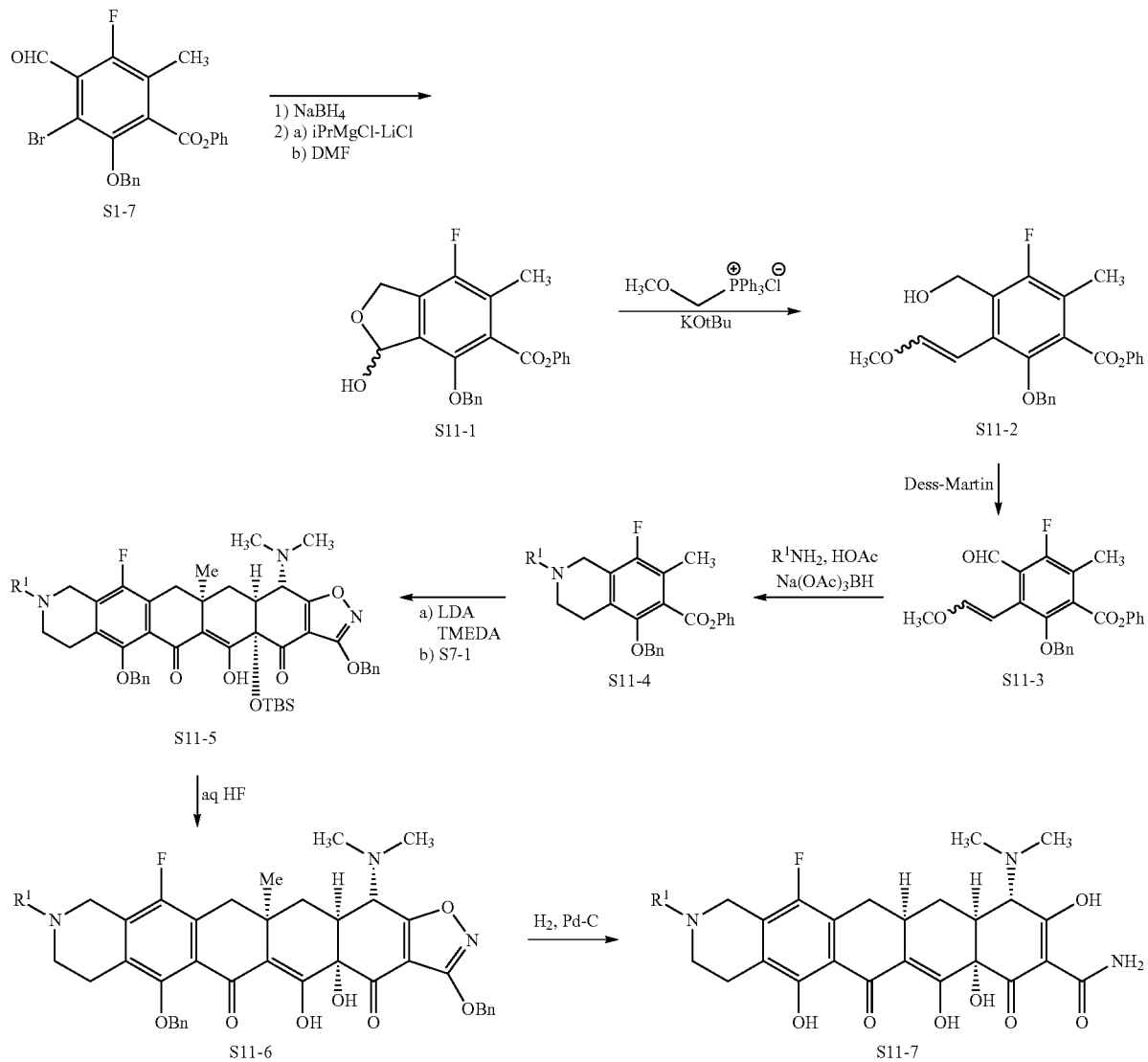
Compounds of Formula V, wherein $R^{7a}$ and $R^{7b}$ are taken together to form =O are synthesized according to Scheme 12.
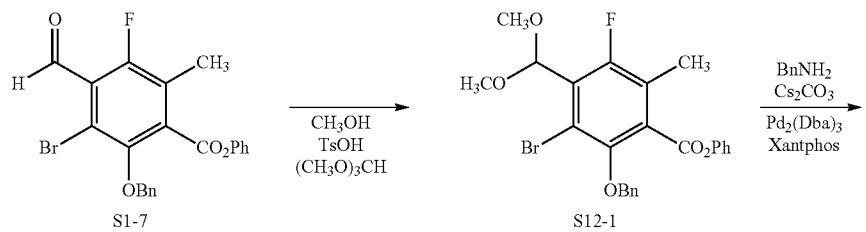

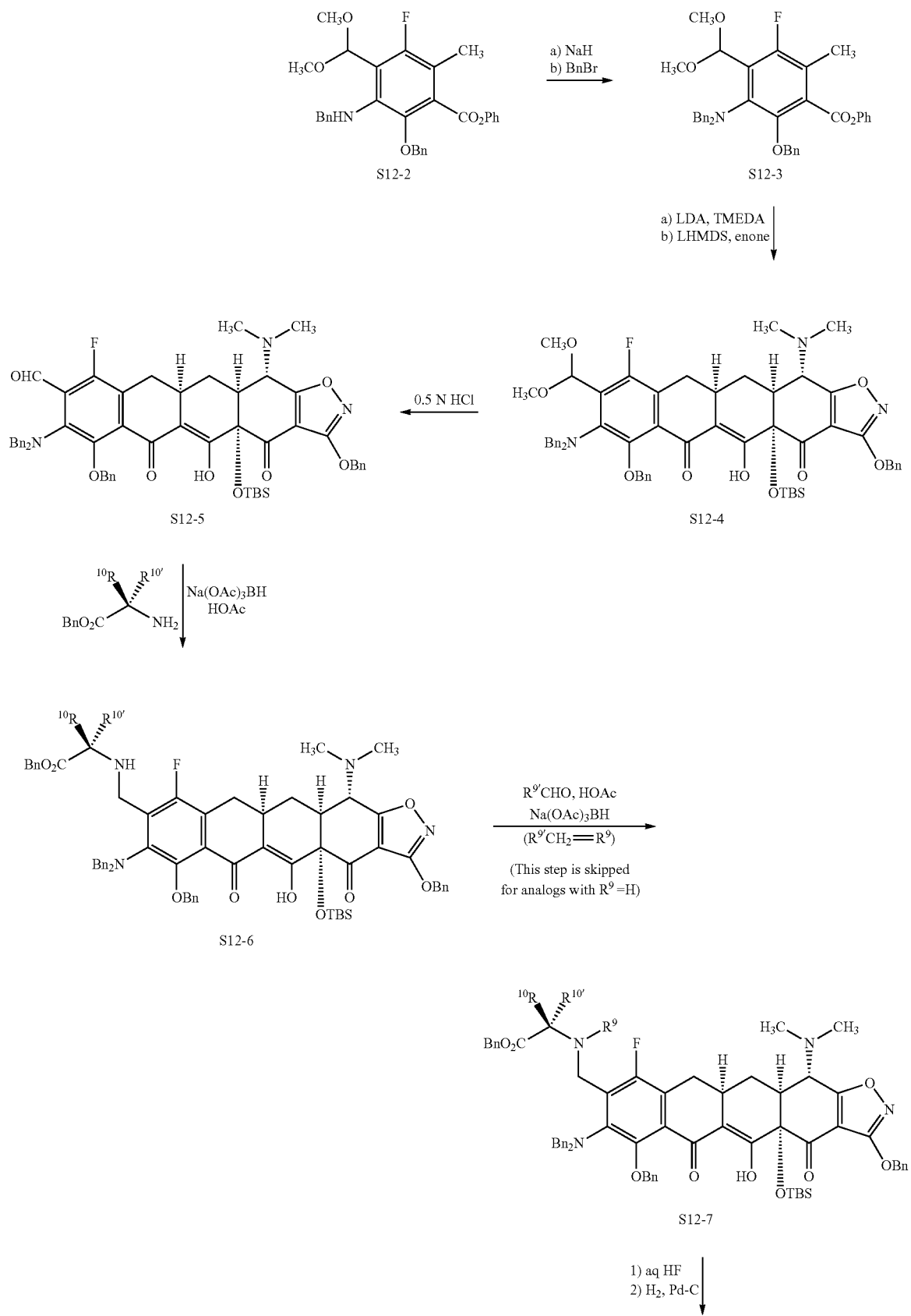

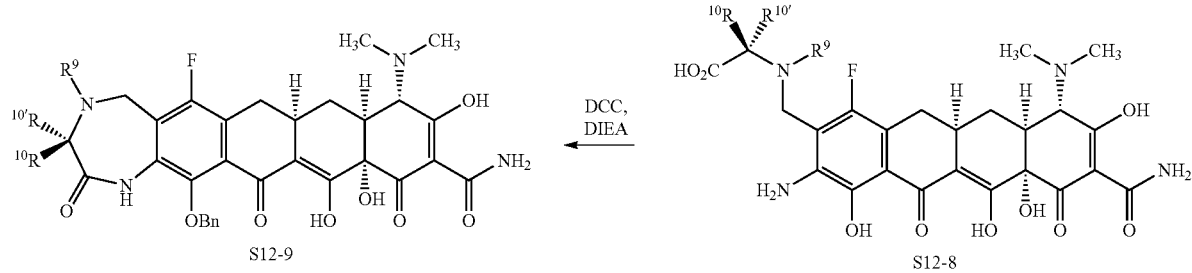
Compounds of Formula V, wherein $R^{7a}$ and $R^{7b}$ are hydrogen are prepared according to Scheme 13
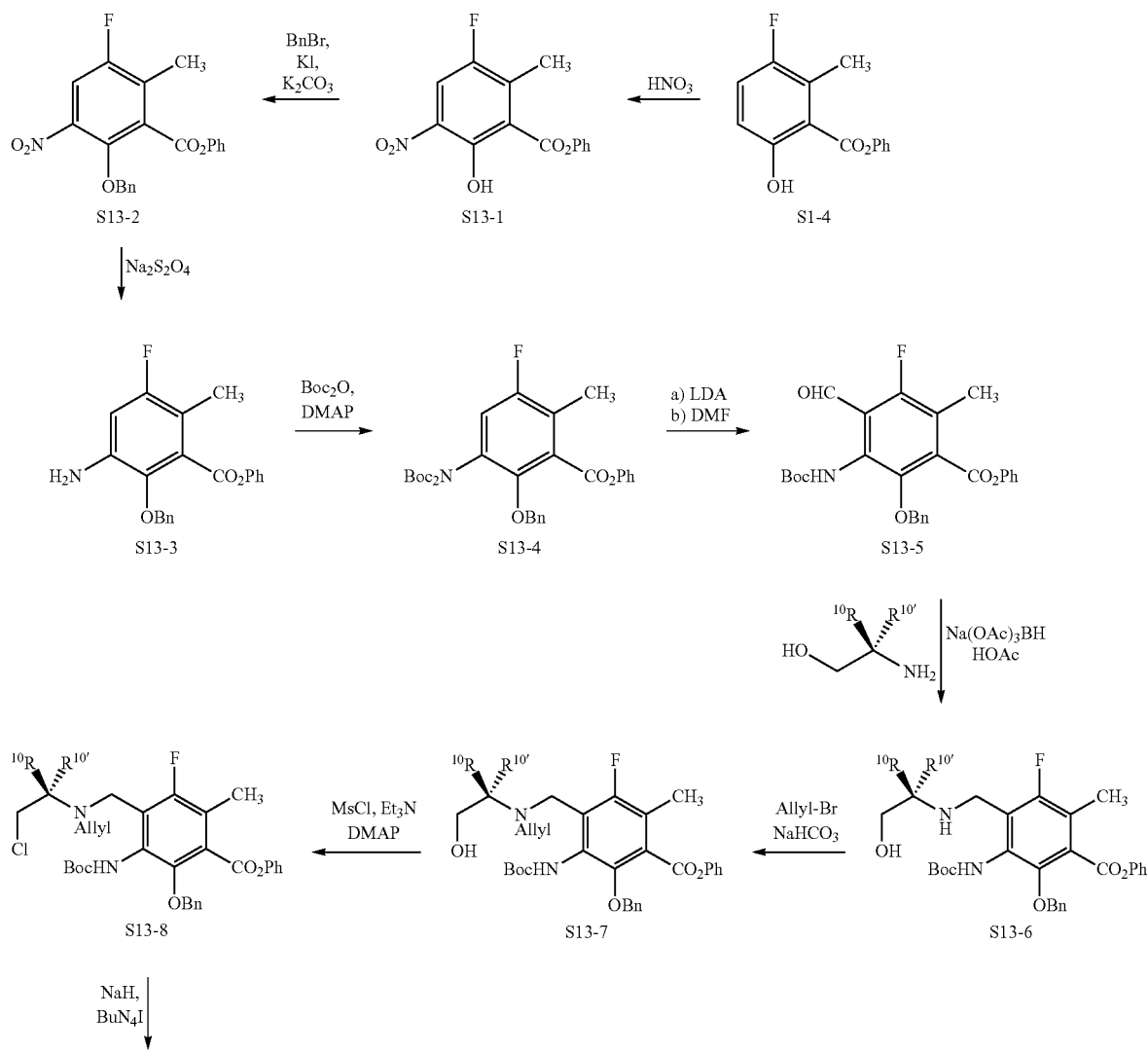

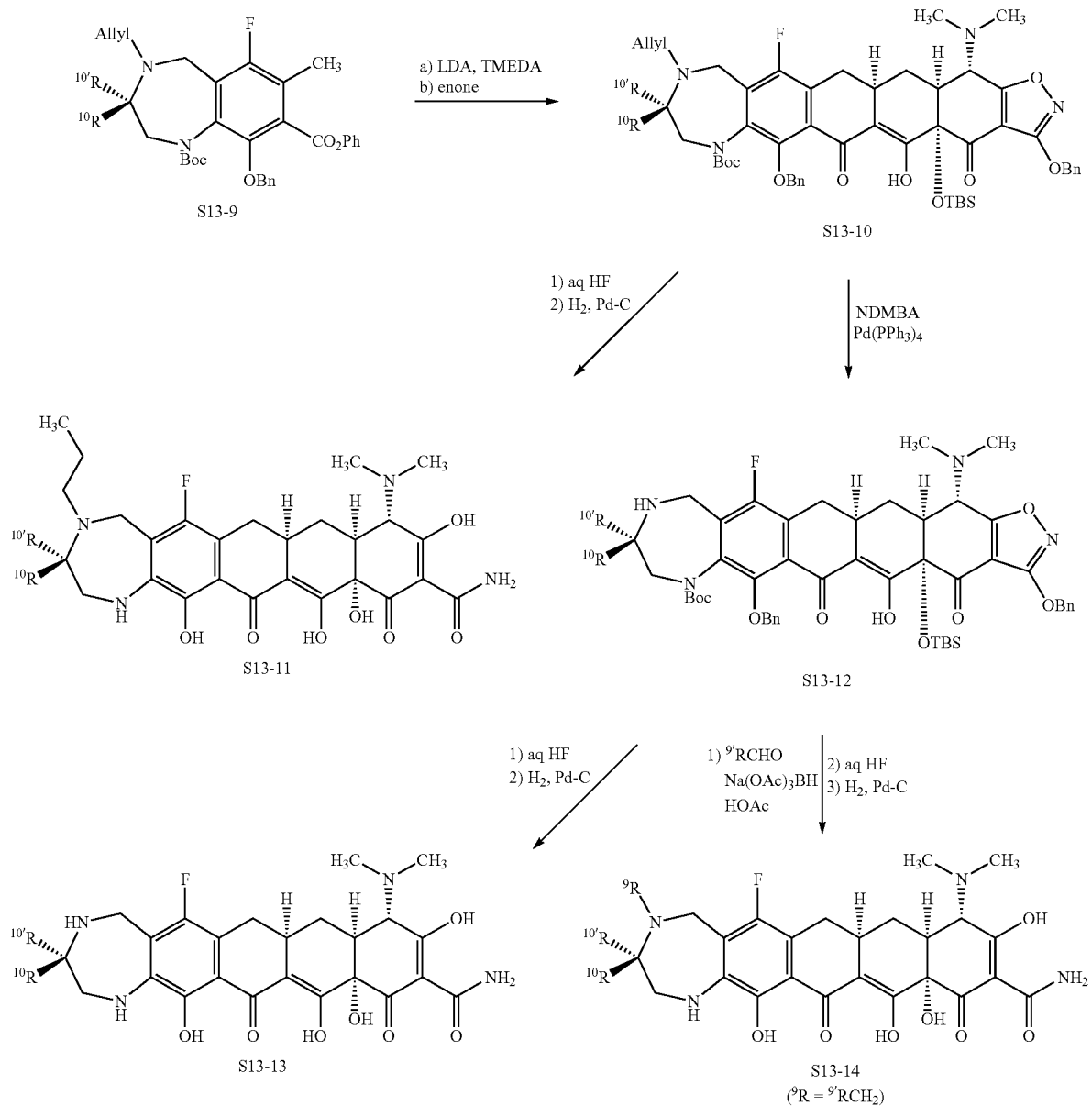

EXAMPLE 1

Preparation of phenyl 4-(benzyloxy)-2-tert-butyl-7-fluoro-6-methylisoindoline-5-carboxylate (S1-11-1)

Synthesis of S1-2

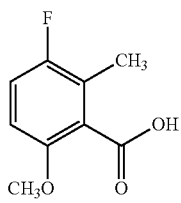

S1-2

To a THF solution of 5-fluoro-2-methoxybenzoic acid (S1-1, 500 mg, 2.94 mmol, Aldrich 523097) cooled at −78° C. was added a THF solution of s-BuLi (4.60 mL, 1.40 M, 6.44 mmol, 2.2 eq) and TMEDA (0.97 mL, 6.47 mmol, 2.2 eq). The reaction was stirred at −78° C. for 2 h. Methyl iodide (1.10 mL, 17.64 mmol, 6 eq) was added to the reaction mixture dropwise. The reaction was allowed to warm to 25° C. over 1 h and stirred at 25° C. for 1 h. NaOH (6 N, 20 mL) was added. The resulting mixture was extracted with t-butylmethyl ether (20 mL×2). The aqueous layer was acidified with HCl (6 N) to pH 1 and extracted with EtOAc (20 mL×4). The combined EtOAc extracts were dried ($Na_2SO_4$) and concentrated to give 510 mg of crude product S1-2: NMR (400 MHz, $CDCl_3$) δ 7.06 (dd, J=9.8, 8.5 Hz, 1 H), 6.75 (dd, J=9.8, 3.7 Hz, 1 H), 3.86 (s, 3 H), 2.34 (d, J=2.4 Hz, 3 H); MS (ESI) m/z 185.12 (M+H).

Synthesis of S1-3

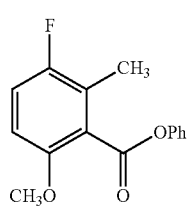

S1-3

Oxalyl chloride (0.95 mL, 11.10 mmol, 5.5 eq) was added to CH$_2$Cl$_2$ solution (15 mL, anhydrous) of S1-2 (510 mg, 2.00 mmol). DMF (0.1 mL) was added to the resulting mixture. The reaction was stirred at 25° C. for 1 h and concentrated. The resulting solid was re-dissolved in 15 mL of anhydrous CH$_2$Cl$_2$. Phenol (520 mg, 5.50 mmol, 2.8 eq), DMAP (670 mg, 5.6 mmol, 2.8 eq), and triethylamine (1.90 mL, 13.90 mmol, 7.0 eq) were added to the reaction mixture. The reaction was stirred at 25° C. for 12 h and concentrated. EtOAc and H$_2$O were added to the residue. The organic layer was washed with NaOH (1 N), H$_2$O, and brine, dried (Na$_2$SO$_4$), and concentrated. Flash chromatography on silica gel (40:1 hexanes/EtOAc) yielded 400 mg of compound S1-3 (52% for 2 steps): $^1$H NMR (400 MHz, CDCl$_3$) δ 7.47-7.41 (m, 2 H), 7.31-7.24 (m, 3 H), 7.08 (dd, J=9.2, 9.2 Hz, 1 H), 6.77 (dd, J=9.2, 3.7 Hz, 1 H), 3.88 (s, 3 H), 2.36 (d, J=2.3 Hz, 3 H); MS (ESI) m/z 261.12 (M+H).

Synthesis of S1-4

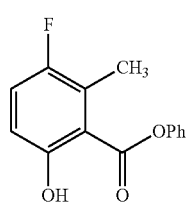

S1-4

BBr$_3$ (1.85 mL, 1 M, 1.85 mmol, 1.2 eq) was added to a CH$_2$Cl$_2$ solution (8 mL) of S1-3 (400 mg, 1.54 mmol) at −78° C. The reaction was stirred from −78° C. to 25° C. for 1.5 h, quenched with saturated NaHCO$_3$ and concentrated. EtOAc and H$_2$O were added to the reaction mixture. The aqueous layer was extracted with EtOAc. The combined EtOAc extracts were dried (Na$_2$SO$_4$) and concentrated to yield 360 mg of crude S1-4: $^1$H NMR (400 MHz, CDCl$_3$) δ 10.66 (s, 1 H), 7.50-7.44 (m, 2 H), 7.36-7.31 (m, 1 H), 7.26-7.18 (m, 3 H), 6.86 (dd, J=9.3, 4.9 Hz, 1 H), 2.60 (d, J=2.4 Hz, 3 H); MS (ESI) m/z 245.11 (M−H).

Synthesis of S1-5

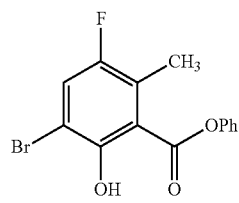

S1-5

Compound S1-4 (4.92 g, 95% purity, 20 mmol) was dissolved in acetic acid (50 mL) and bromine (1.54 mL, 30 mmol) was added via syringe at room temp. After stirred at room temp for 2 hour, LC/MS indicated that the starting material was consumed. This reaction mixture was dilute with ethyl acetate, wash with water (3×100 mL) and brine. The organics were dried over Na$_2$SO$_4$, filtered, and concentrated under reduced pressure. This gave 7.06 g of compound S1-5 as light yellow solid: $^1$H NMR (400 MHz; CDCl$_3$) δ 11.14 (s, 1 H), 7.52 (d, J=9.2 Hz, 1 H), 7.49-7.43 (m, 2 H), 7.36-7.30 (m, 1 H), 7.21-7.16 (m, 2 H), 2.55 (d, J=2.3 Hz, 3 H).

Synthesis of S1-6

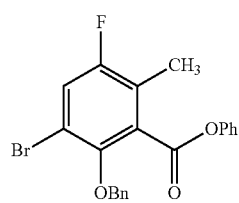

S1-6

Compound S1-5 (crude, 1.06 g, 2.97 mmol) was dissolve in acetone (20 mL) with potassium carbonate (821 mg, 5.94 mmol, 2.0 eq) and cooled to 0° C. in an ice-bath. Benzyl bromide (540 µL, 4.45 mmol, 1.5 eq) was added dropwise. After 2 hrs, LC/MS indicated that the starting material was consumed 40%. The reaction mixture was heated to 50° C. for another hour and the starting material was all consumed. The reaction mixture was diluted with ethyl acetate (100 mL) and washed with water and brine. The organics were dried over Na$_2$SO$_4$, filtered, and concentrated under reduced pressure. This gave 2.2 g of the crude S1-6, which was purified by column chromatography (Biotage 10 g column, 2 to 5% ethyl acetate in hexane gradient), yielding 1.03 g (84% for two steps) of the pure compound S1-6 as an colorless oil: $^1$H NMR (400 MHz, CDCl$_3$) δ 7.50-7.47 (m, 2 H), 7.40-7.33 (m, 6 H), 7.25 (t, J=7.3 Hz, 1 H), 7.04 (d, J=8.6 Hz, 2 H), 5.09 (s, 2 H), 2.32 (d, J=1.8 Hz, 3 H).

Synthesis of S1-7

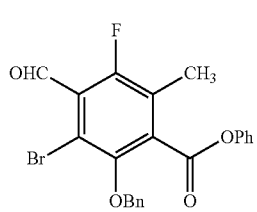

S1-7

LDA solution was prepared by adding n-BuLi (1.6 M, 5.1 mL, 8.16 mmol, 1.5 eq) to diisopropylamine (1.15 mL, 8.16 mmol) in THF (15 mL) at −78° C. The reaction mixture was warmed up to −20° C. and stirred for 15 min. After LDA solution was cooled to −78° C., compound S1-6 (2.26 g, 5.44 mmol) in THF (5 mL) was added dropwise, forming an orange-red solution. After 10 min, DMF (1.26 mL, 16.3 mmol, 3 eq) was added dropwise. The reaction solution was allowed to warm up to −20° C. in 1 hour and was quenched with NH$_4$Cl (aq. Solution). LC/MS indicated that the starting material was all consumed. The reaction mixture was diluted with ethyl acetate (100 mL) and washed with water and brine. The organics were dried over Na$_2$SO$_4$, filtered, and concentrated under reduced pressure. This gave 2.42 g of the crude S1-7, which was purified by column chromatography (Biotage 24 g column, 5 to 10% ethyl acetate in hexane gradient), yielding 2.23 g (92%) of the pure compound S1-7 as light yellow solid. $^1$H NMR (400 MHz, CDCl$_3$) δ 10.37 (s, 1H), 7.51-7.47 (m, 2H), 7.40-7.33 (m, 5H), 7.27 (t, J=7.3 Hz, 1H), 7.06-7.02 (m, 2H), 5.12 (s, 2H), 2.37 (d, J=2.3 Hz, 3H).

Synthesis of S1-8

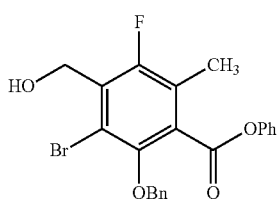

S1-8

Compound S1-7 (416 mg, 0.94 mmol) was dissolved in methanol (5 mL) and sodium borohydride (75.6 mg, 2 mmol) was added in several portions. During the addition, gas evolution was observed. After stirring at rt for 30 min, LC/MS indicated that the starting material was consumed. This reaction mixture was diluted with ethyl acetate and washed with water (2×20 mL) and brine. The organics were dried over Na$_2$SO$_4$, filtered, and concentrated under reduced pressure. The crude material was purified by column chromatography (Biotage 10 g column, 5 to 20% ethyl acetate in hexane gradient), yielding 367 mg (87.7%) of the pure compound S1-8 as a colorless oil. $^1$H NMR (400 MHz, CDCl$_3$) δ 10.37 (s, 1H), 7.49 (dd, J=7.8, 2.3 Hz, 2H), 7.40-7.33 (m, 5H), 7.25 (t, J=7.8 Hz, 1H), 7.07-7.02 (m, 2H), 5.10 (s, 2H), 4.91 (dd, J=6.9, 2.3 Hz, 2H), 2.35 (d, J=2.3 Hz, 3H); MS (ESI) m/z 467.10, 469.08 (M+Na).

Synthesis of S1-9

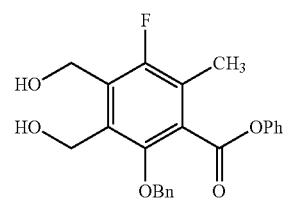

S1-9 i-Propyl magnesium chloride/lithium chloride solution (Chemetall Foote Corporation, 1.2 M solution in THF, 4.4 mL, 5.3 mmol) was added to a −78° C. solution of compound S1-8 (472 mg, 1.06 mmol) in THF (10 mL). The reaction mixture was allowed to warm to 0° C. over 1 hour. Paraformaldehyde (318 mg, 10.6 mmol) was added, and the reaction was allowed to warm to rt. After 1 hour, the reaction mixture was heated to 40° C. After 1 hour, the reaction mixture was quenched with ammonium chloride (saturated, aqueous solution) and was extracted with EtOAc (2×). The combined extracts were dried over Na$_2$SO$_4$, filtered, and concentrated under reduced pressure. The crude material was purified by column chromatography (Biotage 10 g column, 10 to 35% EtOAc in hexane gradient), yielding 337 mg (80%) of S1-9 as a thick oil. $^1$H NMR (400 MHz, CDCl$_3$) δ 7.45-7.34 (m, 7H), 7.30-7.23 (m, 1H), 7.10 (d, J=7.8 Hz, 2H), 5.08 (s, 2H), 4.85 (s, 2H), 4.76 (s, 2H), 2.39 (d, J=2.3 Hz, 3H); MS (ESI) m/z 419.19 (M+Na).

Synthesis of S1-10

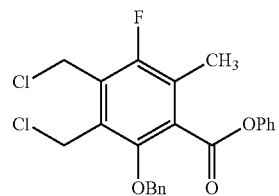

S1-10

To a solution of compound S1-9 (2.98 g, 7.52 mmol, 1 eq) in 1,2-dichloroethane (20 mL) was added thionyl chloride (2.18 mL, 30.1 mmol, 4 eq) and tetrabutylammonium chloride (174 mg, 0.76 mmol, 0.1 eq). The reaction vessel was sealed and the mixture heated to 80° C. for 2 h, then concentrated under reduced pressure. Purification of the resulting crude oil via flash column chromatography on silica gel (Redisep, 80 g, 4 to 6% EtOAc in hexane gradient) provided 2.66 g of S1-10 (81%) as a waxy white solid: $^1$H NMR (400 MHz, CDCl$_3$) δ 7.48-7.42 (m, 2H), 7.41-7.34 (m, 4H), 7.29-7.24 (m, 1H), 7.10-7.05 (m, 2H), 5/13 (s, 2H), 4.81 (s, 4H), 2.44-2.39 (m, 3H); MS (ESI) m/z 431.14, 433.16 (M+H).

Synthesis of S1-11-1

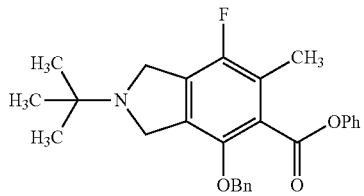

S1-11-1

Compound S1-10 (120 mg, 0.277 mmol), t-butylamine (0.032 mL, 0.305 mmol) and diisopropylethylamine (0.096 mL, 0.554 mmol) were heated to 110° C. in 1,2-dimethoxyethane (1 mL). After 2 hours, additional t-butylamine (0.100 mL, 0.95 mmol) was added. After 2 more hours, additional t-butylamine (0.500 mL, 4.75 mmol) was added, and the reaction mixture was heated overnight. The reaction mixture was concentrated under reduced pressure and was purified by column chromatography (Biotage 10 g column, 5 to 20% EtOAc in hexane gradient), yielding 64.1 mg (53%) of the product. $R_f$=0.25 in 20% EtOAc in hexane; $^1$H NMR (400 MHz, CDCl$_3$) δ 7.42-7.30 (m, 7 H), 7.27-7.20 (m, 1 H), 7.04 (d, J=7.8 Hz, 2 H), 5.02 (s, 2 H), 4.08 (s, 2 H), 4.04 (s, 2 H), 2.33 (d, J=1.8 Hz, 3 H), 1.15 (s, 9 H); MS (ESI) m/z 434.29 (M+H).

The following compounds were prepared by methods similar to those described for S1-11-1.

EXAMPLE 2

S1-11-2

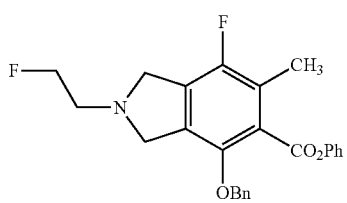

S1-11-2

$^1$H NMR (400 MHz, CDCl$_3$) δ 7.41-7.30 (m, 7 H), 7.25-7.20 (m, 1 H), 7.05-7.00 (m, 2 H), 5.01 (s, 2 H), 4.67 (t, J=4.9 Hz, 1 H), 4.55 (t, J=4.9 Hz, 1 H), 4.08 (s, 4H), 3.08 (t, J=4.9 Hz, 1 H), 3.01 (t, J=4.9 Hz, 1 H), 2.34-2.32 (m, 3 H); MS (ESI) m/z 424.63 (M+H).

EXAMPLE 3

S1-11-3

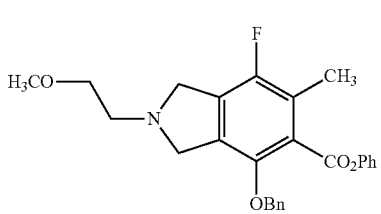

S1-11-3

$^1$H NMR (400 MHz, CDCl$_3$) δ 7.43-7.31 (m, 7 H), 7.25-7.20 (m, 1 H), 7.07-7.01 (m, 2 H), 5.03 (s, 2 H), 4.07 (s, 4 H), 3.57 (t, J=5.5 Hz, 2 H), 3.41 (s, 3 H), 2.95 (t, J=5.5 Hz, 2 H), 2.36-2.34 (m, 3 H); MS (ESI) m/z 436.38 (M+H).

EXAMPLE 4

S1-11-4

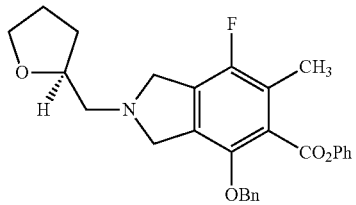

S1-11-4

$^1$H NMR (400 MHz, CDCl$_3$) δ 7.37-7.31m (m, 7 H), 7.29-7.23 (m, 1 H), 7.05-6.99 (m, 2 H), 5.01 (s, 2 H), 3.95 (s, 3 H), 2.47 (d, J=6.1 Hz, 2 H), 2.33 (s, 3 H), 1.83-1.72 (m, 1 H), 0.95 (d, J=5.5 Hz, 6 Hz); MS (ESI) m/z 434.27 (M+H).

EXAMPLE 5

S1-11-5

S1-11-5

$^1$H NMR (400 MHz, CDCl$_3$) δ 7.41-7.32 (m, 7 H), 7.25-7.20 (m, 1 H), 7.07-7.02 (m, 2 H), 5.03 (s, 2 H), 4.16-4.01 (m, 5 H), 3.96-3.87 (m, 1 H), 3.84-3.76 (m, 1 H), 3.37-3.27 (m, 1 H), 2.89-2.77 (m, 2 H), 2.35 (s, 3 H), 1.98-1.83 (m, 2 H), 1.66-1.54 (m, 1 H); MS (ESI) m/z 462.82 (M+H).

EXAMPLE 6

S1-11-6

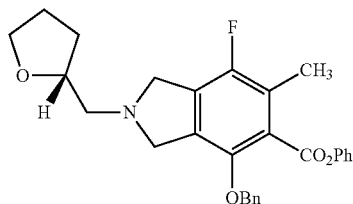

¹H NMR (400 MHz, CDCl₃) δ 7.41-7.32 (m, 7 H), 7.25-7.20 (m, 1 H), 7.07-7.02 (m, 2 H), 5.03 (s, 2 H), 4.16-4.01 (m, 5 H), 3.96-3.87 (m, 1 H), 3.84-3.76 (m, 1 H), 3.37-3.27 (m, 1 H), 2.89-2.77 (m, 2 H), 2.35 (s, 3 H), 1.98-1.83 (m, 2 H), 1.66-1.54 (m, 1 H); MS (ESI) m/z 462.80 (M+H).

EXAMPLE 7

S1-11-7

¹H NMR (400 MHz, CDCl₃) δ 7.44-7.30 (m, 7 H), 7.25-7.20 (m, 1 H), 7.08-7.00 (m, 2 H), 5.04 (s, 2 H), 4.06-3.95 (m, 4 H), 2.82-2.71 (m, 1 H), 2.35 (s, 3 H), 1.18 (d, J=6.1 Hz, 6 H); MS (ESI) m/z 420.62 (M+H).

EXAMPLE 8

S1-11-8

¹H NMR (400 MHz, CDCl₃) δ 7.43-7.30 (m, 7 H), 7.25-7.20 (m, 1 H), 7.08-7.01 (m, 2 H), 5.04 (s, 2 H), 4.06-3.95 (m, 4 H), 2.67-2.56 (m, 1 H), 2.35 (s, 3 H), 1.72-1.57 (m, 1 H), 1.51-1.37 (m, 1 H), 1.13 (d, J=6.1 Hz, 3 H), 0.94 (t, J=7.0 Hz, 3 H); MS (ESI) m/z 434.00 (M+H).

EXAMPLE 9

S1-11-9

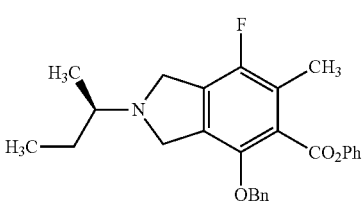

¹H NMR (400 MHz, CDCl₃) δ 7.43-7.29 (m, 7 H), 7.25-7.20 (m, 1 H), 7.08-7.00 (m, 2 H), 5.04 (s, 2 H), 4.05-3.96 (m, 4 H), 2.66-2.55 (m, 1 H) 2.34 (s, 3 H), 1.72-1.57 (m, 1 H), 1.51-1.37 (m, 1 H), 1.13 (d, J=6.1 Hz, 3 H), 0.95 (t, J=7.3 Hz, 3 H); MS (ESI) m/z 434.64 (M+H).

EXAMPLE 10

S1-11-10

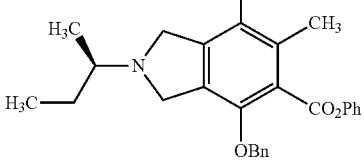

¹H NMR (400 MHz, CDCl₃) δ 7.43-7.29 (m, 7 H), 7.25-7.20 (m, 1 H), 7.08-7.00 (m, 2 H), 5.04 (s, 2 H), 4.05-3.96 (m, 4 H), 2.66-2.55 (m, 1 H) 2.34 (s, 3 H), 1.72-1.57 (m, 1 H), 1.51-1.37 (m, 1 H), 1.13 (d, J=6.1 Hz, 3 H), 0.95 (t, J=7.3 Hz, 3 H); MS (ESI) m/z 434.60 (M+H).

EXAMPLE 11

S1-11-11

¹H NMR (400 MHz, CDCl₃) δ 7.42-7.34 (m, 7 H), 7.29-7.22 (m, 1 H), 7.06-6.99 (m, 2 H), 5.04 (s, 2 H), 4.02-3.95 (m, 4 H), 2.51-2.42 (m, 1 H), 2.34 (s, 3 H), 1.98-1.87 (m, 1 H), 1.01 (d, J=6.1 Hz, 3 H), 0.95 (d, J=6.7 Hz, 3 H), 0.89 (d, J=6.7 Hz, 3H): MS (ESI) m/z 448.85 (M+H).

EXAMPLE 12

S1-11-12

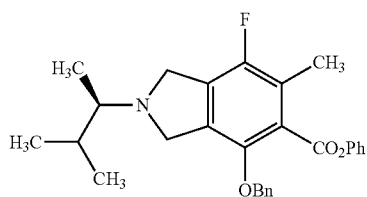

$^1$H NMR (400 MHz, CDCl$_3$) δ 7.42-7.34 (m, 7 H), 7.29-7.22 (m, 1 H), 7.06-6.99 (m, 2 H), 5.04 (s, 2 H), 4.02-3.95 (m, 4 H), 2.51-2.42 (m, 1 H), 2.34 (s, 3 H), 1.98-1.87 (m, 1 H), 1.01 (d, J=6.1 Hz, 3 H), 0.95 (d, J=6.7 Hz, 3 H), 0.89 (d, J=6.7 Hz, 3 H): MS (ESI) m/z 446.48 (M−H).

EXAMPLE 13

S1-11-13

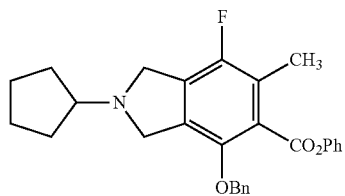

$^1$H NMR (400 MHz, CDCl$_3$) δ 7.41-7.3 (m, 7 H), 7.28-7.19 (m, 1 H), 7.05-7.00 (m, 2 H), 5.01 (s, 2 H), 3.99-3.94 (m, 4 H), 2.93-2.91 (m, 1 H), 2.33 (s, 3 H), 1.93-1.80 (m, 2 H), 1.80-1.67 (m, 2 H), 1.66-1.45 (m, 4 H); MS (ESI) m/z 446.61 (M+H).

EXAMPLE 14

S1-11-14

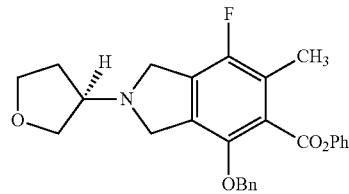

$^1$H NMR (400 MHz, CDCl$_3$) δ 7.41-7.32 (m, 7 H), 7.25-7.20 (m, 1 H), 7.07-7.02 (m, 2 H), 5.03 (s, 2 H), 4.04-3.94 (m, 5 H), 3.93-3.81 (m, 2 H), 3.77-3.70 (m, 1 H), 3.37-3.27 (m, 1 H), 2.37-2.31 (m, 3 H), 2.10-2.05 (m, 1 H), 2.02-2.10 (m, 1 H); MS (ESI) m/z 448.80 (M+H).

EXAMPLE 15

S1-11-15

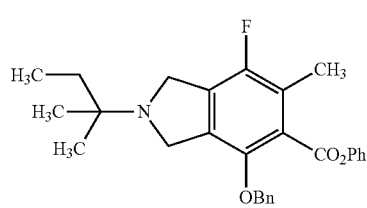

$^1$H NMR (400 MHz, CDCl$_3$) δ 7.40-7.20 (m, 7 H), 7.28-7.25 (m, 1 H), 7.16-7.02 (m, 2 H), 5.02 (s, 2 H), 4.05 (s, 2 H), 4.00 (s, 2 H), 2.33-2.32 (m, 3 H), 1.52 (s, 3 H), 1.49 (q, J=7.3 Hz, 2 H), 1.05 (s, 6 H), 0.90 (t, J=7.3 Hz, 3 H); MS (ESI) m/z 448.25 (M+H).

EXAMPLE 16

S1-11-16

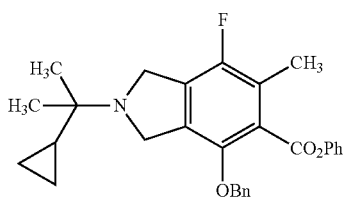

$^1$H NMR (400 MHz, CDCl$_3$) δ 7.40-7.23 (m, 7 H), 7.28-7.25 (m, 1 H), 7.16-7.02 (m, 2 H), 5.03 (s, 2 H), 4.17 (s, 2 H), 4.12 (s, 2 H), 2.34-2.32 (m, 3 H), 1.03-0.98 (m, 7 H), 0.47-0.40 (m, 2 H), 0.31-0.26 (m, 2 H); MS (ESI) m/z 460.28 (M+H).

EXAMPLE 17

S1-11-17

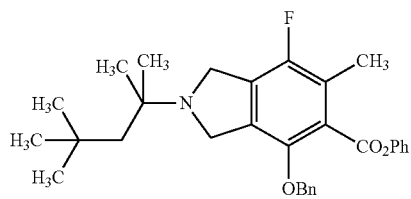

$^1$H NMR (400 MHz, CDCl$_3$) δ 7.42-7.28 (m, 7 H), 7.25-7.20 (m, 1 H), 7.08-7.00 (m, 2 H), 5.03 (s, 2 H), 4.09 (s, 2 H),

EXAMPLE 18

S1-11-18

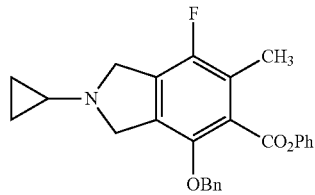

S1-11-18

$^1$H NMR (400 MHz, CDCl$_3$) δ 7.42-7.28 (m, 7 H), 7.25-7.20 (m, 1 H), 7.08-7.00 (m, 2 H), 5.04 (s, 2 H), 4.15 (s, 2 H), 4.13 (s, 2 H), 2.35 (s, 3 H), 2.10-2.02 (m, 1 H), 0.60-0.48 (m, 4 H); MS (ESI) m/z 416.41 (M−H).

EXAMPLE 19

S1-11-19

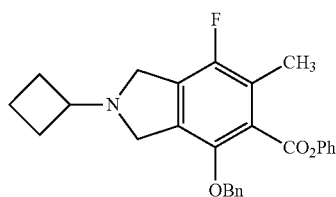

S1-11-19

$^1$H NMR (400 MHz, CDCl$_3$) δ 7.42-7.28 (m, 7 H), 7.25-7.20 (m, 1 H), 7.08-7.00 (m, 2 H), 5.03 (s, 2 H), 3.96 (s, 2 H), 3.94 (s, 2 H), 3.35-3.22 (m, 1 H), 2.35 (s, 3 H), 2.10-2.1.98 (m, 4 H), 1.80-1.70 (m, 2 H); MS (ESI) m/z 430.46 (M−H).

EXAMPLE 20

S1-11-20

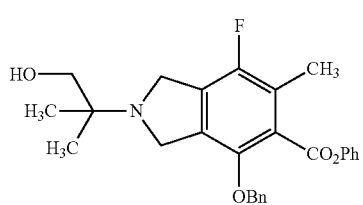

S1-11-20

$^1$H NMR (400 MHz, CDCl$_3$) δ 7.41-7.31 (m, 7 H), 7.27-7.21 (m, 1 H), 7.08-7.03 (m, 2 H), 5.03 (s, 2 H), 4.05 (s, 2 H), 3.94 (s, 2 H), 3.40 (m, 2 H), 2.35 (s, 3 H), 1.11 (s, 6 H); MS (ESI) m/z 448.35 (M−H).

EXAMPLE 21

S1-11-21

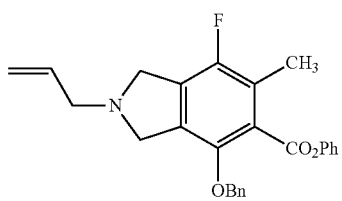

S1-11-21

$^1$H NMR (400 MHz, CDCl$_3$) δ 7.43-7.30 (m, 7 H), 7.25-7.20 (m, 1 H), 7.07-7.01 (m, 2 H), 6.00-5.87 (m, 1 H), 5.33-5.24 (m, 1 H), 5.19 (d, J=10.4, 1H), 5.02 (s, 2 H), 4.00 (s, 4 H), 3.36 (d, J=6.1, 3H), 2.35 (s, 3 H); MS (ESI) m/z 418.26 (M+H).

EXAMPLE 22

Synthesis of S1-11-22

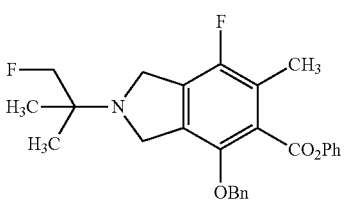

S1-11-22

A solution of alcohol S1-11-20 (92.1 mg, 0.205 mmol, 1 eq) in CH$_2$Cl$_2$ (1 mL) was added dropwise to a solution of pyridine (33.2 μL, 0.410 mmol, 2 eq) and diethylaminosulfur trifluoride (30.1 μL, 0.246 mmol, 1.2 eq) in CH$_2$Cl$_2$ (2 mL) at 0° C. The resulting solution was allowed to warm to ambient temperature and stirred for 2 h. The reaction was diluted with saturated aqueous NH$_4$Cl solution (2 mL), and extracted with EtOAc (2×30 mL). The combined organic layers were dried (Na$_2$SO$_4$), filtered, and concentrated under reduced pressure. Purification of the resulting oil via flash column chromatography on silica gel (Biotage, 25 g, 5 to 30% EtOAc in hexanes gradient) provided 40.0 mg of S1-11-22 (43%) as a clear oil: $^1$H NMR (400 MHz, CDCl$_3$) δ 7.41-7.32 (m, 7 H), 7.25-7.20 (m, 1 H), 7.07-7.02 (m, 2 H), 5.03 (s, 2 H), 4.12 (s, 4 H), 2.89 (s, 1 H), 2.82 (s, 1 H), 2.34 (s, 3 H), 1.44 (s, 3 H), 1.39 (s, 3 H); MS (ESI) m/z 450.45 (M−H).

EXAMPLE 23

Synthesis of S1-11-23

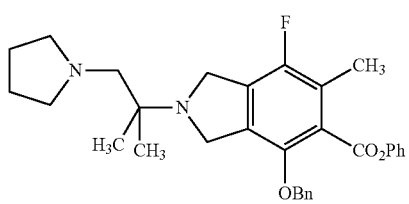

S1-11-23

To a solution of DMSO (23.9 µL, 0.337 mmol, 2 eq) in CH$_2$Cl$_2$ (1 mL) at −70° C. was added oxalyl chloride (17.3 µL, 0.201 mmol, 1.2 eq). After 15 minutes, alcohol S1-11-20 (75.8 mg, 0.168 mmol, 1 eq) in CH$_2$Cl$_2$ (500 µL) was added dropwise. After an additional 20 minutes at −70° C., DIEA (147 µL, 0.84 mmol, 5 eq) was added and the solution removed from the cold bath. After 5 minutes, saturated aqueous NH$_4$Cl solution (800 µL) was added and the mixture was allowed to warm. The solution was further diluted with saturated aqueous NH$_4$Cl solution (4 mL) and extracted with CH$_2$Cl$_2$ (2×7 mL). The combined organic layers were washed with brine (2 mL), dried (Na$_2$SO$_4$), filtered, and concentrated under reduced pressure. The resulting crude oil was dissolved in CH$_2$Cl$_2$ (1 mL) and pyrrolidine (69.7 µL, 0.84 mmol, 5 eq) and acetic acid (48 µL, 0.84 mmol, 5 eq) were added. After 40 minutes, sodium triacetoxyborohydride (178.4 mg, 0.84 mmol, 5 eq) was added. After 50 minutes, the reaction was poured into saturated aqueous NaHCO$_3$ solution (8 mL) and extracted with EtOAc (2×30 mL) The combined organic layers were dried (Na$_2$SO$_4$), filtered, and concentrated under reduced pressure. Purification of the resulting oil via flash column chromatography on silica gel (Biotage, 10 g, 1 to 12% methanol in CH$_2$Cl$_2$ gradient) provided 30.3 mg of S1-11-23 (36%) as a white solid: $^1$H NMR (400 MHz, CDCl$_3$) δ 7.44-7.31 (m, 7 H), 7.26-7.21 (m, 1 H), 7.09-7.02 (m, 2 H), 5.04 (s, 2 H), 4.16 (s, 2 H), 4.12 (s, 2 H). 2.77-2.52 (m, 4 H), 2.35 (s, 3 H), 1.75 (s, 4 H), 1.15 (s, 6 H); MS (ESI) m/z 503.38 (M+H).

EXAMPLE 24

Synthesis of S2-1-1

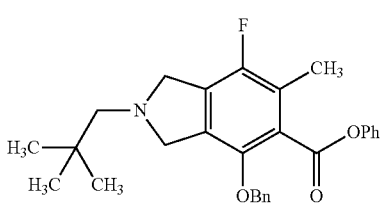

S2-1-1

Methanesulfonyl chloride (0.0446 mL, 0.575 mmol) was added dropwise to a solution of compound S1-9 (76.0 mg, 0.192 mmol) and triethylamine (0.107 mL, 0.768 mmol) in dichloromethane (2 mL). After 1 hour, the reaction mixture was diluted with EtOAc and was washed with water (2×) and brine (1×). The organics were dried over Na$_2$SO$_4$, filtered, and were concentrated under reduced pressure. The material was dissolved in DMF (2 mL), diisopropylethylamine (0.100 mL, 0.575 mmol) and neopentylamine (16.7 mg, 0.192 mmol) were added, and the reaction mixture was heated to 60° C. After heating overnight, the reaction mixture was purified by column chromatography (Biotage 5 g column, 0 to 8% EtOAc in hexane gradient), yielding 26.5 mg (31%) of the product S2-1-1 as a white solid. R$_f$=0.42 in 10% EtOAc in hexane; $^1$H NMR (400 MHz, CDCl$_3$) δ 7.44-7.30 (m, 7 H), 7.28-7.21 (m, 1 H), 7.05 (d, J=7.8 Hz, 2 H), 5.02 (s, 2 H), 4.12 (br s, 4 H), 2.53 (s, 2 H), 2.34 (d, J=1.8 Hz, 3 H), 0.96 (s, 9 H); MS (ESI) m/z 448.32 (M+H).

EXAMPLE 25

Synthesis of phenyl 4-(benzyloxy)-7-chloro-6-methyl-2-tert-pentylisoindoline-5-carboxylate (S3-13-1)

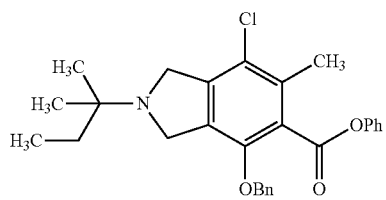

S3-13-1

Synthesis of S3-2

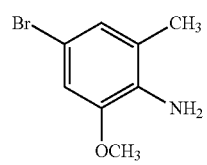

S3-2

To an ice-cooled solution of 2-methoxy-6-methylaniline (S3-1, 25.12 g, 183.1 mmol) in methanol (79 mL) and acetic acid (25 mL) was added a solution of bromine (9.41 mL, 183.1 mmol) in of Acetic acid (79 mL) dropwise via addition funnel. The reaction mixture was allowed to stand for 2 h after complete addition. EtOAc (150 mL) was added, and the solid was collected by filtration and washed with EtOAc, yielding 37.2 g of the HBr salt of compound S3-2 as an off-white solid.

Synthesis of S3-3

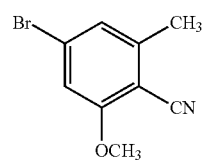

S3-3

4-Bromo-2-methoxy-6-methylaniline (S3-2, 20 g, 92.7 mmol) was suspended in concentrated HCl (22 mL) and crushed ice (76 g) and cooled in an ice-bath. A solution of NaNO$_2$ (6.52 g, 94.6 mmol) in H$_2$O (22 mL) was added dropwise. The resulting mixture was stirred at 0° C. for 30 min and then neutralized with Na$_2$CO$_3$. A suspension of CuCN (10.4 g, 115.9 mmol) in H₂O (44 mL) was mixed with a solution of NaCN (14.4 g, 294.8 mmol) in H₂O (22 mL) and cooled in an ice-bath. The initial diazonium salt mixture was added to the CuCN and NaCN solution along with toluene (180 mL) with vigorous stirring. The reaction mixture was stirred at 0° C. for 1 h, rt for 2 h, and 50° C. for 1 h. After cooling to rt, the layers were separated. The aqueous layer was further extracted with toluene. The combined organic layers were washed with brine, dried over MgSO₄, and concentrated. The residue was passed through a silica gel plug, washed with toluene, and concentrated to give 14.5 g of compound S3-3 as a light yellow solid.

Synthesis of S3-4

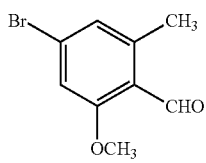

S3-4

To a solution of S3-3 (11.34 g, 50.2 mmol) in THF (100 mL) was added DIBAL-H (1.5 M solution in toluene, 40.1 mL, 60.2 mmol) slowly at −78° C. The reaction mixture was allowed to warm to rt gradually and was stirred overnight. After cooling to 0° C., the reaction was carefully quenched with 1N HCl, and the resulting mixture was stirred at rt for 1 h. The mixture was extracted three times with EtOAc. The combined EtOAc layers were washed with H₂O, saturated, aqueous NaHCO₃, and brine, dried over MgSO₄ and concentrated to provide compound S3-4 as a yellow solid, which was used directly for the next step.

Synthesis of S3-5

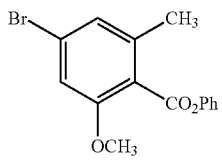

S3-5

To a suspension of S3-4 (assumed 50.2 mmol) in t-BuOH (200 mL) was added a solution of NaClO₂ (11.34 g, 100.3 mmol) and NaH₂PO₄ (34.6 g, 250.8 mmol) in H₂O (100 mL) via addition funnel. After complete addition, 2-methyl-2-butene was added. The resulting homogenous solution was stirred at rt for 30 min, and then the volatiles were removed. The residue was suspended in 150 mL of H₂O. The solution was acidified to pH ~1 with 1N HCl, and was extracted three times with tert-butyl methyl ether. The combined organic solution was extracted three times with 1N NaOH. The combined aqueous solution was acidified with 6N HCl and was extracted three times with EtOAc. The combined EtOAc extracts were washed with brine, dried over MgSO₄, and concentrated to provide 6.84 g benzoic acid (S3-4-a) as an off-white solid. This was pure enough to use directly for the next step.

To a solution of the above benzoic acid (8.64 g, 35.2 mmol) in dichloromethane (70 mL) was added oxalyl chloride (3.76 mL, 42.3 mmol, 1.2 eq), followed by a couple of drops of DMF (caution, gas evolution). The mixture was stirred at rt for 30 min and the reaction mixture was concentrated under reduced pressure. The residue was further dried under high vacuum. The crude benzoyl chloride was re-dissolved in dichloromethane (70 mL). Triethylamine (12.3 mL, 88.1 mmol, 2.5 eq), phenol (3.98 g, 42.3 mmol, 1.2 eq) and DMAP (0.43 g, 3.52 mmol, 0.1 eq) were added. The mixture was stirred at rt for 1 h at which point LC-MS showed all SM was consumed. The solvent was evaporated. The residue was suspended in EtOAc, and the precipitate was filtered off. The organic solution was then washed with 1 N HCl (three times), H₂O, sat. aq. NaHCO₃, and brine, dried over Na₂SO₄, filtered and concentrated. Purification of the residue by Biotage flash chromatography gave compound S3-5 (10.05 g) as an off-white solid: ¹H NMR (400 MHz, CDCl₃) δ 2.42 (s, 3H), 3.87 (s, 3H), 6.97 (d, J=0.9 Hz, 1H), 7.04 (d, J=0.9 Hz, 1H), 7.22-7.27 (m, 3H), 7.41-7.45 (m, 2H); MS (electrospray) m/z 319.0 (M−H), calcd for C₁₅H₁₂BrO₃ 319.0.

Synthesis of S3-6

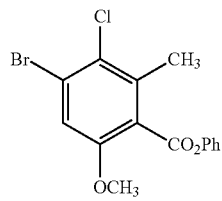

S3-6

To a solution of compound S3-5 (2.52 g, 7.87 mmol) in CH₃CN (16 mL) was added NCS (1.104 g, 8.27 mmol, 1.05 eq) in one portion. The resulting mixture was heated to 60° C. for 45 h. The solvent was evaporated. The residue was suspended in Et₂O (400 mL) and was washed with 1 N NaOH, H₂O, and brine, dried over Na₂SO₄, and concentrated to provide 2.76 g of compound S3-6 as a white solid. This material was used directly for the next step without further purification: ¹H NMR (400 MHz, CDCl₃) δ2.51 (s, 3H), 3.87 (s, 3H), 7.13 (s, 1H), 7.22-7.28 (m, 3H), 7.44 (dd, J=7.8, 7.8 Hz, 2H); MS (electrospray) m/z 353.0 (M−H), calcd for C₁₅H₁₁BrClO₃ 352.97.

Synthesis of S3-7

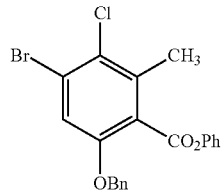

S3-7

Compound S3-6 (2.76 g, 7.76 mmol) was dissolved in anhydrous dichloromethane (78 mL) and a solution of boron tribromide (1.0 M in dichloromethane, 7.76 mL, 7.76 mmol, 1.0 eq) was added at −78° C. The resulting yellow solution was stirred at −78° C. for 15 min and then at 0° C. for 30 min whereupon sat. aq. NaHCO₃ was added. The mixture was stirred at rt for 10 min. and was extracted with EtOAc three times. The combined organic layers were washed with brine, dried over $Na_2SO_4$, and concentrated to provide 2.69 g of the phenol intermediate as an off-white solid. This material was used directly for the next step without further purification: $^1$H NMR (400 MHz, $CDCl_3$) δ2.83 (s, 3H), 7.19 (d, J=7.8 Hz, 2H), 7.27 (s, 1H), 7.32 (dd, J=7.8, 7.8 Hz, 1H), 7.46 (dd, J=7.8, 7.8 Hz, 2H); MS (electrospray) m/z 339.0 (M−H), calcd for $C_{14}H_9BrClO_3$ 338.95.

The above phenol (2.65 g, 7.76 mmol) was dissolved in acetone (40 mL), and $K_2CO_3$ (2.14 g, 15.5 mmol, 2 eq) was added followed by benzylbromide (0.97 mL, 8.15 mmol, 1.05 eq). After stirring overnight at rt, the solution was filtered through a bed of Celite. The solid cake was further washed with three portions of EtOAc. The combined organic solution was concentrated. The residue was purified by Biotage flash chromatography to yield 2.97 g of compound S3-7 as a white solid: $^1$H NMR (400 MHz, $CDCl_3$) δ2.51 (s, 3H), 5.11 (s, 2H), 7.05 (d, J=7.8 Hz, 2H), 7.19-7.26 (m, 2H), 7.33-7.43 (m, 7H); MS (electrospray) m/z 429.0 (M−H), calcd for $C_{21}H_{15}BrClO_3$ 429.00.

Synthesis of S3-8

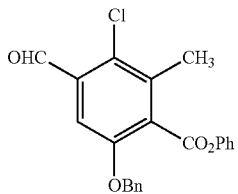

S3-8

To a solution of compound S3-7 (1.98 g, 4.59 mmol) in anhydrous THF (23 mL) was added i-PrMgCl·LiCl (1.2 M in THF, 7.65 mL, 9.18 mmol, 2 eq) dropwise at −78° C. under $N_2$ atmosphere. After 10 min, the temperature was raised to 0° C. After stirring for another 1 h at 0° C., DMF (1.80 mL, 22.9 mmol, 5 eq) was added. Stirring was maintained for 30 min at rt. The reaction was quenched by the addition of saturated, aqueous $NH_4Cl$. The layers were separated, and the aqueous layer was further extracted twice with EtOAc. The combined organic layers were washed with brine, dried over $Na_2SO_4$, filtered, and concentrated. Purification of the residue by Biotage flash chromatography gave compound S3-8 (1.45 g) as a white solid: $^1$H NMR (400 MHz, $CDCl_3$) δ2.51 (s, 3H), 5.19 (s, 2H), 7.05 (d, J=7.8 Hz, 2H), 7.25-7.27 (m, 1H), 7.33-7.44 (m, 8H) 10.51 (s, 1H); MS (electrospray) m/z 379.1 (M−H), calcd for $C_{22}H_{16}ClO_4$ 379.08.

Synthesis of S3-9

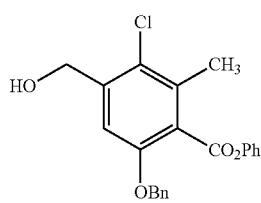

S3-9

Compound S3-8 (2.51 g, 6.59 mmol) was suspended in methanol (25 mL) and sodium borohydride (373 mg, 9.88 mmol) was added in several portions. After gas evolution ceased and complete solution was achieved, the reaction mixture was quenched with $NaHCO_3$ (saturated, aqueous solution) and was extracted with EtOAc (3×). The organics were dried over $Na_2SO_4$, filtered, and concentrated under reduced pressure. This gave 2.49 g (99%) of S3-9 as a white solid. $^1$H NMR (400 MHz, $CDCl_3$) δ 7.46-7.32 (m, 7 H), 7.27-7.21 (m, 1 H), 7.13 (s, 1 H), 7.07 (d, J=8.7 Hz, 2 H), 5.16 (s, 2 H), 4.77 (d, J=6.4 Hz, 2 H), 2.46 (s, 3 H), 2.06 (t, J=6.4 Hz, 1 H); MS (ESI) m/z 405.15 (M+H).

Synthesis of S3-10

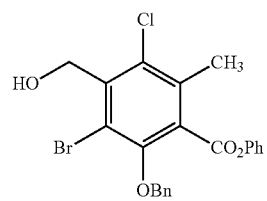

S3-10

10% Palladium on carbon (Degussa, 50 mg) was added to a solution of compound S3-9 (1.85 g, 4.84 mmol) in EtOAc (10 mL), Methanol (10 mL), and chlorobenzene (1.5 mL) and an atmosphere of hydrogen was introduced. After 5 hours, the reaction mixture was purged with nitrogen and was filtered through Celite. The filtrate was concentrated under reduced pressure, yielding the phenol intermediate as a white solid. The intermediate was dissolved in Acetic acid (15 mL) and sodium acetate (0.595 g, 7.26 mmol) was added. Bromine (0.372 mL, 7.26 mmol) was added dropwise over ~3 min. After 10 min, the reaction mixture was quenched with $Na_2S_2O_3$ (5% aqueous solution) and was diluted with EtOAc. The layers were separated, and the EtOAc layer was washed with water (3×) and brine (1×). The organics were dried over $Na_2SO_4$, filtered, and concentrated under reduced pressure. The material was dissolved in acetone (30 mL), and $K_2CO_3$ (1.34 g, 9.68 mmol) and benzyl bromide (0.633 mL, 5.32 mmol) were added. The reaction mixture was heated to 50° C. overnight. Upon cooling to rt, the reaction mixture was diluted with EtOAc and was washed with water (3×) and brine (1×). The organics were dried over $Na_2SO_4$, filtered, and concentrated under reduced pressure. The material was purified by column chromatography (Biotage 50 g column, 7 to 60% EtOAc in hexane gradient), yielding 2.03 g (91%) of S3-10. $^1$H NMR (400 MHz, $CDCl_3$) δ 7.51-7.47 (m, 2 H), 7.41-7.31 (m, 5 H), 7.30-7.23 (m, 1 H), 7.03 (d, J=8.2 Hz, 2 H), 5.12-5.05 (m, 4 H), 2.48 (s, 3 H), 2.18 (t, J=7.1 Hz, 1 H); MS (ESI) m/z 482.99, 484.99, 486.99 (M+Na).

Synthesis of S3-11

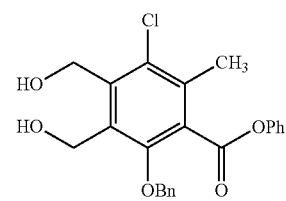

S3-11 i-Propyl magnesium chloride/lithium chloride solution (Chemetall Foote Corporation, 1.2 M solution in THF, 4.4 mL, 5.3 mmol) was added to a −78° C. solution of compound S3-10 (490 mg, 1.06 mmol) in THF (10 mL). The reaction mixture was allowed to warm to 0° C. over 1 hour. Paraformaldehyde (318 mg, 10.6 mmol) was added, and the reaction was heated to 40° C. After 1 hour, the reaction mixture was quenched with ammonium chloride (saturated, aqueous solution) and was extracted with EtOAc (3×). The combined extracts were washed with water (3×) and brine (1×), and were dried over Na$_2$SO$_4$, filtered, and concentrated under reduced pressure. The material was purified by column chromatography (Biotage 25 g column, 7 to 80% EtOAc in hexane gradient), yielding 238 mg (54%) of S3-11 as a thick oil. R$_f$=0.22 in 30% EtOAc in hexane; $^1$H NMR (400 MHz, CDCl$_3$) δ 7.45-7.30 (m, 7 H), 7.28-7.22 (m, 1 H), 7.09 (d, J=8.3 Hz, 2 H), 5.09 (s, 2 H), 5.00 (d, J=6.4 Hz, 2 H), 4.80 (d, J=6.0 Hz, 2 H), 2.73 (t, J=6.4 Hz, 1 H), 2.52 (s, 3 H), 2.48 (t, J=6.0 Hz, 1 H); MS (ESI) m/z 435.12 (M+Na).

Synthesis of S3-12

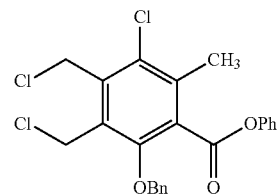

S3-12

To a solution of S3-11 (2.76 g, 6.67 mmol, 1 eq) in 1,2-dichloroethane (25 mL) was added thionyl chloride (1.93 mL, 26.6 mmol, 4 eq) and tetrabutylammonium chloride (154.3 mg, 0.67 mmol, 0.1 eq). The reaction vessel was sealed and the mixture heated to 80° C. for 2 h, then concentrated under reduced pressure. Purification of the resulting crude oil via flash column chromatography on silica gel (Biotage, 100 g, 2 to 18% EtOAc in hexane gradient) provided 2.47 g of S3-12 (82%) as a waxy white solid: $^1$H NMR (400 MHz, CDCl$_3$) δ 7.48-7.37 (m, 7 H), 7.35-7.324 (m, 1 H), 7.10-7.06 (m, 2H), 5.15 (s, 2 H), 4.96 (s, 2 H), 4.83 (s, 2 H), 2.53 (s, 3 H); MS (ESI) m/z 447.28, 449.30 (M+H).

Synthesis of S3-13-1

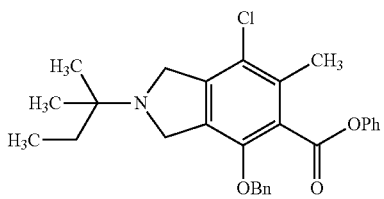

S3-13-1

Compound S3-12 (150 mg, 0.334 mmol), t-amylamine (0.041 mL, 0.35 mmol) and diisopropylethylamine (0.233 mL, 1.34 mmol) were heated to 60° C. in 1,2-dimethoxyethane (0.8 mL). After 1 hour, the reaction mixture was heated to 80° C. overnight. Upon cooling to rt, the reaction mixture was diluted with EtOAc (20 mL) and was washed with NaHCO$_3$ (saturated, aqueous solution, 2×) and brine (1×). The organics were dried over Na$_2$SO$_4$, filtered, and concentrated under reduced pressure. The material was purified by column chromatography (Biotage 25 g column, 2 to 20% EtOAc in hexane gradient), yielding 62.8 mg (40%) of the product. R$_f$=0.42 in 15% EtOAc in hexane; $^1$H NMR (400 MHz, CDCl$_3$) δ 7.45-7.30 (m, 7 H), 7.28-7.20 (m, 1H), 7.01 (d, J=7.8 Hz, 2 H), 5.05 (s, 2 H), 4.15-4.04 (m, 4 H), 2.43 (s, 3 H), 1.49 (q, J=7.8 Hz, 2 H), 1.07 (s, 6 H), 0.91 (t, 7.8 Hz, 3 H); MS (ESI) m/z 464.24, 466.24 (M+H).

The following compounds were prepared by methods similar to those described for S3-13-1.

EXAMPLE 26

Synthesis of S3-13-2

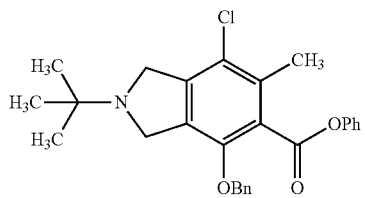

S3-13-2

R$_f$=0.19 in 15% EtOAc in hexane; MS (ESI) m/z 450.21, 452.20 (M+H).

EXAMPLE 27

Synthesis of S3-13-3

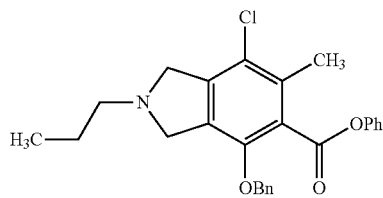

S3-13-3

R$_f$=0.18 in 15% EtOAc in hexane; MS (ESI) m/z 436.21, 438.19 (M+H).

EXAMPLE 28

Synthesis of S3-13-4

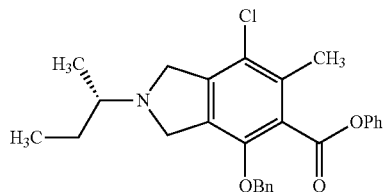

S3-13-4

R$_f$=0.22 in 15% EtOAc in hexane; $^1$H NMR (400 MHz, CDCl$_3$) δ 7.42-7.28 (m, 7 H), 7.26-7.18 (m, 1 H), 7.01 (d, J=7.3 Hz, 2 H), 5.05 (s, 2 H), 4.15-4.00 (m, 4H), 2.43 (s, 3 H), 1.74-1.62 (m, 1 H), 1.50-1.36 (m, 2 H), 1.12 (d, J=6.4 Hz, 3 H), 0.94 (t, 7.6 Hz, 3 H); MS (ESI) m/z 450.26, 452.26 (M+H).

EXAMPLE 29

Synthesis of S3-13-5

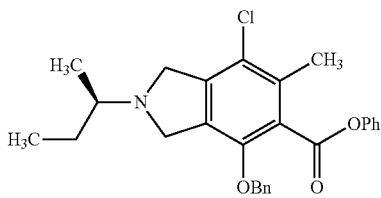

$R_f$=0.22 in 15% EtOAc in hexane; $^1$H NMR (400 MHz, CDCl$_3$) δ 7.44-7.30 (m, 7 H), 7.28-7.20 (m, 1 H), 7.03 (d, J=7.3 Hz, 2 H), 5.07 (s, 2 H), 4.10 (s, 2 H), 4.04 (s, 2 H), 2.45 (s, 3 H), 1.74-1.62 (m, 1 H), 1.50-1.38 (m, 2 H), 1.14 (d, J=6.4 Hz, 3 H), 0.96 (t, 7.6 Hz, 3 H); MS (ESI) m/z 450.21, 452.21 (M+H).

EXAMPLE 30

Synthesis of phenyl 4-(benzyloxy)-2-isopropyl-6-methyl-7-(trifluoromethyl)isoindoline-5-carboxylate (S4-10-1)

Synthesis of S4-1

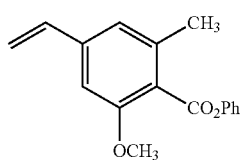

Compound S3-5 (20 g, 62.5 mmol, 1.0 eq), 2,4,6-trivinyl-cyclotriboroxane-pyridine complex (7.8 g, 31.25 mmol, 0.50 eq), Pd(PPh$_3$)$_4$ (2.2 g, 1.88 mmol, 0.030 eq) and K$_2$CO$_3$ (17.25 g, 125 mmol, 2.0 eq) was added to vessel in 1,4-dioxane:H$_2$O (3:1, V:V). The mixture was bubbled with N$_2$ to remove O$_2$ for 6 times. The mixture was heated to reflux for 19 h. The mixture was concentrated. The residue partitioned between EtOAc and water. The organic layer was dried over Na$_2$SO$_4$ and evaporated to dryness. The crude compound was purified by column chromatography on silica gel eluting with (petroleum ether:EtOAc=200:1→100:1→50:1) to yield 14.8 g of compound S4-1 (88%) as a light yellow solid.

Synthesis of S4-2

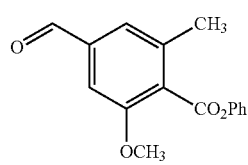

An ozone-enriched stream of oxygen was bubbled through a cold (−78° C.) solution of compound S4-1 (21 g, 78.3 mmol, 1.0 eq) in anhydrous CH$_2$Cl$_2$, and the reaction was monitored by TLC until the starting material was consumed. The solution was purged with argon at −78 C for 10 min to remove the excess O$_3$. CH$_3$SCH$_3$ (50 mL) was added into the reaction mixture and stirred for 1 hour from −78° C. to 25° C. The reaction mixture was concentrated. The crude compound was purified by column chromatography on silica gel elute with (petroleum ether:EtOAc=100:1→50:→30:1) to yield 13 g of compound 4-2 (62%) as a light yellow solid.

Synthesis of S4-3

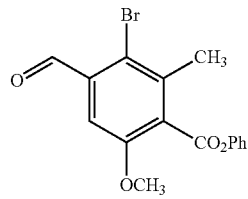

Compound S4-2 (1.8 g, 6.62 mmol, 1 eq) was dissolved in HOAc. Bromine (1.6 mL, 26.5 mmol, 4 eq) was added dropwise into the solution. The reaction mixture was stirred for 1 hour at rt. The mixture was concentrated. The residue was extracted with EtOAc and a saturated NaHCO$_3$, The organic layer was washed with brine and water in return, dried over Na$_2$SO$_4$ and concentrated to dryness. To afford 1.9 g compound S4-3 as a light yellow solid.

Synthesis of S4-4

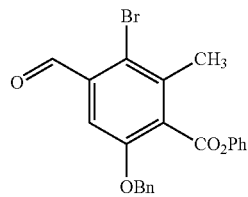

BBr$_3$ (4.9 g, 1.9 mL, 19.5 mmol, 1.5 eq) was added to a CH$_2$Cl$_2$ solution (30 mL) of S4-3 (3.5 g, 13.0 mmol, 1.0 eq) at −78° C. The reaction was stirred from −78° C. to 25° C. for 1.5 h, quenched with saturated NaHCO$_3$ and the reaction mixture was extracted with EtOAc. The combined EtOAc extracts were dried (Na$_2$SO$_4$) and concentrated to yield 3.3 g of the crude phenol intermediate.

K₂CO₃ (3.6 g, 26.0 mmol, 2.0 eq) and BnBr (4.2 g, 26.0 mmol, 2.0 eq) were added to a solution of the above crude phenol (3.3 g, 13.0 mmol, 1.0 eq) in DMF (15 mL). The reaction mixture was stirred at rt for 2 h. The reaction mixture was filtered and washed with EtOAc. Water (150 mL) was added into it and extracted with EtOAc. The organic layer was dried over Na₂SO₄ and concentrated. The crude compound was purified by column chromatography on silica gel elute with (petroleum ether:EtOAc=100:1→50:1) to yield 3.5 g of compound S4-4 (62% for 3 steps) as a light yellow solid.

Synthesis of S4-5

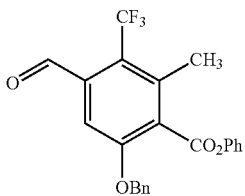

S4-5

A DMF (50 mL) solution of compound S4-4 (5 g, 11.8 mmol, 1.0 eq), MeO₂CCF₂SO₂F (11.3 g, 59 mmol, 5.0 eq) and CuI (4.5 g, 23.6 mmol, 2.0 eq) in a sealed tube was heated to 100° C. for 20 h. The mixture was filtered and the solid was washed with EtOAc. The solution was concentrated and partitioned with EtOAc and water. The organic layer was separated and dried over Na₂SO₄, concentrated to give 7 g of the crude compound S4-5 as brown oil.

Synthesis of S4-6

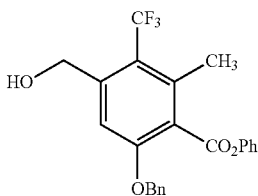

S4-6

To a stirred suspension of S4-5 (3.24 g, 7.81 mmol, 1 eq) in methanol (40 mL) was added sodium borohydride (389 mg, 10.2 mmol, 1.3 eq). Gas evolution was evident; the solution was homogeneous after 5 min. After 2 h the reaction mixture was poured into a saturated aqueous NH₄Cl solution (95 mL), water (5 mL), and extracted with EtOAc (2×80 mL). The combined organic layers were dried (Na₂SO₄), filtered, and concentrated under reduced pressure. MS (ESI) m/z 415.39 (M−H).

Synthesis of S4-7

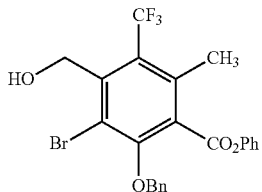

S4-7

Compound S4-6 (crude, 7.81 mmol) was dissolved in methanol:dioxane (40 mL, 15:1). Palladium on carbon (10%, 160 mg) was added, and the vessel was fitted with a septum and evacuated and back-filled with hydrogen gas three times, and then stirred at ambient temperature under a hydrogen balloon. After 2 h, another 100 mg of palladium catalyst was added and the evacuation and back-fill procedure repeated. After 16 h, another 500 mg of palladium catalyst was added, and the reaction vessel, the evacuation and back-fill procedure repeated, and the solution degassed with bubbling hydrogen for 5 min. After an additional 3 h, the suspension was filtered through Celite to remove the palladium catalyst and concentrated under reduced pressure. The resulting oil was suspended in acetic acid (30 mL). Following addition of sodium acetate (958 mg, 11.7 mmol, 1.5 eq) the solution became homogenous. Bromine (602 µL, 11.7 mmol, 1.5 eq) was added dropwise over six minutes. After 1 h, a solution of sodium thiosulfate (5% aqueous, 40 mL) was added and the solution stirred vigorously for 15 minutes. The reaction solution was extracted with EtOAc (2×45 mL) and the combined organic layers washed with water (2×20 mL), brine (20 mL), dried (Na₂SO₄), filtered, and concentrated under reduced pressure. To this crude intermediate in acetone (35 mL), were added benzyl bromide (1.02 mL, 8.59 mmol, 1.1 eq) and potassium carbonate (2.16 g, 15.6 mmol, 2 eq). The flask was fitted with a reflux condenser and heated to 50° C. for 6 h. The reaction solution was diluted with water (30 mL) and extracted with EtOAc (2×100 mL). The combined organic layers were dried (Na₂SO₄), filtered, and concentrated under reduced pressure. Purification of the resulting crude oil via flash column chromatography on silica gel (Biotage, 100 g, 7 to 55% EtOAc in hexane gradient) provided 2.13 g of intermediate 8-benzylalcohol-9-bromo compound S4-7 (55%, 4 steps) as a waxy yellow solid: ¹H NMR (400 MHz, CDCl₃) δ 7.53-7.48 (m, 2 H), 7.42-7.32 (m, 5 H), 7.29-7.24 (m, 1 H), 7.10-6.95 (m, 2 H), 5.14 (s, 2 H), 5.05-4.95 (m, 4 H), 2.58-2.53 (m, 3 H), 2.20-2.13 (m, 1 H); MS (ESI) m/z 493.39, 495.27 (M−H).

Synthesis of S4-8

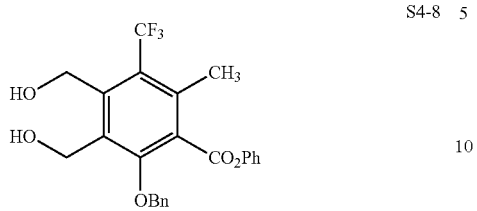

S4-8

Compound S4-7 (2.13 g, 4.30 mmol, 1 eq) was azeotropically dried from toluene three times and dried under vacuum for 18 h. To a solution of this bromide in THF (35 mL) under $N_2$ at −50° C. was added isopropyl magnesium chloride-lithium chloride complex (1.2 M solution in THF, 17.9 mL, 21.5 mmol, 5 eq) dropwise over 10 minutes. The resulting dark yellow solution was allowed to warm to 0° C. over 1 h. Paraformaldehyde (1.27 g, 43.1 mmol, 10 eq) was added as a solid at 0° C., the reaction flask was fitted with a reflux condenser, and the vessel was heated to 40° C. in an oil bath for 2 h. After cooling, the resulting slurry was poured into saturated aqueous $NH_4Cl$ solution (40 mL) and water (15 mL), and extracted with EtOAc (2×90 mL). The combined organic layers were washed with brine (30 mL), dried ($Na_2SO_4$), filtered, and concentrated under reduced pressure. Purification of the resulting crude oil via flash column chromatography on silica gel (Biotage, 100 g, 6 to 55% EtOAc in hexane gradient) provided 1.47 g of S4-8 (76%) as a white solid: $^1$H NMR (400 MHz, $CDCl_3$) δ 7.48-7.35 (m, 7 H), 7.29-7.23 (m, 1 H), 7.10-7.03 (m, 2 H), 5.14 (s, 2 H), 4.92-4.83 (m, 4 H), 2.96 (t, J=6.7 Hz, 1 H), 2.78 (t, J=6.7 Hz, 1 H), 2.62-2.55 (m, 3 H): MS (ESI) m/z 445.38 (M−H).

Synthesis of S4-9

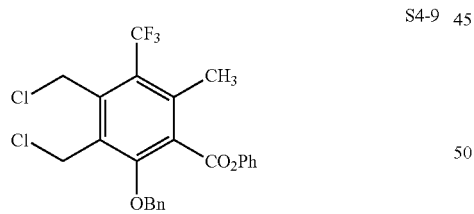

S4-9

To a solution of S4-8 (1.47 g, 3.29 mmol, 1 eq) in 1,2-dichloroethane (13 mL) was added thionyl chloride (956 μL, 13.2 mmol, 4 eq) and tetrabutylammonium chloride (75 mg, 0.33 mmol, 0.1 eq). The reaction vessel was sealed and the mixture heated to 80° C. for 3 h, then concentrated under reduced pressure. Purification of the resulting crude oil via flash column chromatography on silica gel ((Biotage, 50 g, 2 to 20% EtOAc in hexane gradient) provided 1.41 g of S4-9 (89%) as a waxy white solid: $^1$H NMR (400 MHz, $CDCl_3$) δ 7.48-7.35 (m, 7 H), 7.29-7.23 (m, 1 H), 7.10-7.03 (m, 2H), 5.20 (s, 2 H), 4.94-4.86 (m, 4 H), 2.64-2.58 (m, 3 H); MS (ESI) m/z 481.31, 483.30 (M+H).

Synthesis of S4-10-1

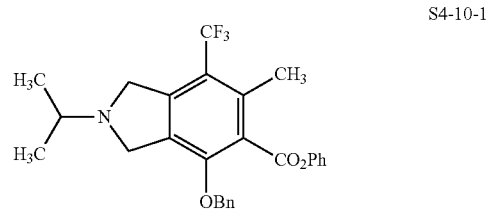

S4-10-1

To a solution of S4-9 (862 mg, 1.78 mmol, 1 eq) in 1,2-dimethoxyethane (10 mL) was added DIEA (930 μL, 5.34 mmol, 3 eq) and isopropylamine (152 μL, 1.78 mmol, 1 eq). The reaction was sealed and heated to 110° C. for 2.5 h. The solution was cooled and another 85 μL isopropylamine (0.99 mmol, 0.55 eq) was added and the reaction replaced in the heating bath. After an additional 15 h, the solution was concentrated under reduced pressure. Purification of the resulting oil via flash column chromatography on silica gel (Biotage 100 g, 5 to 40% EtOAc in hexanes gradient) provided 696 mg of S4-10-1 (83%) as a white solid: $^1$H NMR (400 MHz, $CDCl_3$) δ 7.42-7.29 (m, 7 H), 7.23-7.19 (m, 1 H), 7.00-6.96 (m, 2 H), 5.10 (s, 2 H), 4.13 (s, 2 H), 4.02 (s, 2 H), 2.81-2.72 (m, 1 H), 2.53-2.48 (m, 3 H), 1.17 (d, J=6.1 Hz, 6 H): MS (ESI) m/z 468.39 (M−H).

The following compounds were prepared from S4-9 and the corresponding amines by methods similar to those described for S4-10-1.

EXAMPLE 31

S4-10-2

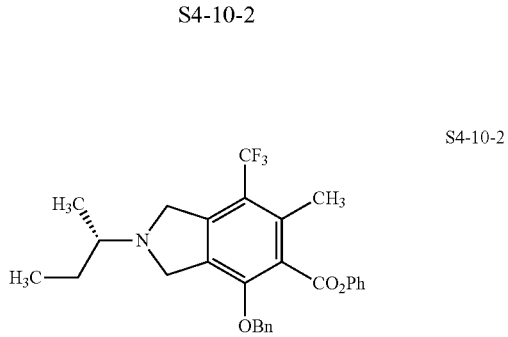

S4-10-2

$^1$H NMR (400 MHz, $CDCl_3$) δ 7.45-7.32 (m, 7 H), 7.28-7.21 (m, 1 H), 5.13 (s, 2 H), 4.16 (m, 2 H), 4.05 (s, 2 H), 2.65-2.60 (s, 1 H), 2.53 (s, 3 H), 1.75-1.62 (m, 1 H), 1.51-1.40 (m, 1 H), 1.14 (d, J=6.7 Hz, 3 H), 0.96 (t, J=7.3 Hz, 3 H): MS (ESI) m/z 482.47 (M−H).

EXAMPLE 32

S4-10-3

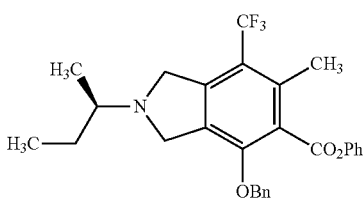

$^1$H NMR (400 MHz, CDCl$_3$) δ 7.42-7.31 (m, 7 H), 7.29-7.21 (m, 1 H), 7.03-6.98 (m, 2 H), 5.13 (s, 2 H), 4.15 (s, 2 H), 4.05 (s, 2 H), 2.66-2.59 (m, 1 H), 2.53 (s, 3 H), 1.75-1.62 (m, 1 H), 1.51-1.40 (m, 1 H), 1.14 (d, J=6.7 Hz, 3 H), 0.96 (t, J=7.3 Hz, 3 H); MS (ESI) m/z 482.48 (M−H).

EXAMPLE 33

S4-10-4

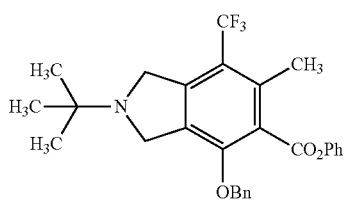

$^1$H NMR (400 MHz, CDCl$_3$) δ 7.42-7.31 (m, 7 H), 7.29-7.19 (m, 1 H), 7.02-6.96 (m, 2 H), 5.10 (s, 2 H), 4.20 (s, 2 H), 4.07 (s, 2 H), 2.51 (s, 3 H), 1.17 (s, 9 H); MS (ESI) m/z 482.48 (M−H).

EXAMPLE 34

S4-10-5

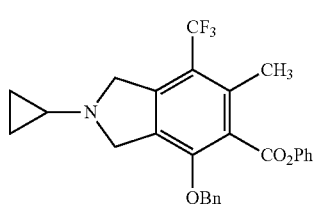

$^1$H NMR (400 MHz, CDCl$_3$) δ 7.45-7.31 (m, 7 H), 7.28-7.19 (m, 1 H), 7.02-6.96 (m, 2 H), 5.13 (s, 2 H), 4.25 (s, 2 H), 4.19 (s, 2 H), 2.53 (s, 3 H), 2.07-1.98 (m, 1 H), 0.60-0.50 (m, 4 H); MS (ESI) m/z 466.43 (M−H).

EXAMPLE 35

S4-10-6

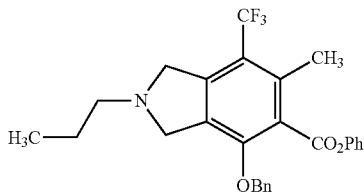

$^1$H NMR (400 MHz, CDCl$_3$) δ 7.45-7.31 (m, 7 H), 7.28-7.21 (m, 1 H), 7.02-6.97 (m, 2 H), 5.12 (s, 2 H), 4.11 (s, 2 H), 4.03 (s, 2 H), 2.68 (t, J=8.6 Hz, 2 H), 2.53 (s, 3 H), 1.65-1.55 (m, 2 H), 0.99 (t, J=7.3 Hz, 3 H); MS (ESI) m/z 481.28 (M−H).

EXAMPLE 36

Preparation of phenyl 4-(benzyloxy)-7-methoxy-6-methyl-2-tert-pentylisoindoline-5-carboxylate (S5-9-1)

Synthesis of S5-1

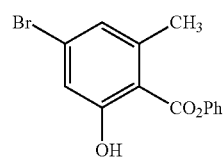

BBr$_3$ (1.0 M solution in CH$_2$Cl$_2$, 28.0 mL, 28.0 mmol) was added to a solution of compound S3-5 (8.98 g, 28.0 mmol) in CH$_2$Cl$_2$ (100 mL) at −78° C. The resulting reaction mixture was stirred at −78° C. for 20 min and at 0° C. for 15 min. NaHCO$_3$ (saturated, aqueous solution, 120 mL) was added slowly. The resulting mixture was stirred at rt for 20 min, and the CH$_2$Cl$_2$ was evaporated. The residue was extracted with ethyl acetate (250 mL), and the combined extracts were dried over MgSO$_4$, filtered, and concentrated under reduced pressure. The material was purified by recrystallization from EtOAc/Hexanes to give 6.76 g of the desired product S5-1 as a white solid. The mother liquor was concentrated and purified by column chromatography (2-10% ethyl acetate in hexanes gradient) to afford an additional 973 mg of product (90% combined yield). $^1$H NMR (400 MHz, CDCl$_3$) δ 11.13 (s, 1 H), 7.47-7.43 (m, 2 H), 7.33-7.29 (m, 1 H), 7.19-7.16 (m, 2 H), 7.08 (d, J=1.8 Hz, 1 H), 6.96 (d, J=1.8 Hz, 1 H), 2.66 (s, 3 H); MS (ESI) m/z 305.05, 307.05 (M−H).

Synthesis of S5-2

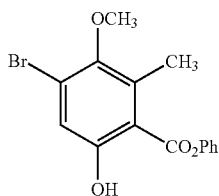

S5-2

A solution of PhI(OAc)₂ (3.77 g, 11.72 mmol) in Methanol (20 mL) was added slowly to a solution of S5-1 (1.71 g, 5.58 mmol) in a mixture of Methanol (30 mL) and 1,4-dioxane (10 mL) at 0° C. The reaction mixture was stirred at rt for 17 h. Acetic acid (6 mL) was added to the reaction mixture. Zinc dust (1.09 g, 16.74 mmol) was added (exothermic), and the reaction mixture was stirred at rt for 20 min. The reaction mixture was filtered through a pad of Celite, and the Celite was washed thoroughly with EtOAc (100 mL). The filtrate was concentrated under reduced pressure. The residue was partitioned between EtOAc (120 mL) and sat. NaHCO₃/brine solution. The organic layer was separated and dried (MgSO₄). The dried solution was filtered, and the filtrate was concentrated. The residue was purified by flash-column chromatography (0-4% ethyl acetate-hexanes gradient) to afford 763 mg (41%) of the desired product S5-2. $^1$H NMR (400 MHz, CDCl₃) δ 10.70 (s, 1 H), 7.47-7.43 (m, 2 H), 7.33-7.30 (m, 1 H), 7.20-7.17 (m, 2 H), 7.16 (s, 1 H), 3.75 (s, 3 H), 2.67 (s, 3 H); MS (ESI) m/z 335.11, 337.14 (M−H).

Synthesis of S5-3

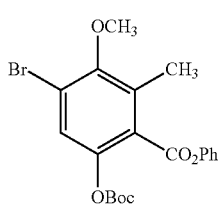

S5-3

Di-tert-butyl dicarbonate (543 mg, 2.49 mmol) and 4-N,N-dimethylamino-pyridine (28 mg, 0.226 mmol) were added to a solution of S5-2 (763 mg, 2.26 mmol) in CH₂Cl₂ (20 mL). The resulting mixture was stirred for 20 min at rt and was concentrated under reduced pressure. The residue was purified by flash-column chromatography (0-5% ethyl acetate-hexanes gradient) to afford 783 mg (79%) of compound S5-3 as a white solid. $^1$H NMR (400 MHz, CDCl₃) δ 7.45-7.41 (m, 2 H), 7.38 (s, 1 H), 7.30-7.26 (m, 1 H), 7.24-7.22 (m, 2 H), 3.81 (s, 3 H), 2.47 (s, 3 H), 1.43 (s, 9 H); MS (ESI) m/z 435.14, 437.15 (M−H).

Synthesis of S5-4

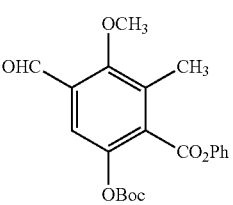

S5-4

Isopropylmagnesium chloride/lithium chloride (Chemetall Foote Corporation, 1.2 M solution in THF, 0.547 mL, 0.657 mmol) was added dropwise to a solution of compound S5-3 (143.6 mg, 0.328 mmol) in THF (3.3 mL) at 0° C. The resulting yellow reaction mixture was then stirred at 0° C. for 1 h. DMF (0.127 mL, 1.64 mmol) was added, and the resulting mixture was stirred at 0° C. for 10 min and then at rt for 20 min. Saturated, aqueous NH₄Cl and brine were added. The resulting mixture was extracted with EtOAc (50 mL), and the organics were dried (MgSO₄), filtered, and concentrated under reduced pressure. The crude product S5-4 was used directly in the next step. $^1$H NMR (400 MHz, CDCl₃) δ 10.38 (s, 1 H), 7.61 (s, 1 H), 7.46-7.42 (m, 2 H), 7.32-7.28 (m, 1 H), 7.26-7.24 (m, 2 H), 3.91 (s, 3 H), 2.46 (s, 3 H), 1.45 (s, 9 H); MS (ESI) m/z 385.24 (M−H).

Synthesis of S5-5

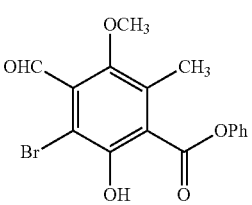

S5-5

Compound S5-4 (3.09 g, 8 mmol) was dissolved in dry dichloromethane (20 mL) TFA (10 mL) was slowly added at 0° C. The solution was stirred at 10° C. for 1 h. LC-MS analysis showed the complete consumption of starting material. The reaction mixture was concentrated under reduced pressure. The material was dissolved in acetic acid (30 mL) and sodium acetate (1.31 g, 16.0 mmol) was added. Bromine (0.49 mL, 9.6 mmol) was added via syringe at 10° C. After stirring at rt for 10 min, LC/MS indicated that the starting material was consumed. Most of the acetic acid was removed under reduced pressure. The material was diluted with EtOAc, was washed with water (3×50 mL) and brine, was dried over sodium sulfate, filtered, and concentrated under reduced pressure. This gave 3.23 g (110% crude yield) of compound S5-5 as an orange oil. MS (ESI) m/z 363.19, 365.21 (M−H).

Synthesis of S5-6

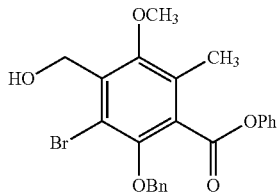

Potassium carbonate (2.21 g, 16.0 mmol) was added to a solution of compound S5-5 (3.23 g, 8.0 mmol) in DMF (20 mL), and the reaction mixture was cooled to 0° C. in an ice-bath. Benzyl bromide (1.14 mL, 9.6 mmol) was added dropwise. After 1 hour, LC/MS indicated that the starting material was completely consumed. The reaction mixture was diluted with EtOAc (100 mL), was washed with water and brine, and was dried over sodium sulfate, filtered, and concentrated under reduced pressure. The material was dissolved in Methanol (50 mL) and was cooled to 0° C. for the addition of NaBH$_4$ (0.355 g, 9.6 mmol). The reaction was stirred at 0° C. for 30 min at which point LC/MS indicated that the starting material was completely consumed. The reaction was quenched with water, and the resulting mixture was extracted with EtOAc. The combined extracts were dried (sodium sulfate) and concentrated under reduced pressure. Flash chromatography on silica gel (10:1 to 4:1 hexanes/EtOAc) yielded 3.52 g (96%, 4 steps) of S5-6. $^1$H NMR (400 MHz, CDCl$_3$) δ 7.52-7.48 (m, 2 H), 7.40-7.32 (m, 5 H), 7.27-7.22 (m, 1 H), 7.07-7.03 (m, 2 H), 5.10 (s, 2 H), 4.90 (s, 2 H), 3.85 (s, 3H), 2.37 (s, 3 H); MS (ESI) m/z 479.26, 481.25 (M+Na).

Synthesis of S5-7

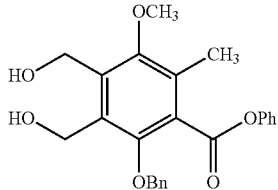

Isopropylmagnesium chloride/lithium chloride (Chemetall Foote Corporation, 1.2 M solution in THF, 31.6 mL, 37.9 mmol) was added to a solution of compound S5-6 (3.47 g, 7.58 mmol) in THF (100 mL) under nitrogen atmosphere at 0° C. The resulting solution was warmed to rt and was stirred for 30 min. After the solution was cooled to 0° C., DMF (5.84 mL, 75.8 mmol) was added slowly via syringe. The reaction was warmed to rt over 1 hour. The reaction mixture was diluted with ethyl acetate (200 mL), was washed with water and brine, and was dried over sodium sulfate, filtered, and concentrated under reduced pressure. The material was dissolved in Methanol (50 mL) and was cooled to 0° C. NaBH$_4$ (0.42 g, 11.4 mmol) was added, and the reaction mixture was stirred at 0° C. for 30 min. The reaction was quenched with water and was extracted with EtOAc. The combined EtOAc extracts were dried (sodium sulfate) and concentrated under reduced pressure to give 3.02 g of crude S5-7. The material was used without further purification. MS (ESI) m/z 407.46 (M–H).

Synthesis of S5-8

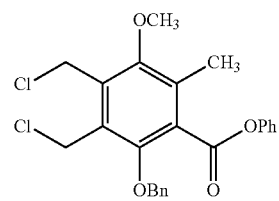

Compound S5-7 (961 mg, 2.35 mmol) was partially dissolved in 1,2-dichloroethane (10 mL) and tetrabutylammonium chloride (64.0 mg, 0.23 mmol) was added. Thionyl chloride (0.683 mL, 9.41 mmol) was added slowly, forming a clear solution. The reaction mixture was heated to 80° C. in a sealed tube and was stirred for 1 hour 30 min. The reaction mixture was concentrated under reduced pressure and was purified by flash chromatography on silica gel (50:1 to 20:1 hexanes/EtOAc). This gave 1.40 g (80%, 3 steps) of compound S5-8. $^1$H NMR (400 MHz, CDCl$_3$) δ 7.50-7.43 (m, 2H), 7.43-7.32 (m, 5 H), 7.29-7.22 (m, 1 H), 7.11-7.06 (m, 2 H), 5.15 (s, 2 H), 4.89 (s, 2H), 4.86 (s, 2 H), 3.89 (d, J=0.72 Hz, 3 H), 2.43 (d, J=0.92 Hz, 3 H); MS (ESI) m/z 467.35 (M+Na).

Synthesis of S5-9-1

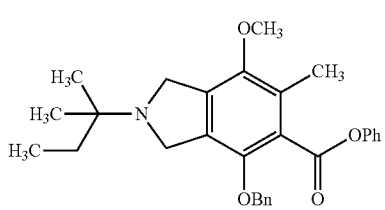

Diisopropylethylamine (2.39 mL, 13.73 mmol) and t-amylamine (0.294 mL, 2.52 mmol) were added to a solution of compound S5-8 (1.02 g, 2.29 mmol) in 1,2-dimethoxyethane (15 mL). The reaction mixture was heated to 110° C. overnight in a sealed tube. The reaction mixture was concentrated under reduced pressure and was purified by flash chromatography on silica gel (20:1 to 1:1 hexanes/EtOAc), yielding 623 mg (59%) of compound S5-9-1. $^1$H NMR (400 MHz, CDCl$_3$) δ 7.42-7.38 (m, 2 H), 7.37-7.30 (m, 5 H), 7.23-7.19 (m, 1 H), 7.06-7.02 (m, 2 H), 5.02 (s, 2 H), 4.10 (s, 2 H), 4.03 (s, 2 H), 3.76 (s, 3 H), 2.34 (s, 3 H), 1.86 (q, J=7.3 Hz, 2 H), 1.08 (s, 6 H), 0.91 (t, J=7.3 Hz, 3 H); MS (ESI) m/z 460.45 (M+H).

The following compounds were prepared from S5-8 and the corresponding amines by methods similar to those described for S5-9-1.

EXAMPLE 37
S5-9-2
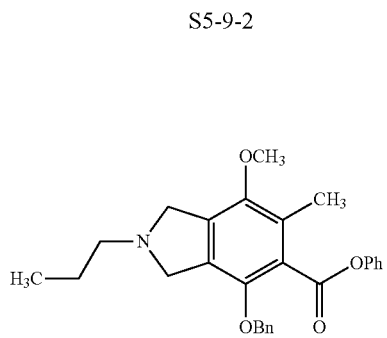
S5-9-2
$R_f$=0.20 in 33% EtOAc in Hexane; MS (ESI) m/z 432.48 (M+H).
EXAMPLE 38
S5-9-3
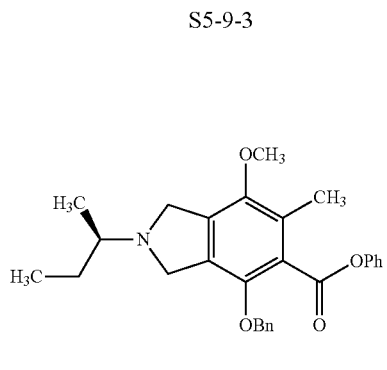
S5-9-3
MS (ESI) m/z 446.45 (M+H):
EXAMPLE 39
S5-9-4
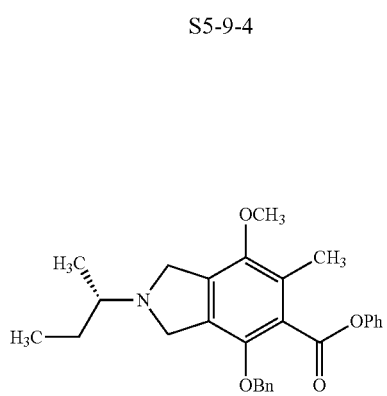
S5-9-4
MS (ESI) m/z 446.48 (M+H).
EXAMPLE 40
S5-9-5
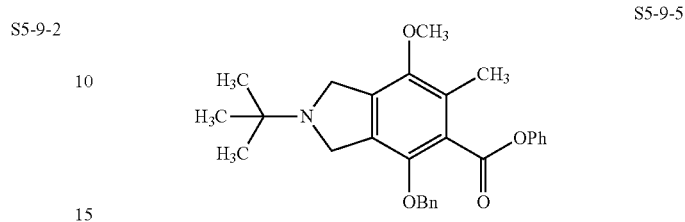
S5-9-5
$R_f$=0.25 in 33% EtOAc in Hexane; $^1$H NMR (400 MHz, CDCl$_3$) δ 7.42-7.38 (m; 2 H), 7.37-7.28 (m, 5 H), 7.23-7.19 (m, 1 H), 7.06-7.01 (m, 2 H), 5.02 (s, 2 H), 4.10 (s, 2 H), 4.04 (s, 2 H), 3.75 (s, 3 H), 2.34 (s, 3 H), 1.16 (s, 9 H); MS (ESI) m/z 446.48 (M+H).
EXAMPLE 41
S5-9-6
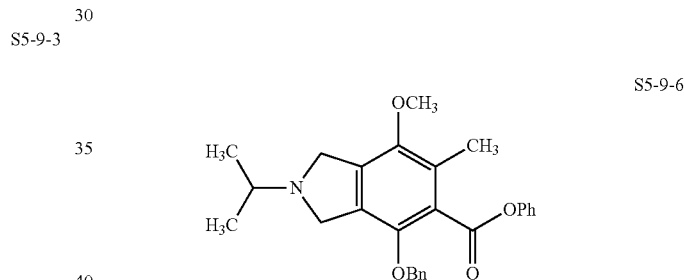
S5-9-6
MS (ESI) m/z 432.48 (M+H).
EXAMPLE 42
S5-9-7
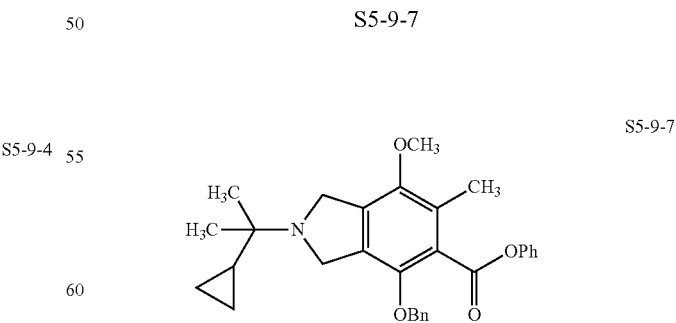
S5-9-7
$R_f$=0.31 in 33% EtOAc in Hexane; MS (ESI) m/z 472.51 (M+H).

EXAMPLE 43

S6-1-1

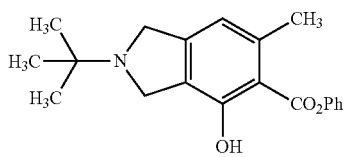

To a solution of S3-13-2 (221 mg, 0.491 mmol, 1 eq) in dioxane:methanol:0.5 N HCl in methanol (1:1:1, 4 mL) was added palladium on carbon (10%, 146 mg). The vessel was evacuated and back-filled with hydrogen gas three times, then degassed with bubbling hydrogen for 4 min, and stirred at ambient temperature under a hydrogen balloon. After 16.5 h, another 80 mg palladium catalyst was added, and the evacuation and degassing procedure repeated. After an additional 4 h, the reaction suspension was filtered through Celite to remove the palladium catalyst and concentrated under reduced pressure. Purification of the resulting crude oil via flash column chromatography on silica gel (Silicycle, 25 g, 1 to 8% methanol in dichloromethane gradient) provided 112.6 mg of compound S6-1-1 (70%) as a waxy white solid: $^1$ H NMR (400 MHz, CDCl$_3$) δ 11.42-11.10 (brs, 1 H), 7.37 (t, J=8.3 Hz, 2 H), 7.28-7.20 (m, 1 H), 7.11 (d, J=7.4 Hz, 2 H), 6.66 (s, 1 H), 4.43-4.32 (m, 4 H), 2.61 (s, 3 H), 1.35 (s, 9 H); MS (ESI) m/z 326.94 (M+H).

EXAMPLE 44

S6-2-1

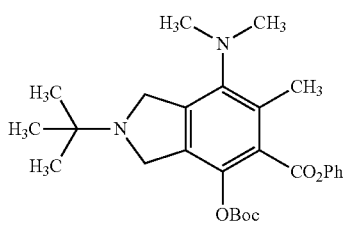

To a solution of S6-1-1 (113 mg, 0.346 mmol, 1 eq) in trifluoroacetic acid (4 mL) at 0° C. was added potassium nitrate (67.4 mg, 0.667 mmol, 1.92 eq). The mixture was allowed to warm to ambient temperature at which point the solution turned orange. After 30 min, the solvent was removed under reduced pressure. To a solution of this crude oil in methanol:THF (1:1, 2.5 mL) was added formaldehyde (37% aq, 64 μL, 0.87 mmol, 2.5 eq) and palladium on carbon (10%, 101 mg). The reaction vessel was evacuated and back-filled with hydrogen gas three times, and the solution stirred at ambient temperature under a hydrogen balloon. After 18 h, the reaction mixture was filtered through Celite and concentrated under reduced pressure. This crude oil was dissolved in dimethylformamide (2 mL), and diisopropylethylamine (241 μL, 1.38 mmol, 4 eq), di-tert-butylcarbonate (226 mg, 1.04 mmol, 3 eq) and a catalytic amount of dimethylaminopyridine were added. The reaction mixture was placed under nitrogen and stirred at ambient temperature. After 2 h, the reaction solution was diluted with saturated aqueous sodium bicarbonate (10 mL) and water (30 mL) and extracted with EtOAc (2×30 mL) The combined organic extracts were washed with brine, dried (Na$_2$SO$_4$), filtered, and concentrated under reduced pressure. Purification of the resulting crude oil via flash column chromatography on silica gel (Silicycle, 12 g, 5 to 30% EtOAc in hexane gradient) provided 72 mg of S6-2-1 (44%) as a white solid: $^1$ H NMR (400 MHz, CDCl$_3$) δ 7.45-7.38 (m, 2 H), 7.29-7.20 (m, 3 H), 4.15 (s, 2 H), 3.93 (s, 3 H), 2.73 (s, 6 H), 2.40 (s, 3 H), 1.42 (s, 9 H), 1.19 (s, 9 H); MS (ESI) m/z 467.47 (M–H).

The following compounds were prepared by methods similar to those described for S6-2-1.

EXAMPLE 45

S6-2-2

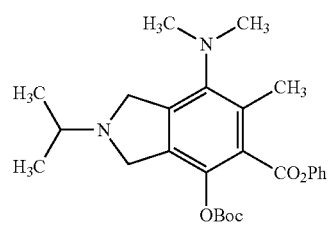

$^1$ H NMR (400 MHz, CDCl$_3$) δ 7.45-7.35 (m, 2 H), 7.28-7.20 (m, 3 H), 4.08 (s, 2 H), 3.86 (s, 2 H), 2.88-2.80 (7 H), 2.40 (s, 3 H), 1.41 (s, 9 H), 1.19 (d, J=4.9 Hz, 6H); MS (ESI) m/z 455.01 (M+H).

EXAMPLE 46

S6-2-3

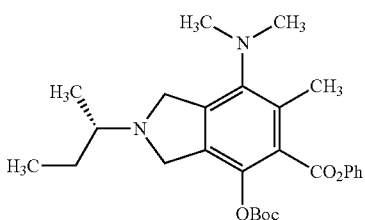

$^1$ H NMR (400 MHz, CDCl$_3$) δ 7.45-7.38 (m, 2 H), 7.29-7.20 (m, 3 H), 4.09 (s, 2 H), 3.87 (s, 2 H), 2.73 (s, 6 H), 2.64-2.54 (m, 1 H), 2.40 (s, 3 H), 1.78-1.60 (m, 2 H), 1.42 (s, 9 H), 1.14 (d, J=8.0 Hz, 3 H), 0.94 (t, J=7.6 Hz, 3 H); MS (ESI) m/z 467.51 (M–H).

EXAMPLE 47

S6-2-4

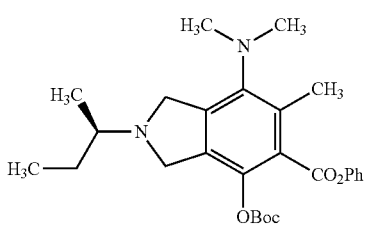

[1] H NMR (400 MHz, CDCl₃) δ 7.45-7.38 (m, 2 H), 7.29-7.20 (m, 3 H), 4.09 (s, 2 H), 3.86 (s, 2 H), 2.73 (s, 6 H), 2.64-2.54 (m, 1 H), 2.39 (s, 3 H), 1.78-1.60 (m, 2 H), 1.42 (s, 9 H), 1.14 (d, J=8.0 Hz, 3 H), 0.94 (t, J=7.6 Hz, 3 H); MS (ESI) m/z 467.55 (M–H).

EXAMPLE 48

S6-2-5

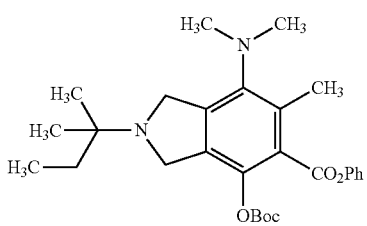

[1] H NMR (400 MHz, CDCl₃) δ 7.49-7.35 (m, 2 H), 7.29-7.20 (m, 3 H), 4.13 (s, 2 H), 3.91 (s, 2 H), 2.73 (s, 6 H), 2.40 (s, 3 H), 1.59-1.48 (m, 2 H), 1.42 (s, 9 H), 1.09 (s, 6 H), 0.92 (t, J=7.3 Hz, 3 H); MS (ESI) m/z 481.48 (M–H).

EXAMPLE 49

Compound 102

Synthesis of S7-2-1

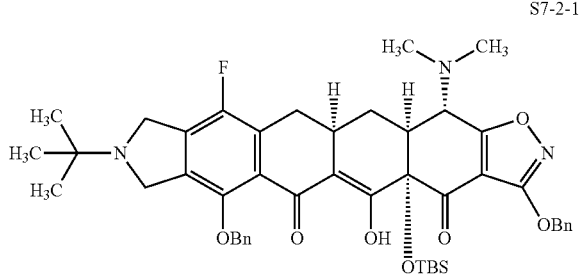 [SMILES: CN(C)[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)CN(C(C)(C)C)C5)C[C@H]3C[C@@H]12]

Lithium diisopropylamide was prepared at –40° C. from n-butyllithium (2.5 M solution in hexane, 0.118 mL, 0.294 mmol) and diisopropylamine (0.0416 mL, 0.294 mmol) in THF (5 mL). The reaction mixture was cooled to –78° C. and TMEDA (0.114 mL, 0.762 mmol) was added followed by the dropwise addition of a solution of compound S1-11-1 (66.5 mg, 0.153 mmol) in THF (2 mL). This resulted in an orange-red colored solution. After 5 min, a solution of enone S7-1 (61.3 mg, 0.127 mmol) in THF (1 mL) was added. After complete addition, the reaction mixture was allowed to warm to –20° C. over 1 h. The reaction was quenched by the addition of ammonium chloride (saturated, aqueous solution) and was extracted with EtOAc (2×). The combined extracts were dried over Na₂SO₄, filtered, and concentrated under reduced pressure. The material was purified on a Waters Autopurification system equipped with a Sunfire Prep C18 OBD column [5 μm, 19×50 mm; flow rate, 20 mL/min; Solvent A: H₂O with 0.1% HCO₂H; Solvent B: CH₃CN with 0.1% HCO₂H; gradient: 20→100% B; mass-directed fraction collection], yielding 17.2 mg (17%) of the desired product S7-2-1 as a yellow solid. [1] H NMR (400 MHz, CDCl₃) δ 16.0 (s, 1 H), 7.52-7.44 (m, 2 H), 7.42-7.26 (m, 8 H), 5.35 (s, 2 H), 4.92 (s, 2 H), 4.32-4.20 (m, 2 H), 4.06-3.90 (m, 3 H), 3.21 (dd, J=15.6, 4.6 Hz, 1 H), 3.03-2.91 (m, 1 H), 2.58-2.36 (m, 9 H), 2.13 (d, J=14.6 Hz, 1 H), 1.18 (s, 9 H), 0.82 (s, 9 H), 0.27 (s, 3 H), 0.12 (s, 3 H); MS (ESI) m/z 822.51 (M+H).

Synthesis of Compound 102

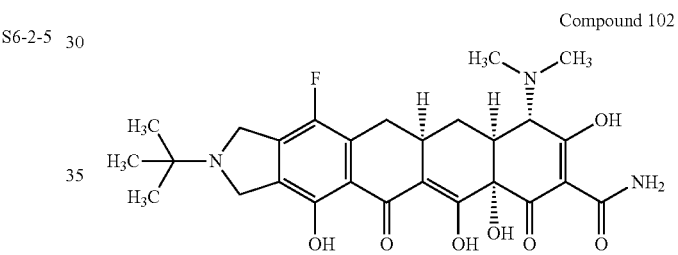

Aqueous HF (0.4 mL, 48%) was added to a solution of S7-2-1 (17.2 mg, 0.0209 mmol) in 1,4-dioxane (0.8 mL) in a plastic vial. After 4 h, the reaction mixture was poured into a solution of K₂HPO₄ (4.8 g) in water (15 mL). The mixture was extracted with EtOAc (3×). The combined EtOAc extracts were dried over Na₂SO₄, filtered and concentrated under reduced pressure. The material was dissolved in Methanol (1 mL), 1,4-dioxane (1 mL) and 0.5 M HCl in Methanol (0.5 mL), and palladium on carbon (Degussa, 10 wt %, ~5 mg) was added. An atmosphere of hydrogen was introduced, and the reaction mixture was stirred for 2 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05N HCl in water; Solvent B: CH₃CN; gradient: 0→70% B; mass-directed fraction collection]. Fractions with the desired MW were collected and freeze-dried to yield 8.7 mg (69%, 2 steps) of the desired product Compound 102 as a yellow solid. [1] H NMR (400 MHz, CD₃OD with 1 drop DCl) δ 4.85 (q, J=15.1 Hz, 2H), 4.73 (s, 2 H), 4.16 (s, 1 H), 3.22-2.95 (m, 9 H), 2.36-2.24 (m, 2H), 1.72-1.56 (m, 1H), 1.53 (s, 9 H); MS (ESI) m/z 530.35 (M+H).

The following compounds were prepared by methods similar to that for Compound 102, substituting the appropriate isoindoline S1-11, S2-1, S3-13, S4-10, S5-9, or S6-2 for S1-11-1.

EXAMPLE 50

Compound 101

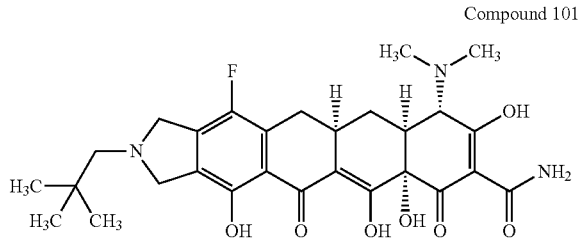 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(CC(C)(C)C)C5]

Compound 101

Prepared from S2-1-1, yellow solid: ¹H NMR (400 MHz, CD₃OD with 1 drop DCl) δ 5.17 (d, J=14.7 Hz, 1 H), 5.08 (d, J=14.2 Hz, 1 H), 4.81 (d, J=14.7 Hz, 1 H), 4.67 (d, J=14.2 Hz, 1 H), 4.15 (s, 1 H), 3.52 (s, 2 H), 3.34-2.95 (m, 9 H), 2.38-2.22 (m, 2 H), 1.61 (q, J=12.5 Hz, 1 H), 1.19 (s, 9 H); MS (ESI) m/z 544.35 (M+H).

EXAMPLE 51

Compound 150

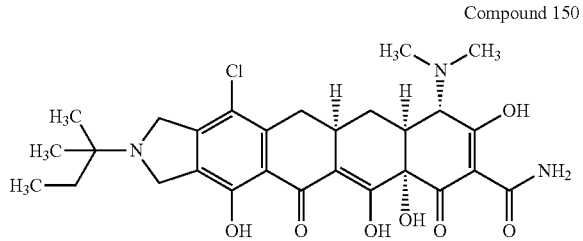 [SMILES: CCC(C)(C)N1Cc2c(O)c3c(c(Cl)c2C1)C[C@H]1C[C@H]2[C@H](N(C)C)C(O)=C(C(N)=O)C(=O)[C@@]2(O)C(O)=C1C3=O]

Compound 150

Prepared from S3-13-1, yellow solid: ¹H NMR (400 MHz, CD₃OD with 1 drop DCl) δ 4.94-4.67 (m, 4 H), 4.18 (s, 1 H), 3.18-2.95 (m, 9 H), 2.40-2.26 (m, 2 H), 1.91 (q, J=7.3 Hz, 2 H), 1.63 (q, J=12.4 Hz, 1 H), 1.48 (s, 6 H), 1.08 (t, J=7.3 Hz, 3 H); MS (ESI) m/z 560.26, 562.27 (M+H).

EXAMPLE 52

Compound 144

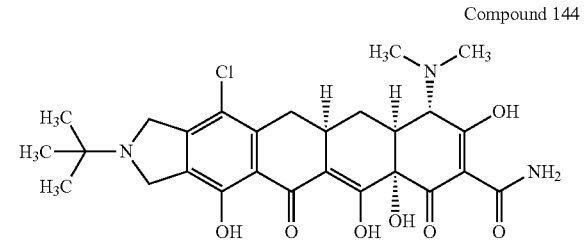 [SMILES: CN(C)[C@@H]1C(O)=C(C(N)=O)C(=O)[C@@]2(O)C(O)=C3C(=O)c4c(O)c5c(c(Cl)c4C[C@H]3C[C@@H]12)CN(C(C)(C)C)C5]

Compound 144

Prepared from S3-13-2, yellow solid: ¹H NMR (400 MHz, CD₃OD with 1 drop DCl) δ 4.90-4.73 (m, 4 H), 4.16 (s, 1 H), 3.17-2.95 (m, 9 H), 2.41-2.24 (m, 2 H), 1.68-1.56 (m, 1 H), 1.53 (s, 9 H); MS (ESI) m/z 546.20, 548.29 (M+H).

EXAMPLE 53

Compound 149

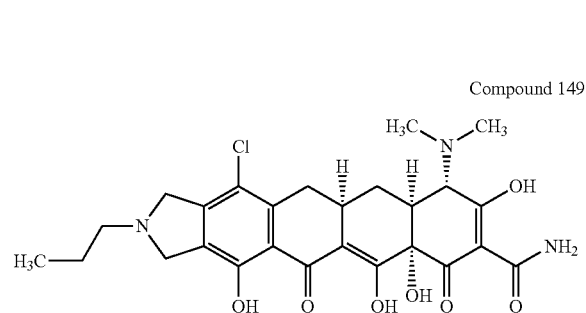 [SMILES: CCCN1Cc2c(O)c3c(c(Cl)c2C1)C[C@H]1C[C@H]2[C@H](N(C)C)C(O)=C(C(N)=O)C(=O)[C@@]2(O)C(O)=C1C3=O]

Compound 149

Prepared from S3-13-3, yellow solid: ¹H NMR (400 MHz, CD₃OD with 1 drop DCl) δ 5.05-4.95 (m, 2 H), 4.71 (d, J=15.1 Hz, 1 H), 4.62 (d, J=14.2 Hz, 1 H), 4.16 (s, 1 H), 3.50-3.42 (m, 2 H), 3.17-2.94 (m, 9 H), 2.42-2.24 (m, 2 H), 1.94-1.82 (m, 2 H), 1.63 (q, J=12.8 Hz, 1 H), 1.07 (t, J=7.3 Hz, 3 H); MS (ESI) m/z 532.23, 534.20 (M+H).

EXAMPLE 54

Compound 110

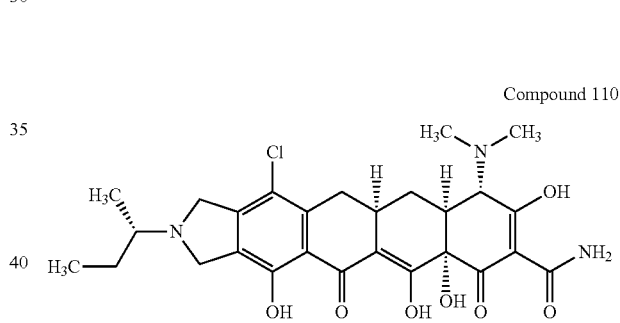

Compound 110

Prepared from S3-13-4, yellow solid: ¹H NMR (400 MHz, CD₃OD with 1 drop DCl) δ 4.98-4.86 (m, 2 H), 4.78 (d, J=16.0 Hz, 1 H), 4.70 (d, J=14.2 Hz, 1 H), 4.15 (s, 1 H), 3.70-3.57 (m, 1 H), 3.17-2.92 (m, 9 H), 2.43-2.24 (m, 2 H), 2.08-1.96 (m, 1 H), 1.79-1.56 (m, 2 H), 1.50-1.42 (m, 3 H), 1.08 (t, J=7.3 Hz, 3 H); MS (ESI) m/z 546.21, 548.23 (M+H).

EXAMPLE 55

Compound 117

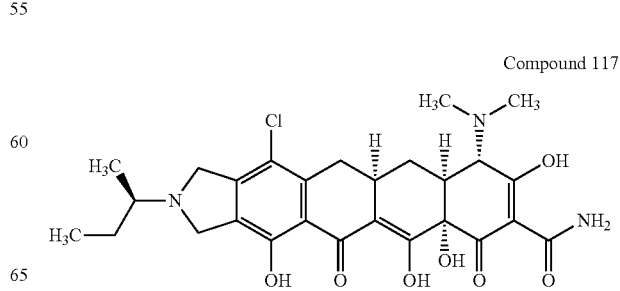

Compound 117

Prepared from S3-13-5, yellow solid: $^1$H NMR (400 MHz, CD$_3$OD with 1 drop DCl) δ 4.98-4.88 (m, 2 H), 4.84-4.64 (m, 2 H), 4.15 (s, 1 H), 3.70-3.57 (m, 1 H), 3.15-2.94 (m, 9 H), 2.43-2.24 (m, 2 H), 2.09-1.96 (m, 1 H), 1.77-1.55 (m, 2 H), 1.45 (d, J=6.4 Hz, 3 H), 1.07 (t, J=7.3 Hz, 3 H); MS (ESI) m/z 546.48, 548.48 (M+H).

EXAMPLE 56

Compound 119

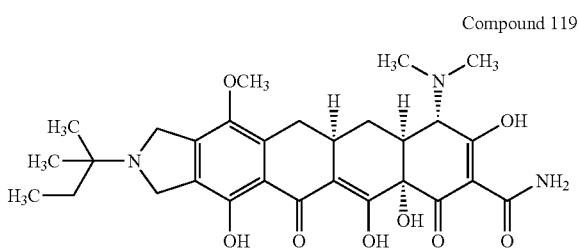 [SMILES: CCC(C)(C)N1Cc2c(O)c3c(c(OC)c2C1)C[C@H]1C[C@H]2[C@H](N(C)C)C(O)=C(C(N)=O)C(=O)[C@@]2(O)C(O)=C1C3=O]

Compound 119

Prepared from S5-9-1, yellow solid: $^1$H NMR (400 MHz, CD$_3$OD) δ 4.87 (s, 2H), 4.71 (s, 2 H), 4.08 (s, 1 H), 3.76 (d, J=4.1 Hz, 3 H), 3.27-3.19 (m, 1 H), 3.03 (s, 3H), 2.95 (s, 3 H), 3.06-2.92 (m, 2 H), 2.37-2.18 (m, 2 H), 1.88 (q, J=7.3 Hz, 2 H), 1.70-1.58 (m, 1 H), 1.47 (s, 6 H), 1.08 (t, J=7.3 Hz, 3 H); MS (ESI) m/z 556.53 (M+H).

EXAMPLE 57

Compound 138

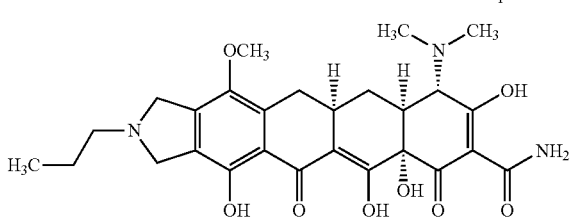

Compound 138

Prepared from S5-9-2: $^1$H NMR (400 MHz, CD$_3$OD) δ 4.87 (s, 2 H), 4.69 (s, 2H), 4.09 (s, 1 H), 3.76 (d, J=3.2 Hz, 3 H), 3.27-3.19 (m, 1 H), 3.04 (s, 3 H), 2.96 (s, 3H), 3.10-2.91 (m, 4 H), 2.36-2.18 (m, 2 H), 2.09-1.97 (m, 1 H), 1.77-1.57 (m, 2 H), 1.08 (t, J=7.3 Hz, 3 H); MS (ESI) m/z 528.51 (M+H).

EXAMPLE 58

Compound 145

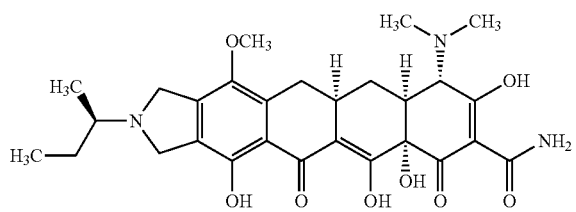

Compound 145

Prepared from S5-9-3: $^1$H NMR (400 MHz, CD$_3$OD) δ 5.00-4.76 (m, 2 H), 4.59 (d, J=14.2 Hz, 1 H), 4.12 (d, J=3.3 Hz, 1 H), 3.76 (d, J=6.0 Hz, 1 H), 3.66-3.55 (m, 1 H), 3.28-3.20 (m, 1 H), 3.10-2.91 (m, 9 H), 2.35-2.19 (m, 2 H), 2.09-1.97 (m, 1 H), 1.77-1.57 (m, 2 H), 1.46 (d, J=6.4 Hz, 3 H), 1.08 (t, J=7.1 Hz, 3 H); MS (ESI) m/z 542.54 (M+H).

EXAMPLE 59

Compound 148

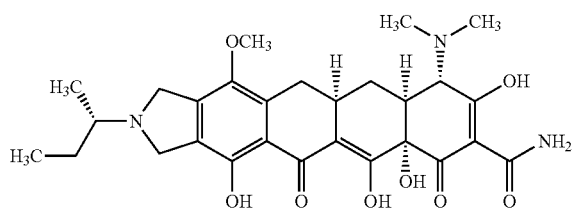

Compound 148

Prepared from S5-9-4: $^1$H NMR (400 MHz, CD$_3$OD) δ 5.00-4.76 (m, 2 H), 4.58 (d, J=14.2 Hz, 1 H), 4.10 (s, 1 H), 3.75 (d, J=6.0 Hz, 1 H), 3.64-3.55 (m, 1 H), 3.27-3.19 (m, 1 H), 3.09-2.90 (m, 9 H), 2.35-2.19 (m, 2 H), 2.09-1.95 (m, 1 H), 1.77-1.57 (m, 2 H), 1.45 (dd, J=6.4, 3.7 Hz, 3 H), 1.07 (t, J=7.2 Hz, 3 H); MS (ESI) m/z 542.52 (M+H).

EXAMPLE 60

Compound 125

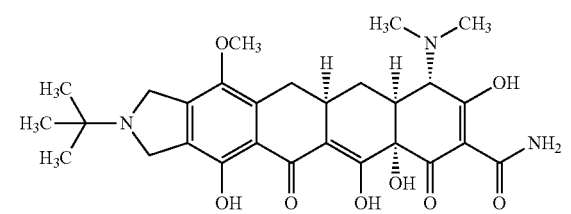

Compound 125

Prepared from S5-9-5: $^1$H NMR (400 MHz, CD$_3$OD) δ 4.87 (s, 2 H), 4.70 (s, 2H), 4.09 (s, 1 H), 3.76 (d, J=3.2 Hz, 3

H), 3.27-3.19 (m, 1 H), 3.04 (s, 3 H), 2.96 (s, 3H), 3.10-2.91 (m, 2 H), 2.36-2.18 (m, 2 H), 1.70-1.58 (m, 1 H), 1.53 (s, 9 H); MS (ESI) m/z 542.56 (M+H).

EXAMPLE 61

Compound 107

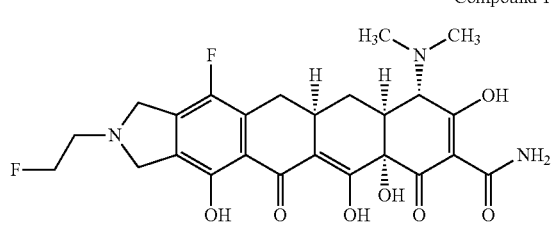

Compound 107

Prepared from S1-11-2: $^1$H NMR (400 MHz, CD$_3$OD) δ 4.99-4.94 (m, 1 H), 4.88-4.82 (m, 1 H), 4.10 (s, 1 H), 3.97-3.92 (m, 1 H), 3.90-3.85 (m, 1 H), 3.25-3.16 (m, 1 H), 3.15-2.92 (m, 11 H), 2.41-2.28 (m, 1 H), 2.28-2.17 (m, 1 H), 1.72-1.59 (m, 1 H); MS (ESI) m/z 520.24 (M+H).

EXAMPLE 62

Compound 134

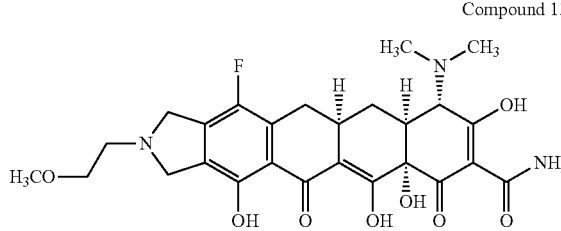

Compound 134

Prepared from S1-11-3: $^1$H NMR (400 MHz, CD$_3$OD) δ 5.07-4.92 (m, 1 H), 4.80-4.55 (m, 1 H), 4.10 (s, 1 H), 3.85-3.75 (m, 2 H), 3.75-3.65 (m, 2 H), 3.46 (s, 3 H), 3.23-3.14 (m, 1 H), 3.13-2.92 (m, 9 H), 2.39-2.19 (m, 2 H), 1.70-1.56 (m, 1 H); MS (ESI) m/z 532.24 (M+H).

EXAMPLE 63

Compound 121

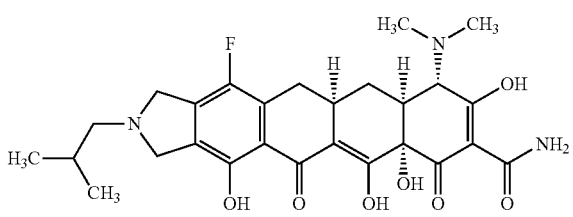

Compound 121

Prepared from S1-11-4: $^1$H NMR (400 MHz, CD$_3$OD) δ 4.78-4.68 (m, 1 H), 4.63-4.51 (m, 1 H), 4.08 (s, 1 H), 3.38-3.34 (m, 2 H), 3.23-3.14 (m, 1 H), 3.14-2.89 (m, 10 H), 2.41-2.28 (m, 1 H), 2.25-2.13 (m, 2 H), 1.72-1.58 (m, 1 H), 1.11 (d, J=6.7 Hz, 6H); MS (ESI) m/z 530.19 (M+H).

EXAMPLE 64

Compound 104

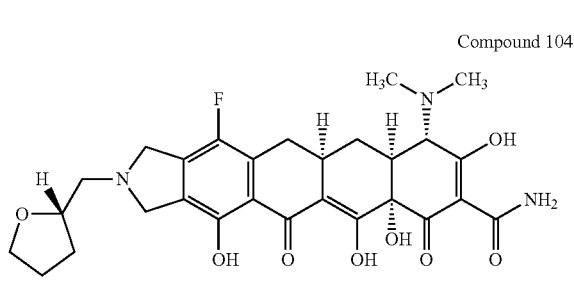 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C[C@@H]1CCCO1)C5]

Compound 104

Prepared from S1-11-5: $^1$H NMR (400 MHz, CD$_3$OD) δ 5.08-4.70 (m, 3 H), 4.69-4.58 (m, 1 H), 4.37-4.27 (m, 1 H), 4.09 (s, 1 H), 4.01-3.92 (m, 1 H), 3.91-3.82 (m, 1 H), 3.67-3.57 (m, 1 H), 3.53-3.43 (m, 1 H), 3.23-3.14 (m, 1 H), 3.14-2.92 (m, 8 H), 2.40-2.27 (m, 1 H), 2.27-2.13 (m, 2 H), 2.05-1.92 (m, 2 H), 1.72-1.57 (m, 2 H); MS (ESI) m/z 558.26 (M+H).

EXAMPLE 65

Compound 108

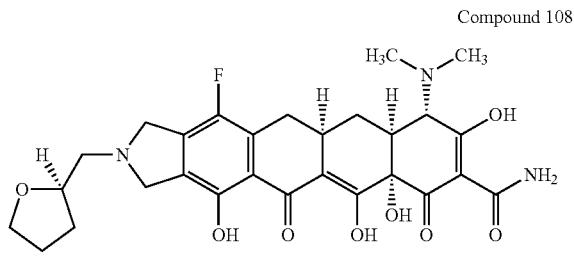 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C[C@H]1CCCO1)C5]

Compound 108

Prepared from S1-11-6: $^1$H NMR (400 MHz, CD$_3$OD) δ 5.07-4.70 (m, 3 H), 4.69-4.58 (m, 1 H), 4.37-4.27 (m, 1 H), 4.09 (s, 1 H), 4.01-3.92 (m, 1 H), 3.91-3.82 (m, 1 H), 3.67-3.57 (m, 1 H), 3.53-3.43 (m, 1 H), 3.23-3.14 (m, 1 H), 3.14-2.92 (m, 8 H), 2.40-2.27 (m, 1 H), 2.27-2.13 (m, 2 H), 2.05-1.92 (m, 2 H), 1.72-1.57 (m, 2 H); MS (ESI) m/z 558.21 (M+H).

EXAMPLE 66

Compound 143

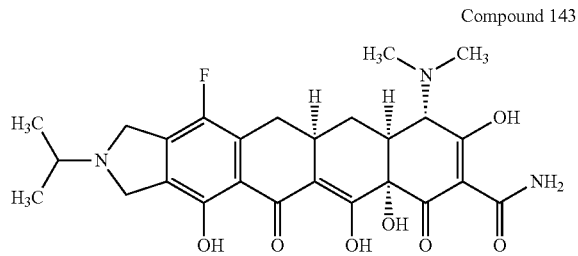

Compound 143

Prepared from S1-11-7: $^1$H NMR (400 MHz, CD$_3$OD) δ 5.05-4.81 (m, 2 H), 4.80-4.70 (m, 1 H), 4.68-4.55 (m, 1 H), 4.08 (s, 1 H), 3.85-3.72 (m, 1 H), 3.24-3.13 (m, 1 H), 3.13-2.90 (m, 8 H), 2.40-2.26 (m, 1 H), 2.25-2.16 (m, 1 H), 1.71-1.56 (m, 1 H), 1.47 (d, J=6.7 Hz, 6 H); MS (ESI) m/z 516.32 (M+H).

EXAMPLE 67

Compound 120

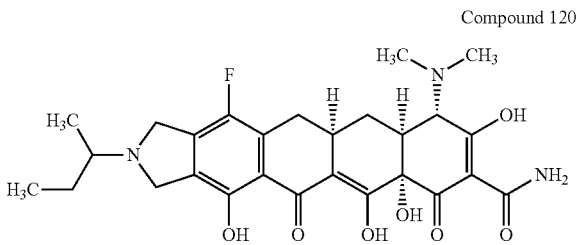

Compound 120

Prepared from S1-11-8: $^1$H NMR (400 MHz, CD$_3$OD) δ 5.10-4.74 (m, 3 H), 4.70-4.58 (m, 1 H), 4.09 (s, 1 H), 3.69-3.54 (m, 1 H), 3.24-2.88 (m, 9 H), 2.40-2.28 (m, 1 H), 2.28-2.19 (m, 1 H), 2.07-1.94 (m, 1 H), 1.77-1.57 (m, 2 H), 1.45 (d, J=6.1 Hz, 3H), 1.08 (t, J=7.9 Hz, 3 H); MS (ESI) m/z 530.27 (M+H).

EXAMPLE 68

Compound 130

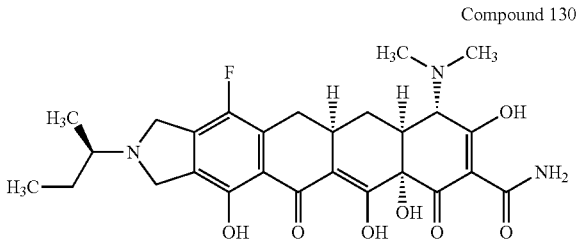

Compound 130

Prepared from S1-11-9: $^1$H NMR (400 MHz, CD$_3$OD) δ 5.03-4.74 (m, 3 H), 4.68-4.58 (m, 1 H), 4.10 (s, 1 H), 3.67-3.55 (m, 1 H), 3.23-2.90 (m, 9 H), 2.37-2.18 (m, 2 H), 2.07-1.94 (m, 1 H), 1.76-1.56 (m, 2 H), 1.44 (d, J=6.1 Hz, 3 H), 1.07 (t, J=7.3 Hz, 3 H); MS (ESI) m/z 530.26 (M+H).

EXAMPLE 69

Compound 123

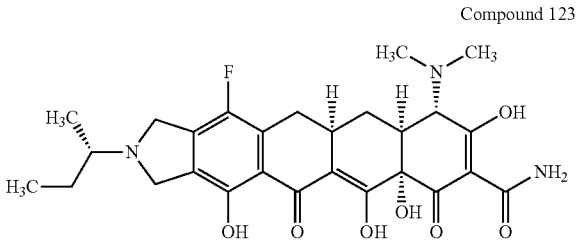 [SMILES: CCC(C)N1Cc2c(O)c3c(c(F)c2C1)C[C@H]1C[C@H]2[C@H](N(C)C)C(O)=C(C(N)=O)C(=O)[C@@]2(O)C(O)=C1C3=O]

Compound 123

Prepared from S1-11-10: $^1$H NMR (400 MHz, CD$_3$OD) δ 5.05-4.73 (m, 3 H), 4.68-4.58 (m, 1 H), 4.09 (s, 1 H), 3.66-3.54 (m, 1 H), 3.23-2.91 (m, 9 H), 2.38-2.28 (m, 1 H), 2.28-2.19 (m, 1 H), 2.07-1.94 (m, 1 H), 1.75-1.57 (m, 2 H), 1.44 (d, J=6.1 Hz, 3H), 1.07 (t, J=7.3 Hz, 3 H); MS (ESI) m/z 530.26 (M+H).

EXAMPLE 70

Compound 137

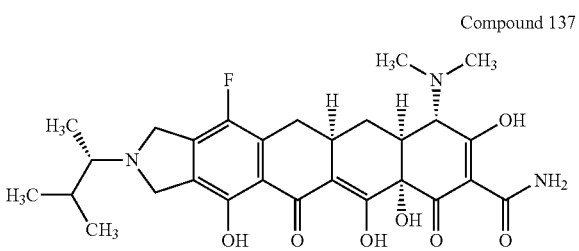 [SMILES: CC(C)[C@H](C)N1Cc2c(O)c3c(c(F)c2C1)C[C@H]1C[C@H]2[C@H](N(C)C)C(O)=C(C(N)=O)C(=O)[C@@]2(O)C(O)=C1C3=O]

Compound 137

Prepared from S1-11-11: $^1$H NMR (400 MHz, CD$_3$OD) δ 5.08-4.73 (m, 3 H), 4.72-4.52 (m, 1 H), 4.09 (s, 1 H), 3.67-3.55 (m, 1 H), 3.23-2.90 (m, 9 H), 2.44-2.27 (m, 2 H), 2.27-2.18 (m, 1 H), 1.70-1.57 (m, 1 H), 1.37 (d, J=6.7 Hz, 3 H), 1.09 (d, J=6.7 Hz, 3 H), 1.07-1.01 (m, 3 H); MS (ESI) m/z 544.32 (M+H).

EXAMPLE 71

Compound 106

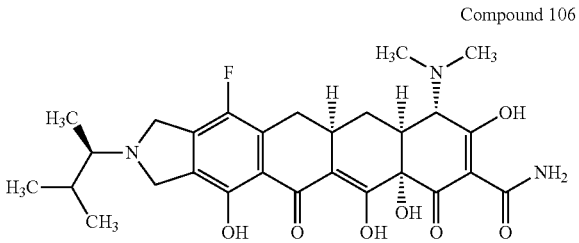 [SMILES: CC(C)[C@@H](C)N1Cc2c(O)c3c(c(F)c2C1)C[C@H]1C[C@H]2[C@H](N(C)C)C(O)=C(C(N)=O)C(=O)[C@@]2(O)C(O)=C1C3=O]

Compound 106

Prepared from S1-11-12: $^1$H NMR (400 MHz, CD$_3$OD) δ 5.10-4.73 (m, 3 H), 4.72-4.58 (m, 1 H), 4.09 (s, 1 H), 3.66-3.56 (m, 1 H), 3.24-2.87 (m, 9 H), 2.45-2.29 (m, 2 H), 2.27-2.19 (m, 1 H), 1.71-1.58 (m, 1 H), 1.38 (d, J=6.7 Hz, 3 H), 1.10 (d, J=7.3 Hz, 3 H), 1.05 (d, J=6.7 Hz, 3 H); MS (ESI) m/z 544.31 (M+H).

EXAMPLE 72

Compound 100

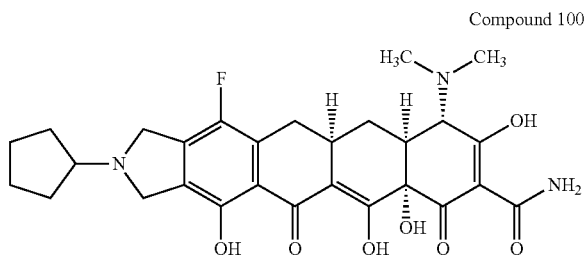 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C1CCCC1)C5]

Compound 100

Prepared from S1-11-13: [1] H NMR (400 MHz, CD$_3$OD) δ 5.10-4.91 (m, 2 H), 4.78-4.69 (m, 1 H), 4.65-4.53 (m, 1 H), 4.10 (s, 1 H), 4.03-3.90 (m, 1 H), 3.24-2.90 (m, 9 H), 2.39-2.18 (m, 4 H), 1.98-1.70 (m, 6 H), 1.70-1.56 (m, 1 H); MS (ESI) m/z 542.27 (M+H).

EXAMPLE 73

Compound 140

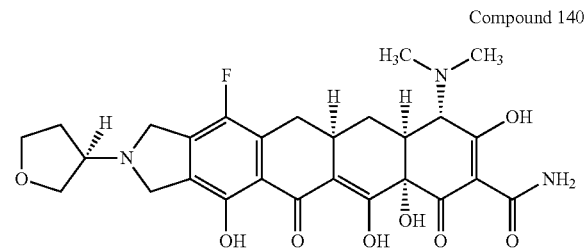 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN([C@@H]1CCOC1)C5]

Compound 140

Prepared from S1-11-14: [1] H NMR (400 MHz, CD$_3$OD) δ 515-5.43 (broad, 4H), 4.41-4.33 (m, 1 H), 4.27-4.19 (m, 1 H), 4.17-4.10 (m, 1 H), 4.08 (s, 1 H), 3.90-3.83 (m, 1 H), 3.80-3.71 (m, 1 H), 3.23-3.14 (m, 1 H), 3.13-2.91 (m, 8 H), 2.57-2.44 (m, 1H), 2.40-2.17 (m, 3 H), 1.71-1.57 (m, 1 H); MS (ESI) m/z 544.21 (M+H).

EXAMPLE 74

Compound 129

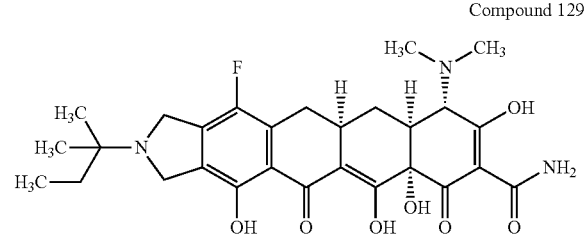 [SMILES: CCC(C)(C)N1Cc2c(O)c3c(c(F)c2C1)C[C@H]1C[C@H]2[C@H](N(C)C)C(O)=C(C(N)=O)C(=O)[C@@]2(O)C(O)=C1C3=O]

Compound 129

Prepared from S1-11-15: [1] H NMR (400 MHz, CD$_3$OD) δ 4.96-4.63 (m, 4 H), 4.10 (s, 1 H), 3.28-2.85 (m, 9 H), 2.41-2.16 (m, 2 H), 1.92-1.82 (m, 2 H), 1.70-1.57 (m, 1 H), 1.46 (s, 6 H), 1.12-1.02 (m, 3 H); MS (ESI) m/z 569.26 (M+H).

EXAMPLE 75

Compound 118

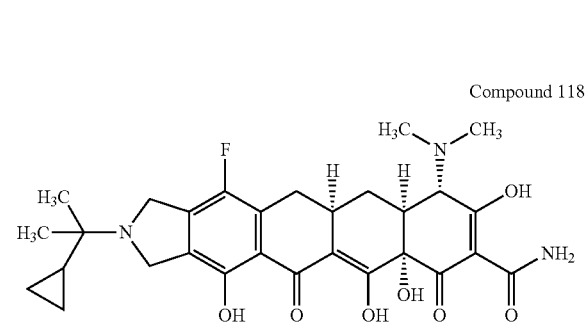 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)C1CC1)C5]

Compound 118

Prepared from S1-11-16: [1] H NMR (400 MHz, CD$_3$OD) δ 5.02-4.74 (m, 4 H), 4.09 (s, 1 H), 3.23-2.91 2.39-2.27 (m, 1 H), 2.27-2.18 (m, 1 H), 1.71-1.57 (m, 1 H), 1.37 (s, 6 H), 1.34-1.25 (m, 1 H), 0.78-0.68 (m, 2 H), 0.68-0.061 (m, 2 H); MS (ESI) m/z 556.36 (M+H).

EXAMPLE 76

Compound 133

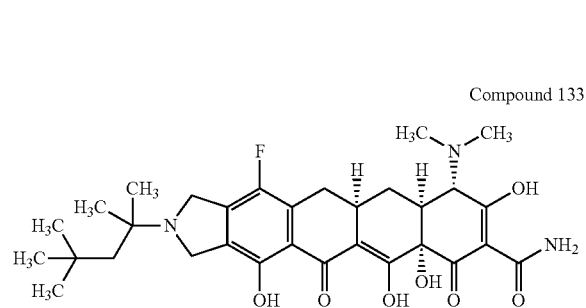 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)CC(C)(C)C)C5]

Compound 133

Prepared from S1-11-17: [1] H NMR (400 MHz, CD$_3$OD) δ 4.99-4.79 (m, 2 H), 4.79-4.69 (m, 2 H), 4.10 (s, 1 H), 3.24-2.92 (m, 9 H), 2.39-2.27 (m, 1 H), 2.27-2.19 (m, 1 H), 1.86 (s, 2 H), 1.70-1.56 (m, 7 H), 1.13 (s, 9 H); MS (ESI) m/z 586.38 (M+H).

EXAMPLE 77

Compound 114

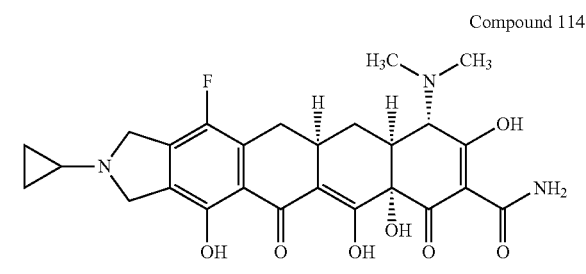 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C1CC1)C5]

Compound 114

Prepared from S1-11-18: [1] H NMR (400 MHz, CD$_3$OD) δ 5.09-4.80 (m, 4 H), 4.10 (s, 1 H), 3.28-2.94 (m, 10 H), 2.40-

2.29 (m, 1 H), 2.28-2.21 (m, 1 H), 1.72-1.59 (m, 1 H), 1.20-1.28 (m, 2 H), 1.18-1.03 (m, 2 H); MS (ESI) m/z 514.47 (M+H).

EXAMPLE 78

Compound 132

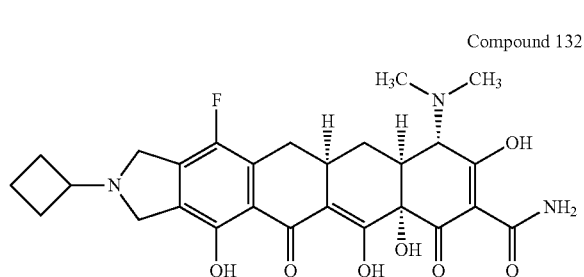 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C1CCC1)C5]
Compound 132

Prepared from S1-11-19: $^1$H NMR (400 MHz, CD$_3$OD) δ 5.04-4.84 (m, 2 H), 4.64-4.56 (m, 1 H), 4.53-4.42 (m, 1 H), 4.18-4.04 (m, 2 H), 3.22-3.15 (m, 1 H), 3.14-2.95 (m, 8 H), 2.50-2.29 (m, 5 H), 2.28-2.20 (m, 1 H), 2.05-1.85 (m, 2 H), 1.71-1.58 (m, 1 H); MS (ESI) m/z 528.49 (M+H).

EXAMPLE 79

Compound 136

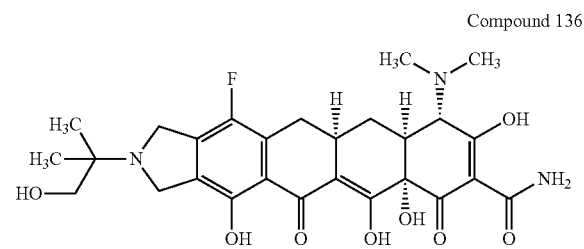 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)CO)C5]
Compound 136

Prepared from S1-11-20: $^1$H NMR (400 MHz, CD$_3$OD) δ 4.97-4.81 (m, 1 H), 4.80-4.65 (m, 3 H), 4.09 (s, 1 H), 3.69 (s, 2 H), 3.23-2.91 (m, 9 H), 2.39-2.27 (m, 1 H), 2.27-2.19 (m, 1 H), 1.70-1.57 (m, 1 H), 1.44 (s, 6 H); MS (ESI) m/z 546.33 (M+H).

EXAMPLE 80

Compound 142

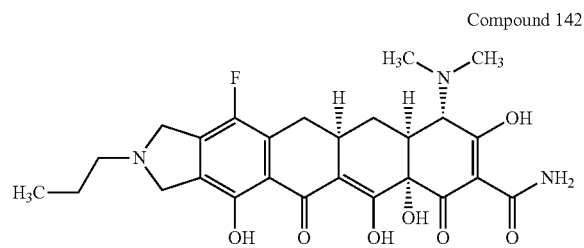 [SMILES: CCCN1Cc2c(O)c3c(c(F)c2C1)C[C@H]1C[C@H]2[C@H](N(C)C)C(O)=C(C(N)=O)C(=O)[C@@]2(O)C(O)=C1C3=O]
Compound 142

Prepared from S1-11-21: $^1$H NMR (400 MHz, CD$_3$OD) δ 5.08-4.81 (m, 2 H), 4.75-4.47 (m, 1 H), 4.08 (s, 1 H), 3.50-3.37 (m, 2 H), 3.21-2.84 (m, 9 H), 2.40-2.27 (m, 1 H), 2.26-2.17 (m, 1 H), 1.92-1.76 (m, 2 H), 1.71-1.57 (m, 1 H), 1.07 (t, J=7.3 Hz, 3H); MS (ESI) m/z 516.24 (M+H).

EXAMPLE 81

Compound 122

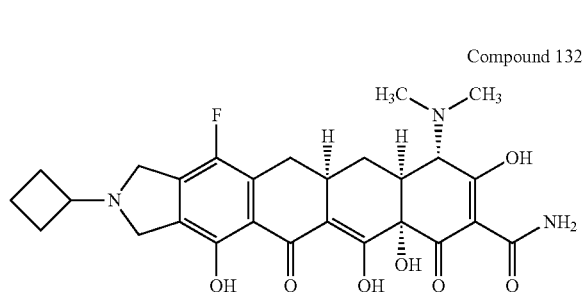
Compound 122

Prepared from S1-11-22: $^1$H NMR (400 MHz, CD$_3$OD) δ 4.96-4.82 (m, 4 H), 4.10 (s, 1 H), 3.89 (m, 1 H), 3.83 (m, 1 H), 3.23-3.15 (m, 1 H), 3.14-2.91 (m, 8 H), 2.40-2.29 (m, 1 H), 2.28-2.20 (m, 1 H), 1.72-1.54 (m, 7 H); MS (ESI) m/z 548.53 (M+H).

EXAMPLE 82

Compound 146

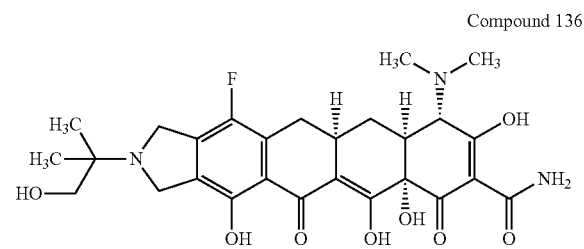 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)CO)C5]
Compound 146

Prepared from S1-11-23: $^1$H NMR (400 MHz, CD$_3$OD) δ 4.92-4.78 (m, 2 H), 4.78-4.66 (m, 2 H), 4.09 (s, 1 H), 3.98-3.85 (m, 2 H), 3.85-3.78 (m, 2 H), 3.22-3.12 (m, 1 H), 3.14-2.90 (m, 8 H), 2.40-2.27 (m, 1 H), 2.27-2.01 (m, 7 H), 1.74-1.56 (m, 7 H); MS (ESI) m/z 599.29 (M+H).

EXAMPLE 83

Compound 126

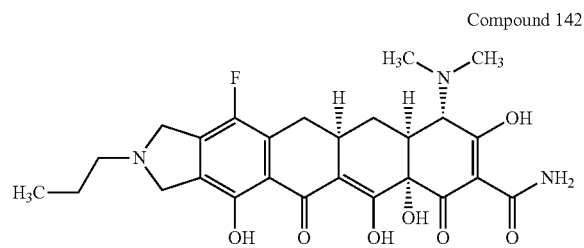 [SMILES: CCCN1Cc2c(O)c3c(c(F)c2C1)C[C@H]1C[C@H]2[C@H](N(C)C)C(O)=C(C(N)=O)C(=O)[C@@]2(O)C(O)=C1C3=O]
Compound 126

Prepared from S4-10-1: $^1$H NMR (400 MHz, CD$_3$OD) δ 5.13-4.96 (m, 1 H), 4.64-4.51 (m, 1 H), 4.11 (s, 1 H), 3.86-

3.74 (m, 1 H), 3.24-2.89 (m, 11 H), 2.66-2.52 (m, 1 H), 2.27-2.18 (m, 1 H), 1.69-1.59 (m, 1 H), 1.47 (s, 6 H); MS (ESI) m/z 566.26 (M+H).

EXAMPLE 84

Compound 113

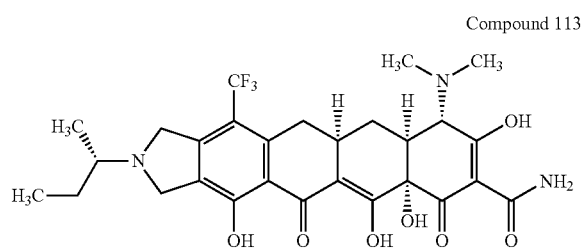 [SMILES: CC[C@H](C)N1Cc2c(O)c3c(c(C(F)(F)F)c2C1)C[C@H]1C[C@H]2[C@H](N(C)C)C(O)=C(C(N)=O)C(=O)[C@@]2(O)C(O)=C1C3=O]

Compound 113

Prepared from S4-10-2: $^1$H NMR (400 MHz, CD$_3$OD) δ 5.08-4.93 (m, 1 H), 4.80-4.60 (m, 1 H), 4.12 (s, 1 H), 3.67-3.55 (m, 1 H), 3.27-3.17 (m, 1 H), 3.16-2.85 (m, 10 H), 2.65-2.52 (m, 1 H), 2.28-2.19 (m, 1 H), 2.08-1.95 (m, 1 H), 1.77-1.58 (m, 2 H), 1.45 (d, J=6.7 Hz, 3 H), 1.07 (t, J=7.6 Hz, 3 H); MS (ESI) m/z 580.26 (M+H).

EXAMPLE 85

Compound 128

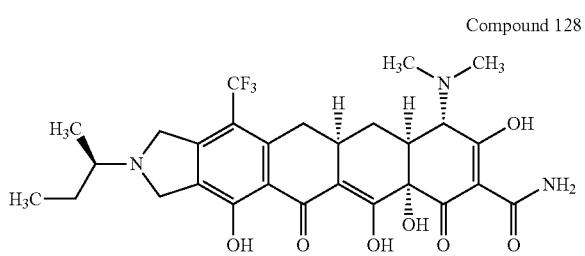

Compound 128

Prepared from S4-10-3: $^1$H NMR (400 MHz, CD$_3$OD) δ 5.08-4.91 (m, 1 H), 4.70-4.51 (m, 1 H), 4.13 (s, 1 H), 3.66-3.56 (m, 1 H), 3.26-3.17 (m, 1 H), 3.16-2.86 (m, 10 H), 2.66-2.53 (m, 1 H), 2.28-2.19 (m, 1 H), 2.09-1.94 (m, 1 H), 1.77-1.57 (m, 2 H), 1.45 (d, J=6.1 Hz, 3 H), 1.07 (t, J=7.3 Hz, 3 H); MS (ESI) m/z 580.26 (M+H).

EXAMPLE 86

Compound 112

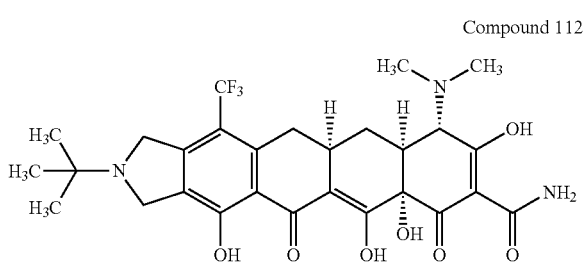 [SMILES: CN(C)[C@@H]1C(O)=C(C(N)=O)C(=O)[C@@]2(O)C(O)=C3C(=O)c4c(O)c5c(c(C(F)(F)F)c4C[C@H]3C[C@@H]12)CN(C(C)(C)C)C5]

Compound 112

Prepared from S4-10-4: $^1$H NMR (400 MHz, CD$_3$OD) δ 4.98-4.86 (m, 1 H), 4.78-4.66 (m, 1 H), 4.12 (s, 1 H), 3.25-2.89 (m, 12 H), 2.68-2.52 (m, 1 H), 2.27-2.18 (m, 1 H), 1.72-1.59 (m, 1 H), 1.53 (s, 9 H); MS (ESI) m/z 580.26 (M+H).

EXAMPLE 87

Compound 116

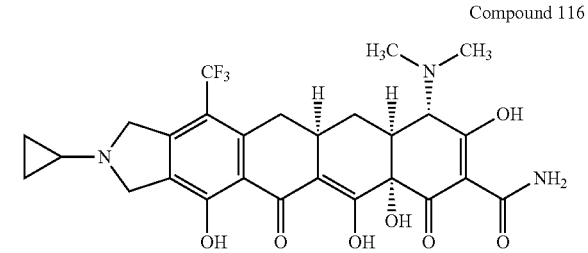 [SMILES: CN(C)[C@@H]1C(O)=C(C(N)=O)C(=O)[C@@]2(O)C(O)=C3C(=O)c4c(O)c5c(c(C(F)(F)F)c4C[C@H]3C[C@@H]12)CN(C1CC1)C5]

Compound 116

Prepared from S4-10-5: $^1$H NMR (400 MHz, CD$_3$OD) δ 5.17-5.01 (m, 2 H), 4.12 (s, 1 H), 3.27-3.19 (2 H), 3.16-2.84 (m, 10 H), 2.66-2.54 (m, 1 H), 2.27-2.19 (m, 1H), 1.72-1.59 (m, 1 H), 1.20-1.13 (m, 2 H), 1.09-1.02 (m, 2 H); MS (ESI) m/z 564.17 (M+H).

EXAMPLE 88

Compound 141

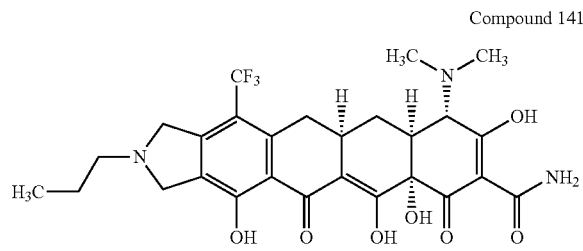 [SMILES: CCCN1Cc2c(O)c3c(c(C(F)(F)F)c2C1)C[C@H]1C[C@H]2[C@H](N(C)C)C(O)=C(C(N)=O)C(=O)[C@@]2(O)C(O)=C1C3=O]

Compound 141

Prepared from S4-10-6: $^1$H NMR (400 MHz, CD$_3$OD) δ 5.20-5.07 (m, 1 H), 4.58-4.47 (m, 1 H), 4.13 (s, 1 H), 3.51-3.38 (m, 2 H), 3.28-3.17 (m, 1 H), 3.16-2.90 (m, 10 H), 2.67-2.51 (m, 1 H), 2.28-2.19 (m, 1 H), 1.94-1.80 (m, 2 H), 1.72-1.59 (m, 1 H), 1.08 (t, J=7.4 Hz, 3 H); MS (ESI) m/z 566.26 (M+H).

EXAMPLE 89

Compound 115

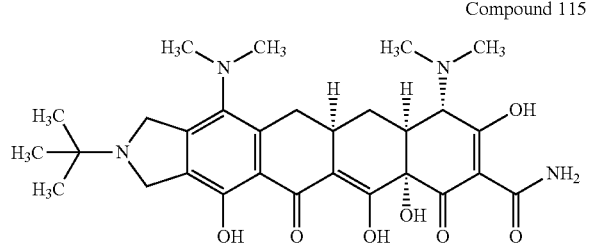 [SMILES: CN(C)c1c2c(c(O)c3c1C[C@H]1C[C@H]4[C@H](N(C)C)C(O)=C(C(N)=O)C(=O)[C@@]4(O)C(O)=C1C3=O)CN(C(C)(C)C)C2]

Compound 115

Prepared from S6-2-1: $^1$H NMR (400 MHz, CD$_3$OD) δ 5.16-4.96 (m, 2 H), 4.78-4.62 (m, 2 H), 4.16 (s, 1 H), 3.28-

EXAMPLE 90

Compound 135

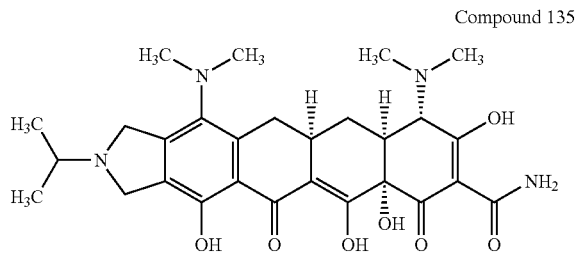 [SMILES: CC(C)N1Cc2c(O)c3c(c(N(C)C)c2C1)C[C@H]1C[C@H]2[C@H](N(C)C)C(O)=C(C(N)=O)C(=O)[C@@]2(O)C(O)=C1C3=O]

Compound 135

Prepared from S6-2-2: $^1$H NMR (400 MHz, CD$_3$OD) δ 5.19-5.03 (m, 1 H), 4.60-4.46 (m, 1 H), 4.13 (s, 1 H), 3.88-3.75 (m, 1 H), 3.13-2.82 (m, 17 H), 2.48-2.21 (m, 2 H), 1.73-1.59 (m, 1 H), 1.57-1.44 (m, 6 H); MS (ESI) m/z 541.24 (M+H).

EXAMPLE 91

Compound 124

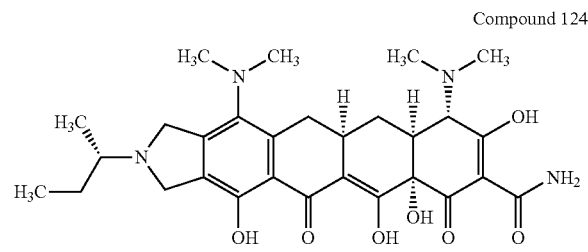 [SMILES: CC[C@H](C)N1Cc2c(O)c3c(c(N(C)C)c2C1)C[C@H]1C[C@H]2[C@H](N(C)C)C(O)=C(C(N)=O)C(=O)[C@@]2(O)C(O)=C1C3=O]

Compound 124

Prepared from S6-2-3: $^1$H NMR (400 MHz, CD$_3$OD) δ 5.10-4.96 (m, 1 H), 4.58-4.46 (m, 1 H), 4.10 (s, 1 H), 3.68-3.55 (m, 1 H), 3.10-2.68 (m, 18 H), 2.40-2.18 (m, 1 H), 2.11-1.98 (m, 1 H), 1.78-1.57 (m, 2 H), 1.46 (d, J=6.1 Hz, 3 H), 1.09 (t, J=6.7 Hz, 3 H); MS (ESI) m/z 555.33 (M+H).

EXAMPLE 92

Compound 127

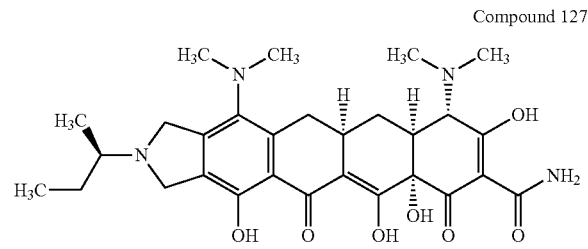 [SMILES: CC[C@@H](C)N1Cc2c(O)c3c(c(N(C)C)c2C1)C[C@H]1C[C@H]2[C@H](N(C)C)C(O)=C(C(N)=O)C(=O)[C@@]2(O)C(O)=C1C3=O]

Compound 127

Prepared from S6-2-4: $^1$H NMR (400 MHz, CD$_3$OD) δ 5.14-4.96 (m, 1 H), 4.58-4.44 (m, 1 H), 4.16 (s, 1 H), 3.66-3.54 (m, 1 H), 3.10-2.69 (m, 18 H), 2.38-2.19 (m, 1 H), 2.14-1.99 (m, 1 H), 1.76-1.57 (m, 1 H), 1.53-1.40 (m, 3 H), 1.08 (t, J=7.3 Hz, 3 H); MS (ESI) m/z 555.39 (M+H).

EXAMPLE 93

Compound 103

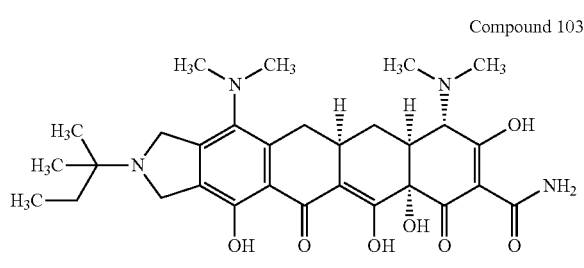 [SMILES: CCC(C)(C)N1Cc2c(O)c3c(c(N(C)C)c2C1)C[C@H]1C[C@H]2[C@H](N(C)C)C(O)=C(C(N)=O)C(=O)[C@@]2(O)C(O)=C1C3=O]

Compound 103

Prepared from S6-2-5: $^1$H NMR (400 MHz, CD$_3$OD) δ 5.12-4.98 (m, 2 H), 4.71 (s, 2 H), 4.16 (s, 1 H), 3.25-2.91 (m, 15 H), 2.61-2.38 (m, 1 H), 2.35-2.25 (m, 1 H), 1.99-1.89 (m, 2 H), 1.73-1.60 (m, 1 H), 1.52 (s, 6 H), 1.10 (t, J=7.3 Hz, 3 H); MS (ESI) m/z 569.26 (M+H).

EXAMPLE 94

Compound 105

Synthesis of S8-1

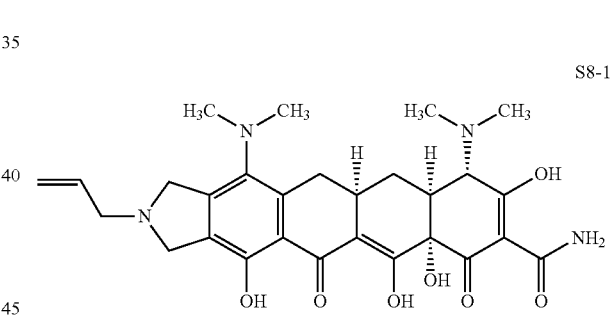

S8-1

To a solution of lithium diisopropylamide (1.8 M in hexanes, 446 μL, 0.804 mmol, 2.2 eq) and TMEDA (328 μL, 2.19 mmol, 6 eq) in THF (8 mL) at –78° C. was added a solution of compound S1-11-21 (168 mg, 0.402 mmol, 1.1 eq) in THF (1 mL) by dropwise addition. This resulted in a dark red colored solution. After 30 min, a solution of enone S7-1 (175 mg, 0.362 mmol, 1 eq) in THF (1.2 mL) was added. After complete addition, the reaction mixture was allowed to warm to –15° C. over 1 h. The reaction was quenched by the addition of ammonium chloride (saturated, aqueous solution, 15 mL) and was extracted with EtOAc (2×30 mL). The combined organic extracts were dried over Na$_2$SO$_4$, filtered, and concentrated under reduced pressure. Purification of the resulting oil via flash column chromatography on silica gel (Silicycle, 25 g, 10 to 25% EtOAc in hexanes gradient) provided 208 mg of S8-1 (71%) as a white solid: $^1$H NMR (400 MHz, CDCl$_3$) δ 16.05 (s, 1 H), 7.53-7.43 (m, 2 H), 7.42-7.28 (m, 8 H), 5.95-5.79 (m, 1 H), 5.35 (s, 2 H), 5.27-5.12 (m, 2 H), 4.90 (q, J=10.4 Hz, 2 H), 4.01-3.74 (m, 4 H), 3.29 (d, J=6.1 Hz, 1 H), 3.25-3.18 (m, 1 H), 3.03-2.92 (m, 1 H), 2.58-2.34 (m, 9 H), 2.13 (d, J=14.7 Hz, 1 H), 0.82 (s, 9 H), 0.27 (s, 3 H), 0.12 (s, 3 H); MS (ESI) m/z 806.38 (M+H).

Synthesis of S8-2

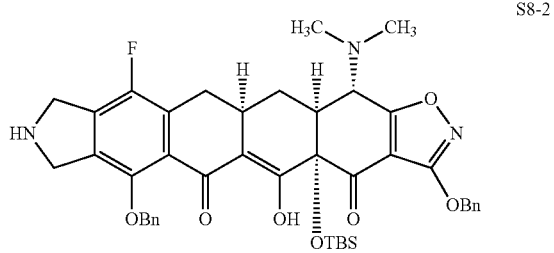 [SMILES: CN(C)[C@@H]1c2onc(OCc3ccccc3)c2C(=O)[C@@]2(O[Si](C)(C)C(C)(C)C)C(O)=C3C(=O)c4c(c(F)c5c(c4OCc4ccccc4)CNC5)C[C@H]3C[C@@H]12]

A flame-dried vial was charged with N,N-dimethylbarbituric acid (103 mg, 0.66 mmol, 2.6 eq) and tetrakis(triphenylphosphine)palladium(0) (20.1 mg, 0.017 mmol, 0.07 eq). The vial was evacuated and back-filled with nitrogen three times. A solution of S8-1 (205 mg, 0.254 mmol, 1 eq) in dichloromethane (degassed, 4 mL) under nitrogen was transferred via syringe to the prepared vial. The resulting heterogeneous solution was placed in a 35° C. heating block. After 1 h, the reaction mixture was concentrated under reduced pressure. Purification of the resulting oil via flash column chromatography on silica gel (Silicycle, 12 g, 20 to 60% EtOAc in hexanes gradient) provided 176 mg of S8-2 (90%) as an orange solid: [1] H NMR (400 MHz, CD$_3$OD) δ 7.52-7.45 (m, 2 H), 7.41-7.28 (m, 8 H), 5.36 (s, 2 H), 4.91 (s, 2 H), 4.34-4.20 (m, 2 H), 4.19-3.99 (m, 2 H), 3.96 (d. J=10.4 Hz, 1 H), 3.36-3.27 (m, 1 H), 3.23 (dd, J=4.9, 15.2 Hz, 1 H), 3.04-2.93 (m, 1 H), 2.59-2.36 (m, 9 H), 2.14 (d, J=14.7 Hz, 1 H), 0.82 (s, 9 H), 0.27 (s, 3 H), 0.13 (s, 3 H); MS (ESI) m/z 766.33 (M+H).

Synthesis of Compound 105

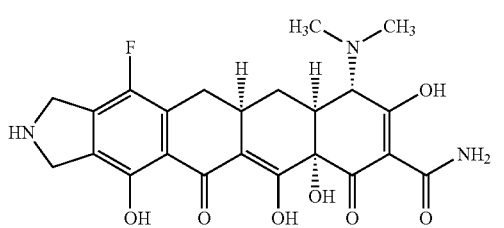

To a solution of S8-2 (9.6 mg, 0.012 mmol, 1 eq) in 1,4-dioxane (1 mL) was added an aqueous solution of HF (50%, 150 µL). After two hours, the reaction mixture was poured into an aqueous K$_2$HPO$_4$ solution (2.4 g in 25 mL) and extracted with EtOAc (2×30 mL). The combined organic layers were dried (Na$_2$SO$_4$), filtered, and concentrated under reduced pressure. Palladium on carbon (10%, 8 mg) was added to a solution of this crude oil in dioxane:MeOH:0.5 N HCl in Methanol (5:4:1, 1 mL). The flask was fitted with a septum and evacuated and back-filled three times with hydrogen gas, and then the solution was degassed with bubbling hydrogen for 3 minutes. The reaction was stirred under an atmosphere (balloon) of hydrogen gas for 2 h. The reaction mixture was filtered through Celite to remove the palladium catalyst and concentrated under reduced pressure. Preparative reverse phase HPLC of the resulting oil was performed on a Waters Autopurification system using a Polymerx 10µ RP-γ 100 R column [30×21.20 mm, 10 micron, solvent A: 0.05 N HCl in water, solvent B: Methanol; injection volume: 1.5 mL (0.05 N HCl in water); gradient: 20→80% B over 20 min; mass-directed fraction collection]. Fractions with the desired MW, eluting at 6.75-7.5 min, were collected and freeze-dried to provide 2.0 mg of the desired compound Compound 105 (33%): [1] H NMR (400 MHz, CD$_3$OD) δ 4.74 (s, 2H), 4.64 (s, 2 H), 4.09 (s, 1 H), 3.25-3.14 (m, 1 H), 3.14-2.88 (m, 8 H), 2.40-2.28 (m, 1H), 2.27-2.18 (m, 1 H), 1.71-1.59 (m, 1 H); MS (ESI) m/z 474.13 (M+H).

EXAMPLE 95

Compound 111

Synthesis of S8-4-1

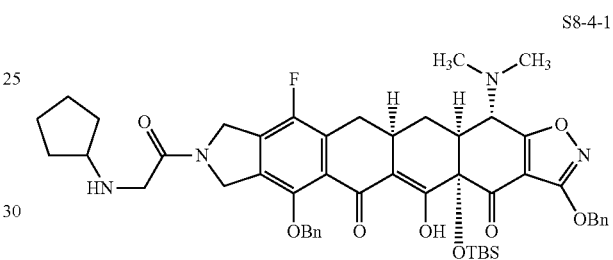

To a solution of S8-2 (30.3 mg, 0.040 mmol, 1 eq) in THF (1 mL) was added bromoacetylbromide (3.6 µL, 0.041 mmol, 1.05 eq). After 5 min, 0.75 µL bromoacetylbromide (0.008 mmol, 0.2 eq) was added, followed by cyclopentylamine (19.5 µL, 0.197 mmol, 5 eq). After 1 h, the reaction was complete, and the mixture was concentrated under reduced pressure to produce crude S8-4-1, which was used without further purification Synthesis of Compound 111

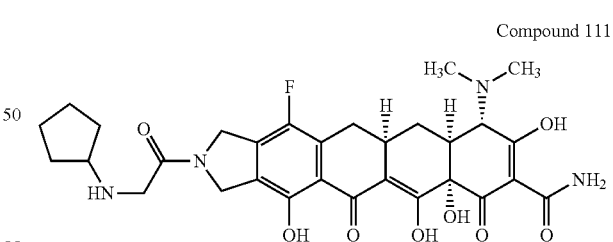

To a solution of this crude oil in 1,4-dioxane (1.8 mL) was added an aqueous solution of HF (50%, 250 µL). After 1.5 h, the reaction mixture was poured into an aqueous K$_2$HPO$_4$ solution (3.6 g in 30 mL) and extracted with EtOAc (2×30 mL). The combined organic layers were dried (Na$_2$SO$_4$), filtered, and concentrated under reduced pressure. Palladium on carbon (10%, 15.1 mg) was added to a solution of this crude oil in dioxane:MeOH (1:1, 1 mL). The flask was fitted with a septum and evacuated and back-filled three times with hydrogen gas. The reaction was stirred under an atmosphere (balloon) of hydrogen gas for 3 h. The reaction mixture was filtered through Celite to remove the palladium catalyst and concentrated under reduced pressure. Preparative reverse phase HPLC of the resulting oil was performed on a Waters Autopurification system using a Polymerx 10μ RP-γ 100 R column [30×21.20 mm, 10 micron, solvent A: 0.05 N HCl in water, solvent B: CH₃CN; injection volume: 2.4 mL (0.05 N HCl in water); gradient: 20→80% B over 20 min; mass-directed fraction collection]. Fractions with the desired MW, eluting at 11.0-12.5 min, were collected and freeze-dried to provide 2.4 mg of the desired compound Compound 111 (9%): ¹ H NMR (400 MHz, CD₃OD) δ 5.04-4.75 (m, 4 H), 4.17-4.06 (m, 3 H), 3.68-3.56 (m, 1 H), 3.24-290 (m, 9H), 2.38-2.26 (m, 1 H), 2.26-2.04 (m, 3 H), 1.91-1.57 (m, 7 H); MS (ESI) m/z 599.28 (M+H).

EXAMPLE 96

Compound 131

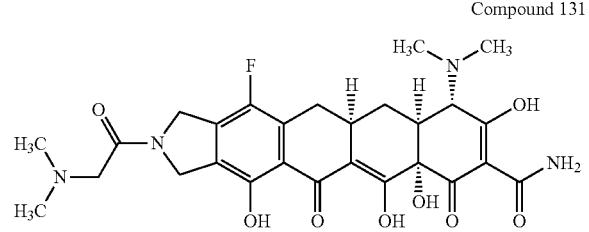 [SMILES: CN(C)CC(=O)N1Cc2c(O)c3c(c(F)c2C1)C[C@H]1C[C@H]2[C@H](N(C)C)C(O)=C(C(N)=O)C(=O)[C@@]2(O)C(O)=C1C3=O]

Compound 131

To a solution of S8-2 (20.1 mg, 0.026 mmol, 1 eq) in THF (1 mL) was added dimethylaminoacetyl chloride hydrochloride (85%, 7.4 mg, 0.039 mmol, 1.5 eq). After 2.5 h, the reaction mixture was diluted with sodium bicarbonate solution (saturated, aqueous, 3 mL) and extracted with EtOAc (2×7 mL). The combined organic layers were washed with brine (2 mL), dried (Na₂SO₄), filtered, and concentrated under reduced pressure to produce S8-4-2 (not shown). To a solution of this crude oil in 1,4-dioxane (1.5 mL) was added an aqueous solution of HF (50%, 300 μL). After 1.5 h, the reaction mixture was poured into an aqueous K₂HPO₄ solution (3.6 g in 30 mL) and extracted with EtOAc (2×25 mL). The combined organic layers were dried (Na₂SO₄), filtered, and concentrated under reduced pressure. Palladium on carbon (10%, 12 mg) was added to a solution of this crude oil in dioxane:MeOH (1:1, 1 mL) The flask was fitted with a septum and evacuated and back-filled three times with hydrogen gas. The reaction mixture was stirred under an atmosphere (balloon) of hydrogen gas for 2.5 h, then was filtered through Celite to remove the palladium catalyst and concentrated under reduced pressure. Preparative reverse phase HPLC of the resulting oil was performed on a Waters Autopurification system using a Polymerx 10μ RP-γ 100 R column [30×21.20 mm, 10 micron, solvent A: 0.05 N HCl in water, solvent B: Methanol; injection volume: 2.0 mL (20% Methanol in 0.05 N HCl in water); gradient: 20→80% B over 20 min; mass-directed fraction collection]. Fractions with the desired MW, eluting at 8.0-10.2 min, were collected and freeze-dried to provide 7.0 mg of the desired compound Compound 131 (42%): ¹ H NMR (400 MHz, CD₃OD) δ 4.99-4.73 (m, 4 H), 4.37-4.27 (m, 2 H), 4.09 (s, 1 H), 3.22-2.91 (m, 15 H), 2.37-2.16 (m, 2 H), 1.71-1.56 (m, 1 H); MS (ESI) m/z 559.19 (M+H).

EXAMPLE 97

Compound 139

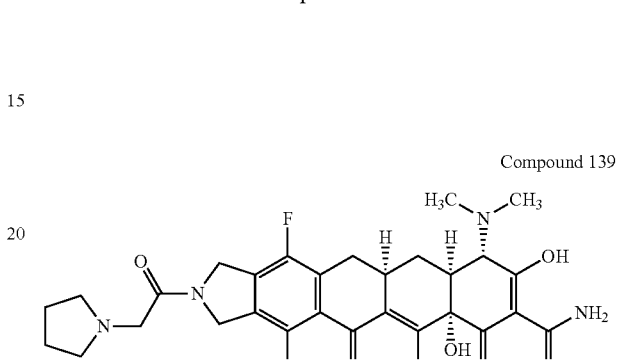

Compound 139

To a solution of S8-2 (21.0 mg, 0.027 mmol, 1 eq) in THF (1 mL) was added pyrrolidineacetylchloride hydrochloride (8.4 mg, 0.045 mmol, 1.7 eq). After 1 h, the reaction mixture was diluted with sodium bicarbonate solution (saturated, aqueous, 3.5 mL) and extracted with EtOAc (2×7 mL). The combined organic layers were washed with brine (2 mL), dried (Na₂SO₄), filtered, and concentrated under reduced pressure to produce S8-4-3 (not shown). To a solution of this crude oil in 1,4-dioxane (1.7 mL) was added an aqueous solution of HF (50%, 300 μL). After 1.5 h, the reaction mixture was poured into an aqueous K₂HPO₄ solution (3.6 g in 30 mL) and extracted with EtOAc (2×25 mL). The combined organic layers were dried (Na₂SO₄), filtered, and concentrated under reduced pressure. Palladium on carbon (10%, 15 mg) was added to a solution of this crude oil in dioxane:MeOH (5:4, 0.90 mL). The flask was fitted with a septum and evacuated and back-filled three times with hydrogen gas. The reaction mixture was stirred under an atmosphere (balloon) of hydrogen gas for 2.5 h, then was filtered through Celite to remove the palladium catalyst and concentrated under reduced pressure. Preparative reverse phase HPLC of the resulting oil was performed on a Waters Autopurification system using a Polymerx 10μ RP-γ 100 R column [30×21.20 mm, 10 micron, solvent A: 0.05 N HCl in water, solvent B: Methanol; injection volume: 2.0 mL (20% Methanol in 0.05 N HCl in water); gradient: 20→80% B over 20 min; mass-directed fraction collection]. Fractions with the desired MW, eluting at 9.4-11.1 min, were collected and freeze-dried to provide 3.5 mg of the desired compound Compound 139 (19%): ¹ H NMR (400 MHz, CD₃OD) δ 5.00-4.74 (m, 4 H), 4.43-4.35 (m, 2 H), 4.09 (s, 1 H), 3.84-3.73 (m, 2 H), 3.27-2.90 (m, 11 H), 2.37-2.00 (m, 6 H), 1.70-1.56 (m, 1 H); MS (ESI) m/z 585.28 (M+H).

EXAMPLE 98

Compound 147

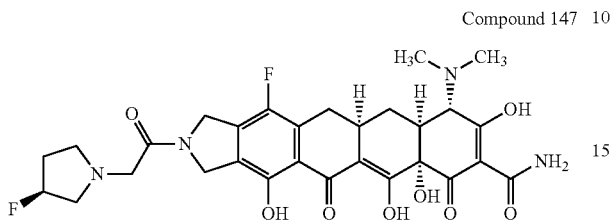

Compound 147

To a solution of S8-2 (33.0 mg, 0.043 mmol, 1 eq) in THF (1 mL) was added bromoacetylbromide (4.1 µL, 0.047 mmol, 1.1 eq). After 40 min, (S)-(+)-3-fluoropyrrolidine hydrochloride salt (15.6 mg, 0.124 mmol, 3 eq) was added, followed by triethylamine (18 µL, 0.126 mmol, 3 eq). After an additional 19 h, additional pyrrolidine salt (32 mg, 0.254 mmol, 6 eq) and triethylamine (54 µL, 0.387 mmol, 9 eq) were added. After 20 h, the mixture was diluted with brine (8 mL), water (1.5 mL), and extracted with EtOAc (2×30 mL) The combined organic layers were dried ($Na_2SO_4$), filtered, and concentrated under reduced pressure to produce S8-4-4 (not shown). To a solution of this crude oil in 1,4-dioxane (1 mL) was added an aqueous solution of HF (50%, 250 µL). After 1.5 h, the reaction mixture was poured into an aqueous $K_2HPO_4$ solution (3 g in 30 mL) and extracted with EtOAc (2×30 mL). The combined organic layers were dried ($Na_2SO_4$), filtered, and concentrated under reduced pressure. Palladium on carbon (10%, 16.5 mg) was added to a solution of this crude oil in dioxane:MeOH (1:1, 1 mL). The flask was fitted with a septum and evacuated and back-filled three times with hydrogen gas. The reaction was stirred under an atmosphere (balloon) of hydrogen gas for 2 h. The reaction mixture was filtered through Celite to remove the palladium catalyst and concentrated under reduced pressure. Preparative reverse phase HPLC of the resulting oil was performed on a Waters Autopurification system using a Polymerx 10µ RP-γ 100 R column [30×21.20 mm, 10 micron, solvent A: 0.05 N HCl in water, solvent B: $CH_3CN$; injection volume: 2.4 mL (0.05 N HCl in water); gradient: 10→60% B over 15 min; mass-directed fraction collection]. Fractions with the desired MW, eluting at 6.3-7.3 min, were collected and freeze-dried to provide 7.8 mg of the desired compound Compound 147 (27%): [1] H NMR (400 MHz, $CD_3OD$) δ 5.61-5.34 (m, 1 H), 5.02-4.77 (m, 4 H), 4.58-4.38 (m, 2 H), 4.18-3.90 (m, 3 H), 3.74-3.38 (m, 2 H), 3.24-2.89 (m, 9 H), 2.59-2.28 (m, 4 H), 2.27-2.18 (m, 1 H), 1.71-1.58 (m, 1 H); MS (ESI) m/z 603.35 (M+H).

EXAMPLE 99

Compound 109

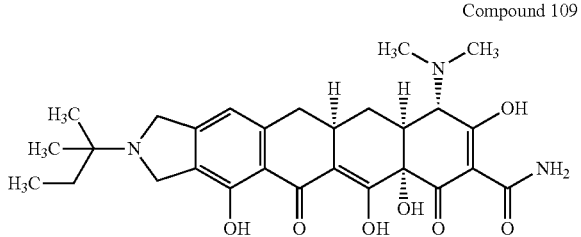

Compound 109

Compound 150 (7.9 mg, 0.013 mmol) was dissolved in Methanol (1 mL) and 1,4-dioxane (1 mL) and 0.5 M HCl in Methanol (0.2 mL), and palladium on carbon (Degussa, 10 wt %, ~2 mg) was added. An atmosphere of hydrogen was introduced, and the reaction mixture was stirred overnight. The reaction mixture was filtered through Celite, and the filtrate was concentrated under reduced pressure. The material was dissolved in Methanol (1 mL) and palladium on carbon (Degussa, 10 wt %, ~20 mg) was added. An atmosphere of hydrogen was introduced, and the reaction mixture was stirred overnight. The reaction mixture was filtered through Celite, and the filtrate was concentrated under reduced pressure. The material was purified on a Waters Autopurification system equipped with a Phenomenex Polymerx 10µ RP 100 A column [10 µm, 30×21.20 mm; flow rate, 20 mL/min; Solvent A: 0.05N HCl in water; Solvent B: Methanol; gradient: 20→100% B; mass-directed fraction collection]. Fractions with the desired MW were collected and freeze-dried to yield 1.2 mg (16%, 2 steps) of the desired product Compound 109 as a yellow solid. [1] H NMR (400 MHz, $CD_3OD$ with 1 drop DCl) δ 6.84 (s, 1 H), 4.85-4.65 (m, 4 H), 4.13 (s, 1 H), 3.15-2.88 (m, 9 H), 2.61-2.50 (m, 1 H), 2.28-2.20 (m, 1 H), 1.92-1.82 (m, 2 H), 1.65-1.50 (m, 1 H), 1.44 (s, 6 H), 1.06 (t, J=7.3 Hz, 3 H); MS (ESI) m/z 526.30 (M+H).

EXAMPLE 100

Compound 201

Synthesis of S10-1

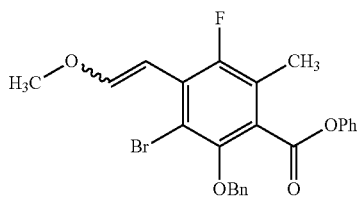

S10-1

(Methoxymethyl)triphenylphosphonium chloride (1.55 g, 4.51 mmol) was added to a suspension of potassium t-butoxide (0.506 g, 4.51 mmol) in THF (15 mL), giving an immediate red colored solution. After 15 min, a solution of compound S1-7 (1.00 g, 2.26 mmol) in THF (5 mL) was added. After 2 h, the reaction mixture was quenched with water and was extracted with EtOAc (2×). The combined extracts were dried over $Na_2SO_4$, filtered, and concentrated under reduced pressure. The material was purified by column chromatography (Biotage 20 g column, 0 to 6% EtOAc in hexane gradient), yielding 986 mg (93%) of the compound S10-1 as a mixture of two isomers. MS (ESI) m/z 493.04, 495.04 (M+Na).

Synthesis of S10-2

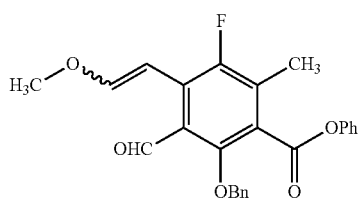

S10-2 i-Propyl magnesium chloride/lithium chloride solution (Chemetall Foote Corporation, 1.2 M solution in THF, 8.5 mL, 10.2 mmol) was added to a −50° C. solution of compound S10-1 (956 mg, 2.03 mmol) in THF (20 mL). The reaction mixture was allowed to warm to 0° C. over 1 h. N,N-Dimethylformamide (1.25 mL, 16.2 mmol) was added, and the reaction was allowed to warm to rt. After 1 hour, the reaction mixture was quenched with ammonium chloride (saturated, aqueous solution) and was extracted with EtOAc (2×). The combined extracts were dried over $Na_2SO_4$, filtered, and concentrated under reduced pressure. The material was purified by column chromatography (Biotage 25 g column, 5 to 40% EtOAc in hexane gradient), yielding 205 mg (24%) of compound S10-2. $R_f$=0.23 in 20% EtOAc in hexane; $^1$H NMR (400 MHz, $CDCl_3$) δ 10.3 (s, 1 H), 7.45-7.30 (m, 7 H), 7.28-7.24 (m, 1 H), 7.10-7.02 (m, 3H), 6.67 (d, J=12.8 Hz, 1 H), 5.09 (s, 2 H), 3.77 (s, 3 H), 2.43 (d, J=4.6 Hz, 3 H); MS (ESI) m/z 443.18 (M+Na).

Synthesis of S10-3-1

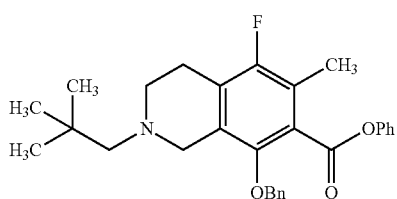

S10-3-1

Neopentylamine (0.077 mL, 0.66 mmol) was added to a solution of compound S10-2 (55.5 mg, 0.132 mmol) in $CH_2Cl_2$ (5 mL) and Acetic acid (0.038 mL, 0.66 mmol). After 5 min, sodium triacetoxyborohydride (83.9 mg, 0.396 mmol) was added. After 1 hour, the reaction mixture was diluted with EtOAc and was washed with $NaHCO_3$ (saturated, aqueous solution, 2×). The organics were dried over $Na_2SO_4$, filtered, and concentrated under reduced pressure, yielding 53.3 mg (88% crude) of compound S10-3-1. $^1$H NMR (400 MHz, $CDCl_3$) δ 7.46-7.30 (m, 7 H), 7.26-7.20 (m, 1H), 7.10-7.04 (m, 2 H), 4.96 (s, 2 H), 3.72 (s, 2 H), 2.86-2.75 (m, 4 H), 2.35 (d, J=1.8 Hz, 3 H), 2.23 (s, 2 H), 0.89 (s, 9 H); MS (ESI) m/z 462.28 (M+H).

Synthesis of S10-4-1

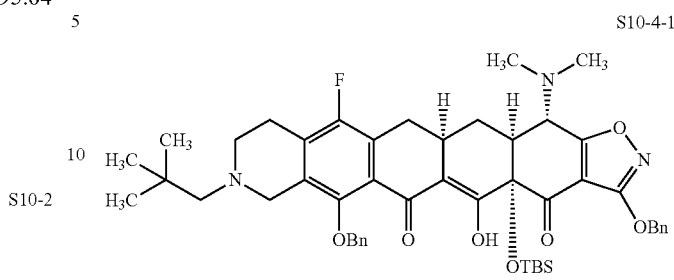

S10-4-1

Lithium diisopropylamide was prepared at −40° C. from n-butyllithium (2.5 M solution in hexane, 0.045 mL, 0.11 mmol) and diisopropylamine (0.016 mL, 0.11 mmol) in THF (2 mL). The reaction mixture was cooled to −78° C. and TMEDA (0.040 mL, 0.27 mmol) was added followed by the dropwise addition of a solution of compound S10-3-1 (24.9 mg, 0.0539 mmol) in THF (1 mL). No color change was observed, so additional lithium diisopropylamide (2.0M solution in THF, 0.060 mL, 0.12 mmol) was added until a deep red colored solution persisted. After 15 min, a solution of enone S7-1 (21.7 mg, 0.045 mmol) in THF (0.5 mL) was added. After complete addition, the reaction mixture was allowed to warm to −20° C. over 1 h. The reaction was quenched by the addition of ammonium chloride (saturated, aqueous solution) and was extracted with EtOAc (2×). The combined extracts were dried over $Na_2SO_4$, filtered, and concentrated under reduced pressure. The material was purified on a Waters Autopurification system equipped with a Sunfire Prep C18 OBD column [5 μm, 19×50 mm; flow rate, 20 mL/min; Solvent A: $H_2O$ with 0.1% $HCO_2$ H; Solvent B: $CH_3CN$ with 0.1% $HCO_2$ H; gradient: 50→100% B; mass-directed fraction collection], yielding 18.9 mg (49%) of the desired product S10-4-1 as a yellow solid. $^1$H NMR (400 MHz, $CDCl_3$) δ 16.0 (s, 1 H), 7.52-7.44 (m, 2 H), 7.40-7.28 (m, 8 H), 5.36 (s, 2 H), 4.94 (d, J=11.0 Hz, 1 H), 4.78 (d, J=10.4 Hz, 1 H), 4.10-3.89 (m, 3 H), 3.29-3.15 (m, 2 H), 3.06-2.96 (m, 2 H), 2.65-2.40 (m, 11 H), 2.15 (d, J=14.6 Hz, 1 H), 0.98 (s, 9 H), 0.82 (s, 9 H), 0.27 (s, 3 H), 0.12 (s, 3 H); MS (ESI) m/z 850.39 (M+H).

Synthesis of Compound 201

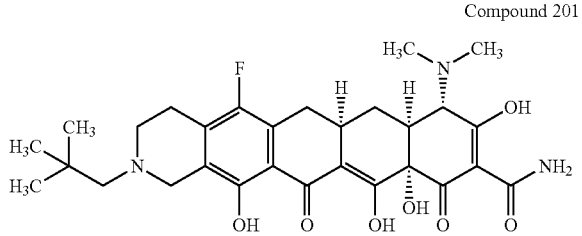 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CCN(CC(C)(C)C)C5]

Compound 201

Aqueous HF (0.4 mL, 48%) was added to a solution of S10-4-1 (18.9 mg, 0.022 mmol) in 1,4-dioxane (1 mL) in a plastic vial. After stirring overnight, the reaction mixture was poured into a solution of $K_2 HPO_4$ (4.8 g) in water (15 mL). The mixture was extracted with EtOAc (3×). The combined EtOAc extracts were dried over $Na_2SO_4$, filtered and concentrated under reduced pressure. The material was dissolved in Methanol (2 mL), 1,4-dioxane (2 mL) and 0.5M HCl in Methanol (0.5 mL), and palladium on carbon (Degussa, 10 wt %, ~5 mg) was added. An atmosphere of hydrogen was introduced, and the reaction mixture was stirred for 2 h. The reaction mixture was filtered through Celite, and the filtrate was concentrated under reduced pressure. The material was purified on a Waters Autopurification system equipped with a Phenomenex Polymerx 10μ RP 100 A column [10 μm, 30×21.20 mm; flow rate, 20 mL/min; Solvent A: 0.05N HCl in water; Solvent B: $CH_3CN$; gradient: 0→70% B; mass-directed fraction collection]. Fractions with the desired MW were collected and freeze-dried to yield 7.8 mg (57%, 2 steps) of the desired product Compound 201 as a yellow solid. [1] H NMR (400 MHz, $CD_3OD$ with 1 drop DCl) δ 4.60 (t, J=14.4 Hz, 1H), 4.32 (dd, J=16.0, 7.8 Hz, 1 H), 4.15 (s, 1 H), 3.88-3.79 (m, 1 H), 3.62-3.50 (m, 1H), 3.36-3.16 (m, 5 H), 3.15-2.96 (m, 8 H), 2.35-2.24 (m, 2 H), 1.61 (q, J=12.7 Hz, 1H), 1.20 (s, 9 H); MS (ESI) m/z 558.26 (M+H).

The following compounds were prepared by methods similar to that for Compound 201, substituting the appropriate tetrahydroisoquinoline for S10-3-1. The appropriate tetrahydroisoquinolines were prepared by methods similar to that for S10-3-1, substituting the appropriate amine for neopentylamine.

EXAMPLE 101

Compound 200

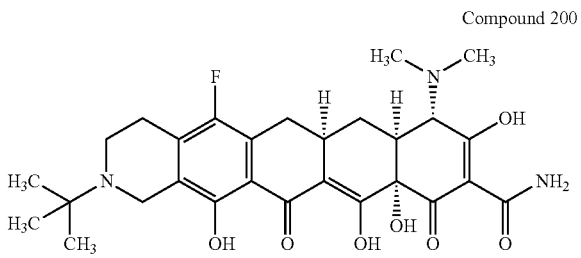 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CCN(C(C)(C)C)C5]

Compound 200

Yellow solid: [1] H NMR (400 MHz, $CD_3OD$ with 1 drop DCl) δ 4.53 (t, J=15.8 Hz, 1 H), 4.24 (dd, J=16.0, 3.7 Hz, 1 H), 4.14 (s, 1 H), 4.04-3.96 (m, 1 H), 3.34-3.14 (m, 4 H), 3.14-2.90 (m, 8 H), 2.34-2.23 (m, 2 H), 1.69-1.52 (m, 10 H); MS (ESI) m/z 544.27 (M+H).

Prepared from S10-3-2,

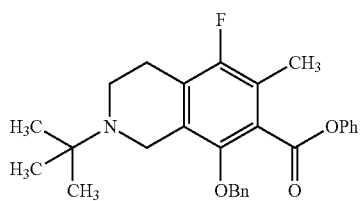

S10-3-2

[1] H NMR (400 MHz, $CDCl_3$) δ 7.45-7.30 (m, 7 H), 7.29-7.22 (m, 1 H), 7.12-7.08 (m, 2 H), 4.96 (s, 2 H), 3.70 (s, 2 H), 2.86-2.80 (m, 2 H), 2.78-2.72 (m, 2 H), 2.33 (s, 3 H), 1.11 (s, 9 H); MS (ESI) m/z 448.31 (M+H).

EXAMPLE 102

Compound 202

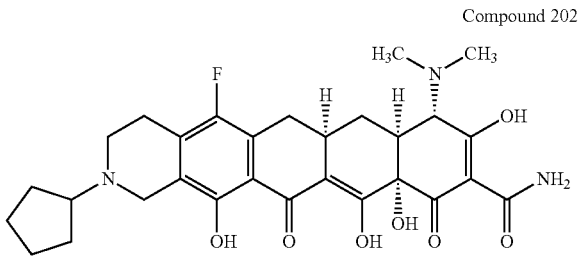 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CCN(C1CCCC1)C5]

Compound 202

Yellow solid: [1] H NMR (400 MHz, $CD_3OD$ with 1 drop DCl) δ 4.59 (t, J=15.3 Hz, 1 H), 4.22 (dd, J=16.3, 5.7 Hz, 1 H), 4.14 (s, 1 H), 3.94-3.86 (m, 1 H), 3.86-3.75 (m, 1 H), 3.44-3.34 (m, 1 H), 3.33-2.96 (m, 11 H), 2.35-2.22 (m, 4 H), 2.00-1.84 (m, 4H), 1.80-1.70 (m, 2 H), 1.68-1.55 (m, 1 H); MS (ESI) m/z 556.26 (M+H).

Prepared from S10-3-3,

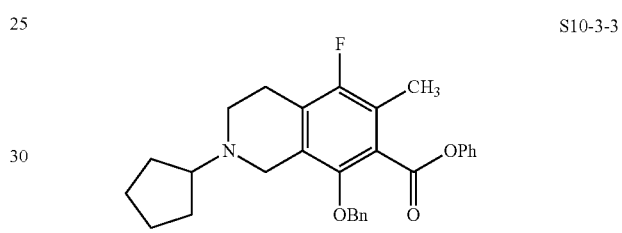

S10-3-3

[1] H NMR (400 MHz, $CDCl_3$) δ 7.45-7.30 (m, 7 H), 7.29-7.22 (m, 1 H), 7.12-7.08 (m, 2 H), 4.96 (s, 2 H), 3.66 (s, 2 H), 2.90-2.83 (m, 2 H), 2.78-2.72 (m, 2 H), 2.71-2.62 (m, 1 H), 2.34 (d, J=1.4 Hz, 3 H), 1.96-1.86 (m, 2 H), 1.76-1.64 (m, 2 H), 1.63-1.42 (m, 4 H); MS (ESI) m/z 460.54 (M+H).

EXAMPLE 103

Preparation of phenyl 5-(benzyloxy)-8-fluoro-7-methyl-2-propyl-1,2,3,4-tetrahydroisoquinoline-6-carboxylate (S11-4-1)

Synthesis of S11-1

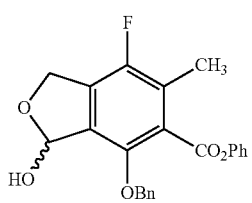

S11-1

To a stirred suspension of compound S1-7 (3.99 g, 8.99 mmol, 1 eq) in methanol (50 mL) was added sodium borohydride (420 mg, 11.1 mmol, 1.3 eq). Gas evolution was evident; the solution was homogeneous after 5 min. After 40 min the reaction was complete. The mixture was poured into a saturated aqueous $NH_4Cl$ solution (40 mL), water (10 mL), and extracted with EtOAc (3×75 mL). The combined organic layers were dried ($Na_2SO_4$), filtered, and concentrated under reduced pressure. The crude material (2.13 g, 4.30 mmol, 1 eq) was azeotropically dried from toluene three times and dried under vacuum for 2 h. To a solution of this bromide in THF (90 mL) under $N_2$ at −50° C. was added isopropyl magnesium chloride-lithium chloride complex (1.2 M solution in THF, 37.4 mL, 44.9 mmol, 5 eq) dropwise over 10 minutes. The resulting dark yellow solution was allowed to warm to 0° C. over 1 h. Dimethylformamide (5.57 mL, 71.9 mmol, 8 eq) was added dropwise, and the solution was heated to 40° C. for 1.5 h. The reaction solution was poured into a saturated aqueous $NH_4Cl$ solution (45 mL), water (20 mL), and extracted with EtOAc (2×100 mL). The combined organic layers were dried ($Na_2SO_4$), filtered, and concentrated under reduced pressure. MS (ESI) m/z 393.32 (M−H).

Synthesis of S11-2

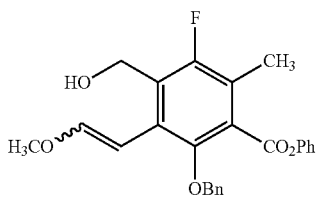

S11-2

A flame-dried flask was cooled under nitrogen and charged with potassium tert-butoxide (1.78 g, 15.8 mmol, 2 eq), evacuated and back-filled with $N_2$, charged with THF (80 mL), and cooled to 0° C. To this solution was added (methoxymethyl)triphenylphosphonium chloride (5.43 g, 15.8 mmol, 2 eq). The resulting red solution was allowed to warm to room temperature for 30 min, and a solution of S11-1 (3.11 g, 7.88 mmol, 1 eq) in THF (15 mL) was added slowly. After 1.5 h, the reaction was diluted with water (45 mL) and extracted with EtOAc (2×75 mL). The combined organic layers were washed with brine, dried ($Na_2SO_4$), filtered, and concentrated under reduced pressure. Purification of the resulting crude oil via flash column chromatography on silica gel (Redisep, 220 g, 5 to 40% EtOAc in hexane gradient) provided 1.57 g and 949 mg of the E and Z isomers of S11-2, respectively (75% total, 1.65:1 E:Z) as yellow oils: [1] H NMR (E-isomer, 400 MHz, $CDCl_3$) δ 7.45-7.30 (m, 7 H), 7.28-7.20 (m, 1 H), 7.14-7.03 (m, 3 H), 5.88 (d, J=13.4 Hz, 1 H), 5.05 (s, 2 H), 4.76 (s, 2 H), 3.63 (s, 3 H), 2.35 (s, 3 H); MS (ESI) m/z 421.37 (E-isomer, M−H); [1] H NMR (Z-isomer, 400 MHz, $CDCl_3$) δ 7.42-7.29 (m, 7 H), 7.04 (d, J=7.3 Hz, 2H), 6.31 (d, J=7.3 Hz, 1 H), 5.48 (d, J=7.3 Hz, 1 H), 4.97 (s, 2 H), 4.65 (s, 2 H), 3.70 (s, 3 H), 2.36 (s, 3 H); MS (ESI) m/z 421.34 (Z-isomer, M−H).

Synthesis of S11-3

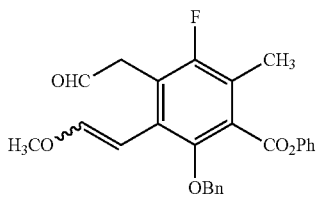

S11-3

To a solution of S11-2 (196 mg, 0.464 mmol, 1 eq) in dichloromethane (4.6 mL) was added Dess-Martin periodinane (239 mg, 0.563 mmol, 1.2 eq). After 1 h, the solution was diluted with saturated aqueous sodium bicarbonate (25 mL) and extracted with EtOAc (2×30 mL). The combined organic layers were washed with saturated aqueous sodium bicarbonate (10 mL), brine (20 mL), dried ($Na_2SO_4$), filtered, and concentrated under reduced pressure. The material was used immediately in the next reaction without further purification or characterization.

Synthesis of S11-4-1

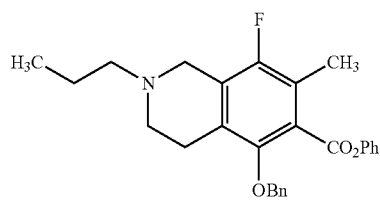

S11-4-1

To the crude compound S11-3 (0.116 mmol) in dichloromethane (1.5 mL) was added acetic acid (33 μL, 0.58 mmol, 5 eq) and propylamine (48 μL, 0.58 mmol, 5 eq) were added. After 50 min, the solution was deep red in color. After 2 h, sodium triacetoxyborohydride (123 mg, 0.58 mmol, 5 eq) was added to the reaction mixture. The solution color faded to yellow. After an additional 17.5 h, the reaction mixture was diluted with saturated aqueous sodium bicarbonate (4 mL) and extracted with EtOAc (2×8 mL). The combined organic layers were washed with brine (3 mL), dried ($Na_2SO_4$), filtered, and concentrated under reduced pressure. Purification of the resulting crude oil via flash column chromatography on silica gel (Biotage, 10 g, 2 to 20% EtOAc in hexane gradient) provided 29 mg of S11-4-1 (57%) as a clear oil: [1] H NMR (400 MHz, $CDCl_3$) δ 7.47-7.40 (m, 2 H), 7.40-7.30 (m, 5 H), 7.27-7.21 (m, 1 H), 7.07 (d, J=7.3 Hz, 2 H), 4.97 (s, 2 H), 3.66 (s, 2 H), 2.99-2.89 (m, 2 H), 2.76-2.63 (m, 2 H), 2.58-2.48 (m, 5 H), 2.38 (s, 3 H) 1.72-1.58 (m, 2 H), 0.97 (d, J=7.3 Hz, 3 H); MS (ESI) m/z 432.40 (M−H).

The following intermediates were prepared according to the methods used to synthesize S11-4-1.

EXAMPLE 104

S11-4-2

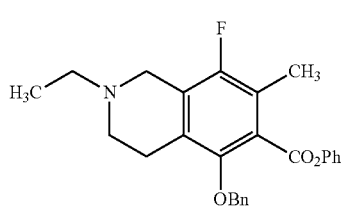

S11-4-2

[1] H NMR (400 MHz, $CDCl_3$) δ 7.48-7.30 (m, 7 H), 7.28-7.21 (m, 1 H), 7.06 (d, J=7.3 Hz, 2 H), 4.97 (s, 2 H), 3.66 (s, 2 H), 2.98-292 (m, 2 H), 2.73-2.60 (m, 4 H), 2.35 (s, 3 H) 1.21 (t, J=7.3 Hz, 3 H); MS (ESI) m/z 418.41 (M−H).

EXAMPLE 105

S11-4-3

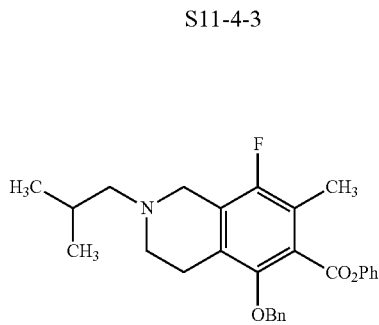

$^1$H NMR (400 MHz, CDCl$_3$) δ 7.47-7.40 (m, 2 H), 7.40-7.30 (m, 5 H), 7.27-7.21 (m, 1 H), 7.07 (d, J=7.3 Hz, 2 H), 4.98 (s, 2 H), 3.61 (s, 2 H), 2.96-2.85 (m, 2 H), 2.70-2.60 (m, 2 H), 2.38-2.25 (m, 5 H), 1.91-1.85 (m, 1 H), 0.95 (d, J=6.1 Hz, 6 H); MS (ESI) m/z 446.40 (M−H).

EXAMPLE 106

S11-4-4

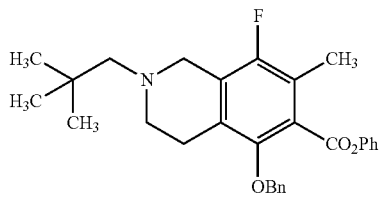

$^1$H NMR (400 MHz, CDCl$_3$) δ 7.45-7.40 (m, 2 H), 7.40-7.30 (m, 5 H), 7.28-7.22 (m, 1 H), 7.07 (d, J=7.3 Hz, 2 H), 5.00 (s, 2 H), 3.73 (s, 2 H), 2.92-2.85 (m, 2 H), 2.79-2.70 (m, 2 H), 2.34 (s, 3 H), 2.28 (s, 2 H), 0.92 (s, 9 H); MS (ESI) m/z 460.41 (M−H).

EXAMPLE 107

S11-4-5

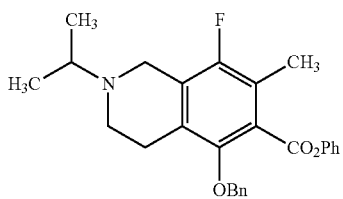

$^1$H NMR (400 MHz, CDCl$_3$) δ 7.48-7.29 (m, 7 H), 7.28-7.20 (m, 1 H), 7.06 (d, J=8.6 Hz, 2 H), 4.97 (s, 2 H), 3.76 (s, 2 H), 3.04-2.87 (m, 3 H), 2.80-2.69 (m, 2 H), 2.35 (s, 3 H), 1.16 (d, J=6.7 Hz, 6 H); MS (ESI) m/z 432.39 (M−H).

EXAMPLE 108

S11-4-6

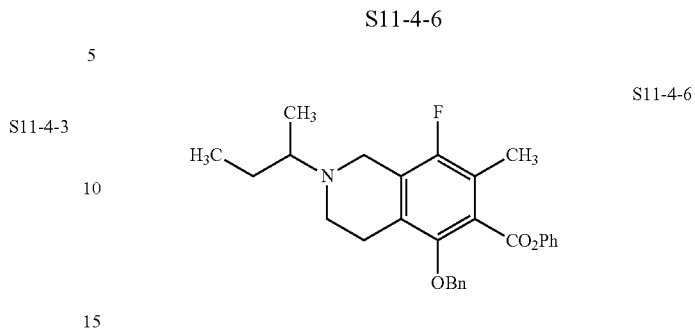

$^1$H NMR (400 MHz, CDCl$_3$) δ 7.48-7.40 (m, 2 H), 7.40-7.29 (m, 5 H), 7.27-7.22 (m, 1 H), 7.07 (d, J=7.3 Hz, 2 H), 4.97 (s, 2 H), 3.85-3.67 (m, 2 H), 3.00-2.85 (m, 2 H), 2.81-2.65 (m, 3 H), 2.34 (s, 3 H), 1.75-1.60 (m, 1 H), 1.49-1.36 (m, 1 H), 1.09 (d, J=6.7 Hz, 3 H), 0.95 (d, J=7.3 Hz, 3 H); MS (ESI) m/z 446.43 (M−H).

EXAMPLE 109

S11-4-7

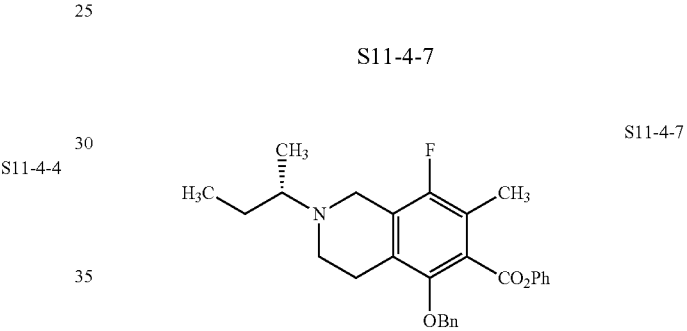

$^1$H NMR (400 MHz, CDCl$_3$) δ 7.48-7.40 (m, 2 H), 7.40-7.29 (m, 5 H), 7.27-7.22 (m, 1 H), 7.07 (d, J=7.3 Hz, 2 H), 4.97 (s, 2 H), 3.85-3.67 (m, 2 H), 3.00-2.85 (m, 2 H), 2.81-2.65 (m, 3 H), 2.34 (s, 3 H), 1.75-1.60 (m, 1 H), 1.49-1.36 (m, 1 H), 1.09 (d, J=6.7 Hz, 3 H), 0.95 (d, J=7.3 Hz, 3 H); MS (ESI) m/z 446.46 (M−H).

EXAMPLE 110

S11-4-8

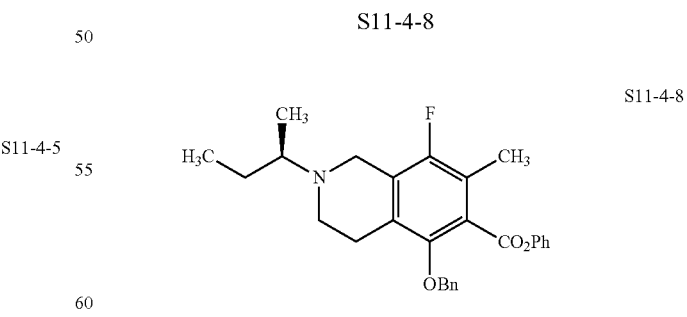

$^1$H NMR (400 MHz, CDCl$_3$) δ 7.48-7.40 (m, 2 H), 7.40-7.29 (m, 5 H), 7.27-7.22 (m, 1 H), 7.07 (d, J=7.3 Hz, 2 H), 4.97 (s, 2 H), 3.85-3.67 (m, 2 H), 3.00-2.85 (m, 2 H), 2.81-2.65 (m, 3 H), 2.34 (s, 3 H), 1.75-1.60 (m, 1 H), 1.49-1.36 (m, 1 H), 1.09 (d, J=6.7 Hz, 3 H), 0.95 (d, J=7.3 Hz, 3 H); MS (ESI) m/z 446.46 (M−H).

EXAMPLE 111

S11-4-9

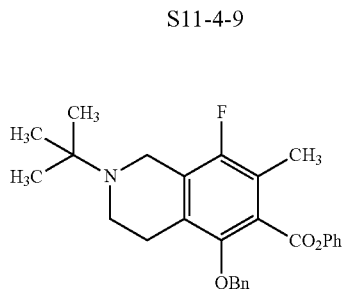

$^1$ H NMR (400 MHz, CDCl$_3$) δ 7.47-7.40 (m, 2 H), 7.40-7.30 (m, 5 H), 7.28-7.22 (m, 1 H), 7.07 (d, J=7.3 Hz, 2 H), 4.97 (s, 2 H), 3.00-2.92 (m, 2 H), 2.81-2.70 (m, 2 H), 2.34 (s, 3 H), 1.20 (s, 9 H); MS (ESI) m/z 446.47 (M−H).

EXAMPLE 112

Compound 304

Synthesis of S11-5-1

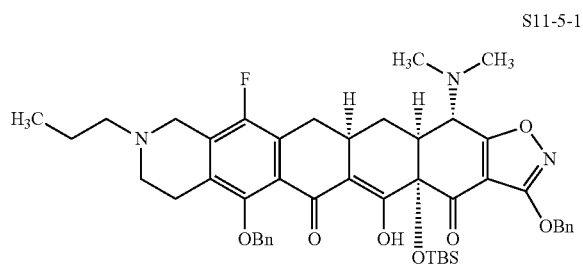 [SMILES: CCCN1CCc2c(c(F)c3c(c2OCc2ccccc2)C(=O)C2=C(O)[C@]4(O[Si](C)(C)C(C)(C)C)C(=O)c5c(OCc6ccccc6)noc5[C@@H](N(C)C)[C@@H]4C[C@@H]2C3)C1]

To a solution of lithium diisopropylamide (1.8 M in hexanes, 73 μL, 0.132 mmol, 2.4 eq) and TMEDA (41 μL, 0.275 mmol, 6 eq) in THF (2 mL) at −78° C. was added a solution of compound S11-4-1 (29 mg, 0.065 mmol, 1.1 eq) in THF (400 μL) by dropwise addition. This resulted in a dark red colored solution. After 10 min, a solution of enone S7-1 (27 mg, 0.055 mmol, 1 eq) in THF (400 μL) was added. After complete addition, the reaction mixture was allowed to warm to −20° C. over 1 h. The reaction was quenched by the addition of ammonium chloride (saturated, aqueous solution, 800 μL) and was extracted with EtOAc (2×30 mL) The combined organic extracts were dried over Na$_2$SO$_4$, filtered, and concentrated under reduced pressure. Purification of the resulting oil via flash column chromatography on silica gel (Biotage, 10 g, 5 to 40% EtOAc in hexanes gradient) provided 25 mg of S11-5-1 (55%): $^1$ H NMR (400 MHz, CDCl$_3$) δ 7.51-7.46 (m, 2 H), 7.46-7.41 (m, 2 H), 7.40-7.29 (m, 6 H), 5.35 (s, 2 H), 4.90-4.75 (m, 2 H), 3.96 (d, J=11.0 Hz, 1 H), 3.80-3.42 (m, 2 H), 3.26-3.16 (m, 1 H), 3.02-2.64 (m, 3 H), 2.62-2.40 (m, 10 H), 2.14 (d, J=14.0 Hz, 1 H), 0.97-0.92 (3 H), 0.89-0.77 (m, 10 H), 0.27 (s, 3 H), 0.12 (s, 3 H); MS (ESI) m/z 820.71 (M−H).

Synthesis of Compound 304

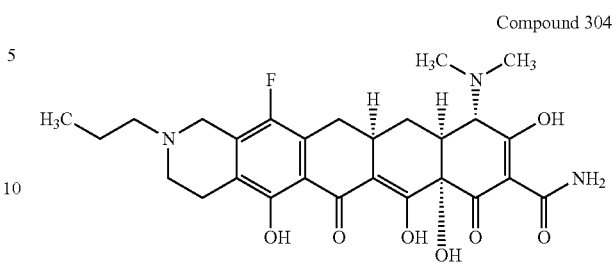

To a solution of S11-5-1 (25 mg, 0.030 mmol, 1 eq) in 1,4-dioxane (1 mL) was added an aqueous solution of HF (50%, 300 μL). After 15.5 h, the reaction mixture was poured into an aqueous K$_2$HPO$_4$ solution (3.6 g in 30 mL) and extracted with EtOAc (2×30 mL). The combined organic layers were dried (Na$_2$SO$_4$), filtered, and concentrated under reduced pressure. Palladium on carbon (10%, 16 mg) was added to a solution of this crude oil in dioxane:MeOH (1:1, 1 mL). The flask was fitted with a septum and evacuated and back-filled three times with hydrogen gas. The reaction was stirred under an atmosphere (balloon) of hydrogen gas for 1 h. The reaction mixture was filtered through Celite to remove the palladium catalyst and concentrated under reduced pressure. Preparative reverse phase HPLC of the resulting oil was performed on a Waters Autopurification system using a Polymerx 10μ RP-γ 100 R column [30×21.20 mm, 10 micron, solvent A: 0.05 N HCl in water, solvent B: Methanol; injection volume: 1.5 mL (0.05 N HCl in water); gradient: 30→70% B over 15 min; mass-directed fraction collection]. Fractions with the desired MW, eluting at 6.0-8.3 min, were collected and freeze-dried to provide 8.4 mg of the desired compound Compound 304 (45%): $^1$ H NMR (400 MHz, CD$_3$OD) δ 4.73-4.62 (m, 1 H), 4.41-4.27 (m, 1 H), 4.10 (s, 1 H), 3.93-3.81 (m, 1 H), 3.43-3.24 (m, 1 H), 3.24-2.88 (m, 13 H), 2.36-2.18 (m, 2 H), 1.97-1.83 (m, 2 H), 1.70-1.54 (m, 1 H), 1.07 (t, J=7.3 Hz, 3 H); MS (ESI) m/z 530.34 (M−H).

The following compounds of Formula IV were prepared according to the methods of Compound 304, using the appropriate N-substituted phenyl 5-(benzyloxy)-8-fluoro-7-methyl-1,2,3,4-tetrahydroisoquinoline-6-carboxylate intermediate in place of S11-4-1

EXAMPLE 113

Compound 307

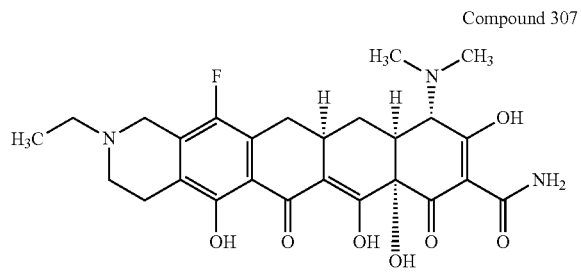 [SMILES: CCN1CCc2c(O)c3c(c(F)c2C1)C[C@H]1C[C@H]2[C@H](N(C)C)C(O)=C(C(N)=O)C(=O)[C@@]2(O)C(O)=C1C3=O]

Prepared from S11-4-2: $^1$ H NMR (400 MHz, CD$_3$OD) δ 4.74-4.62 (m, 1 H), 4.37-4.26 (m, 1 H), 4.09 (s, 1 H), 3.92-3.83 (m, 1 H), 3.49-3.34 (m, 4 H), 3.23-2.92 (m, 10 H), 2.38-2.27 (m, 1 H), 2.26-2.18 (m, 1 H), 1.72-1.58 (m, 1 H), 1.48 (t, J=7.3 Hz, 3H); MS (ESI) m/z 516.31 (M–H).

EXAMPLE 114

Compound 306

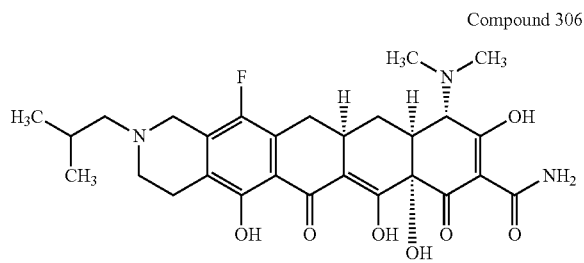 [SMILES: CC(C)CN1CCc2c(O)c3c(c(F)c2C1)C[C@H]1C[C@H]2[C@H](N(C)C)C(O)=C(C(N)=O)C(=O)[C@@]2(O)C(O)=C1C3=O]
Compound 306

Prepared from S11-4-3: $^1$H NMR (400 MHz, CD$_3$OD) δ 4.72-4.61 (m, 1 H), 4.40-4.29 (m, 1 H), 4.08 (s, 1 H), 3.93-3.83 (m, 1 H), 3.42-3.30 (m, 1 H), 3.24-2.92 (m, 13 H), 2.37-2.26 (m, 3 H), 1.70-1.58 (m, 1 H), 1.10 (t, J=6.7 Hz, 6 H); MS (ESI) m/z 544.36 (M–H).

EXAMPLE 115

Compound 306

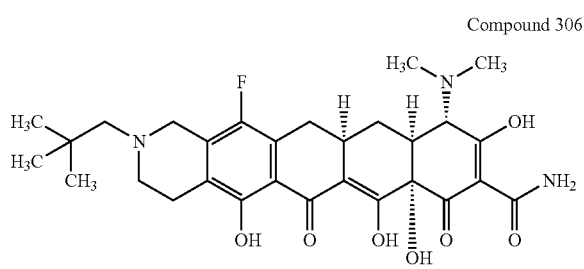 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(CC(C)(C)C)CC5]
Compound 306

Prepared from S11-4-4: $^1$H NMR (400 MHz, CD$_3$OD) δ 4.71-4.61 (m, 1 H), 4.51-4.40 (m, 1 H), 4.09 (s, 1 H), 3.91-3.82 (m, 1 H), 3.59-3.49 (m, 1 H), 3.27-2.92 (m, 12 H), 2.38-2.17 (m, 2 H), 1.71-1.59 (m, 1 H), 1.19 (s, 9 H); MS (ESI) m/z 558.35 (M–H).

EXAMPLE 116

Compound 300

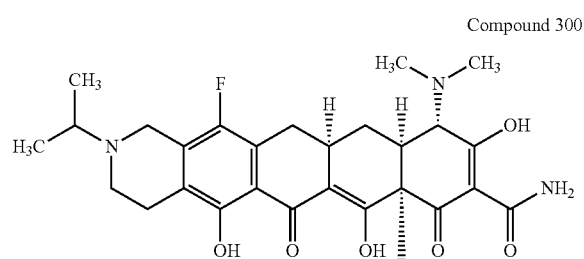
Compound 300

Prepared from S11-4-5: $^1$H NMR (400 MHz, CD$_3$OD) δ 4.57-4.39 (m, 2 H0, 4.09 (s, 1 H), 3.88-3.75 (m, 2 H), 3.39-

3.26 (m, 1 H), 3.24-2.92 (m, 11 H), 2.37-2.18 (m, 2 H), 1.70-1.58 (m, 1 H), 1.48 (d, 5.9 Hz, 6 H); MS (ESI) m/z 530.32 (M–H).

EXAMPLE 117

Compound 301

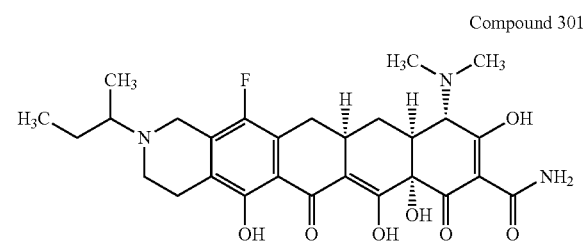 [SMILES: CC[C@H](C)N1CCc2c(O)c3c(c(F)c2C1)C[C@H]1C[C@H]2[C@H](N(C)C)C(O)=C(C(N)=O)C(=O)[C@@]2(O)C(O)=C1C3=O]
Compound 301

Prepared from S11-4-6: $^1$H NMR (400 MHz, CD$_3$OD) δ 4.51-4.41 (m, 2 H), 4.09 (s, 1 H), 3.84-3.74 (m, 1 H), 3.61-3.49 (m, 1 H), 3.43-3.39 (m, 1 H), 3.24-2.89 (m, 11 H), 2.36-2.17 (m, 2 H), 2.06-1.92 (m, 1 H), 1.83-1.57 (m, 2 H), 1.48-1.41 (m, 3 H), 1.09 (t, J=7.3 Hz, 3 H); MS (ESI) m/z 544.36 (M–H).

EXAMPLE 118

Compound 305

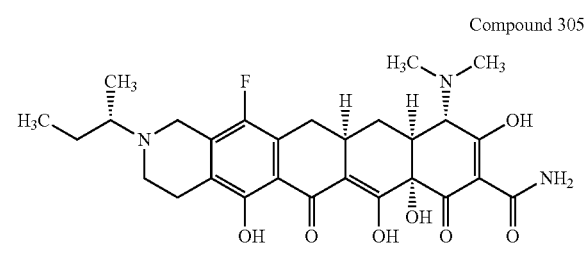
Compound 305

Prepared from S11-4-7: $^1$H NMR (400 MHz, CD$_3$OD) δ 4.56-4.41 (m, 2 H), 4.08 (s, 1 H), 3.84-3.74 (m, 1 H), 3.61-3.50 (m, 1 H), 3.43-3.39 (m, 1 H), 3.24-2.89 (m, 11 H), 2.36-2.17 (m, 2 H), 2.04-1.90 (m, 1 H), 1.81-1.57 (m, 2 H), 1.48-1.40 (m, 3 H), 1.09 (t, J=7.3 Hz, 3 H); MS (ESI) m/z 544.36 (M–H).

EXAMPLE 119

Compound 302

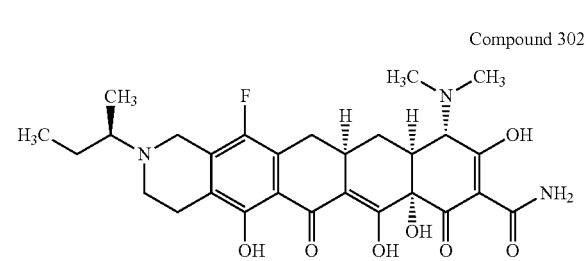 [SMILES: CC[C@@H](C)N1CCc2c(O)c3c(c(F)c2C1)C[C@H]1C[C@H]2[C@H](N(C)C)C(O)=C(C(N)=O)C(=O)[C@@]2(O)C(O)=C1C3=O]
Compound 302

Prepared from S11-4-8: $^1$H NMR (400 MHz, CD$_3$OD) δ 4.56-4.41 (m, 2 H), 4.08 (s, 1 H), 3.84-3.74 (m, 1 H), 3.61-3.52 (m, 1 H), 3.43-3.39 (m, 1 H), 3.24-2.92 (m, 11 H), 2.36-2.17 (m, 2 H), 2.04-1.91 (m, 1 H), 1.81-1.54 (m, 2 H), 1.48-1.40 (m, 3 H), 1.10 (t, J=7.3 Hz, 3 H); MS (ESI) m/z 544.43 (M−H).

EXAMPLE 120

Compound 308

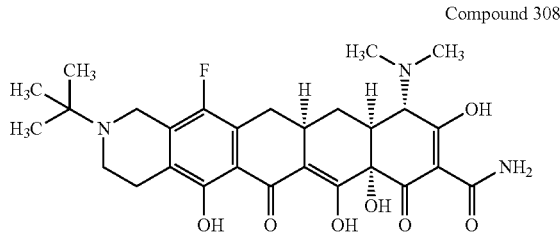 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)C)CC5]

Compound 308

Prepared from S11-4-9: [1] H NMR (400 MHz, CD$_3$OD) δ 4.61-4.37 (m, 2 H), 4.07-3.99 (m, 2 H), 3.27-2.91 (m, 12 H), 2.37-2.18 (m, 2 H), 1.72-1.49 (m, 10 H); MS (ESI) m/z 544.3 (M−H).

EXAMPLE 121

Compound 400

Synthesis of S12-1

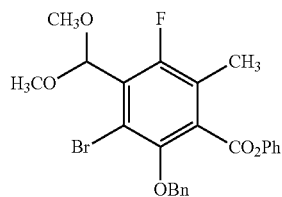

S12-1

To a solution of compound S1-7 (10 g, 22.60 mmol, 1.0 equiv) in MeOH was added trimethylorthoformate (4.8 g, 45.20 mmol, 2.0 equiv) and TsOH.H$_2$O (0.13 g, 0.68 mmol, 0.03 equiv) at rt. The reaction mixture was heated to reflux overnight and concentrated under reduced pressure. The residue was diluted with H$_2$O and extracted with EtOAc. The organic layer was dried over sodium sulfate and evaporated to dryness. The crude product was purified by column chromatography on silica gel (petroleum ether:EtOAc from 100:1 to 30:1) to afford compound S12-1 as a light yellow solid (10 g, 91%): [1] H NMR (400 MHz, CDCl$_3$) δ 7.41-7.45 (m, 2 H), 7.25-7.35 (m, 5 H), 7.16-7.21 (m, 1 H), 6.98 (d, J=8.0 Hz, 2 H), 5.71 (s, 1 H), 5.04 (s, 2 H), 3.46 (s, 6 H), 2.29 (d, J=2.4 Hz, 3 H).

Synthesis of S12-2

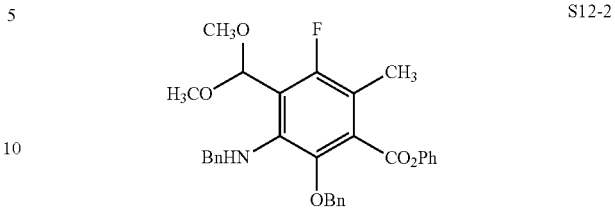

S12-2

To bromide S12-1 (500 mg, 1.02 mmol, 1 eq) in anhydrous 1,4-dioxan1 (5 mL) was added benzylamine (0.165 mL, 1.50 mmol, 1.5 eq), cesium carbonate (0.585 g, 1.80 mmol, 1.8 eq), XantPhos (70 mg, 0.12 mmol, 0.12 eq), and Pd$_2$(dba)$_3$ (20 mg, 0.02 mmol, 0.02 eq). The mixture was sealed, degassed by bubbling dry nitrogen through for 5 min with gentle stirring, and heated at 160° C. in a Biotage microwave reactor for 25 min, and cooled to room temperature. LC/MS analysis indicated complete consumption of the starting material and the appearance of the desired secondary amine S12-2 as the major product.

A total of 2.45 g of bromide S12-1 was processed in 500 mg batches per the above procedure. The reaction mixtures were combined, diluted with saturated aqueous sodium bicarbonate (100 mL), and extracted with EtOAc (200 mL×1, 50 mL×2). The EtOAc extracts were combined, dried over sodium sulfate, and concentrated under reduced pressure. Flash column chromatography on silica gel using 0% to 10% EtOAc/hexane yielded the desired product S12-2 as an orange oil (1.68 g, 65%): R$_f$ 0.70 (20% EtOAc/hexane); [1] H NMR (400 MHz, CDCl$_3$) δ 7.20-7.45 (m, 13 H), 7.05 (d, J=8.6 Hz, 2 H), 5.55 (s, 1 H), 5.24 (br t, J=6.1 Hz, 1 H), 5.14 (s, 2 H), 4.43 (d, J=6.1 Hz, 2 H), 3.37 (s, 6 H), 2.26 (s, 3 H); MS (ESI) m/z 516.3 (M+H), calcd for C$_{31}$H$_{31}$FNO$_5$ 516.2.

Synthesis of S12-3

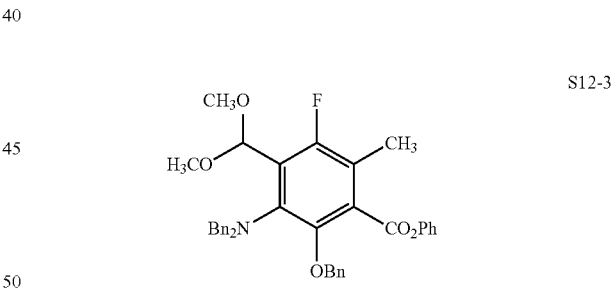

S12-3

To secondary amine S12-1 (1.47 g, 2.85 mmol, 1 eq) in anhydrous DMF (6 mL) was added NaH (250 mg, 60% in mineral oil, 6.30 mmol, 2.2 eq). The yellow suspension was stirred at rt for 30 min. NaI (43 mg, 0.28 mmol, 0.1 eq) and benzyl bromide (0.82 mL, 6.90 mmol, 2.4 eq) were added. The reaction (deep-orange) was stirred at rt for 24 h, diluted with EtOAc (100 mL), washed with saturated aqueous sodium bicarbonate (100 mL×2) and brine (50 mL×1), dried over sodium sulfate, and concentrated in under reduced pressure. Flash column chromatography on silica gel using 0% to 10% EtOAc/hexane yielded the desired tertiary amine S12-3 as a pale oil (1.16 g, 67%): R$_f$ 0.33 (10% EtOAc/hexane); [1] H NMR (400 MHz, CDCl$_3$) δ 7.20-7.40 (m, 18 H), 6.99 (d, J=8.0 Hz, 2 H), 5.72 (s, 1 H), 4.68 (s, 2 H), 4.20-4.40 (br m, 4 H), 3.32 (s, 6 H), 2.34 (s, 3 H); MS (ESI) m/z 606.3 (M+H), calcd for C$_{38}$H$_{37}$FNO$_5$ 606.3.

The compound was contaminated with the corresponding benzyl ester (instead of phenyl ester), which was not removed prior to the next step.

Synthesis of S12-4

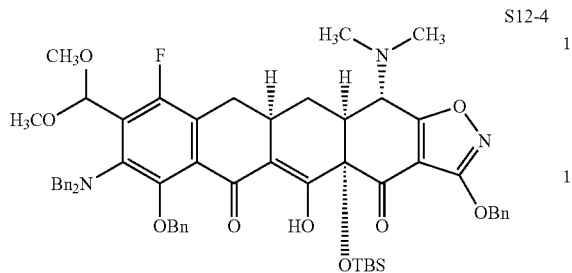

The diisopropylamine (0.30 mL, 2.12 mmol, 1.1 eq) in anhydrous THF (10 mL) at −78° C. was added n-BuLi (1.33 mL, 1.6 M/hexane, 2.12 mmol, 1.1 eq) dropwise. The pale solution was stirred at 0° C. for 30 min and cooled to −78° C. TMEDA (0.35 mL, 2.33 mmol, 1.2 eq) was added, followed by the addition of compound S12-3 (1.16 g, 1.92 mmol, 1 eq, in 30 mL THF) dropwise over a period of 5 min. The deep-red solution was stirred at −78° C. for 30 min LHMDS (2.12 mL, 1.0 M/THF, 1.1 eq) was added, followed by the addition of enone S7-1 (0.96 g, 1.92 mmol, in 10 mL THF) dropwise over a period of 2 min. The resulting yellow solution was slowly warm up to 0° C. over a period of 3 h, diluted with EtOAc (200 mL) and saturated aqueous sodium bicarbonate (100 mL). The EtOAc layer was collected. The aqueous layer was extracted with more EtOAc (50 mL×2). The combined EtOAc solution was dried over sodium sulfate and concentrated in under reduced pressure. Flash column chromatography on silica gel using 0% to 15% EtOAc/hexane yielded the desired product as a yellow solid (0.77 g, 40%): $R_f$ 0.50 (20% EtOAc/hexane); $^1$H NMR (400 MHz, CDCl$_3$) δ 15.82 (s, 1H), 7.00-7.50 (m, 20 H), 5.79 (s, 1 H), 5.38 (s, 2 H), 5.04 (d, J=10.4 Hz, 1 H), 4.50 (d, J=10.4 Hz, 1 H), 4.00-4.40 (m, 4 H), 3.95 (d, J=10.4 Hz, 1 H), 3.35 (s, 3 H), 3.20-3.30 (m, 3 H), 3.13 (s, 3 H), 2.95-3.05 (m, 1 H), 2.55-2.65 (m, 1 H), 2.50 (s, 6 H), 2.15-2.20 (m, 1 H), 0.85 (s, 9 H), 0.30 (s, 3 H), 0.14 (s, 3 H); MS (ESI) m/z 994.5 (M+H), calcd for $C_{58}H_{65}FN_3O_9Si$ 994.6.

0.52 g of compound S12-3 was also recovered.

Synthesis of S12-5

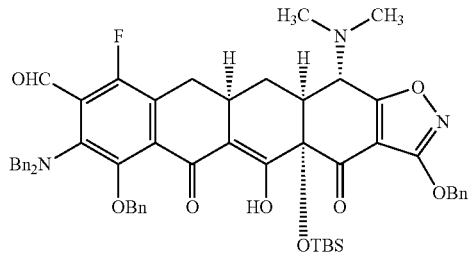

To compound S12-4 (0.77 g, 0.78 mmol, 1 eq) in THF (10 mL) was added 3 N HCl/water (2 mL, final [HCl]=0.5 M). The deep yellow solution was stirred at rt for 2 h, diluted with EtOAc (100 mL), washed with saturated aqueous sodium bicarbonate (100 mL×2) and brine (50 mL×1), dried over sodium sulfate, and concentrated in under reduced pressure to yield the crude product as a deep-orange solid (0.72 g, 97%): MS (ESI) m/z 948.4 (M+H), calcd for $C_{56}H_{59}FN_3O_8Si$ 948.4.

Synthesis of S12-7-1

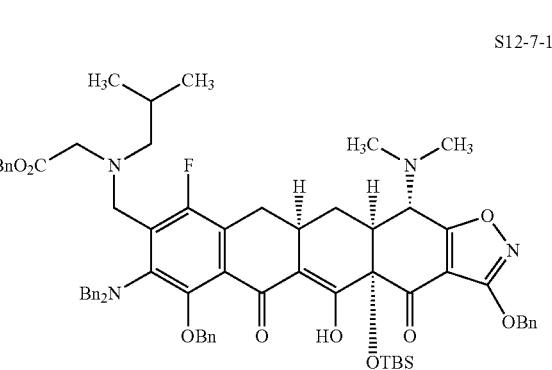

To aldehyde S12-5 (95 mg, 0.10 mmol, 1 eq) in 1,2-dichloroethane (2 mL) was added glycine benzyl ester (50 mg, TsOH salt, 0.15 mmol, 1.5 eq), triethylamine (0.022 mL, 0.16 mmol, 1.6 eq), HOAc (0.024 mL, 0.42 mmol, 4 eq), and Na(OAc)$_3$BH (32 mg, 0.15 mmol, 1.5 eq). The deep-red solution became yellow and was stirred at rt for 1 h. Isobutyraldehyde (0.032 mL, 0.35 mmol, 3.5 eq) and Na(OAc)$_3$BH (82 mg, 0.40 mmol, 4 eq) were added. The reaction was stirred at rt for 1 h, diluted with EtOAc (20 mL), washed with saturated aqueous sodium bicarbonate (10 mL×1) and brine (10 mL×1), dried over sodium sulfate, and concentrated in under reduced pressure to yield the crude product (S12-7-1) as a yellow residue: MS (ESI) m/z 1153.5 (M+H), calcd for $C_{69}H_{78}FN_4O_9Si$ 1153.6.

Synthesis of S12-8-1

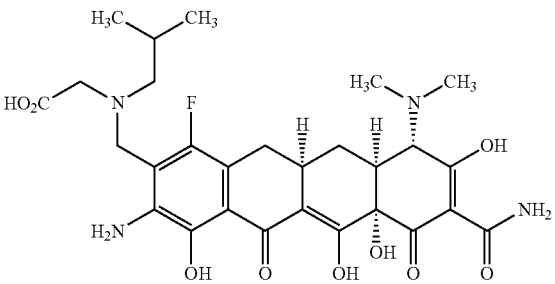

Crude compound S12-7-1 was dissolved in THF (1.5 mL) and added with 50% HF/water (0.5 mL). The yellow solution was stirred at rt for 2 h and added into K$_2$HPO$_4$/water (5 g in 20 mL water) with stirring. The mixture was extracted with EtOAc (20 mL×3). The EtOAc extracts were combined, dried over sodium sulfate, and concentrated in under reduced pressure to yield the crude product as a yellow residue: MS (ESI) m/z 1039.5 (M+H), calcd for $C_{63}H_{63}FN_4O_9$ 1038.5.

The above crude product (0.10 mmol, 1 eq) was dissolved in methanol (3 mL) and 1,4-dioxane (1 mL). 10% Pd—C (21 mg, 0.01 mmol, 0.1 eq) and 0.5 N HCl/methanol (1 mL) were added. The mixture was purged with hydrogen and stirred under 1 atm hydrogen at rt for 1 h. The catalyst was filtered off with a small Celite pad and washed with methanol (2 mL×3). The yellow methanol solution was concentrated in under reduced pressure to afford the crude product, which was purified with HPLC to yield the desired product S12-8-1) as a yellow solid (26 mg, HCl salt, 37% overall): $^1$H NMR (400 MHz, CD$_3$OD) δ 4.52 (s, 2 H), 4.08 (s, 1 H), 4.02 (s, 2 H), 2.90-3.50 (m, 8H), 2.10-2.30 (m, 3 H), 1.55-1.70 (m, 1 H), 1.00 (d, J=6.1 Hz, 6 H): MS (ESI) m/z 591.4 (M+H), calcd for C$_{28}$H$_{36}$FN$_4$O$_9$ 591.3.

Synthesis of Compound 400

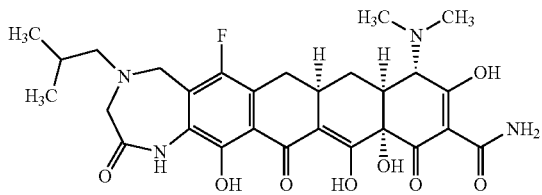

Compound 400

The above amino acid S12-8-1 (20 mg, HCl salt, 0.029 mmol, 1 eq) was dissolved in anhydrous DMF (5 mL) DIEA (0.0067 mL, 0.039 mmol, 1.3 eq) and DCC (12 mg, 0.058 mmol, 2 eq) were added. The reaction was stirred at rt for 24 h. 0.5 N HCl/methanol (0.5 mL) was added. The reaction mixture was added dropwise into ether (500 mL) with vigorous stirring. The yellow precipitates were collected onto a small Celite pad, washed with more ether (10 mL×3), and eluted with methanol (10 mL×3). The yellow methanol solution was concentrated in under reduced pressure to afford the crude product, which was purified by HPLC to yield the desired product Compound 400 as an orange solid (8 mg, 43%): $^1$H NMR (400 MHz, CD$_3$OD) δ 4.52 (s, 2 H), 4.10 (s, 1 H), 3.86 (br s, 2 H), 2.90-3.50 (m, 8 H), 2.37 (t, J=14.6 Hz, 1 H), 2.15-2.30 (m, 2H), 1.60-1.70 (m, 1 H), 1.08 (d, J=6.7 Hz, 6 H); MS (ESI) m/z 573.5 (M+H), calcd for C$_{28}$H$_{34}$FN$_4$O$_8$ 573.2.

The following compounds were prepared similarly to Compound 400 using the appropriate intermediate S12-6 or S12-7.

EXAMPLE 122

Compound 426

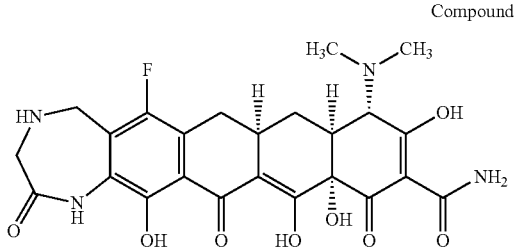

Compound 426

$^1$H NMR (400 MHz, CD$_3$OD) δ 4.43 (s, 2 H), 4.10 (s, 1 H), 3.80 (s, 2 H), 2.90-3.40 (m, 9 H), 2.31-2.41 (m, 1 H), 2.22-2.30 (m, 1 H), 1.60-1.72 (m, 1 H); MS (ESI) m/z 517.4 (M+H), calcd for C$_{24}$H$_{26}$FN$_4$O$_8$ 517.2.

EXAMPLE 123

Compound 416

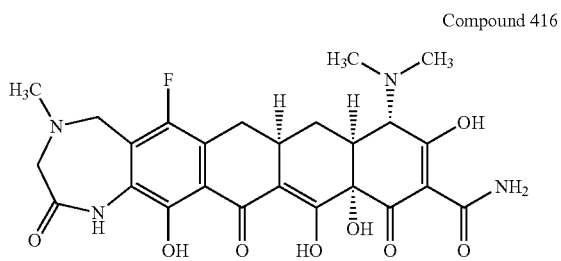 [SMILES: CN1CC(=O)Nc2c(O)c3c(c(F)c2C1)C[C@H]1C[C@H]2[C@H](N(C)C)C(O)=C(C(N)=O)C(=O)[C@@]2(O)C(O)=C1C3=O]

Compound 416

$^1$H NMR (400 MHz, CD$_3$OD) δ 4.53 (br s, 2 H), 4.17 (s, 1 H), 3.87 (br, s, 2 H), 2.90-3.30 (m, 12 H), 2.32-2.42 (m, 1 H), 2.23-2.30 (m, 1 H), 1.60-1.72 (m, 1 H); MS (ESI) m/z 531.3 (M+H), calcd for C$_{25}$H$_{28}$FN$_4$O$_8$ 531.2.

EXAMPLE 124

Compound 403

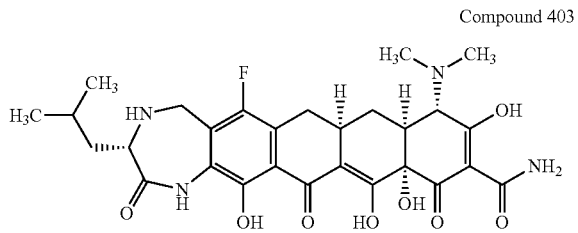 [SMILES: CC(C)C[C@@H]1NCc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3]

Compound 403

$^1$H NMR (400 MHz, CD$_3$OD) δ 4.65 (d, J=14.4 Hz, 1 H), 4.05-4.15 (m, 2 H), 3.80 (dd, J=4.3, 9.8 Hz, 1 H), 2.90-3.30 (m, 9 H), 2.32-2.42 (m, 1 H), 2.23-2.30 (m, 1H), 2.10-2.20 (m, 1 H), 1.60-1.73 (m, 2 H), 1.38-1.45 (m, 1 H), 0.92 (d, J=6.7 Hz, 3H), 0.87 (d, J=6.7 Hz, 3 H); MS (ESI) m/z 573.4 (M+H), calcd for C$_{28}$H$_{34}$FN$_4$O$_8$ 573.2.

EXAMPLE 125

Compound 411

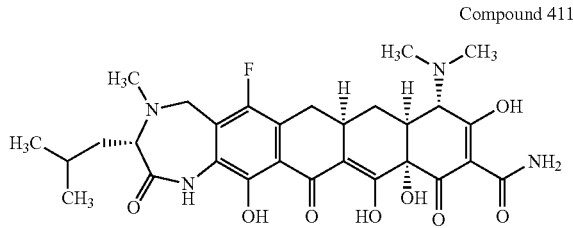 [SMILES: CC(C)C[C@H]1C(=O)Nc2c(O)c3c(c(F)c2CN1C)C[C@H]1C[C@H]2[C@H](N(C)C)C(O)=C(C(N)=O)C(=O)[C@@]2(O)C(O)=C1C3=O]

Compound 411

$^1$H NMR (400 MHz, CD$_3$OD) δ 4.22 (br s, 1 H), 4.11 (s, 1 H), 3.96 (br s, 1 H), 2.95-3.45 (m, 12 H), 2.35-2.45 (m, 1 H), 2.20-2.30 (m, 2 H), 1.61-1.72 (m, 1 H), 1.52-1.60 (m, 1 H), 1.42-1.50 (m, 1 H), 0.93 (d, J=6.7 Hz, 3 H), 0.85 (d, J=6.7 Hz, 3 H); MS (ESI) m/z 587.5 (M+H), calcd for C$_{29}$H$_{36}$FN$_4$O$_8$ 587.2.

EXAMPLE 126

Compound 419

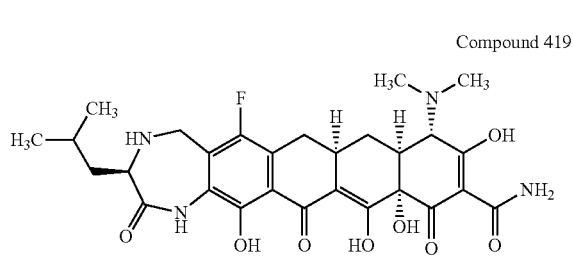 [SMILES: CC(C)C[C@H]1NCc2c(F)c3c(c(O)c2NC1=O)C(=O)C1=C(O)[C@]2(O)C(=O)C(C(N)=O)=C(O)[C@@H](N(C)C)[C@@H]2C[C@@H]1C3]

$^1$H NMR (400 MHz, CD$_3$OD) δ 4.66 (d, J=14.0 Hz, 1 H), 4.11 (s, 1 H), 4.09 (d, J=14.0 Hz, 1 H), 3.78 (dd, J=4.3, 9.2 Hz, 1 H), 2.85-3.30 (m, 9 H), 2.30-2.42 (m, 1H), 2.21-2.30 (m, 1 H), 2.10-2.20 (m, 1 H), 1.58-1.70 (m, 2 H), 1.37-1.46 (m, 1 H), 0.91 (d, J=6.7 Hz, 3 H), 0.85 (d, J=6.7 Hz, 3 H); MS (ESI) m/z 573.3 (M+H), calcd for C$_{28}$H$_{34}$FN$_4$O$_8$ 573.2.

EXAMPLE 127

Compound 428

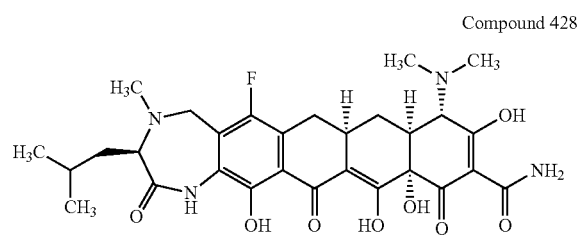 [SMILES: CC(C)C[C@@H]1C(=O)Nc2c(O)c3c(c(F)c2CN1C)C[C@H]1C[C@H]2[C@H](N(C)C)C(O)=C(C(N)=O)C(=O)[C@@]2(O)C(O)=C1C3=O]

$^1$H NMR (400 MHz, CD$_3$OD) δ 4.20 (br s, 1 H), 4.11 (s, 1 H), 3.85 (br s, 1 H), 2.95-3.30 (m, 12 H), 2.35-2.45 (m, 1 H), 2.20-2.30 (m, 2 H), 1.61-1.72 (m, 1 H), 1.52-1.60 (m, 1 H), 1.43-1.51 (m, 1 H), 0.93 (d, J=6.7 Hz, 3 H), 0.85 (d, J=6.7 Hz, 3 H); MS (ESI) m/z 587.3 (M+H), calcd for C$_{29}$H$_{36}$FN$_4$O$_8$ 587.2.

EXAMPLE 128

Compound 410

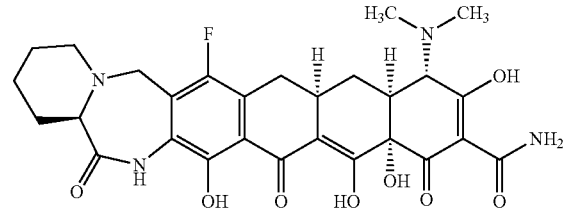

$^1$H NMR (400 MHz, CD$_3$OD) δ 4.58 (d, J=13.6 Hz, 1 H), 4.40 (d, J=14.4 Hz, 1 H), 4.12 (s, 1 H), 3.81 (d, J=9.2 Hz, 1 H), 4.41 (d, J=9.2 Hz, 1 H), 3.17-2.99 (m, 10H), 2.43-2.35 (m, 1 H), 2.29-2.26 (m, 1 H), 2.05-1.89 (m, 6 H), 1.69-1.65 (m, 1 H); MS (ESI) m/z 571.1 (M+H), calcd for C$_{28}$H$_{32}$FN$_4$O$_8$ 571.2.

EXAMPLE 129

Compound 418

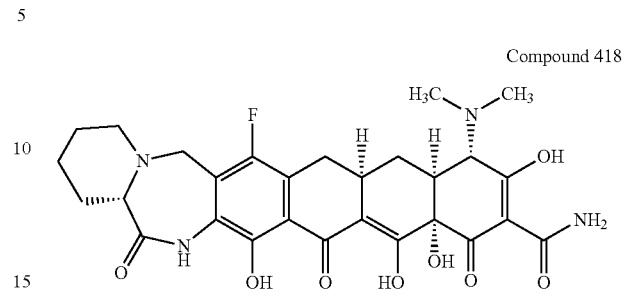

$^1$H NMR (400 MHz, CD$_3$OD) δ 4.55 (d, J=14.4 Hz, 1 H), 4.41 (d, J=14.4 Hz, 1 H), 4.14 (s, 1 H), 3.83 (d, J=10.4 Hz, 1 H), 4.41 (d, J=10.4 Hz, 1 H), 3.13-2.98 (m, 10 H), 2.43-2.36 (m, 1 H), 2.29-2.26 (m, 1 H), 1.99-1.90 (m, 6 H), 1.72-1.61 (m, 1 H); MS (ESI) m/z 571.1 (M+H), calcd for C$_{28}$H$_{32}$FN$_4$O$_8$ 571.2.

EXAMPLE 130

Compound 401

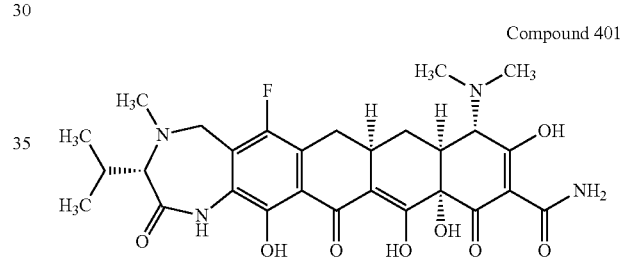

$^1$H NMR (400 MHz, CD$_3$OD) δ 4.13 (s, 1 H), 3.86 (d, J=8.4 Hz, 1 H), 3.22-2.99 (m, 13 H), 2.41-2.15 (m, 3 H), 1.68-1.62 (m, 1 H), 1.06 (d, J=6.4 Hz, 3 H), 0.99 (d, J=4.4 Hz, 3 H); MS (ESI) m/z 573.0 (M+H), calcd for C$_{28}$H$_{34}$FN$_4$O$_8$ 573.2.

EXAMPLE 131

Compound 402

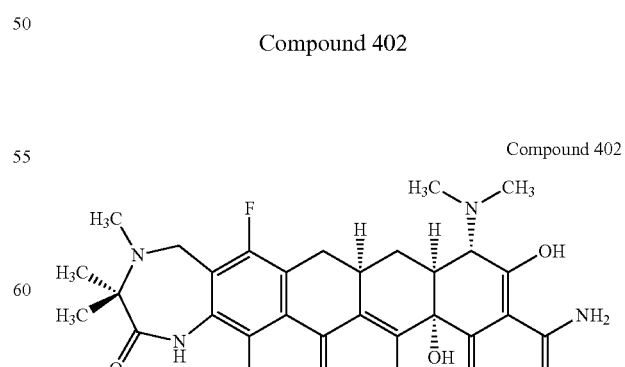

$^1$H NMR (400 MHz, CD$_3$OD) δ 4.58 (s, 2 H), 4.12 (s, 1 H), 3.21-2.86 (m, 13 H), 2.42-2.34 (m, 1 H), 2.27-2.18 (m, 1 H), 1.74-1.62 (m, 1 H), 1.30 (s, 6 H); MS (ESI) m/z 559.1 (M+H), calcd for C$_{27}$H$_{32}$FN$_4$O$_8$ 559.2.

EXAMPLE 132

Compound 422

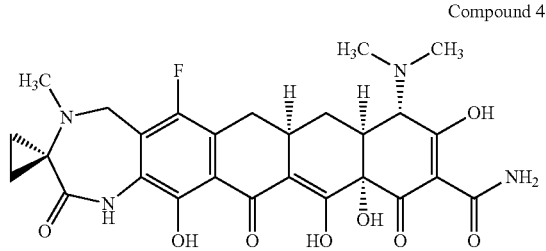
Compound 422

$^1$H NMR (400 MHz, CD$_3$OD) δ 4.64-4.63 (m, 2 H), 4.12 (s, 1 H), 3.21-2.98 (m, 12 H), 2.40-2.33 (m, 1 H), 2.28-2.25 (m, 1 H), 1.71-1.62 (m, 1 H), 1.32-1.29 (m, 4 H); MS (ESI) m/z 557.0 (M+H), calcd for C$_{27}$H$_{30}$FN$_4$O$_8$ 557.2.

EXAMPLE 133

Compound 425

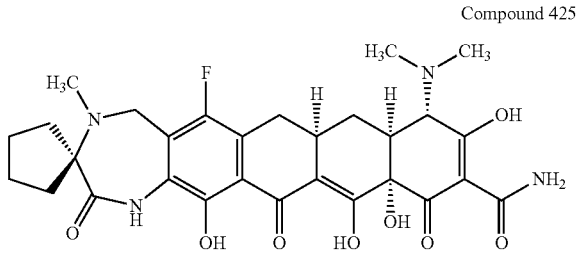
Compound 425

$^1$H NMR (400 MHz, CD$_3$OD) δ 4.57 (s, 2 H), 4.11 (s, 1 H), 3.06-2.98 (m, 12 H), 2.43-2.25 (m, 3 H), 1.84-1.55 (m, 6 H), 1.32-1.29 (m, 2 H); MS (ESI) m/z 585.1 (M+H), calcd for C$_{29}$H$_{34}$FN$_4$O$_8$ 585.2.

EXAMPLE 134

Compound 407

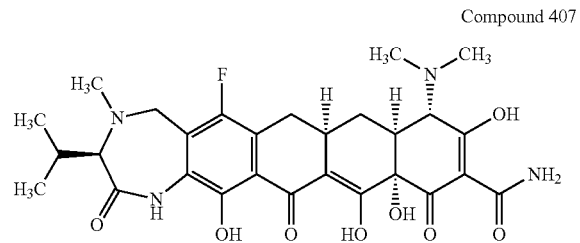 [SMILES: CC(C)[C@@H]1C(=O)Nc2c(O)c3c(c(F)c2CN1C)C[C@H]1C[C@H]2[C@H](N(C)C)C(O)=C(C(N)=O)C(=O)[C@@]2(O)C(O)=C1C3=O]
Compound 407

$^1$H NMR (400 MHz, CD$_3$OD) δ 4.12 (s, 1 H), 3.83 (d, J=8.4 Hz, 1 H), 3.35-2.84 (m, 14 H), 2.40-2.33 (m, 3 H), 1.71-1.61 (m, 1 H), 1.07-1.06 (d, J=6.4 Hz, 3 H), 0.99 (d, J=6.4 Hz, 3 H); MS (ESI) m/z 573.0 (M+H), calcd for C$_{28}$H$_{34}$FN$_4$O$_8$ 573.2.

EXAMPLE 135

Compound 413

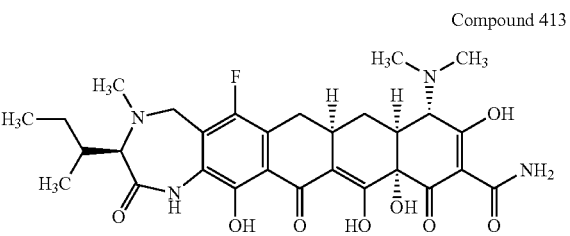 [SMILES: CCC(C)[C@@H]1C(=O)Nc2c(O)c3c(c(F)c2CN1C)C[C@H]1C[C@H]2[C@H](N(C)C)C(O)=C(C(N)=O)C(=O)[C@@]2(O)C(O)=C1C3=O]
Compound 413

$^1$H NMR (400 MHz, CD$_3$OD) δ 4.11 (s, 1 H), 3.85 (d, J=10.0 Hz, 1 H), 3.24-2.91 (m, 14 H), 2.40-2.16 (m, 3 H), 1.70-1.56 (m, 2 H), 1.07-1.06 (m, 1 H), 0.98-0.83 (m, 6 H); MS (ESI) m/z 587.1 (M+H), calcd for C$_{29}$H$_{36}$FN$_4$O$_8$ 581.2.

EXAMPLE 136

Compound 424

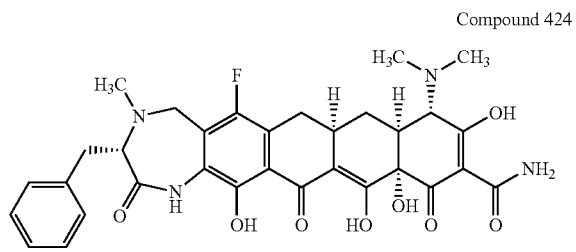 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C)[C@@H](Cc1ccccc1)C(=O)N5]
Compound 424

$^1$H NMR (400 MHz, CD$_3$OD) δ 7.26-7.25 (m, 5 H), 4.23-4.14 (m, 2 H), 4.09 (s, 1 H), 3.53 (t, J=10.8 Hz, 1 H), 3.14-2.97 (m, 14 H), 2.39-2.23 (m, 2 H), 1.67-1.60 (m, 1 H); MS (ESI) m/z 621.0 (M+H), calcd for C$_{32}$H$_{34}$FN$_4$O$_8$ 621.2.

EXAMPLE 137

Compound 421

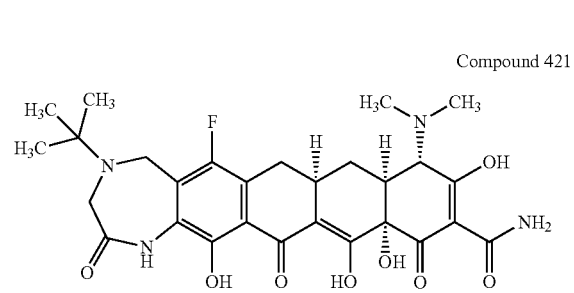 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)C)CC(=O)N5]
Compound 421

¹H NMR (400 MHz, CD₃OD) δ 4.45 (s, 2 H), 4.02 (s, 1 H), 3.89 (s, 2 H), 3.04-2.87 (m, 9 H), 2.60-2.52 (m, 1 H), 2.31-2.14 (m, 2 H), 1.49 (s, 9 H); MS (ESI) m/z 573.2 (M+H), calcd for C₂₈H₃₄FN₄O₈ 573.2.

EXAMPLE 138

Compound 415

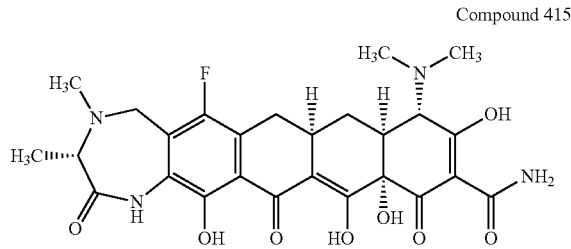 [SMILES: C[C@H]1C(=O)Nc2c(O)c3c(c(F)c2CN1C)C[C@H]1C[C@H]2[C@H](N(C)C)C(O)=C(C(N)=O)C(=O)[C@@]2(O)C(O)=C1C3=O]
Compound 415

¹H NMR (400 MHz, CD₃OD) δ 4.11 (s, 1 H), 3.36-3.25 (m, 5 H), 3.05-2.97 (m, 9 H), 2.48-2.36 (m, 1 H), 2.27-2.24 (m, 1 H), 1.74-1.62 (m, 1 H), 1.48 (d, J=6.0 Hz, 3H); MS (ESI) m/z 545.0 (M+H), calcd for C₂₆H₃₀FN₄O₈ 545.2.

EXAMPLE 139

Compound 406

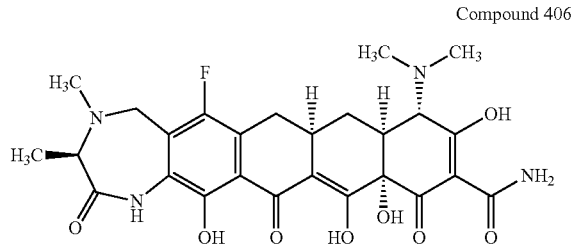 [SMILES: C[C@@H]1C(=O)Nc2c(O)c3c(c(F)c2CN1C)C[C@H]1C[C@H]2[C@H](N(C)C)C(O)=C(C(N)=O)C(=O)[C@@]2(O)C(O)=C1C3=O]
Compound 406

¹H NMR (400 MHz, CD₃OD) δ 4.12 (s, 1 H), 3.25-2.86 (m, 14 H), 2.43-2.25 (m, 2 H), 1.71-1.61 (m, 1 H), 1.49 (d, J=6.0 Hz, 3 H); MS (ESI) m/z 545.0 (M+H), calcd for C₂₆H₃₀FN₄O₈ 545.2.

EXAMPLE 140

Compound 423

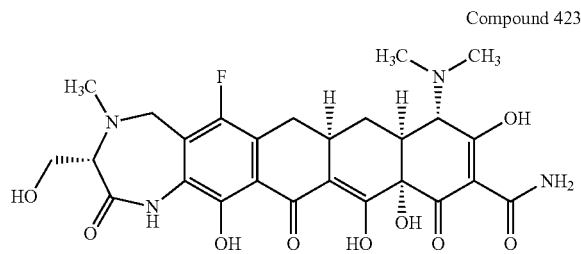 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C)[C@@H](CO)C(=O)N5]
Compound 423

¹H NMR (400 MHz, CD₃OD) δ 4.11 (s, 3 H), 3.90 (d, J=7.6 Hz, 1 H), 3.25-2.97 (m, 14 H), 2.41-2.25 (m, 2H), 1.71-1.61 (m, 1H); MS (ESI) m/z 561.4 (M+H), calcd for C₂₆H₃₀FN₄O₉ 561.2.

EXAMPLE 141

Compound 420

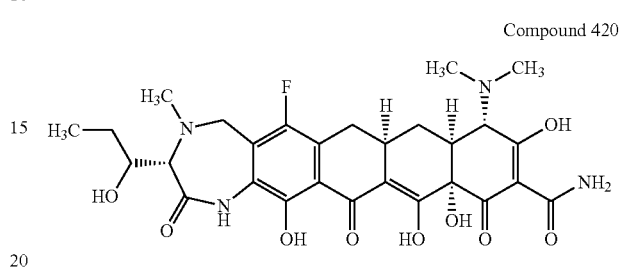
Compound 420

¹H NMR (400 MHz, CD₃OD) δ 4.09 (s, 1 H), 3.85 (d, J=9.6 Hz, 1 H), 3.19-2.95 (m, 12 H), 2.39-2.32 (m, 2 H), 2.24-2.19 (m, 1 H), 1.69-1.52 (m, 4 H), 1.51-1.28 (m, 1 H), 1.16-1.14 (m, 2 H), 0.97-0.95 (m, 6 H); MS (ESI) m/z 587.3 (M+H), calcd for C₂₉H₃₆FN₄O₈ 587.2.

EXAMPLE 142

Compound 409

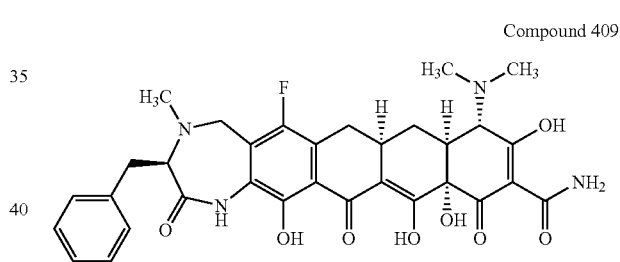
Compound 409

¹H NMR (400 MHz, CD₃OD) δ 7.26-7.25 (m, 5 H), 4.17-4.11 (m, 3 H), 3.53 (t, J=10.8 Hz, 1 H), 3.15-2.97 (m, 14 H), 2.38-2.24 (m, 2H), 1.66-1.63 (m, 1H); MS (ESI) m/z 621.0 (M+H), calcd for C₃₂H₃₄FN₄O₈ 621.2.

EXAMPLE 143

Compound 405

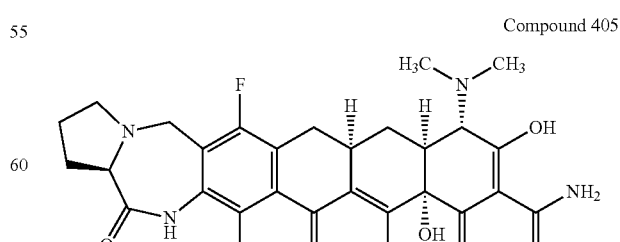
Compound 405

¹H NMR (400 MHz, CD₃OD) δ 4.51 (d, J=12.8 Hz, 1 H), 4.20 (d, J=12.8 Hz, 1 H), 4.11 (s, 1 H), 3.84 (t, J=11.2 Hz, 1

H), 3.21-2.81 (m, 11 H), 2.37-2.33 (m, 4 H), 2.06-2.04 (m, 2 H), 1.71-1.64 (m, 1H); MS (ESI) m/z 557.3 (M+H), calcd for $C_{27}H_{30}FN_4O_8$ 557.2.

EXAMPLE 144

Compound 412

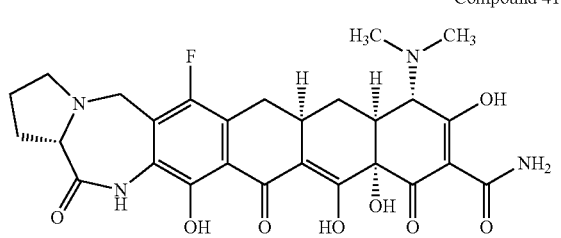

Compound 412

$^1$ H NMR (400 MHz, CD$_3$OD) δ 4.48-4.46 (m, 1H), 4.18 (d, J=13.6 Hz, 1H), 4.12 (s, 1 H), 3.86-3.83 (m, 1 H), 3.35-3.29 (m, 2 H), 3.24-2.97 (m, 9 H), 2.81-2.77 (m, 2 H), 2.38-2.24 (m, 3 H), 2.12-2.01 (m, 2 H), 1.66 (m, 1 H); MS (ESI) m/z 557.0 (M+H), calcd for $C_{27}H_{30}FN_4O_8$ 557.2.

EXAMPLE 145

Compound 404

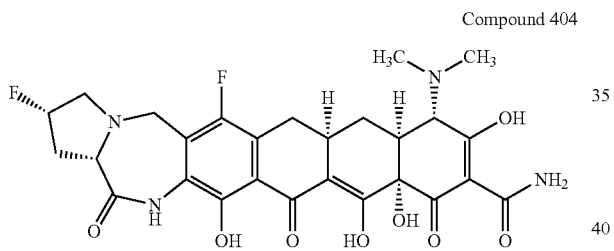

Compound 404

$^1$ H NMR (400 MHz, CD$_3$OD) δ 5.52, 5.40 (m, 1 H Total), 4.63 (d, J=14.0 Hz, 1H), 4.52 (d, J=14.0 Hz, 1 H), 4.10 (s, 1 H), 4.06-3.97 (m, 1 H), 3.86-3.81 (m, 1 H), 3.04-2.96 (m, 10 H), 2.60-2.48 (m, 1 H), 2.49-2.26 (m, 3 H), 1.69-1.59 (m, 1 H); MS (ESI) m/z 575.1 (M+H), calcd for $C_{27}H_{29}F_2N_4O_8$ 575.2.

EXAMPLE 146

Compound 414

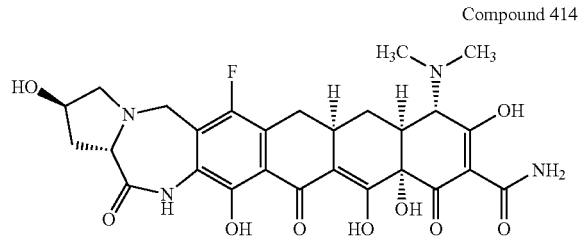 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN1C[C@H](O)C[C@H]1C(=O)N5]

Compound 414

$^1$ H NMR (400 MHz, CD$_3$OD) δ 4.72-4.62 (m, 2 H), 4.28-4.17 (m, 1 H), 4.12 (s, 1 H), 3.75-3.67 (m, 1 H), 3.49-3.40 (m, 1 H), 3.28-2.94 (m, 10 H), 2.42-2.33 (m, 1 H), 2.31-2.22 (m, 1 H), 2.09-1.99 (m, 1 H), 1.71-1.60 (m, 1 H), 1.39-1.34 (m, 1 H); MS (ESI) m/z 573.1 (M+H), calcd for $C_{27}H_{30}F_2N_4O_9$ 573.2.

EXAMPLE 147

Compound 417: $^1$ H NMR (400 MHz, CD$_3$OD) δ 4

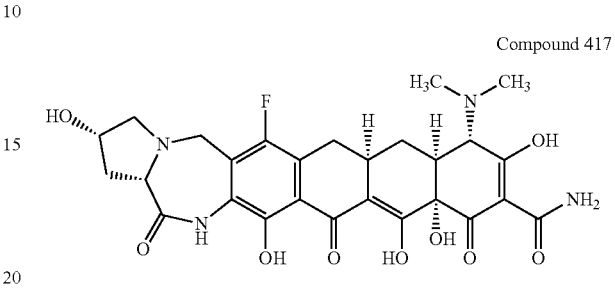

Compound 417

72-4.62 (m, 2 H), 4.21 (d, J=13.2 Hz, 1 H), 4.13 (s, 1 H), 3.72 (d, J=13.2 Hz, 1 H), 3.49-3.40 (m, 1 H), 3.27-2.94 (m, 10 H), 2.40-2.22 (m, 2 H), 2.10-1.99 (m, 2 H), 1.71-1.60 (m, 1 H); MS (ESI) m/z 573.0 (M+H), calcd for $C_{27}H_{30}F_2N_4O_9$ 573.2.

EXAMPLE 148

Compound 427

Synthesis of S13-1

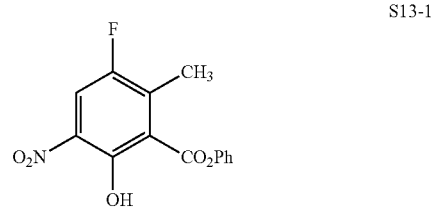

S13-1

To a 250 mL round bottom flask was added compound S1-4 (14.47 g, 56.30 mmol, 1.0 equiv, crude), tetrabutylammonium bromide (0.90 g, 2.80 mmol, 0.05 equiv), 1,2-dichloroethane (60 mL), and water (60 mL). The clear bi-layer was cooled in a 20° C. water bath. Nitric acid (7.2 mL, 70 wt %, 112.60 mmol, 2.0 equiv) was added. After the addition, the reaction temperature slowly rose to 26° C. The reaction was stirred at room temperature overnight (19 hrs). TLC (heptane/EtOAc=9.5/0.5) showed the reaction was complete. The organic layer was separated, washed with water (60 mL×2) and brine, and dried over anhydrous sodium sulfate. The solvent was removed to give compound S13-1 as a brown oil, which solidified on standing (17.71 g, quantitative). The crude product was used directly for the next step.

Synthesis of S13-2

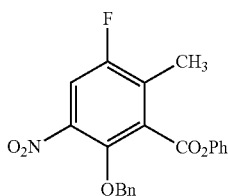

S13-2

To a 250 mL round bottom flask was added compound S13-1 (17.7 g, 56.30 mmol 1.0 equiv), acetone (177 mL), anhydrous potassium carbonate (15.6 g, 113.00 mmol, 2.0 equiv), and potassium iodide (0.47 g, 2.80 mmol, 0.05 equiv). To the stirred suspension at room temperature was added benzyl bromide (7.03 mL, 59.10 mmol, 1.05 equiv). The suspension was then heated to 56° C. for 4 hrs. TLC (heptane/EtOAc=9/1) showed the reaction was complete. The solid was removed by filtration and washed with acetone (30 mL). The filtrated was concentrated to give a paste. The paste was partitioned between methyl t-butyl ether (MTBE, 120 mL) and water (80 mL). The organic layer was washed with water (80 mL) and brine, dried over anhydrous sodium sulfate, and concentrated to give compound S13-2 as a brown oil (21.09 g, 98%). The crude product was used directly for the next step.

Synthesis of S13-3

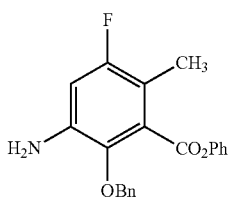

S13-3

To a 1 L round bottom flask was added compound S13-2 (21.08 g, 55.40 mmol, 1.0 equiv) and THF (230 mL). The solution was cooled in a cold water bath to 10° C. To another 500 mL round bottom flask containing water (230 mL), sodium hydrosulfite ($Na_2S_2O_4$, 56.7 g, 276.80 mmol, 5.0 equiv) was added slowly with stirring. The aqueous solution of sodium hydrosulfite was added to the THF solution of compound S13-2. The temperature quickly rose from 10° C. to 20.4° C. after the addition. The yellow suspension was stirred while the cold water bath slowly warmed up to room temperature overnight to give an orange cloudy solution. The reaction temperature during this period was between 15° C. to 19° C. TLC (heptane/EtOAc=9/1) showed the reaction was complete. The orange cloudy solution was diluted with EtOAc (460 mL). The organic layer was washed with water (150 mL×2) and brine, dried over anhydrous sodium sulfate, and concentrated under reduced pressure to give the crude product as a brown oil. The crude product was purified by flash silica gel column eluted with heptane/EtOAc 9/1 to yield the desired product S13-3 (15.83 g, 80%, 3 steps).

Synthesis of S13-4

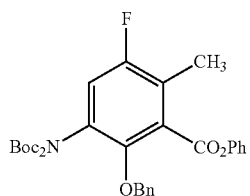

S13-4

To compound S13-3 5.50 g, 16.65 mmol, 1 eq in DMF (30 mL) was added $Boc_2O$ (8.54 g, 39.13 mmol, 2.5 eq), DIEA (8.18 mL, 46.96 mmol, 3 eq), and DMAP (102 mg, 0.84 mmol, 0.05 eq). The reaction solution was stirred at rt for overnight, diluted with ethyl acetate (300 mL), washed with water (500 mL), saturated aqueous sodium bicarbonate (100 mL) and brine (100 mL), dried over sodium sulfate, and concentrated under reduced pressure. Flash column chromatography on silica gel (0%→5% ethyl acetate/hexanes) yielded the desired product S13-4 as a white solid (6.12 g, 71%): $R_f$ 0.80 (20% ethyl acetate/hexanes); MS (electrospray) m/z 574.3 (M+Na), calcd for $C_{31}H_{34}FNNaO_7$ 574.2.

Synthesis of S13-5

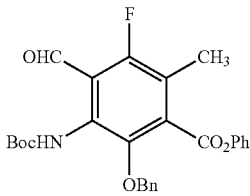

S13-5

To diisopropylamine (1.70 mL, 12.00 mmol, 1.2 eq) in THF (10 mL) at −78° C. was added nBuLi (4.80 mL, 2.5 M/hexane, 12.00 mmol, 1.2 eq) dropwise. The reaction was stirred at 0° C. for 10 min and re-cooled to −78° C. Compound S13-4 (5.52 g, 10.00 mmol, 1 eq) in THF (10 mL) was added dropwise over a period of 5 min. The resulting deep orange solution was stirred at −78° C. for 30 min. Anhydrous DMF (0.98 mL, 12.50 mmol, 1.25 eq) was added dropwise. The resulting light yellow solution was stirred at −78° C. for 30 min. Acetic acid (0.90 mL) was added at −78° C. The reaction was warmed to rt, diluted with saturated aqueous sodium bicarbonate (100 mL), and extracted with ethyl acetate (50 mL×3). The organic extracts were combined, dried over sodium sulfate, and concentrated under reduced pressure. Flash column chromatography with ethyl acetate/hexanes (0%→10%) yielded the desired product S13-5 as an orange foam (2.04 g, 43%): $R_f$ 0.45 (20% ethyl acetate/hexane); MS (electrospray) m/z 534.3 (M+$CH_3OH$+Na), calcd for $C_{28}H_{30}FNNaO_7$ 534.2.

Synthesis of S13-6-1

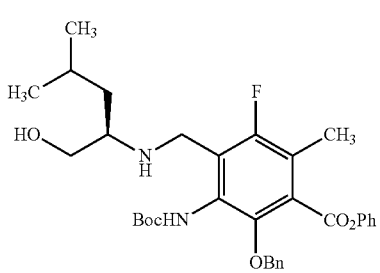

S13-6-1

To compound S13-5 (1.00 g, 2.08 mmol, 1 eq) in 1,2-dichloroethane (10 mL) was added (R)-(−)-leucinol (0.27 g, 2.30 mmol, 1.1 eq), acetic acid (0.30 mL, 5.24 mmol, 2.5 eq), and sodium triacetoxyborohydride (0.66 g, 3.11 mmol, 1.5 eq). The reaction mixture was stirred at rt for 1 h, diluted with ethyl acetate (50 mL), washed with saturated aqueous sodium bicarbonate (50 mL) and brine (50 mL), dried over sodium sulfate, and concentrated under reduced pressure to give the crude product as a yellow solid (quantitative): $R_f$ 0.55 (ethyl acetate); MS (electrospray) m/z 581.1 (M+H), calcd for $C_{33}H_{42}FN_2O_6$ 581.3.

Synthesis of S13-7-1

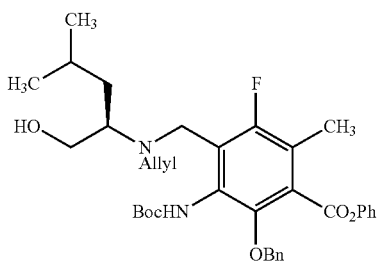

S13-7-1

To compound S13-6-1 (0.52 g, 0.90 mmol) in acetonitrile (20 mL) was added sodium bicarbonate (0.16 g, 1.95 mmol, 2.2 eq), allyl bromide (0.15 mL, 1.80 mmol, 2.0 eq), and tetrabutylammonium iodide (33 mg, 0.09 mmol, 0.1 eq). The reaction mixture was heated at 70° C. for 24 h, cooled to rt, diluted with water (100 mL), and extracted with ethyl acetate (100 mL×1, 50 mL×2). The ethyl acetate extracts were combined, dried over sodium sulfate, and concentrated under reduced pressure. Flash column chromatography on silica gel (0%→60% ethyl acetate/hexanes) yielded the desired product S13-7-1 as a white solid (0.37 g, 66%): $R_f$ 0.60 (30% ethyl acetate/hexane); $^1$H NMR (400 MHz, CDCl$_3$) δ 7.25-7.35 (m, 8 H), 7.06 (d, J=8.6 Hz, 2 H), 5.70-5.81 (m, 1 H), 5.18 (d, J=17.1 Hz, 1 H), 5.10 (d, J=10.4 Hz, 1 H), 5.00 (d, J=10.4 Hz, 1 H), 4.85 (d, J=10.4 Hz, 1 H), 3.45-3.80 (m, 4 H), 3.10-3.28 (m, 1 H), 2.99 (dd, J=8.0, 14.0 Hz, 1 H), 2.80-2.90 (m, 1 H), 2.33 (d, J=2.4 Hz, 3 H), 1.43 (s, 9H), 1.35-1.60 (m, 2 H), 1.05-1.15 (m, 1 H), 0.90 (d, J=6.7 Hz, 3 H), 0.87 (d, J=6.7 Hz, 3 H); MS (electrospray) m/z 621.5 (M+H), calcd for $C_{36}H_{46}FN_2O_6$ 621.3.

Synthesis of S13-8-1

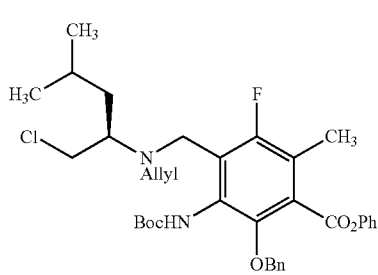

S13-8-1

To compound S13-7-1 (0.35 g, 0.56 mmol, 1 eq) in methylene chloride (10 mL) was added triethylamine (0.16 mL, 1.15 mmol, 2 eq), DMAP (14 mg, 0.11 mmol, 0.2 eq), and methanesulfonyl chloride (65 µL, 0.84 mmol, 1.5 eq). The reaction solution was stirred at rt for 1 h, diluted with ethyl acetate (100 mL), washed with saturated aqueous sodium bicarbonate (50 mL×2) and brine (50 mL), dried over sodium sulfate, and concentrated under reduced pressure. Flash column chromatography on silica gel (0%→10% ethyl acetate/hexanes) gave the desired product as a yellow oil (0.36 g, 80%): $R_f$ 0.60 (20% ethyl acetate/hexane); $^1$H NMR (400 MHz, CDCl$_3$) δ 7.97, 7.83 (br s, 1 H, combined), 7.20-7.50 (m, 8 H), 7.05 (d, J=7.3 Hz, 2 H), 5.90-6.08 (m, 1 H), 5.19-5.20 (m, 2 H), 4.92-5.03 (m, 2 H), 3.94-4.02, 3.45-3.75, 3.15-3.30, 3.00-3.10, 2.55-2.80 (m, 7 H combined), 2.33 (d, J=1.8 Hz, 3 H), 1.30-1.90 (m, 3 H), 1.46 (s, 9H), 0.80-0.92 (m, 6 H); MS (electrospray) m/z 639.2 (M+H), calcd for $C_{36}H_{45}ClFN_2O_5$ 639.3.

Synthesis of S13-9-1

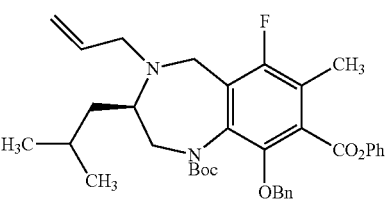

S13-9-1

To compound S13-8-1 (0.22 g, 0.34 mmol, 1 eq) in anhydrous DMF (15 mL) was added tetrabutylammonium iodide (25 mg, 0.068 mmol, 0.2 eq) and sodium hydride (27 mg, 60% in mineral oil, 0.68 mmol, 2 eq). The reaction mixture was stirred at rt for 5 h, diluted with ethyl acetate (200 mL), washed with saturated aqueous sodium bicarbonate (200 mL), water (200 mL) and brine (100 mL), dried over sodium sulfate, and concentrated under reduced pressure. Flash column chromatography on silica gel (0%→8% ethyl acetate/hexanes) yielded the desired product S13-9-1 as a colorless oil (85 mg, 42%): $R_f$ 0.75 (15% ethyl acetate/hexane); $^1$H NMR (400 MHz, CDCl$_3$) mixture of tautomers, complex; MS (electrospray) m/z 603.5 (M+H), calcd for $C_{36}H_{44}FN_2O_5$ 603.3.

Synthesis of S13-10-1

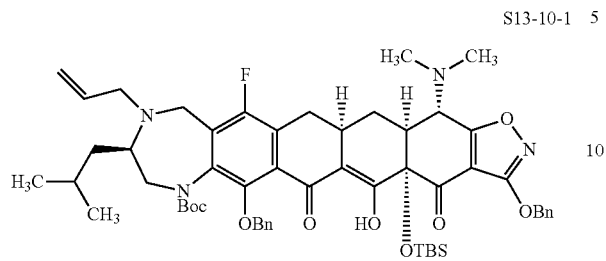

S13-10-1

To diisopropylamine (44 µL, 0.31 mmol, 2.2 eq) in anhydrous THF (1 mL) at −78° C. was added nBuLi (0.20 mL, 1.6 M/hexanes, 0.32 mmol, 2.2 eq) dropwise. The reaction solution was stirred at 0° C. for 10 min and re-cooled to −78° C. TMEDA (53 µL, 0.35 mmol, 2.5 eq) was added, followed by dropwise addition of compound S13-9-1 (85 mg, 0.14 mmol, 1 eq) in anhydrous THF (2 mL) over a period of 3 min. The resulting deep red solution was stirred at −78° C. for 30 min. Enone S7-1 (68 mg, 0.14 mmol) in anhydrous THF (2 mL) was added dropwise. The resulting light brown solution was gradually warmed up with stirring from −78° C. to −20° C. over a period of 1 h. Acetic acid (0.1 mL) was added. The reaction mixture was diluted with ethyl acetate, washed with saturated aqueous sodium bicarbonate (50 mL) and brine (50 mL), dried over sodium sulfate, and concentrated under reduced pressure. Flash column chromatography on silica gel (0%→20% ethyl acetate/hexanes) yielded the desired product S13-10-1 as a yellow oil (103 mg, 74%): $R_f$ 0.20 (10% ethyl acetate/hexane); $^1$H NMR (400 MHz, CDCl$_3$) mixture of tautomers, complex; MS (electrospray) m/z 991.8 (M+H), calcd for $C_{56}H_{72}FN_4O_9Si$ 991.5.

Synthesis of Compound 427

Compound 427

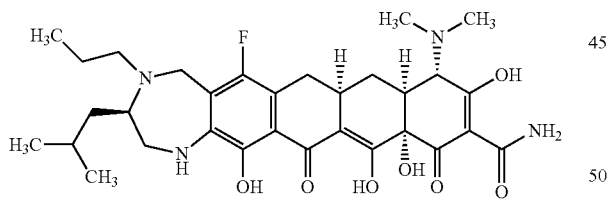

To compound S13-10-1 (21 mg, 0.021 mmol) in THF (1 mL) was added 48% aqueous HF (1 mL). After stirring at rt for overnight, the yellow reaction solution was slowly added to 25% aqueous K$_2$HPO$_4$ (40 mL) with rapid stirring. The mixture was extracted with ethyl acetate (20 mL×3). The organic extracts were combined, dried over sodium sulfate, and concentrated under reduced pressure to give the crude product as a yellow residue: MS (electrospray) m/z 777.6 (M+H), calcd for $C_{56}H_{72}FN_4O_9Si$ 777.4.

To the above intermediate in methanol (3 mL) and 1,4-dioxane (1 mL) was added 0.5 M HCl/methanol (1 mL) and 10% Pd—C (9 mg, 0.004 mmol, 0.2 eq). The mixture was purged with hydrogen and stirred under 1 atm hydrogen atmosphere at rt for 2 h. The catalyst was filtered off with a small Celite pad and washed with methanol (1 mL×3). The filtrate was concentrated under reduced pressure. Preparative HPLC purification yielded the desired product Compound 427 as a bright yellow solid (4.1 mg, 33% overall): $^1$H NMR (400 MHz, CD$_3$OD) δ 4.83 (s, 1 H), 4.66 (s, 1 H), 4.08 (s, 1H), 2.80-3.70 (m, 15 H), 2.05-2.30 (m, 1 H), 1.70-1.90 (m, 3 H), 1.45-1.75 (m, 1 H), 0.97-1.10 (m, 9 H); MS (electrospray) m/z 601.5 (M+H), calcd for $C_{31}H_{42}FN_4O_7$ 601.3.

EXAMPLE 149

Compound 408

Synthesis of S13-12-1

S13-12-1

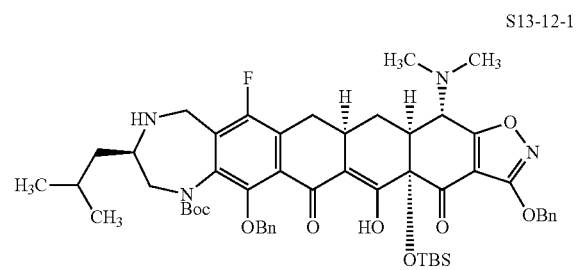 [SMILES: CC(C)C[C@@H]1CN(C(=O)OC(C)(C)C)c2c(c(F)c3c(c2OCc2ccccc2)C(=O)C2=C(O)[C@]4(O[Si](C)(C)C(C)(C)C)C(=O)c5c(OCc6ccccc6)noc5[C@@H](N(C)C)[C@@H]4C[C@@H]2C3)CN1]

To compound S13-10-1 (80 mg, 0.081 mmol, 1 eq) in methylene chloride (2 mL) was added N,N-dimethylbarbituric acid (31 mg, 0.25 mmol, 3 eq) and Pd(PPh$_3$)$_4$ (4.7 mg, 0.004 mmol, 0.05 eq). The reaction mixture was degassed by bubbling nitrogen through for 2 min and heated at 40° C. with stirring for 24 h. Stirring was continued at rt for another 24 h. Saturated aqueous sodium bicarbonate (10 mL) was added. The mixture was extracted with ethyl acetate (10 mL×3). The organic extracts were combined, dried over sodium sulfate, and concentrated under reduced pressure to yield the crude product as a yellow solid: MS (electrospray) m/z 951.8 (M+H), calcd for $C_{53}H_{68}FN_4O_9Si$ 951.5.

Synthesis of Compound 408

Compound 408

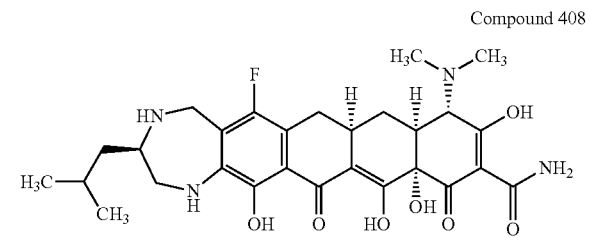 [SMILES: CC(C)C[C@@H]1CNc2c(O)c3c(c(F)c2CN1)C[C@H]1C[C@H]2[C@H](N(C)C)C(O)=C(C(N)=O)C(=O)[C@@]2(O)C(O)=C1C3=O]

Prepared from compound S13-12-1 (0.027 mmol) using similar procedures for Compound 427 (orange solid, 4.6 mg, 30% overall): $^1$H NMR (400 MHz, CD$_3$OD) δ 4.56 (d, J=15.9 Hz, 1 H), 4.36 (d, J=15.9 Hz, 1 H), 4.08 (s, 1 H), 3.75 (dd, J=3.6, 15.3 Hz, 1 H), 3.60-3.68 (m, 1 H), 2.85-3.15 (m, 11 H), 2.15-2.25 (m, 1 H), 1.50-1.85 (m, 4 H), 1.03 (d, J=6.7 Hz, 3 H), 1.00 (d, J=6.7 Hz, 3 H); MS (electrospray) m/z 559.5 (M+H), calcd for $C_{28}H_{36}FN_4O_7$ 559.3.

EXAMPLE 150

Compound 429

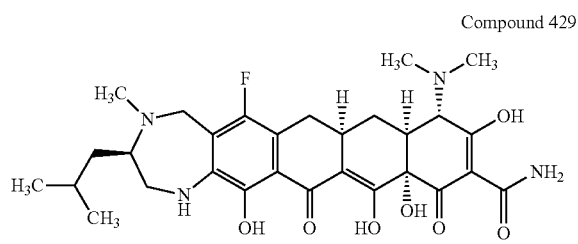 [SMILES: CC(C)C[C@@H]1CNc2c(O)c3c(c(F)c2CN1C)C[C@H]1C[C@H]2[C@H](N(C)C)C(O)=C(C(N)=O)C(=O)[C@@]2(O)C(O)=C1C3=O]

To compound S13-12-1 (0.054 mmol) in 1,2-dichloroethane (5 mL) was added acetic acid (10 µL, 0.17 mmol, 3 eq), formaldehyde (8 µL, 36.5% aqueous solution, 0.11 mmol, 2 eq), and sodium triacetoxyborohydride (27 mg, 0.13 mmol, 2.5 eq). The reaction mixture was stirred at rt for 4 h. Additional formaldehyde (8 µL, 36.5% aqueous solution, 0.11 mmol, 2 eq) and sodium triacetoxyborohydride (10 mg, 0.048 mmol, 0.9 eq) were added. The reaction mixture was stirred at rt for another 20 min. Saturated aqueous sodium bicarbonate (20 mL) was added. The mixture was extracted with ethyl acetate (20 mL×3). The organic extracts were combined, dried over sodium sulfate, and concentrated under reduced pressure to yield the crude product as a yellow solid: MS (electrospray) m/z 965.4 (M+H), calcd for $C_{54}H_{70}FN_4O_9Si$ 965.5.

The above intermediate was then deprotected using similar procedures for Compound 427 to give the desired product Compound 429 as an orange solid (5.6 mg, 15% overall): $^1$H NMR (400 MHz, $CD_3OD$) δ 4.55-5.00 (m, 2 H), 4.09 (s, 1 H), 3.45-3.85 (m, 4 H), 2.85-3.20 (m, 12 H), 2.05-2.30 (m, 2 H), 1.50-1.85 (m, 3 H), 1.00-1.10 (m, 6 H); MS (electrospray) m/z 573.5 (M+H), calcd for $C_{29}H_{38}FN_4O_7$ 573.3.

EXAMPLE 151

Antibacterial Activity

The antibacterial activities for the compounds of the invention were studied according to the following protocols.
Minimum Inhibitory Concentration (MIC) Assay MICs were determined according to the Clinical and Laboratory Standards Institute (CLSI) guidances (e.g., CLSI. Performance standards for antimicrobial susceptibility testing; nineteenth information supplement. CLSI document M100-S19, CLSI, 940 West Valley Road, Suite 1400, Wayne, Pa. 19087-1898, USA, 2009). Briefly, frozen bacterial strains were thawed and subcultured onto Mueller Hinton Broth (MHB) or other appropriate media (Streptococcus requires blood and *Haemophilus* requires hemin and NAD). Following incubation overnight, the strains were subcultured onto Mueller Hinton Agar and again incubated overnight. Colonies were observed for appropriate colony morphology and lack of contamination. Isolated colonies were selected to prepare a starting inoculum equivalent to a 0.5 McFarland standard. The starting inoculum was diluted 1:125 (this is the working inoculum) using MHB for further use. Test compounds were prepared by dilution in sterile water to a final concentration of 5.128 mg/mL. Antibiotics (stored frozen, thawed and used within 3 hours of thawing) and compounds were further diluted to the desired working concentrations.

The assays were run as follows. Fifty µL of MHB was added to wells 2-12 of a 96-well plate. One hundred µL of appropriately diluted antibiotics was added to well 1. Fifty µL of antibiotics was removed from well 1 and added to well 2 and the contents of well 2 mixed by pipetting up and down five times. Fifty µL of the mixture in well 2 was removed and added to well 3 and mixed as above. Serial dilutions were continued in the same manner through well 12. Fifty µL, was removed from well 12 so that all contained 50 µL. Fifty µL of the working inoculum was then added to all test wells. A growth control well was prepared by adding 50 µL of working inoculum and 50 µL of MHB to an empty well. The plates were then incubated at 37° C. overnight, removed from the incubator and each well was read on a plate reading mirror. The lowest concentration (MIC) of test compound that inhibited the growth of the bacteria was recorded.

Example:

|  | 1 | 2 | 3 | 4 | 5 | 6 | 7 | 8 | 9 | 10 | 11 | 12 |
|---|---|---|---|---|---|---|---|---|---|---|---|---|
| [Abt] | 32 | 16 | 8 | 4 | 2 | 1 | 0.5 | 0.25 | 0.125 | 0.06 | 0.03 | 0.015 |
| Growth | − | − | − | − | − | + | + | + | + | + | + | + |

[abt] = antibiotic concentration in the well in µg/ml
Growth = bacterial growth (cloudiness)
Interpretation: MIC = 2 µg/mL Protocol for Determining Inoculum Concentration (Viable Count)

Fifty 50 µl of the inoculum was pipetted into well 1. Ninety µl of sterile 0.9% NaCl was pipetted into wells 2-6 of a 96-well microtiter plate. Ten µL from was removed from well 1 and added it to well 2 followed by mixing. Ten µL was removed from well two and mixed with the contents of well 3 and so on creating serial dilutions through well 6. Ten µL was removed from each well and spotted onto an appropriate agar plate. The plate was placed into an incubator overnight. The colonies in spots that contain distinct colonies were counted. Viable count was calculated by multiplying the number of colonies by the dilution factor.

| Spot from Well | 1 | 2 | 3 | 4 | 5 | 6 |
|---|---|---|---|---|---|---|
| Dilution Factor | $10^2$ | $10^3$ | $10^4$ | $10^5$ | $10^6$ | $10^7$ |

Bacterial Strains

The following bacterial strains, listed below, were examined in minimum inhibitory concentration (MIC) assays.

| ORGANISM | STRAIN DESIGNATION | KEY PROPERTIES |
| --- | --- | --- |
| *Staphylococcus aureus* | SA100 | ATCC 13709, MSSA, Smith strain |
| *Staphylococcus aureus* | SA101 | ATCC 29213, CLSI quality control strain, MSSA |
| *Staphylococcus aureus* | SA191 | HA-MRSA, tetracycline-resistant, lung infection model isolate |
| *Staphylococcus aureus* | SA161 | HA-MRSA, tetracycline-resistant, tet(M) |
| *Staphylococcus aureus aaaureusaureus* | SA158 | Tetracycline-resistant tet(K) |
| *Staphylococcus epidermidis* | SE164 | ATCC 12228, CLSI quality control strain, tetracycline-resistant |
| *Enterococcus faecalis* | EF103 | ATCC 29212, tet-I/R, control strain |
| *Enterococcus faecalis* | EF159 | Tetracycline-resistant, tet(M) |
| *Streptococcus pneumoniae* | SP106 | ATCC 49619, CLSI quality control strain |
| *Streptococcus pneumoniae* | SP160 | Tetracycline-resistant, tet(M) |
| Streptococcus pyogenes | SP312 | 2009 clinical isolate, tet(M) |
| Streptococcus pyogenes | SP193 | *S. pyogenes* for efficacy models; tetS; sensitive to sulfonamides |
| *Haemophilus influenzae* | HI262 | Tetracycline-resistant, ampicillin-resistant |
| *Moraxella catarrhalis* | MC205 | ATCC 8176, CLSI quality control strain |
| *Escherichia coli* | EC107 | ATCC 25922, CLSI quality control strain |
| *Escherichia coli* | EC155 | Tetracycline-resistant, tet(A) |
| *Enterobacter cloacae* | EC108 | ATCC 13047, wt |
| *Klebsiella pneumoniae* | KP109 | ATCC 13883, wt |
| *Klebsiella pneumoniae* | KP153 | Tetracycline-resistant, tet(A), MDR, ESBL+ |
| *Klebsiella pneumoniae* | KP457 | 2009 ESBL+, CTX-M, OXA |
| *Proteus mirabilis* | PM112 | ATCC 35659 |
| *Pseudomonas aeruginosa* | PA111 | ATCC 27853, wt, control strain |
| *Pseudomonas aeruginosa* | PA169 | Wt, parent of PA170-173 |
| *Pseudomonas aeruginosa* | PA173 | PA170 ΔmexX; MexXY-(missing a functional efflux pump) |
| *Pseudomonas aeruginosa* | PA555 | ATCC BAA-47, wild type strain PAO1 |
| *Pseudomonas aeruginosa* | PA556 | Multiple-Mex efflux pump knockout strain |
| *Acinetobacter baumannii* | AB110 | ATCC 19606, wt |
| *Acinetobacter baumannii* | AB250 | Cystic fibrosis isolate, MDR |
| *Stenotrophomonas maltophilia* | SM256 | Cystic fibrosis isolate, MDR |
| *Burkholderia cenocepacia* | BC240 | Cystic fibrosis isolate, MDR |

*MDR, multidrug-resistant; MRSA, methicillin-resistant *S. aureus*; MSSA, methicillin-sensitive *S. aureus*; HA-MRSA, hospital-associated MRSA; tet(K), major gram-positive tetracycline efflux mechanism; tet(M), major gram-positive tetracycline ribosome-protection mechanism; ESBL+, extended spectrum β-lactamase Results Values of minimum inhibition concentration (MIC) for the compounds of the invention are provided in Tables 5-7.

TABLE 5

MIC Values for Compounds of the Invention Compared to Sancycline, Minocycline and Tigecycline.

| Cmpd No. | SA101 29213 | SA100 13709 | SA161 MRSA tetM | SA158 tetK | EF103 29212 | EF159 tetM | SP106 49619 | SP160 tetM |
| --- | --- | --- | --- | --- | --- | --- | --- | --- |
| 100 | B | B | B | B | B | B | B | B |
| 101 | B | B | B | B | B | B | C | B |
| 102 | C | B | B | B | B | B | B | B |
| 104 | C | C | B | B | B | B | B | B |
| 105 | B | B | C | B | B | B | B | B |
| 106 | B | B | B | B | B | B | B | B |
| 107 | B | B | B | B | B | B | B | B |
| 108 | C | C | B | B | B | B | B | B |
| 109 | C | C | B | B | B | B | B | B |
| 110 | B | B | B | B | B | B | B | B |
| 111 | C | B | B | B | B | B | B | B |
| 117 | C | C | B | B | B | B | B | B |
| 118 | B | B | B | B | B | B | B | B |
| 120 | B | B | B | B | B | B | B | B |
| 121 | B | B | B | B | B | B | B | B |

TABLE 5-continued

MIC Values for Compounds of the Invention Compared to Sancycline, Minocycline and Tigecycline.

| | | | | | | | | |
|---|---|---|---|---|---|---|---|---|
| 123 | B | B | B | B | B | B | B | B |
| 129 | B | B | B | B | B | B | B | B |
| 130 | B | B | B | B | B | B | B | B |
| 131 | B | B | B | B | B | B | B | B |
| 133 | C | B | B | B | B | B | C | B |
| 134 | B | B | B | B | B | B | B | B |
| 136 | C | B | B | B | B | B | B | B |
| 137 | B | B | B | B | B | B | B | B |
| 139 | B | B | B | B | B | B | B | B |
| 140 | B | B | B | B | B | B | B | B |
| 142 | B | B | B | B | B | B | B | B |
| 143 | B | B | B | B | B | B | B | B |
| 144 | B | B | B | B | B | B | B | B |
| 146 | C | C | B | B | B | B | B | B |
| 147 | B | B | B | B | B | B | B | B |
| 149 | B | B | B | B | B | B | B | B |
| 150 | B | B | B | B | B | B | B | B |
| 200 | C | C | B | NT | B | B | B | B |
| 201 | B | B | B | B | B | B | C | B |
| 202 | C | B | B | B | B | B | B | B |

| Cmpd No. | EC107 25922 | EC155 tetA | AB110 19606 | PA111 27853 | EC108 13047 | KP109 13883 | KP153 tetA |
|---|---|---|---|---|---|---|---|
| 100 | B | B | A | B | B | B | B |
| 101 | B | B | C | B | C | B | B |
| 102 | B | B | B | B | B | B | B |
| 104 | B | B | C | B | B | B | B |
| 105 | B | C | C | B | B | B | B |
| 106 | B | B | B | B | B | B | B |
| 107 | B | B | B | B | B | B | B |
| 108 | B | B | C | B | C | B | B |
| 109 | B | B | C | B | B | B | B |
| 110 | B | B | A | B | B | B | B |
| 111 | B | B | C | B | B | B | B |
| 117 | B | B | B | B | B | B | B |
| 118 | B | B | A | B | B | B | B |
| 120 | B | B | A | B | B | B | B |
| 121 | B | B | A | B | B | B | B |
| 123 | B | B | A | B | B | B | B |
| 129 | B | B | A | B | B | B | B |
| 130 | B | B | A | B | B | B | B |
| 131 | B | B | C | B | B | B | B |
| 133 | B | C | C | B | C | B | C |
| 134 | B | B | B | B | B | B | B |
| 136 | B | C | C | B | B | B | B |
| 137 | B | B | B | B | B | B | B |
| 139 | B | B | C | B | B | B | B |
| 140 | B | C | C | B | C | B | C |
| 142 | B | B | A | B | B | B | B |
| 143 | B | B | A | B | B | B | B |
| 144 | B | B | A | B | B | B | B |
| 146 | B | B | C | B | B | B | B |
| 147 | B | B | C | B | B | B | B |
| 149 | B | B | A | B | B | B | B |
| 150 | B | B | C | B | B | B | B |
| 200 | B | B | C | B | B | B | B |
| 201 | B | B | C | B | B | B | B |
| 202 | B | B | C | B | C | B | B |

A = lower than or equal to lowest MIC among three control compounds;
B = greater than lowest MIC among three control compounds, but lower than highest MIC among three control compounds;
C = greater than MIC of all three control compounds.

TABLE 6

MIC Values for Compounds of the Invention Compared to Sancycline, Minocycline and Tigecycline.

| Cmpd No. | SA 101 29213 | SA 100 13709 | SA 161 tetM | SA 158 tetK | SE 164 12228 | EF 159 tetM | SP 106 49619 | SP 160 tetM | SP 193 8668 | HI 262 33929 |
|---|---|---|---|---|---|---|---|---|---|---|
| 112 | C | B | B | B | A | B | A | B | B | C |
| 113 | C | B | B | B | B | B | A | B | B | B |

TABLE 6-continued

MIC Values for Compounds of the Invention Compared to Sancycline, Minocycline and Tigecycline.

| | | | | | | | | | | |
|---|---|---|---|---|---|---|---|---|---|---|
| 114 | B | B | B | B | B | B | A | B | B | C |
| 115 | B | B | B | B | A | B | A | B | B | B |
| 116 | C | B | B | B | B | B | B | B | C | C |
| 119 | B | B | B | B | B | B | A | B | B | C |
| 122 | C | B | B | B | B | B | B | B | C | C |
| 125 | B | B | B | B | A | B | A | B | B | A |
| 126 | B | B | B | B | B | B | A | B | B | A |
| 128 | B | B | B | B | B | B | A | B | A | B |
| 132 | B | B | B | B | A | B | A | B | A | B |
| 138 | B | B | B | B | B | B | A | B | A | A |
| 141 | C | A | B | B | B | B | A | B | A | A |
| 145 | B | B | B | B | A | B | A | B | A | B |
| 148 | B | B | B | B | A | B | A | B | A | B |
| 300 | C | B | B | B | B | B | NT | B | C | C |
| 301 | C | B | B | B | B | B | B | B | C | C |
| 302 | C | C | C | B | B | B | C | B | C | C |
| 303 | C | B | B | B | B | B | NT | B | C | NT |
| 304 | C | B | B | B | B | B | B | B | B | C |
| 305 | C | C | B | B | B | B | B | B | C | C |
| 306 | C | B | B | B | B | B | C | B | C | C |
| 307 | C | B | B | B | B | B | B | B | B | C |
| 308 | C | B | B | B | B | B | B | B | B | C |
| 400 | B | A | B | B | NT | A | B | B | NT | NT |
| 403 | C | B | B | B | NT | B | B | B | NT | NT |
| 405 | B | A | B | B | B | B | A | B | B | A |
| 406 | B | A | B | A | B | B | A | B | B | A |
| 407 | C | NT | B | B | B | B | A | B | NT | C |
| 408 | B | B | B | B | A | B | B | B | B | C |
| 409 | C | NT | B | B | B | B | A | B | NT | C |
| 411 | B | B | B | B | NT | B | B | B | NT | NT |
| 412 | A | A | B | A | A | B | A | A | A | A |
| 413 | C | NT | B | B | B | B | A | B | NT | C |
| 415 | B | B | C | B | NT | C | B | B | NT | NT |
| 416 | A | A | B | B | NT | B | B | B | NT | NT |
| 419 | A | A | B | B | NT | B | B | A | NT | NT |
| 420 | C | B | B | B | NT | B | B | B | NT | NT |
| 421 | B | A | B | A | A | B | A | A | A | B |
| 423 | C | C | B | B | B | B | B | B | C | A |
| 424 | C | B | B | B | B | B | A | B | B | C |
| 426 | B | B | B | B | NT | B | B | B | NT | NT |
| 427 | B | B | B | B | B | B | B | B | B | C |
| 428 | A | A | A | A | NT | B | B | A | NT | NT |
| 429 | B | B | B | B | B | B | B | B | B | C |

| Cmpd No. | MC 205 8176 | EC 107 25922 | EC 155 tetA | KP 153 tetA | PM 112 35659 | PA 169 | PA 173 | AB 250 | SM 256 | BC 240 |
|---|---|---|---|---|---|---|---|---|---|---|
| 112 | C | B | B | B | B | C | B | A | C | C |
| 113 | C | B | B | B | C | C | B | A | C | B |
| 114 | B | B | B | B | B | C | B | A | C | C |
| 115 | C | B | B | B | C | C | B | B | C | C |
| 116 | C | C | B | C | C | C | B | B | C | C |
| 119 | C | B | B | B | B | C | B | A | C | C |
| 122 | C | C | C | C | C | C | B | C | C | C |
| 125 | B | B | B | B | B | C | NT | A | B | B |
| 126 | B | B | B | B | B | B | B | A | B | B |
| 128 | C | B | B | B | B | C | B | A | C | B |
| 132 | B | B | B | B | B | B | B | A | C | B |
| 138 | B | B | B | B | C | C | B | A | C | B |
| 141 | B | B | B | B | B | C | B | A | C | B |
| 145 | B | B | B | B | B | C | B | A | C | B |
| 148 | C | B | B | B | B | C | B | A | C | B |
| 300 | C | B | B | B | B | B | B | A | C | C |
| 301 | B | B | B | B | C | B | B | B | C | C |
| 302 | C | C | B | B | C | B | B | C | C | C |
| 303 | B | C | B | B | C | B | B | C | C | C |
| 304 | C | B | B | B | B | B | B | A | C | C |
| 305 | C | B | B | B | C | B | B | C | C | C |
| 306 | B | B | B | B | C | B | B | C | C | C |
| 307 | C | B | B | B | B | B | B | A | C | C |
| 308 | C | B | B | B | B | B | B | C | C | C |
| 400 | NT | B | B | B | NT | NT | NT | NT | NT | NT |
| 403 | NT | B | B | B | NT | NT | NT | NT | NT | NT |
| 405 | B | B | C | C | B | C | B | B | C | C |
| 406 | B | B | C | C | B | A | B | C | C | C |
| 407 | C | C | C | C | C | NT | NT | C | C | C |

TABLE 6-continued

MIC Values for Compounds of the Invention Compared to Sancycline, Minocycline and Tigecycline.

| 408 | C | B | B | B | B | B | B | A | C | B |
| 409 | C | C | C | C | C | NT | NT | C | C | C |
| 411 | NT | B | B | C | NT | NT | NT | NT | NT | NT |
| 412 | A | B | C | C | B | C | B | A | C | B |
| 413 | C | C | C | C | C | NT | NT | C | C | C |
| 415 | NT | B | C | C | NT | NT | NT | NT | NT | NT |
| 416 | NT | B | C | C | NT | NT | NT | NT | NT | NT |
| 419 | NT | B | B | B | NT | NT | NT | NT | NT | NT |
| 420 | NT | C | C | C | NT | NT | NT | NT | NT | NT |
| 421 | B | B | B | B | C | B | B | A | C | C |
| 423 | C | C | C | C | C | C | B | C | C | C |
| 424 | C | C | C | C | C | C | B | C | C | C |
| 426 | NT | B | C | C | NT | NT | NT | NT | NT | NT |
| 427 | C | B | B | B | B | C | B | A | C | C |
| 428 | NT | B | B | C | NT | NT | NT | NT | NT | NT |
| 429 | B | B | B | B | C | C | B | A | C | B |

A = lower than or equal to lowest MIC among three control compounds;
B = greater than lowest MIC among three control compounds, but lower than highest MIC among three control compounds;
C = greater than MIC of all three control compounds.

TABLE 7

MIC Values for Compounds of the Invention Compared to Sancycline, Minocycline and Tigecycline.

| Cmpd No. | SA 101 29213 | SA 191 | SA 161 tetM | SA 158 tetK | SE 164 12228 | EF 159 tetM | SP 106 49619 | SP 160 tetM | SP 312 tetM | HI 262 33929 | MC 205 8176 |
|---|---|---|---|---|---|---|---|---|---|---|---|
| 103 | C | B | B | B | A | B | A | B | B | C | C |
| 124 | C | B | B | B | A | B | A | B | B | B | C |
| 127 | C | B | B | B | A | B | A | B | B | B | C |
| 135 | B | B | B | B | A | B | A | B | B | A | B |
| 401 | C | B | B | B | B | B | B | B | B | C | C |
| 402 | C | B | C | B | B | B | B | B | B | C | C |
| 404 | C | B | C | B | B | B | A | B | B | A | C |
| 410 | B | A | B | A | A | A | A | B | B | A | B |
| 414 | C | C | C | B | C | C | C | C | C | C | C |
| 417 | C | C | C | B | B | B | C | B | B | A | C |
| 418 | C | C | C | B | B | C | B | B | B | C | C |
| 422 | B | B | B | A | A | B | A | B | B | B | B |
| 425 | C | B | B | B | B | B | B | B | B | C | C |

| Cmpd No. | EC 107 25922 | EC 155 tetA | KP 153 tetA | KP 457 | PM 112 35659 | PA 555 | PA 556 | AB 250 | SM 256 | BC 240 |
|---|---|---|---|---|---|---|---|---|---|---|
| 103 | B | B | B | NT | C | C | C | B | C | C |
| 124 | B | B | B | NT | C | C | C | A | C | C |
| 127 | B | B | B | NT | C | C | C | A | C | C |
| 135 | B | B | B | NT | B | C | B | A | C | C |
| 401 | C | C | C | C | C | C | C | C | C | C |
| 402 | C | B | B | C | C | B | C | C | C | C |
| 404 | B | C | C | C | B | C | C | C | C | C |
| 410 | B | B | B | C | C | C | B | C | C | C |
| 414 | C | C | C | C | C | C | C | C | C | C |
| 417 | C | C | C | C | C | C | C | C | C | C |
| 418 | C | C | C | C | C | C | C | C | C | C |
| 422 | B | C | C | C | C | C | C | B | C | C |
| 425 | C | C | C | C | C | C | C | C | C | C |

A = lower than or equal to lowest MIC among three control compounds;
B = greater than lowest MIC among three control compounds, but lower than highest MIC among three control compounds;
C = greater than MIC of all three control compounds.

EXAMPLE 152

In Vivo Models

A. Mouse Systemic Infection Protocol

Compounds were screened for antibacterial activity in vivo in a mouse systemic infection (septicemia) model. In the model, CD-1 female mice (18-22 grams) were injected IP with a *S. aureus* Smith inoculum that results in 0% survival within 24 to 48 hours. The bacterial dose required to achieve this effect was previously been established through virulence studies. At one hour post infection, mice received either 3 mg/ml IV or 30 mg/ml PO. Typically, six mice were treated per dose group. Animal survival was assessed and recorded for 48 hours. Percent survival at 48 hours was recorded for each compound in Table 8.

TABLE 8

Percent survival at 48 hours for tested compounds.

| Cmpd No. | IV (3 mg/kg) | PO (30 mg/kg) |
|---|---|---|
| 102 | 100% | 83% |
| 143 | 83% | 100% |
| 130 | 33% | 83% |
| 123 | 33% | 67% |
| 132 | 50% | 50% |
| 106 | 17% | 20% |
| 137 | 33% | 33% |
| 131 | 100% | 17% |
| 147 | 83% | 0% |
| 118 | 17% | 50% |
| 129 | 50% | 0% |
| 150 | 0 | 0 |
| 144 | 50% | 0% |
| 110 | 33% | 50% |
| 149 | 17% | 0% |
| 125 | 100% | 33% |
| 119 | 83% | 75% |
| 112 | 100% | 20% |
| 126 | 83% | 100% |
| 128 | 17% | 0% |
| 115 | 100% | 100% |
| 103 | 83% | 100% |
| 135 | 100% | 100% |
| 304 | 0% | 17% |
| 410 | 100% | 50% |
| 419 | 100% | 40% |
| 416 | 100% | 20% |
| 400 | 100% | 0% |
| 428 | 50% | 0% |
| 412 | 100% | 40% |
| 406 | 100% | 40% |
| 408 | 100% | 0% |

B. Neutropenic Respiratory Infection Models for *S. pneumoniae*

Compounds were tested in a neutropenic BALB/c murine model of lung infection challenged with tetracycline-resistant tet(M) *S. pneumoniae* strain SP160. Mice were made neutropenic by pre-treatment with cyclophosphamide and infected with SP160 via intranasal administration. Mice were dosed orally with 30 mg/kg compound or IV with 10 mg/kg compound at 2 and 12 hours post-infection. At 24 hours following initiation of treatment, mice were euthanized and bacterial reduction in the lung was quantified by plating lung homogenates. Data was recorded as $\log_{10}$ reduction in lung colony forming units versus an untreated control group. The results of the testing are shown in FIG. 1.

FIG. 1 shows that Compounds 102 and 135 were as orally efficacious (reduced the bacterial burden in the lung) as linezolid in the *S. pneumoniae* SP160 lung model; and Compounds 143, 130, and 126 did not significantly reduce the lung bacterial burden when orally administered. Compound 102 was also efficacious when administered intravenously (IV); linezolid did not substantially reduce the lung bacterial burden when administered as a control at 5 mg/kg IV. Doxycycline was ineffective, as *S. pneumoniae* SP160 is tetracycline-resistant, carrying a tet(M) ribosomal protection mechanism.

C. Non-neutropenic Respiratory Infection Model for *S. pneumoniae*.

Compound 102 was tested in an immunocompetent CD-1 murine model of lung infection challenged with *S. pneumoniae* strain SP514. Mice were infected with SP514 via intranasal administration and dosed orally with 30 mg/kg compound at 5, 24 and 36 hours post-infection. At 48 hours following initiation of treatment, mice were euthanized and bacterial reduction in the lung was quantified by plating lung homogenates. Data was recorded as $\log_{10}$ reduction in lung colony forming units versus an untreated control group.

Figure 2:
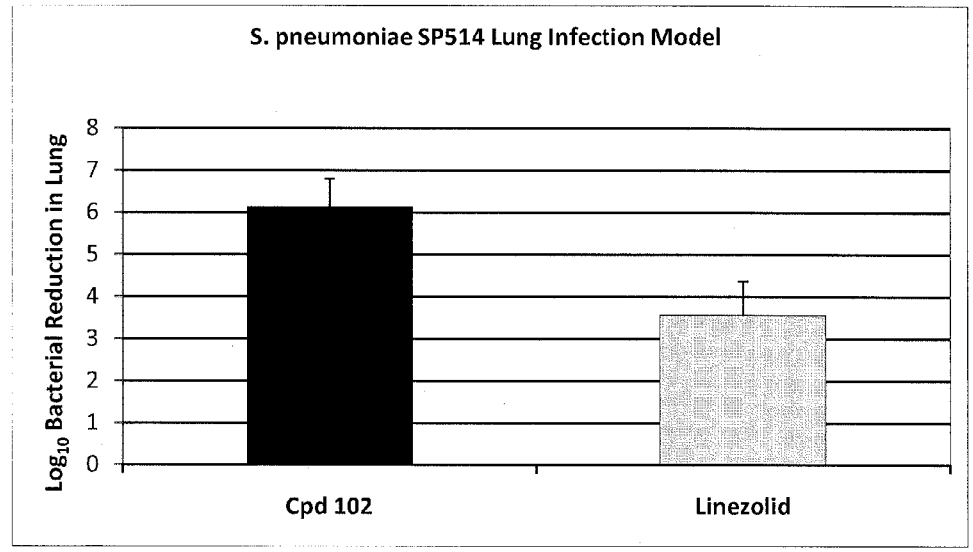
FIG. 2 is a bar graph demonstrating the Compound 102 in the immunocompetent mouse lung infection model with *S. pneumoniae* SP514, oral dosing.

In this model, orally dosed Compound 102 produced a 6.14+/−0.66 $\log_{10}$ reduction in CFU versus the 48 hour untreated control (FIG. 2). Linezolid as a comparator produced a 3.56±0.63 $\log_{10}$ reduction (FIG. 2).

D. Neutropenic Respiratory Infection Model for MRSA

Compounds were tested in a neutropenic BALB/c murine model of lung infection challenged with a tetracycline-resistant tet(M) MRSA strain SA191 infected via intranasal administration. At 2 and 12 hours mice were either dosed orally with 50 mg/kg compound or via IV administration, at 10 mg/kg. At 24 hours following initiation of treatment, mice were euthanized and bacterial reduction in the lung was quantified by plating lung homogenates. Data was recorded as $\log_{10}$ reduction in lung colony forming units versus an untreated control group. The results of the testing are shown in FIG. 3.

Figure 3:
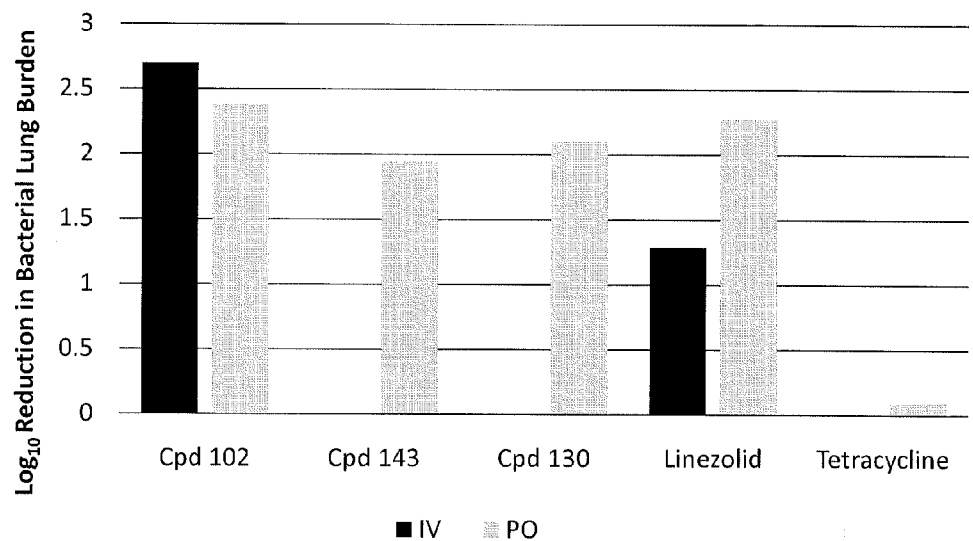
FIG. 3 is a bar graph demonstrating efficacy of Compounds 102, 143, and 130 in the MRSA SA191 lung model. Compounds 102, 143, and 130 and linezolid were evaluated at 10 mg/kg IV, BID. All compounds were tested at 50 mg/kg, BID orally except linezolid. Linezolid was evaluated at 30 mg/kg, BID orally.

FIG. 3 shows that Compounds 102, 143 and 130 were as orally efficacious (reduced the bacterial burden in the lung) as linezolid in the MRSA SA191 lung model. Compound 102 was more efficacious when administered intravenously (IV) than linezolid was. Tetracycline was ineffective as the MRSA strain SA191 is tetracycline-resistant, carrying a tet(M) ribosomal protection mechanism.

E. Respiratory Infection Model for *H. influenzae*

Figure 4:
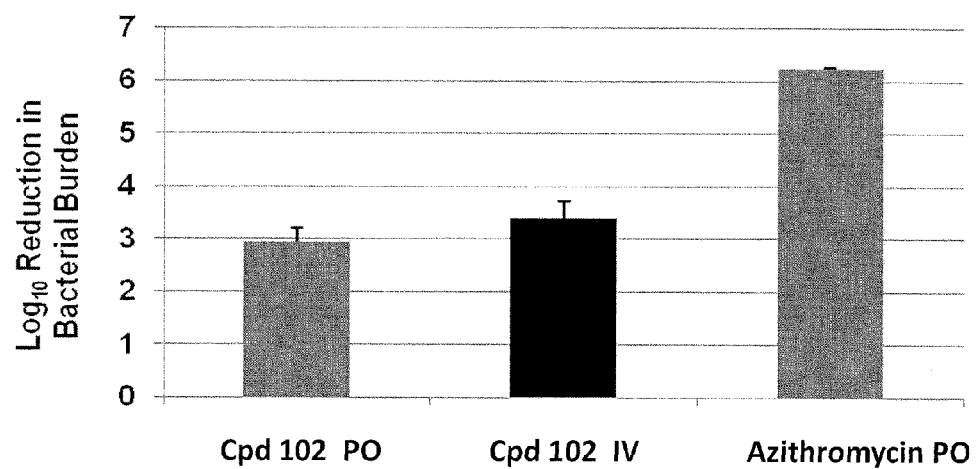
FIG. 4 is a bar graph demonstrating the efficacy of Compound 102 in a Rat lung infection model with *H. influenzae* HI551.

Compound 102 was tested in a rat lung infection challenged with *H. influenzae* via intratracheal administration. At 5, 24, and 48 hours rats were dosed orally with 100 mg/kg compound and azithromycin was dosed at 50 mg/kg. For IV administration, Compound 102 was dosed at 25 mg/kg at 5, 24 and 48 hours. At 72 hours following initiation of treatment, rats were euthanized and bacterial reduction in the lung was quantified by plating lung homogenates. Data was recorded as $\log_{10}$ reduction in lung colony forming units versus an untreated control group. In this model, orally administered Compound 102 produced a 2.93±0.27 $\log_{10}$ reduction in CFU versus the 72 hour untreated control (FIG. 4). Azithromycin, dosed orally, produced 6.24±0.03 reduction. Dosed via the IV route, Compound 102 produced a 3.40±0.31 $\log_{10}$ reduction in CFU versus the 72 hour untreated control.

F. In Vitro Activity of Compound 102 for Selected Gram-Negative and Gram-Positive Pathogens The in vitro activity (by broth microdilution MIC) of Compound 102 against clinically important species of Gram-positive and Gram-negative pathogens was studied. As part of this study, the minimum bactericidal concentration (MBC) was also determined against a subset of the evaluated isolates to determine mode of action.

Methods

All isolates were non-duplicate, non-consecutive, clinically significant isolates and were tested by broth microdilution in accordance with CLSI M7-A8 (See Clinical and Laboratory Standards Institute. *Methods for dilution antimicrobial susceptibility tests for bacteria that grow aerobically; approved standard—8$^{th}$ ed.* CLSI document M7-A8. CLSI, Wayne, Pa. January 2009, the entire teachings of which are incorporated herein by reference).

Quality control and interpretations of results were performed according with CLIS M100-S20, where available (See Clinical and Laboratory Standards Institute. *Performance standards for antimicrobial susceptibility testing; twentieth informational supplement.* CLSI document M100-S20. CLSI, Wayne, Pa. January 2010, the entire teachings of which are incorporated herein by reference).

A subset of isolates were concurrently tested for MBC in accordance with CLSI M26-A (See Clinical and Laboratory Standards Institute. Methods for Determining Bactericidal Activity of Antimicrobial Agents; Approved Guideline. NCCLS document M26-A [ISBN 1-56238-384-1]. NCCLS, 940 West Valley Road, Suite 1400, Wayne, Pa. 19087 USA, 1999.) MBCs were evaluated based on quantitation of the growth in wells beyond the MIC to determine the well where a 3-log reduction in CFU relative to the initial inoculum was observed.

Results for all MIC testing were within the acceptable standards based on the CLSI recommended QC ranges for each comparator agent evaluated and the appropriate ATCC control strains with the exception of colistin which tested one dilution lower than the provisional QC breakpoints established by CLSI for *E. coli* ATCC 25922 and *P. aeruginosa* ATCC 27853.

Summary of Results

The data is presented in Tables 9-11. Table 9 is the antimicrobial susceptibility of all agents tested against all Gram-negative and Gram-positive organisms. Table 10 is the activity profile of Compound 102, tigecycline, and tetracycline by tetracycline resistance phenotype. Table 11 is a summary of MIC and MBC results for Compound 102 against selected strains.

TABLE 9

Antimicrobial susceptibility of all agents tested against all Gram-negative and Gram-positive organisms

| Organism | Agent | Total n | MIC$_{50}$ (μg/ml) | MIC$_{90}$ (μg/ml) |
|---|---|---|---|---|
| *Escherichia coli*[a] | Compound 102 | 40 | 2 | 4 |
| | Tigecycline[b] | | 0.5 | 2 |
| | Tetracycline | | >8 | >8 |
| | Ceftazidime | | 64 | >64 |
| | Ceftazidime/clavulanate | | 4 | 32 |
| | Colistin | | 0.25 | 0.5 |
| | Ertapenem | | ≤1 | ≤1 |
| | Gentamicin | | 2 | >8 |
| | Levofloxacin | | ≤0.25 | >4 |
| | Piperacillin/Tazobactam | | 8 | >64 |
| *Klebsiella pneumoniae*[a] | Compound 102 | 27 | 4 | 16 |
| | Tigecycline[b] | | 2 | 4 |
| | Tetracycline | | 8 | >8 |
| | Ceftazidime | | >64 | >64 |
| | Ceftazidime/clavulanate | | 16 | >32 |
| | Colistin | | 0.25 | 0.5 |
| | Ertapenem | | ≤1 | 8 |
| | Gentamicin | | >8 | >8 |
| | Levofloxacin | | 1 | >4 |
| | Piperacillin/Tazobactam | | >64 | >64 |
| *Klebsiella oxytoca* | Compound 102 | 30 | 1 | 4 |
| | Tigecycline[b] | | 0.5 | 2 |
| | Tetracycline | | 0.5 | 4 |
| | Ceftazidime | | ≤0.5 | ≤0.5 |
| | Ceftazidime/clavulanate | | ≤0.25 | 0.5 |
| | Colistin | | ≤0.12 | 0.25 |
| | Ertapenem | | ≤1 | ≤1 |
| | Gentamicin | | 0.5 | 2 |
| | Levofloxacin | | ≤0.25 | 4 |
| | Piperacillin/Tazobactam | | 2 | 8 |
| *Proteus vulgaris* | Compound 102 | 29 | 8 | >16 |
| | Tigecycline[b] | | 2 | 4 |
| | Tetracycline | | 8 | >8 |
| | Ceftazidime | | ≤0.5 | >64 |
| | Ceftazidime/clavulanate | | ≤0.25 | ≤0.25 |
| | Colistin | | >2 | >2 |
| | Ertapenem | | ≤1 | ≤1 |
| | Gentamicin | | 1 | >8 |
| | Levofloxacin | | ≤0.25 | 1 |
| | Piperacillin/Tazobactam | | ≤0.5 | 2 |

TABLE 9-continued

Antimicrobial susceptibility of all agents tested against all Gram-negative and Gram-positive organisms

| Organism | Agent | Total n | MIC$_{50}$ (μg/ml) | MIC$_{90}$ (μg/ml) |
|---|---|---|---|---|
| *Enterobacter aerogenes* | Compound 102 | 30 | 2 | 2 |
| | Tigecycline[b] | | 0.5 | 0.5 |
| | Tetracycline | | 1 | 2 |
| | Ceftazidime | | ≤0.5 | 16 |
| | Ceftazidime/clavulanate | | ≤0.25 | 16 |
| | Colistin | | ≤0.12 | ≤0.12 |
| | Ertapenem | | ≤1 | ≤1 |
| | Gentamicin | | ≤0.25 | 0.5 |
| | Levofloxacin | | ≤0.25 | ≤0.25 |
| | Piperacillin/Tazobactam | | 2 | 16 |
| *Enterobacter cloacae* | Compound 102 | 29 | 4 | 8 |
| | Tigecycline[b] | | 1 | 4 |
| | Tetracycline | | 4 | >8 |
| | Ceftazidime | | >64 | >64 |
| | Ceftazidime/clavulanate | | >32 | >32 |
| | Colistin | | ≤0.12 | >2 |
| | Ertapenem | | ≤1 | >8 |
| | Gentamicin | | 0.5 | >8 |
| | Levofloxacin | | 1 | >4 |
| | Piperacillin/Tazobactam | | >64 | >64 |
| *Serratia marcescens* | Compound 102 | 30 | 4 | 8 |
| | Tigecycline[b] | | 1 | 2 |
| | Tetracycline | | >8 | >8 |
| | Ceftazidime | | ≤0.5 | ≤0.5 |
| | Ceftazidime/clavulanate | | ≤0.25 | 0.5 |
| | Colistin | | >2 | >2 |
| | Ertapenem | | ≤1 | ≤1 |
| | Gentamicin | | 0.5 | 1 |
| | Levofloxacin | | ≤0.25 | 2 |
| | Piperacillin/Tazobactam | | 2 | 8 |
| *Morganella morganii* | Compound 102 | 30 | 8 | 16 |
| | Tigecycline[b] | | 2 | 4 |
| | Tetracycline | | 2 | >8 |
| | Ceftazidime | | ≤0.5 | 4 |
| | Ceftazidime/clavulanate | | 4 | 16 |
| | Colistin | | >2 | >2 |
| | Ertapenem | | ≤1 | ≤1 |
| | Gentamicin | | 1 | >8 |
| | Levofloxacin | | ≤0.25 | 4 |
| | Piperacillin/Tazobactam | | ≤0.5 | 1 |
| *Salmonella* species | Compound 102 | 30 | 2 | 2 |
| | Tigecycline[b] | | 0.25 | 0.5 |
| | Tetracycline | | 1 | >8 |
| | Ceftazidime | | ≤0.5 | ≤0.5 |
| | Ceftazidime/clavulanate | | ≤0.25 | ≤0.25 |
| | Colistin | | ≤0.12 | 0.5 |
| | Ertapenem | | ≤1 | ≤1 |
| | Gentamicin | | 0.5 | 1 |
| | Levofloxacin | | ≤0.25 | ≤0.25 |
| | Piperacillin/Tazobactam | | 2 | 4 |
| *Shigella* species | Compound 102 | 30 | 0.5 | 2 |
| | Tigecycline[b] | | 0.25 | 0.5 |
| | Tetracycline | | >8 | >8 |
| | Ceftazidime | | ≤0.5 | ≤0.5 |
| | Ceftazidime/clavulanate | | ≤0.25 | ≤0.25 |
| | Colistin | | ≤0.12 | ≤0.12 |
| | Ertapenem | | ≤1 | ≤1 |
| | Gentamicin | | 1 | 1 |
| | Levofloxacin | | ≤0.25 | 0.5 |
| | Piperacillin/Tazobactam | | 2 | 2 |

TABLE 9-continued

Antimicrobial susceptibility of all agents tested against all Gram-negative and Gram-positive organisms

| Organism | Agent | Total n | MIC$_{50}$ | MIC$_{90}$ |
|---|---|---|---|---|
| Acinetobacter lwoffii | Compound 102 | 29 | 0.12 | 0.5 |
|  | Tigecycline |  | 0.12 | 0.5 |
|  | Tetracycline |  | 0.5 | 4 |
|  | Ceftazidime |  | 1 | 16 |
|  | Ceftazidime/ clavulanate |  | ≤0.25 | 4 |
|  | Colistin |  | ≤0.12 | >2 |
|  | Ertapenem |  | ≤1 | 4 |
|  | Gentamicin |  | ≤0.25 | 1 |
|  | Levofloxacin |  | ≤0.25 | ≤0.25 |
|  | Piperacillin/ Tazobactam |  | ≤0.5 | 8 |
| Stenotrophomonas maltophilia | Compound 102 | 29 | 0.5 | 2 |
|  | Tigecycline |  | 0.5 | 2 |
|  | Tetracycline |  | 8 | >8 |
|  | Ceftazidime |  | 8 | >64 |
|  | Ceftazidime/ clavulanate |  | 32 | >32 |
|  | Colistin |  | 0.25 | >2 |
|  | Ertapenem |  | >8 | >8 |
|  | Gentamicin |  | >8 | >8 |
|  | Levofloxacin |  | 0.5 | >4 |
|  | Piperacillin/ Tazobactam |  | 32 | >64 |
| Staphylococcus aureus (MRSA PVL+) | Compound 102 | 30 | 0.25 | 0.25 |
|  | Tigecycline[b] |  | 0.12 | 0.12 |
|  | Tetracycline |  | 0.25 | 0.25 |
|  | Clindamycin |  | 0.06 | 0.12 |
|  | Daptomycin |  | 0.5 | 1 |
|  | Ertapenem |  | 4 | 8 |
|  | Erythromycin |  | >4 | >4 |
|  | Gentamicin |  | 0.25 | 0.5 |
|  | Levofloxacin |  | 0.25 | >2 |
|  | Linezolid |  | 1 | 2 |
|  | Vancomycin |  | 1 | 1 |
| Staphylococcus aureus MRSA[c] | Compound 102 | 105 | 0.5 | 2 |
|  | Tigecycline |  | 0.13 | 0.25 |
|  | Tetracycline |  | 0.25 | >32 |
|  | Levofloxacin |  | >2 | >2 |
|  | Linezolid |  | 2 | 4 |
|  | Vancomycin |  | 1 | 1 |
| Streptococcus anginosus | Compound 102 | 20 | 0.06 | 0.25 |
|  | Tigecycline[b] |  | 0.03 | 0.06 |
|  | Tetracycline |  | 0.12 | >4 |
|  | Clindamycin |  | ≤0.015 | 0.03 |
|  | Daptomycin |  | 0.25 | 0.25 |
|  | Ertapenem |  | 0.12 | 0.25 |
|  | Erythromycin |  | 0.03 | >0.5 |
|  | Levofloxacin |  | 0.5 | 0.5 |
|  | Linezolid |  | 0.5 | 1 |
|  | Penicillin |  | ≤0.12 | ≤0.12 |
|  | Vancomycin |  | 0.5 | 0.5 |
| Streptococcus intermedius | Compound 102 | 30 | 0.12 | 0.12 |
|  | Tigecycline[b] |  | 0.03 | 0.12 |
|  | Tetracycline |  | 0.25 | >4 |
|  | Clindamycin |  | ≤0.015 | 0.06 |
|  | Daptomycin |  | 0.5 | 1 |
|  | Ertapenem |  | 0.06 | 0.5 |
|  | Erythromycin |  | 0.06 | >0.5 |
|  | Levofloxacin |  | 1 | 2 |
|  | Linezolid |  | 1 | 1 |
|  | Penicillin |  | ≤0.12 | 0.25 |
|  | Vancomycin |  | 0.5 | 0.5 |
| Streptococcus mitis | Compound 102 | 29 | 0.12 | 0.25 |
|  | Tigecycline[b] |  | 0.03 | 0.12 |
|  | Tetracycline |  | 0.5 | >4 |
|  | Clindamycin |  | 0.03 | 0.06 |
|  | Daptomycin |  | 0.5 | 1 |
|  | Ertapenem |  | 0.25 | >1 |
|  | Erythromycin |  | >0.5 | >0.5 |
|  | Levofloxacin |  | 1 | 2 |
|  | Linezolid |  | 1 | 1 |
|  | Penicillin |  | 0.25 | 2 |
|  | Vancomycin |  | 0.5 | 0.5 |
| Streptococcus sanguis | Compound 102 | 18 | 0.06 | 0.12 |
|  | Tigecycline[b] |  | 0.03 | 0.06 |
|  | Tetracycline |  | 0.25 | >4 |
|  | Clindamycin |  | 0.03 | 0.06 |
|  | Daptomycin |  | 0.5 | 1 |
|  | Ertapenem |  | 0.12 | 0.5 |
|  | Erythromycin |  | 0.03 | >0.5 |
|  | Levofloxacin |  | 0.5 | 2 |
|  | Linezolid |  | 0.5 | 1 |
|  | Penicillin |  | ≤0.12 | ≤0.12 |
|  | Vancomycin |  | 0.5 | 1 |

[a] 37 E. coli and 24 K. pneumoniae genetically characterized for beta-lactamase production were tested in a separate laboratory on the same study panels
[b] FDA breakpoints for Enterobacteriaceae were applied: ≤2 μg/ml (S), 4 μg/ml (I), ≥8 μg/ml (R); for S. aureus: ≤0.5 μg/ml (S); for Streptococcus spp. (other than S. pneumoniae: ≤0.25 μg/ml (S)
[c] Staphylococcus aureus MRSA includes the data from the Staphylococcus aureus (MRSA PVL+) group.

TABLE 10

Activity profile of Compound 102, tigecycline, and tetracycline by tetracycline resistance phenotype

| Organism | Agent | Phenotype | Total_n | MIC$_{50}$ | MIC$_{90}$ |
|---|---|---|---|---|---|
| Enterobacteriaceae | Compound 102 | TET S | 168 | 2 | 8 |
|  | Compound 102 | TET NS | 137 | 4 | 16 |
|  | Tigecycline | TET S | 168 | 1 | 2 |
|  | Tigecycline | TET NS | 137 | 1 | 4 |
|  | Tetracycline | TET S | 168 | 1 | 4 |
|  | Tetracycline | TET NS | 137 | >8 | >8 |
| S. maltophila | Compound 102 | TET S | 10 | 0.5 | 0.5 |
|  | Compound 102 | TET NS | 19 | 1 | 4 |
|  | Tigecycline | TET S | 10 | 0.25 | 0.5 |
|  | Tigecycline | TET NS | 19 | 0.5 | 2 |
|  | Tetracycline | TET S | 10 | 4 | 4 |
|  | Tetracycline | TET NS | 19 | >8 | >8 |
| Viridans group streptococci | Compound 102 | TET S | 65 | 0.06 | 0.12 |
|  | Compound 102 | TET NS | 32 | 0.12 | 0.25 |
|  | Tigecycline | TET S | 65 | 0.03 | 0.06 |
|  | Tigecycline | TET NS | 32 | 0.03 | 0.12 |
|  | Tetracycline | TET S | 65 | 0.25 | 0.5 |
|  | Tetracycline | TET NS | 32 | >4 | >4 |

TET S = Tetracycline susceptible;
TET NS = Tetracycline non-susceptible

TABLE 11

Summary of MIC and MBC results

| | Study | Compound 102 | | |
|---|---|---|---|---|
| Organism | Isolate ID | MIC | MBC | MBC:MIC |
| Acinetobacter lwoffii | 2919857 | 0.12 | 0.5 | 4 |
| Acinetobacter lwoffii | 2919860 | 0.12 | 16 | 128 |
| Acinetobacter lwoffii | 2919873 | 0.25 | 0.25 | 1 |
| Acinetobacter lwoffii | 2919875 | 0.06 | 0.25 | 4 |
| Enterobacter aerogenes | 2919897 | 2 | 4 | 2 |

TABLE 11-continued

Summary of MIC and MBC results

| | | Compound 102 | | |
|---|---|---|---|---|
| Organism | Study Isolate ID | MIC | MBC | MBC:MIC |
| Enterobacter aerogenes | 2919900 | 1 | 8 | 8 |
| Enterobacter aerogenes | 2919909 | 2 | 8 | 4 |
| Enterobacter aerogenes | 2919913 | 1 | 16 | 16 |
| Enterobacter cloacae | 2920072 | 8 | 16 | 2 |
| Enterobacter cloacae | 2920082 | 2 | 8 | 4 |
| Enterobacter cloacae | 2920119 | 2 | 2 | 1 |
| Klebsiella oxytoca | 2919956 | 1 | 8 | 8 |
| Klebsiella oxytoca | 2919964 | 1 | 4 | 4 |
| Klebsiella oxytoca | 2919972 | 2 | 4 | 2 |
| Klebsiella oxytoca | 2919983 | 1 | 8 | 8 |
| Morganella morganii | 2919931 | 4 | >16 | >4 |
| Morganella morganii | 2919935 | 4 | >16 | >4 |
| Morganella morganii | 2919945 | 8 | >16 | >2 |
| Proteus vulgaris | 2919822 | 16 | >16 | >1 |
| Proteus vulgaris | 2919827 | 8 | >16 | >2 |
| Proteus vulgaris | 2919835 | 4 | >16 | >4 |
| Proteus vulgaris | 2919836 | 2 | 8 | 4 |
| Salmonella species | 2919986 | 2 | 8 | 4 |
| Salmonella species | 2919990 | 2 | 8 | 4 |
| Salmonella species | 2920006 | 2 | 8 | 4 |
| Salmonella species | 2920008 | 2 | 8 | 4 |
| Serratia marcescens | 2920092 | 4 | 16 | 4 |
| Serratia marcescens | 2920094 | 4 | >16 | >4 |
| Serratia marcescens | 2920100 | 8 | 16 | 2 |
| Serratia marcescens | 2920109 | 4 | 16 | 4 |
| Shigella species | 2919892 | 1 | 4 | 4 |
| Shigella species | 2919894 | 0.25 | 4 | 16 |
| Shigella species | 2920018 | 0.25 | 0.5 | 2 |
| Shigella species | 2920026 | 0.5 | 16 | 32 |
| Shigella species | 2920028 | 0.5 | 4 | 8 |
| Staphylococcus aureus | 2919648 | 0.25 | >4 | >16 |
| Staphylococcus aureus | 2919649 | 0.25 | >4 | >16 |
| Staphylococcus aureus | 2919650 | 0.25 | >4 | >16 |
| Stenotrophomonas maltophilia | 2920035 | 2 | >16 | >8 |
| Stenotrophomonas maltophilia | 2920051 | 2 | 16 | 8 |
| Streptococcus anginosus | 2919722 | 0.25 | 2 | 8 |
| Streptococcus anginosus | 2919742 | 0.12 | 2 | 16 |
| Streptococcus anginosus | 2919797 | 0.25 | 2 | 8 |
| Streptococcus intermedius | 2919756 | 0.06 | 1 | 16 |
| Streptococcus intermedius | 2919759 | 0.03 | 2 | 64 |
| Streptococcus intermedius | 2919784 | 0.12 | 2 | 16 |
| Streptococcus intermedius | 2919819 | 0.25 | 1 | 4 |
| Streptococcus mitis | 2919763 | 0.12 | 0.5 | 4 |
| Streptococcus mitis | 2919781 | 0.12 | 0.12 | 1 |
| Streptococcus mitis | 2919798 | 0.06 | 0.06 | 1 |
| Streptococcus mitis | 2919803 | 0.12 | 1 | 8 |
| Streptococcus sanguis | 2919749 | 0.06 | 0.25 | 4 |
| Streptococcus sanguis | 2919752 | 0.25 | 0.5 | 2 |
| Streptococcus sanguis | 2919758 | 0.12 | 2 | 16 |
| Escherichia coli | 2921525 | 1 | >16 | >16 |
| Escherichia coli | 2921526 | 2 | 16 | 8 |
| Klebsiella pneumonia | 2921528 | 2 | >16 | >8 |
| Klebsiella pneumoniae | 2921529 | 2 | >16 | >8 |

Against the evaluated Gram-negative and Gram-positive pathogens, Compound 102 MICs were generally 2-4 fold higher than those of tigecycline.

Compound 102 had comparable MICs relative to tetracycline against the evaluated *S. aureus* and Enterobacteriaceae excluding *Shigella* spp. where Compound 102 was more potent. Compound 102 also had 2-4 fold lower MICs than tetracycline against *Acinetobacter lwoffii, S. maltophila*, and streptococci.

Compound 102 was more potent by $MIC_{50}/MIC_{90}$ against Gram-positive pathogens relative to Gram-negative pathogens.

Compound 102 and tigecycline MICs were not notably altered against evaluated tetracycline resistant isolates relative to tetracycline susceptible isolates, and Compound 102 maintained potency against tetracycline resistant *Shigella* spp., *S. maltophila*, and streptococci.

MBC:MIC ratios for Compound 102 indicated bacteriostatic mode of action (ratio>2 for 89.3% of evaluated isolates).

G. In Vitro Activity of Compound 102 for selected Respiratory Pathogens

The in vitro activity (by broth microdilution MIC) of Compound 102 against clinically important Gram-positive and Gram-negative species that cause respiratory tract or acute bacterial skin and skin structure infections was studied.

Methods

All isolates were non-duplicate, non-consecutive, clinically significant isolates and were tested by broth microdilution in accordance with CLSI M7-A8 (See Clinical and Laboratory Standards Institute. *Methods for dilution antimicrobial susceptibility tests for bacteria that grow aerobically; approved standard—8th ed.* CLSI document M7-A8. CLSI, Wayne, Pa. January 2009, the entire teachings of which are incorporated herein by reference); CLSI M45-A (See Clinical and Laboratory Standards Institute. *Methods for antimicrobial dilution and disk susceptibility testing of infrequently isolated or fastidious bacteria; approved guideline.* CLSI document M45-A. CLSI, Wayne, Pa. May 2006, the entire teachings of which are incorporated herein by reference).

Quality control and interpretations of results were performed according with CLSI M100-S20, where available. (See Clinical and Laboratory Standards Institute. *Performance standards for antimicrobial susceptibility testing; twentieth informational supplement.* CLSI document M100-S20. CLSI, Wayne, Pa. January 2010, the entire teachings of which are incorporated herein by reference).

Results for all MIC testing were within the acceptable standards based on the CLSI recommended QC ranges for each comparator agent evaluated and the appropriate ATCC control strains on each day of testing.

Summary of Results

The activity profiles are presented in Tables 12-14. Table 12 is the activity profile of Compound 102 and other comparator agents against evaluated Gram-positive pathogens. Table 13 is the activity profile of Compound 102 and other comparator agents against evaluated Gram-negative pathogens. Table 14 is the activity profile of Compound 102 and other comparator agents against evaluated pathogen by tetracycline phenotype.

TABLE 12

Activity profile of Compound 102 and other comparator agents against evaluated Gram-positive pathogens

| | | | MIC (mg/mL) | |
|---|---|---|---|---|
| Organism | Phenotype | Drug | $MIC_{50}$ | $MIC_{90}$ |
| S. aureus (n = 50) | MSSA (n = 50)[1] | Compound 102 | 0.25 | 0.5 |
| | | Tigecycline[3] | 0.12 | 0.25 |
| | | Tetracycline | 0.25 | 0.5 |
| | | Azithromycin | 2 | >4 |
| | | Ceftriaxone | 4 | 4 |
| | | Clindamycin | 0.12 | 0.12 |
| | | Gentamicin | 0.25 | 0.5 |
| | | Imipenem | ≤0.25 | ≤0.25 |
| | | Levofloxacin | 0.25 | 1 |
| | | Linezolid | 2 | 4 |
| | | Vancomycin | 1 | 1 |
| CoNS (n = 52) | MSCoNS (n = 26)[1] | Compound 102 | 0.25 | 1 |
| | | Tigecycline | 0.06 | 0.25 |
| | | Tetracycline | 0.5 | 2 |
| | | Azithromycin | 0.25 | >4 |
| | | Ceftriaxone | 1 | 2 |
| | | Clindamycin | 0.06 | 0.06 |
| | | Gentamicin | 0.12 | 0.5 |
| | | Imipenem | ≤0.25 | ≤0.25 |
| | | Levofloxacin | 0.25 | >4 |
| | | Linezolid | 1 | 1 |
| | | Vancomycin | 2 | 2 |

TABLE 12-continued

Activity profile of Compound 102 and other comparator agents against evaluated Gram-positive pathogens

| Organism | Phenotype | Drug | MIC (mg/mL) | |
|---|---|---|---|---|
| | | | MIC$_{50}$ | MIC$_{90}$ |
| | MRCoNS (n = 26)[1] | Compound 102 | 0.25 | 1 |
| | | Tigecycline | 0.06 | 0.12 |
| | | Tetracycline | 0.25 | 2 |
| | | Azithromycin | >4 | >4 |
| | | Ceftriaxone | 16 | >64 |
| | | Clindamycin | 0.12 | >2 |
| | | Gentamicin | 0.25 | >8 |
| | | Imipenem | 1 | >8 |
| | | Levofloxacin | >4 | >4 |
| | | Linezolid | ≤0.5 | 1 |
| | | Vancomycin | 1 | 2 |
| S. saprophyticus (n = 36) | | Compound 102 | 0.25 | 0.5 |
| | | Tigecycline | 0.12 | 0.25 |
| | | Tetracycline | 0.5 | 0.5 |
| | | Azithromycin | 1 | >4 |
| | | Ceftriaxone | 8 | 16 |
| | | Clindamycin | 0.06 | 0.12 |
| | | Gentamicin | ≤0.06 | ≤0.06 |
| | | Imipenem | ≤0.25 | ≤0.25 |
| | | Levofloxacin | 0.5 | 0.5 |
| | | Linezolid | 2 | 4 |
| | | Vancomycin | 1 | 1 |
| S. pneumoniae (n = 100) | PEN S (n = 39)[2] | Compound 102 | 0.06 | 0.12 |
| | | Tigecycline | 0.06 | 0.06 |
| | | Tetracycline | 0.12 | 0.5 |
| | | Azithromycin | 0.12 | >4 |
| | | Ceftriaxone | ≤0.03 | 0.06 |
| | | Clindamycin | 0.06 | 0.06 |
| | | Imipenem | ≤0.015 | ≤0.015 |
| | | Levofloxacin | 0.5 | 1 |
| | | Linezolid | 1 | 1 |
| | | Penicillin (oral) | ≤0.12 | ≤0.12 |
| | | Vancomycin | 0.5 | 0.5 |
| | PEN I (n = 11)[2] | Compound 102 | 0.12 | 0.25 |
| | | Tigecycline | 0.06 | 0.06 |
| | | Tetracycline | 8 | 32 |
| | | Azithromycin | >4 | >4 |
| | | Ceftriaxone | 0.12 | 0.5 |
| | | Clindamycin | 0.06 | >0.5 |
| | | Imipenem | 0.03 | 0.25 |
| | | Levofloxacin | 0.5 | 1 |
| | | Linezolid | 1 | 1 |
| | | Penicillin (oral) | 0.25 | 1 |
| | | Vancomycin | 0.5 | 0.5 |
| | PEN R (n = 50)[2] | Compound 102 | 0.06 | 0.12 |
| | | Tigecycline | 0.06 | 0.06 |
| | | Tetracycline | 16 | 16 |
| | | Azithromycin | >4 | >4 |
| | | Ceftriaxone | 1 | 2 |
| | | Clindamycin | >0.5 | >0.5 |
| | | Imipenem | 0.5 | 0.5 |
| | | Levofloxacin | 0.5 | 1 |
| | | Linezolid | 1 | 1 |
| | | Penicillin (oral) | 2 | >2 |
| | | Vancomycin | 0.25 | 0.5 |
| S. pyogenes (n = 50) | | Compound 102 | 0.12 | 0.25 |
| | | Tigecycline | 0.06 | 0.06 |
| | | Tetracycline | 0.25 | 32 |
| | | Azithromycin | 0.12 | >4 |
| | | Ceftriaxone | ≤0.03 | ≤0.03 |
| | | Clindamycin | 0.06 | 0.06 |
| | | Imipenem | ≤0.015 | ≤0.015 |
| | | Levofloxacin | 0.5 | 0.5 |
| | | Linezolid | 1 | 1 |
| | | Penicillin | ≤0.12 | ≤0.12 |
| | | Vancomycin | 0.5 | 0.5 |
| S. agalactiae (n = 50) | | Compound 102 | 0.5 | 0.5 |
| | | Tigecycline | 0.12 | 0.12 |
| | | Tetracycline | 32 | >32 |
| | | Azithromycin | 0.06 | >4 |
| | | Ceftriaxone | 0.06 | 0.06 |
| | | Clindamycin | 0.06 | >0.5 |
| | | Imipenem | ≤0.015 | 0.03 |
| | | Levofloxacin | 0.5 | 1 |
| | | Linezolid | 1 | 1 |
| | | Penicillin | ≤0.12 | ≤0.12 |
| | | Vancomycin | 0.5 | 0.5 |
| E. faecalis (n = 101) | VAN S (n = 53) | Compound 102 | 0.5 | 0.5 |
| | | Tigecycline | 0.12 | 0.12 |
| | | Tetracycline | >32 | >32 |
| | | Azithromycin | >4 | >4 |
| | | Ceftriaxone | >64 | >64 |
| | | Clindamycin | >2 | >2 |
| | | Gentamicin | >8 | >8 |
| | | Imipenem | 1 | 1 |
| | | Levofloxacin | 1 | >4 |
| | | Linezolid | 2 | 2 |
| | | Vancomycin | 1 | 2 |
| | VAN NS (n = 48) | Compound 102 | 0.5 | 1 |
| | | Tigecycline | 0.06 | 0.12 |
| | | Tetracycline | >32 | >32 |
| | | Azithromycin | >4 | >4 |
| | | Ceftriaxone | >64 | >64 |
| | | Clindamycin | >2 | >2 |
| | | Gentamicin | >8 | >8 |
| | | Imipenem | 1 | 2 |
| | | Levofloxacin | >4 | >4 |
| | | Linezolid | 2 | 2 |
| | | Vancomycin | >16 | >16 |
| E. faecium (n = 100) | VAN S (n = 49) | Compound 102 | 0.12 | 0.5 |
| | | Tigecycline | 0.06 | 0.06 |
| | | Tetracycline | 0.25 | >32 |
| | | Azithromycin | >4 | >4 |
| | | Ceftriaxone | >64 | >64 |
| | | Clindamycin | >2 | >2 |
| | | Gentamicin | 8 | >8 |
| | | Imipenem | >8 | >8 |
| | | Levofloxacin | >4 | >4 |
| | | Linezolid | 2 | 2 |
| | | Vancomycin | 0.5 | 1 |
| | VAN NS (n = 51) | Compound 102 | 0.12 | 0.5 |
| | | Tigecycline | 0.06 | 0.12 |
| | | Tetracycline | 0.25 | >32 |
| | | Azithromycin | >4 | >4 |
| | | Ceftriaxone | >64 | >64 |
| | | Clindamycin | >2 | >2 |
| | | Gentamicin | 8 | >8 |
| | | Imipenem | >8 | >8 |
| | | Levofloxacin | >4 | >4 |
| | | Linezolid | 2 | 2 |
| | | Vancomycin | >16 | >16 |

[1]As oxacillin was not tested as part of the current study, methicillin phenotype was based off of prior oxacillin testing performed on these isolates
[2]Penicillin MICs from prior testing were utilized to determine penicillin phenotype, as penicillin was only tested as low as 0.12 mg/mL, and isolates with MICs of ≤0.12 mg/mL can not be interpreted as either susceptible or intermediate
[3]No CLSI/FDA criteria available for interpretation of MIC MSSA: methicillin-susceptible S. aureus;

MSCoNS: methicillin-susceptible coagulase-negative staphylococci;

MRCoNS: methicillin-resistant coagulase-negative staphylococci

PEN: penicillin;

VAN: vancomycin;

S: susceptible;

I: intermediate;

R: resistant;

NS: non-susceptible;

NA: not applicable

TABLE 13

Activity profile of Compound 102 and other comparator agents against evaluated Gram-negative pathogens

| Organism | Drug | MIC (mg/mL) | |
|---|---|---|---|
| | | MIC$_{50}$ | MIC$_{90}$ |
| H. influenzae (n = 50) | Compound 102 | 0.5 | 1 |
| | Tigecycline | 0.12 | 0.25 |
| | Tetracycline | 0.5 | 0.5 |
| | Ampicillin | ≤0.5 | 8 |
| | Azithromycin | 1 | 2 |
| | Ceftriaxone | ≤0.03 | ≤0.03 |
| | Imipenem | 1 | 2 |
| | Levofloxacin | 0.03 | 0.03 |
| M. catarrhalis (n = 50) | Compound 102 | 0.12 | 0.12 |
| | Tigecycline | 0.06 | 0.12 |
| | Tetracycline | 0.12 | 0.25 |
| | Azithromycin | ≤0.12 | ≤0.12 |
| | Ceftriaxone | ≤0.5 | ≤0.5 |
| | Clindamycin | 1 | 2 |
| | Gentamicin | 0.12 | 0.12 |
| | Imipenem | ≤0.25 | ≤0.25 |
| | Levofloxacin | 0.06 | 0.06 |

TABLE 14

Activity profile of Compound 102 and other comparator agents against evaluated pathogen by tetracycline phenotype

| Organism | Drug | Phenotype | N | MIC (mg/mL) | |
|---|---|---|---|---|---|
| | | | | MIC$_{50}$ | MIC$_{90}$ |
| S. pneumoniae | Compound 102 | TET S | 54 | 0.06 | 0.12 |
| | | TET NS | 46 | 0.12 | 0.12 |
| | Tigecycline | TET S | 54 | 0.06 | 0.06 |
| | | TET NS | 46 | 0.06 | 0.06 |
| | Tetracycline | TET S | 54 | 0.12 | 0.25 |
| | | TET NS | 46 | 16 | 32 |
| S. pyogenes | Compound 102 | TET S | 44 | 0.12 | 0.12 |
| | | TET NS | 6 | 0.25 | NA |
| | Tigecycline | TET S | 44 | 0.06 | 0.06 |
| | | TET NS | 6 | 0.06 | NA |
| | Tetracycline | TET S | 44 | 0.12 | 0.25 |
| | | TET NS | 6 | 32 | NA |
| S. agalactiae | Compound 102 | TET S | 11 | 0.12 | 0.12 |
| | | TET NS | 39 | 0.5 | 0.5 |
| | Tigecycline | TET S | 11 | 0.12 | 0.12 |
| | | TET NS | 39 | 0.12 | 0.12 |
| | Tetracycline | TET S | 11 | 0.25 | 0.25 |
| | | TET NS | 39 | 32 | >32 |
| E. faecalis | Compound 102 | TET S | 30 | 0.12 | 0.25 |
| | | TET NS | 71 | 0.5 | 1 |
| | Tigecycline | TET S | 30 | 0.06 | 0.12 |
| | | TET NS | 71 | 0.12 | 0.12 |
| | Tetracycline | TET S | 30 | 0.25 | 0.5 |
| | | TET NS | 71 | >32 | >32 |
| E. faecium | Compound 102 | TET S | 60 | 0.12 | 0.12 |
| | | TET NS | 40 | 0.25 | 0.5 |
| | Tigecycline | TET S | 60 | 0.06 | 0.06 |
| | | TET NS | 40 | 0.06 | 0.12 |
| | Tetracycline | TET S | 60 | 0.25 | 0.25 |
| | | TET NS | 40 | >32 | >32 |

NA: not applicable;
TET: tetracycline;
S: susceptible;
NS: non-susceptible

Against the evaluated Gram-positive aerobic pathogens, Compound 102 MICs were comparable to those of tetracycline against staphylococci and were several-fold lower than those of tetracycline against pneumococci and beta-hemolytic streptococci; Compound 102 MICs were generally 2-4 fold higher than those of tigecycline.

Against the evaluated Gram-negative respiratory pathogens, Compound 102 had similar MICs to those of tetracycline; Compound 102 MICs were generally 2-4-fold higher than those of tigecycline.

There was minimal impact of tetracycline resistance on the overall activity profile of Compound 102, as Compound 102 MICs were at most 2-4-fold higher against tetracycline resistant isolates relative to tetracycline susceptible isolates.

H. Antibacterial Activity Against *E. coli* DH10B Recombinantly Expressing Tetracycline-Resistance Genes.

Genes encoding tet(A), tet(B), tet(K), tet(M), tet(X), and *E. coli* β-galactosidase (lacZ) as a control were amplified by PCR from clinical isolates confirmed by gene sequencing to have these tetracycline-resistance determinants and cloned into an L-arabinose inducible expression system without any affinity tags (pBAD-Myc-His, Invitrogen, Carlsbad, Calif.). Plasmids were transformed and expressed in *E. coli* DH10B cells (Invitrogen, Carlsbad, Calif.). Cloned inserts were sequenced to verify the tetracycline resistance gene sequence and compared to reported sequences in GenBank (accession numbers; tet(A), AJ419171; tet(B), AP0961; tet(K), AJ888003; tet(M), X90939.1; tet(X), M37699). Cells were grown in Mueller Hinton Broth containing ampicillin, 50 mg/ml, pre-induced for 30 minutes with 1% arabinose (tet (A), tet(B), tet(M), tet(X)) or 0.1% arabinose (tet(K)) at 30° C. prior to use as inocula in MIC assays containing ampicillin, 50 mg/ml. MIC assays were incubated at 35° C. and otherwise followed Clinical Laboratory Standards Institute guidelines, and the resultant data is shown in Table 15.

TABLE 15

MIC values for *E. coli* DH10B recombinantly expressing tetracycline-resistance genes.

| Compound | EC971 LacZ | EC1153 Tet(X) | EC969 TetM | EC970 TetK | EC1082 TetA | EC1083 TetB |
|---|---|---|---|---|---|---|
| Minocycline | 0.5 | 4 | 64 | 1 | 8 | 16 |
| Tetracycline | 2 | >32 | 64 | 64 | >128 | >128 |
| Tigecycline | 0.0625 | 2 | 0.125 | 0.0625 | 1 | 0.0625 |
| Compound 102 | 2 | 4 | 1 | 0.5 | 2 | 1 |
| Ceftriaxone | 0.125 | 0.125 | 0.5 | 0.0625 | 0.0625 | 0.0625 | tet(X) encodes an inactivating enzyme for many tetracyclines called a flavin-dependent monooxygenase.
tet(A) and tet(B) encode tetracycline-specific efflux pumps usually found in gram-negative bacteria.
tet(K) encodes a tetracycline-specific efflux pump found predominantly in gram-positive bacteria.
tet(M) encodes a tetracycline-specific ribosomal protection mechanism that is wide-spread in both gram-negatives and gram-positives.

I. Determination of Resistance Development In vitro

To estimate resistance development in vivo, Compound 102 was analyzed for the propensity to select for resistance in vitro. The spontaneous resistance frequency was determined by plating dense suspensions of *S. aureus* SA101 and *S. pneumoniae* SP106 (~$10^{10}$ colony forming units (CFU) per plating) in replicates on Mueller Hinton agar plates containing compound at 5× the MIC. Plates were supplemented with 5% defibrinated sheep blood for SP106 testing. Resistance frequencies were calculated by dividing the number of colonies that grew at a given drug concentration divided by the total number of plated CFU. For SA101 and SP106, the spontaneous resistance frequencies for Compound 102 were <$2.2 \times 10^{-10}$ and $1 \times 10^{-8}$, respectively. For SA101 and SP106, the spontaneous resistance frequencies for the levofloxacin (negative) control were <$2.2 \times 10^{-10}$ and <$3.13 \times 10^{-9}$, respectively. For SA101 and SP106, the spontaneous resistance frequencies for the rifampin (positive) control were $2.0 \times 10^{-8}$ and $2.88 \times 10^{-7}$, respectively. Thus, neither *S. aureus* nor *S. pneumoniae* appear to have large pre-existing populations that are nonsusceptible to Compound 102.

J. Non-GLP Monkey Pharmacokinetics

As a result of promising pharmacokinetic data in Sprague Dawley rats,[a] Compound 102 was evaluated in 3 non-naïve cynomolgus monkeys. Each animal received a single IV dose of 1 mg/kg and after a 7-day washout, and received a single PO dose of 10 mg/kg. Nine to ten plasma samples were drawn for each dosing route up to 24 hours into heparin-coated vacutainer tubes. Dose formulations were verified with a 5-point calibration curve. The plasma concentration of the compound was quantified by LC/MS/MS using an internal standard. Quality control (QC) samples (low, medium, high; minimum of 6 standards with LLOQ <3 ng/mL) and standard curves (in duplicate) were included in the bioanalytical run. WinNonLin was used to determine individual and mean PK parameters ±standard deviation (F, Cmax, Tmax, T1/2, CL, Vss, AUC(0-t), AUC(0-∞), and MRT). The results are presented in Table 16.

TABLE 16

Pharmacokinetic parameters for Compound 102 in non-naïve cynomologus monkeys

| A. IV dosing | | | B. PO dosing | | |
|---|---|---|---|---|---|
| Parameter | Average | SD | Parameter | Average | SD |
| Dose (mg/kg) | 1 | | Dose (mg/kg) | 10 | |
| Co (ng/ml) | 3170 | 1126 | Cmax (ng/ml) | 1260 | 497 |
| T½ (h) | 23.33 | 3.85 | Tmax (h) | 4 | 0 |
| Vdss (L/kg) | 3.40 | 0.38 | T½ (h) | 24.84 | 8.26 |
| Cl (ml/hr/kg) | 111.6 | 26.46 | AUC last (ng · h/ml) | 16333 | 4937 |
| AUC last (ng · h/ml) | 4853 | 551 | AUC inf (ng · h/ml) | 35433 | 19111 |
| AUC inf (ng · h/ml) | 9310 | 2201 | % Oral bioavailability | 33.7 | 9.1 |

[a]Initial preliminary testing in Sprague Dawley rats (n = 3) resulted an oral bioavailability (% F) of 48.3 ± 31.2.

K. Evaluation of Mammalian Phototoxicity

To estimate its potential to produce phototoxicity in vivo, Compound 102 was tested in validated in vivo and in vitro models of acute phototoxic activity at Charles River Laboratories (See Spielmann, H., et al., *The second ECVAM workshop on phototoxicity testing. The report and recommendations of ECVAM workshop* 42. Altern Lab Anim, 2000. 28(6): p. 777-814; and Peters, B. and H. G. Holzhutter, *In vitro phototoxicity testing: development and validation of a new concentration response analysis software and biostatistical analyses related to the use of various prediction models.* Altern Lab Anim, 2002. 30(4): p. 415-32, the entire teachings of both are incorporated herein by reference). Results showed that, unlike doxycycline, Compound 102 findings in vitro in the neutral red uptake 3T3 assay did not translate to a phototoxic effect in the in vivo model, which is considered to be a better mimic of clinically-relevant UVA exposure of high-level intradermal accumulation of compound.

For in vivo evaluation in the Crl:SKH1-hr hairless mouse model of phototoxicity, mice (n=3 per group) were injected intracutaneously along the back (two dorsal injection sites per mouse) with Compound 102 and control compounds (doxycycline, minocycline, levofloxacin) at either 0.0375 mg/mouse or 0.375 mg/mouse. A vehicle control group was injected with normal saline. The pH of compound formulations was adjusted to 6.5±0.5 prior to injection. Immediately after administration, mice were lightly anesthetized via intraperitoneal injection of chloral hydrate in deionized water and then positioned on plastic tubing with laboratory tape. An aluminum foil mask with a single hole with a diameter of 1.3 cm (1.3 cm²) was placed over the mid-dorsum injection site before UVA exposure. The distal administration site was shielded from UVA exposure. A UVA dose of no less than 20.0 and no more than 20.1 J/cm² at an intensity of 5±1 mW/cm² at the level of the mice was delivered during the exposure period. Mice were observed before formulation administration, after completion of administration, 60±10 minutes and 4 hours ±30 minutes after the completion of UVR exposure and 1, 2 and 3 days after UVR exposure for general appearance, clinical observations and signs of skin responses at the site of UVR exposure and the non-UVA-exposed site. Results showed that administration of the positive control, doxycycline, resulted in dosage-dependent phototoxicity (erythema, edema) at the site of UVA exposure, validating the assay. Minocycline, administered as a negative control, produced no skin reaction at either dose. Administration of levofloxacin resulted in dosage-dependent phototoxicity (erythema, edema, flaking) in the site of UVA exposure. Compound 102 at either 0.0375 or 0.375 mg/mouse resulted in no skin reactions indicative of phototoxicity on the day of UVA exposure or the following three days of observation.

L. In Vitro Susceptibility Study of Compound 102 in *Legionella pneumophila*

*Legionella* organisms are often associated with respiratory infections, and *Legionella pneumophila* results in significant mortality unless it is promptly and effectively treated. In a recent FDA workshop on Clinical Trial Design for Community-Acquired Bacterial Pneumonia (Dec. 9, 2009), the panel voted to include patients with documented *L. pneumophila* in non-inferiority community-acquired bacterial pneumonia (CABP) trials. Because *L. pneumophila* can result in an overall case mortality of 15%, it was important to determine its susceptibility to the compounds of the invention, such as Compound 102.

Methods

The in vitro activity of Compound 102 was compared to tetracycline and erythromycin against a total of 70 *L. pneumophila* isolates (serogroup 1 (n=20), 2 (n=10), 3 (n=10), 4 (n=10), 5 (n=10) and 6 (n=10)) by standard agar dilution using buffered yeast extract agar containing BCYE growth supplement (BYE).

The *Legionella pneumophila* strains were isolated from the respiratory tract from 1992 to 2010 and identified by standard methods described by Murray et al., Manual of Clinical Microbiology, 9rd ed., 2007, A.S.M., the entire teachings of which are incorporated herein by reference. Isolates from six serogroups were tested for a total number of 70 *L. pneumophila*. Buffered Yeast extract (BYE) (with original *Legionella* BCYE Growth supplement) was used as the medium to test *Legionella* strains.

A pilot test to determine if Compound 102 and tetracycline activity were impacted artificially by BCYE supplement or iron was done by testing of *Staphylococcus aureus* ATCC29213 on BYE (Original BYE), BYE without ferric pyrophosphate (modified BYE) and cation-adjusted Mueller-Hinton agar (MH).

Determination of Minimal Inhibitory Concentrations (MICs)

MICs were determined using the CLSI agar dilution method ((See Performance standards for antimicrobial susceptibility testing; Seventeenth Informational Supplement; CLS1, M100-S17 VOL 27 number 1, Clinical and Laboratory Standards Institute, Wayne, Pa., January 2007, the teachings of which are incorporated herein by reference; and Method for dilution antimicrobial susceptibility tests for bacteria that grow aerobically; approved standard 17th edition, M7-A7, Clinical and Laboratory Standards Institute (CLSI), Wayne, Pa., 2006), the entire teachings of which are incorporated herein by reference)), with replicate plating of the organisms onto a series of agar plates of increasing concentrations of compound from 0.004 mg/L to 64 μg/mL. Erythromycin and tetracycline were obtained from Sigma Chemicals, Mississauga, Ont.

Results

Only original BYE supported *L. pneumophila* growth. The pilot tests indicated that BYE resulted in a 16- to 64-fold increase in MICs relative to MH for *S. aureus* ATCC29213 (Tables 17 and 18). These results suggest that the MIC values of Compound 102 obtained in original BYE for *L. pneumophila* were artificially elevated due to media effects.

TABLE 17

Pilot Study with original BYE, Modified BYE and Cation-adjusted Mueller Hinton media for *L. pneumophila* ATCC33152.

| | | | Compound | | |
|---|---|---|---|---|---|
| Media used | Incubation Time | Assay No. | Compound 102 | Tetra-cycline | Erythromycin |
| Original BYE | 24 hours | 1 | NG | NG | NG |
| | | 2 | NG | NG | NG |
| | 48 hours | 1 | 16 | 8 | 0.5 |
| | | 2 | 16 | 8 | 0.25 |
| Modified BYE | 24 hours | 1 | NG | NG | NG |
| | | 2 | NG | NG | NG |
| | 48 hours | 1 | NG | NG | NG |
| | | 2 | NG | NG | NG |
| Cation adjusted Mueller-Hinton | 24 hours | 1 | NG | NG | NG |
| | | 2 | NG | NG | NG |
| Expected MIC Range | | | Unknown | Un-known | 0.25-0.5*** |

NG = no growth

TABLE 18

Pilot Study with original BYE, Modified BYE and Cation-adjusted Mueller Hinton media for *Staphylococcus aureus* ATCC29213.

| | | | Compound | | |
|---|---|---|---|---|---|
| Media used | Incubation Time | Assay No. | Compound 102 | Tetra-cycline | Erythro-mycin |
| Original BYE | 24 hours | 1 | 4 | 2 | 0.5 |
| | | 2 | 4 | 2 | 0.5 |
| | 48 hours | 1 | >64 | 32 | 0.5 |
| | | 2 | >64 | 32 | 0.5 |
| Modified BYE | 24 hours | 1 | 2 | 0.25 | 0.5 |
| | | 2 | 2 | 0.25 | 0.5 |
| | 48 hours | 1 | 8 | 0.5 | 0.5 |
| | | 2 | 8 | 0.5 | 0.5 |
| Cation adjusted Mueller-Hinton | 24 hours | 1 | 0.25 | 0.5 | 1 |
| | 48 hours | 1 | 0.25 | 0.5 | 1 |
| Expected MIC Range | | | 0.25-1* | 0.12-1** | 0.25-1** |

NG = No Growth

*Expected MIC Range with Cation adjusted Mueller-Hinton

**Expected MIC Range with Cation Mueller-Hinton.

***Expected MIC Range with original BYE, data obtained from previous studies.

The activity of Compound 102, tetracycline and erythromycin against all *Legionella pneumophila* serogroups is shown in Table 19. The $MIC_{90}$ values for Compound 102, tetracycline, and erythromycin against strains from all serogroups of *L. pneumophila* were 8, 8, and 0.5 mg/L, respectively, using the original BYE media.

TABLE 19

Susceptibility of *Legionella pneumophila* all serogroups in original BYE Media

| | | MIC (mg/L) | |
|---|---|---|---|
| Serogroup (no. tested) | Antibiotic | $MIC_{50}$ | $MIC_{90}$ |
| All Serogroups (70) | Compound 102 | 2 | 8 |
| | Tetracycline | 4 | 8 |
| | Erythromycin | 0.25 | 0.5 |

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of Structural Formula I:

(I)

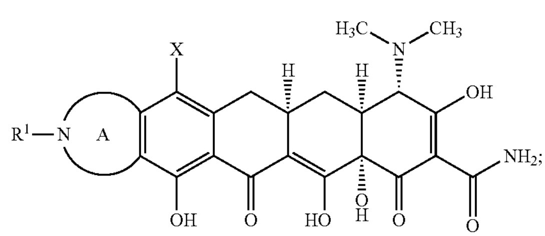

or a pharmaceutically acceptable salt thereof, wherein:

X is selected from halo, $(C_1\text{-}C_6)$alkyl, carbocyclyl, or heterocyclyl, —OR, —SR, $—S(O)_mR$, $—N(R)_2$, —N(R)C(O)R, N(R)C(O)OR', and $N(R)S(O)_mR'$, wherein:

each R is independently selected from H, $(C_1\text{-}C_6)$alkyl, carbocyclyl, or heterocyclyl; or two R groups taken together with the atom or atoms to which they are bound form a 4-7 membered non-aromatic heterocyclyl; and
R' is $(C_1-C_6)$alkyl, carbocyclyl, or heterocyclyl;
ring A is

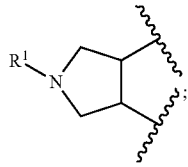

$R^1$ is selected from —$(C_1-C_8)$alkyl, —$(C_0-C_6)$alkylene-carbocyclyl, —$(C_0-C_6)$alkylene-heterocyclyl, —$(C_1-C_6)$alkylene-O—$(C_1-C_6)$alkyl, —$(C_2-C_6)$alkylene-O-carbocyclyl, —$(C_2-C_6)$alkylene-O-heterocyclyl, —$S(O)_m$—$(C_1-C_6)$alkyl, —$S(O)_m$-carbocyclyl, —$S(O)_m$-heterocyclyl, —$(C_2-C_4)$alkylene-$S(O)_m$-carbocyclyl, —$(C_2-C_4)$alkylene-$S(O)_m$-heterocyclyl, —C(O)—$[C(R^4)(R^4)]_{0-4}$—$N(R^2)(R^3)$, —C(O)—$(C_1-C_6)$alkyl, —C(O)-heterocyclyl, —C(O)-carbocyclyl, —$S(O)_m$—$[C(R^4)(R^4)]_{0-4}$—$N(R^2)(R^3)$, and —$S(O)_m$—$(C_1-C_4)$alkylene-carbocyclyl, —$S(O)_m$—$(C_1-C_4)$alkylene-heterocyclyl;

each of $R^2$ and $R^3$ is independently selected from hydrogen, $(C_1-C_8)$alkyl, —$(C_0-C_6)$alkylene-carbocyclyl, —$(C_0-C_6)$alkylene-heterocyclyl, —$(C_2-C_6)$alkylene-O-carbocyclyl, —$(C_2-C_6)$alkylene-O-heterocyclyl, —$S(O)_m$—$(C_1-C_6)$alkyl, —$S(O)_m$-carbocyclyl, —$S(O)_m$-heterocyclyl, —$(C_2-C_4)$alkylene-$S(O)_m$-carbocyclyl, and -$(C_2-C_4)$alkylene-$S(O)_m$-heterocyclyl; or $R^2$ and $R^3$, taken together with the nitrogen atom to which they are bound form a heterocyclyl, wherein the heterocyclyl optionally comprises 1 to 4 additional heteroatoms independently selected from N, S and O;

each $R^4$ is independently selected from hydrogen, $(C_1-C_6)$alkyl, carbocyclyl, heterocyclyl or a naturally occurring amino acid side chain moiety, or two $R^4$ taken together with a common carbon atom to which they are bound form a 3-7 membered non-aromatic carbocyclyl or a 4-7 membered non-aromatic heterocyclyl, wherein the heterocyclyl formed by two $R^4$ comprises one to three heteroatoms independently selected from N, S and O;

any substitutable carbon atom on ring A is optionally:
(i) substituted with one to two substituents independently selected from —$(C_1-C_4)$alkyl, and —$(C_0-C_4)$alkylene-carbocyclyl; or
(ii) substituted with =O;

each alkyl or alkylene in Structural Formula I is optionally and independently substituted with one or more substituents independently selected from halo, —OH, =O, —O—$(C_1-C_4)$alkyl, fluoro-substituted-$(C_1-C_4)$alkyl, —$S(O)_m$—$(C_1-C_4)$alkyl and —$N(R^5)(R^5)$;

each carbocyclyl or heterocyclyl portion of a substituent of ring A or the saturated heterocyclic ring fused to ring A is optionally and independently substituted with one or more substituents independently selected from halo, —$(C_1-C_4)$alkyl, —OH, =O, —O—$(C_1-C_4)$alkyl, —$(C_1-C_4)$alkylene-O—$(C_1-C_4)$alkyl, halo-substituted-$(C_1-C_4)$alkyl, halo-substituted-O—$(C_1-C_4)$alkyl, —C(O)—$(C_1-C_4)$alkyl, —C(O)-(fluoro-substituted-$(C_1-C_4)$alkyl), —$S(O)_m$—$(C_1-C_4)$alkyl, —$N(R^5)(R^5)$ and CN;

each $R^5$ is independently selected from hydrogen and $(C_1-C_4)$alkyl, wherein each alkyl in the group represented by $R^5$ is optionally and independently substituted with one or more substituents independently selected from —$(C_1-C_4)$alkyl, $(C_3-C_6)$cycloalkyl, halo, —OH, —O—$(C_1-C_4)$alkyl, and —$(C_1-C_4)$alkylene-O—$(C_1-C_4)$alkyl; and each m is independently 1 or 2.

2. The compound of claim 1, wherein X is selected from fluoro, chloro, methoxy, methyl, trifluoromethyl, trifluoromethoxy and dimethylamino.

3. The compound of claim 1, wherein X is selected from fluoro, chloro, methoxy, methyl, trifluoromethyl, trifluoromethoxy and dimethylamino.

4. The compound of any one of claims 1, 2, or 3, wherein $R^1$ is selected from —$(C_1-C_8)$alkyl, —$(C_2-C_4)$alkylene-O—$(C_1-C_4)$alkyl, —$(C_0-C_3)$alkylene-(saturated heterocycle), —$(C_0-C_3)$alkylene-$(C_3-C_7)$cycloalkyl, —C(O)—$(CH_2)_{1-3}$—$N(R^2)(R^3)$; wherein:
any alkyl or alkylene portion of $R^1$ is optionally substituted with fluoro or hydroxy;
$R^2$ is selected from hydrogen and $(C_1-C_3)$alkyl;
$R^3$ is selected from $(C_1-C_3)$alkyl and $(C_3-C_7)$cycloalkyl, or
$R^2$ and $R^3$, taken together with the nitrogen atom to which they are bound form a 4-7 membered saturated heterocyclyl, wherein the heterocyclyl is optionally substituted with fluoro.

5. The compound of claim 4, wherein $R^1$ is selected from $(C_1-C_3)$ straight alkyl, optionally substituted with one or more of: 1 to 5 methyl groups, a single hydroxy group, a single methoxy group, and 1 to 3 fluoro groups; $(C_3-C_7)$ cycloalkyl; tetrahydrofuranyl; and —C(O)—$CH_2$—$N(R^2)(R^3)$, wherein $R^2$ and $R^3$ are simultaneously methyl; $R^2$ is hydrogen and $R^3$ is $C_3-C_7$ cycloalkyl; or $R^2$ and $R^3$, taken together with the nitrogen atom to which they are bound form a pyrrolidinyl ring optionally substituted with fluoro.

6. The compound of claim 1, wherein:
X is selected from fluoro, chloro, methoxy, trifluoromethyl, and dimethylamino; and
$R^1$ is selected from ethyl, propyl, $(C_3-C_5)$branched alkyl, $(C_3-C_5)$cycloalkyl, $(C_1-C_3)$ alkylene-cyclopropyl, —$C(O)CH_2NH$-cyclopentyl, and —$C(O)CH_2$-pyrrolidin-1-yl, wherein $R^1$ is optionally substituted with fluoro.

7. The compound of claim 6, wherein:
$R^1$ is selected from 2-fluoroethyl, propyl, isopropyl, sec-butyl, tert-butyl, $(C_3-C_5)$cycloalkyl, —$C(CH_3)_2$-cyclopropyl, —$C(O)CH_2NH$-cyclopentyl, —$C(O)CH_2$-(3-fluoropyrrolidin-1-yl); and when X is methoxy or dimethylamino, $R^1$ is further selected from tert-pentyl.

8. The compound of claim 1, represented by structural formula:

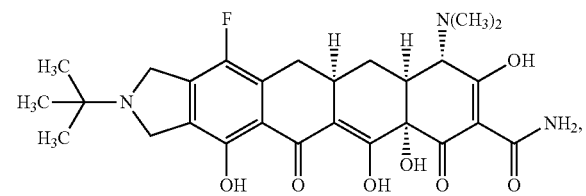

or a pharmaceutically acceptable salt thereof.

9. A compound represented by a structural formula selected from:
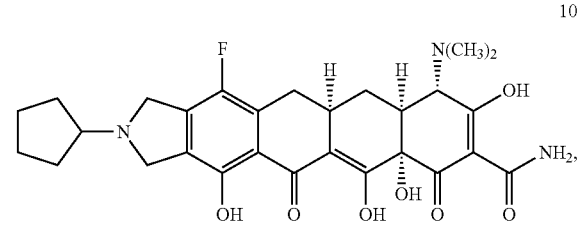
100
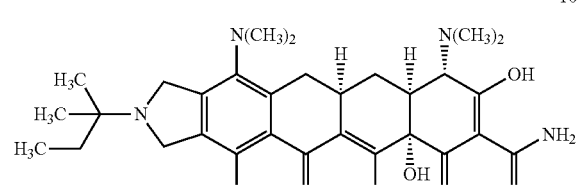
103
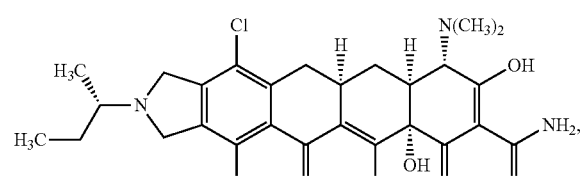
110
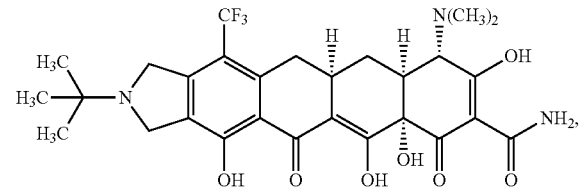 [SMILES: CN(C)[C@@H]1C(O)=C(C(N)=O)C(=O)[C@@]2(O)C(O)=C3C(=O)c4c(O)c5c(c(F)c4C[C@H]3C[C@@H]12)CN(C(C)(C)C)C5]
112
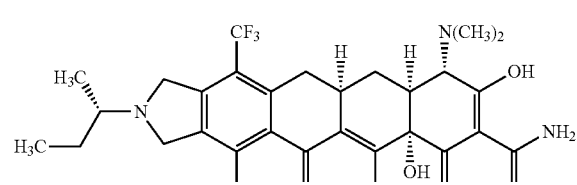
113
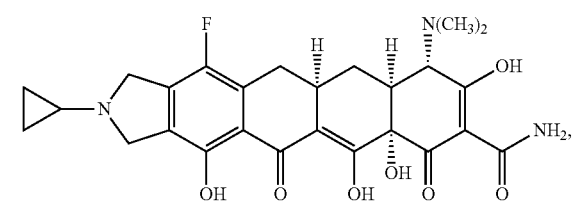
114
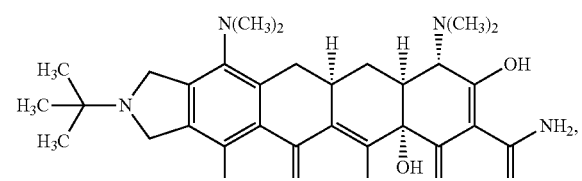
115
-continued
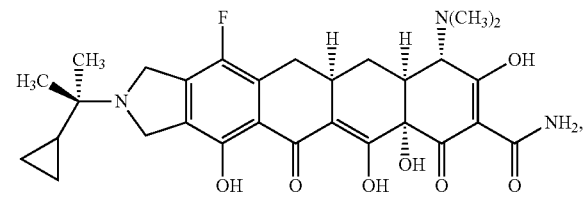
118
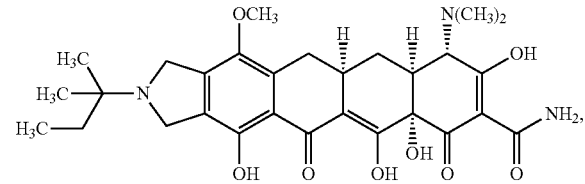
119
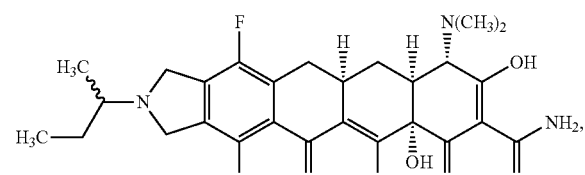
120
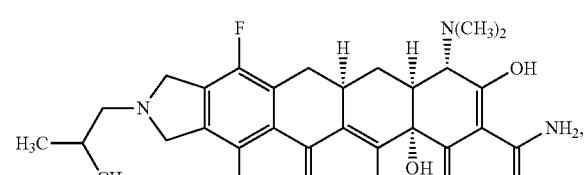
121
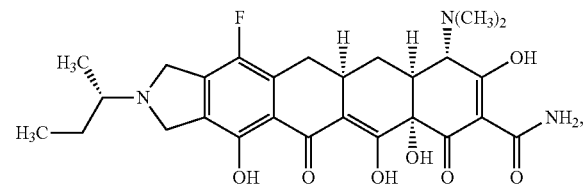
123
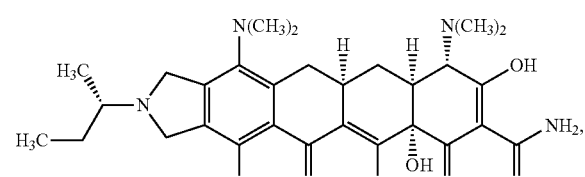
124
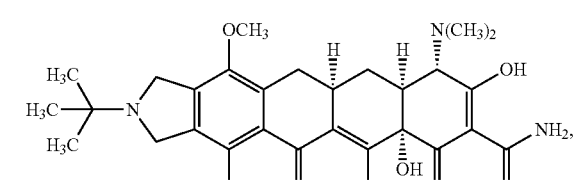
125

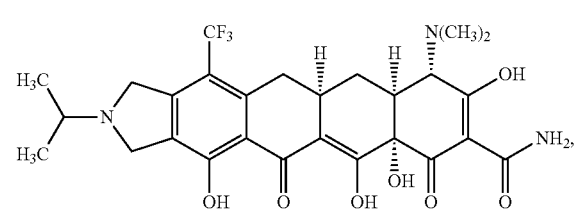
126
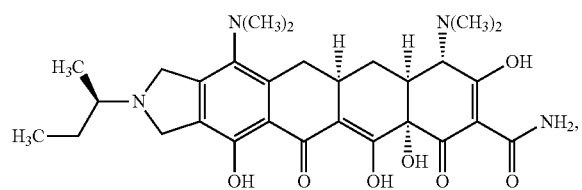
127
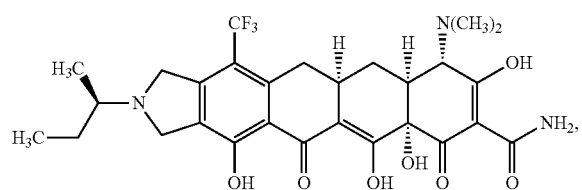
128
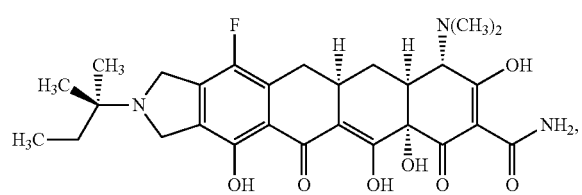
129
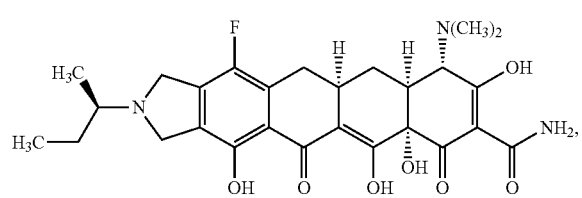
130
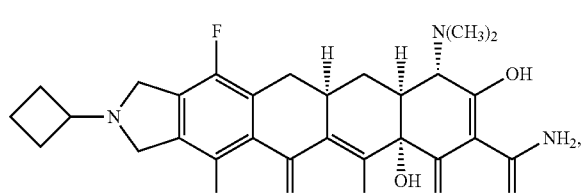
132
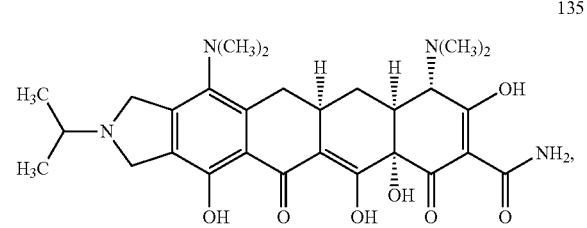
135
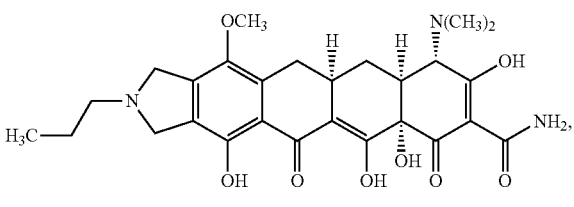
138
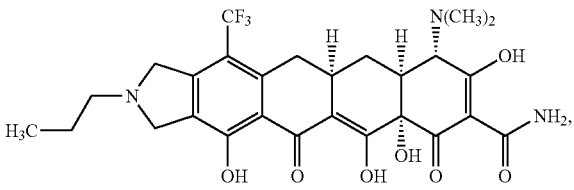
141
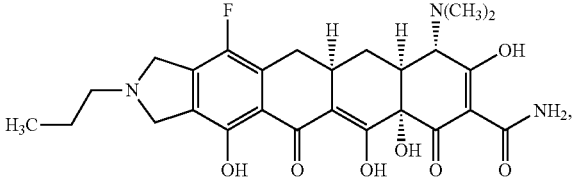 [SMILES: CCCN1Cc2c(O)c3c(c(Cl)c2C1)C[C@H]1C[C@H]2[C@H](N(C)C)C(O)=C(C(N)=O)C(=O)[C@@]2(O)C(O)=C1C3=O]
142
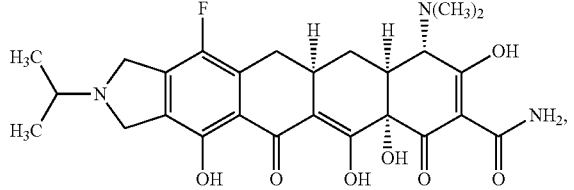
143
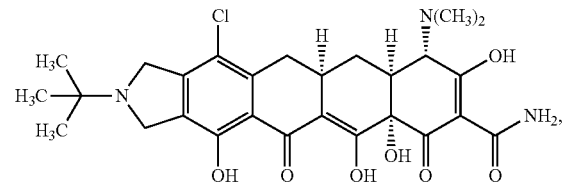
144
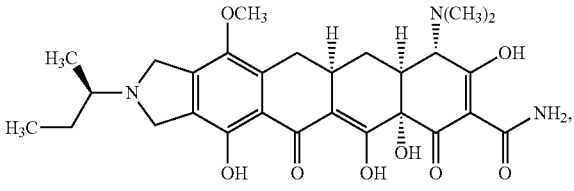
145
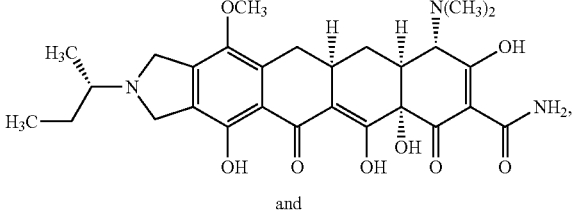
148
and -continued
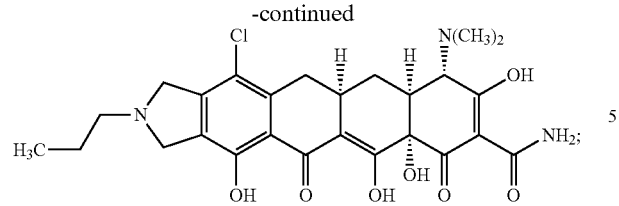
5
or a pharmaceutically acceptable salt thereof.
10. A pharmaceutical composition comprising a pharmaceutically acceptable carrier or diluent and a compound of claim 1.
* * * * *